United States Patent
Kudithipudi et al.

(10) Patent No.: US 11,384,361 B2
(45) Date of Patent: Jul. 12, 2022

(54) COMPOSITIONS AND METHODS BASED ON PMT ENGINEERING FOR PRODUCING TOBACCO PLANTS AND PRODUCTS HAVING ALTERED ALKALOID LEVELS

(71) Applicant: ALTRIA CLIENT SERVICES LLC, Richmond, VA (US)

(72) Inventors: Chengalrayan Kudithipudi, Midlothian, VA (US); Dong Qi, Henrico, VA (US); Yanxin Shen, Henrico, VA (US); Ujwala Warek, Richmond, VA (US); James A. Strickland, Virginia Beach, VA (US); Dongmei Xu, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 18 days.

(21) Appl. No.: 16/523,326

(22) Filed: Jul. 26, 2019

(65) Prior Publication Data

US 2020/0029522 A1    Jan. 30, 2020

Related U.S. Application Data

(60) Provisional application No. 62/848,159, filed on May 15, 2019, provisional application No. 62/703,775, filed on Jul. 26, 2018.

(51) Int. Cl.

| | |
|---|---|
| *A01H 5/12* | (2018.01) |
| *C12N 15/00* | (2006.01) |
| *C12N 15/82* | (2006.01) |
| *A01H 6/82* | (2018.01) |
| *C12Q 1/6827* | (2018.01) |

(52) U.S. Cl.
CPC ........... *C12N 15/8243* (2013.01); *A01H 5/12* (2013.01); *A01H 6/823* (2018.05); *C12Q 1/6827* (2013.01)

(58) Field of Classification Search
None
See application file for complete search history.

(56) References Cited

U.S. PATENT DOCUMENTS

| | | | |
|---|---|---|---|
| 4,516,590 A | 5/1985 | Teng | |
| 4,528,993 A | 7/1985 | Sensabaugh, Jr. et al. | |
| 4,660,577 A | 4/1987 | Sensabaugh et al. | |
| 4,732,856 A | 3/1988 | Federuff | |
| 4,848,373 A | 7/1989 | Lenkey | |
| 4,987,907 A | 1/1991 | Townend | |
| 5,013,658 A | 5/1991 | Dooner et al. | |
| 5,149,645 A | 9/1992 | Hoekema et al. | |
| 5,372,149 A | 12/1994 | Roth et al. | |
| 5,491,081 A | 2/1996 | Webb | |
| 5,689,035 A | 11/1997 | Webb | |
| 8,124,851 B2 | 2/2012 | Dewey et al. | |
| 8,319,011 B2 | 11/2012 | Xu et al. | |
| 9,187,759 B2 | 11/2015 | Dewey et al. | |
| 9,228,194 B2 | 1/2016 | Dewey et al. | |
| 9,228,195 B2 | 1/2016 | Dewey et al. | |
| 9,247,706 B2 | 2/2016 | Dewey et al. | |
| 2004/0118422 A1 | 6/2004 | Lundin et al. | |
| 2005/0178398 A1 | 8/2005 | Breslin et al. | |
| 2006/0191548 A1 | 8/2006 | Strickland et al. | |
| 2007/0240728 A1 | 10/2007 | Hashimoto et al. | |
| 2008/0120737 A1 | 5/2008 | Hashimoto et al. | |
| 2015/0322451 A1* | 11/2015 | Kudithipudi | A24D 1/00 131/329 |
| 2017/0130239 A1 | 5/2017 | Liedschulte et al. | |
| 2017/0233756 A1 | 8/2017 | Beeemann et al. | |
| 2018/0119163 A1 | 5/2018 | Kudithipudi et al. | |

FOREIGN PATENT DOCUMENTS

| | | |
|---|---|---|
| WO | WO 00/67558 | 11/2000 |
| WO | WO 2004/041006 A1 | 5/2004 |
| WO | WO 2005/113821 A1 | 12/2005 |
| WO | WO 2011/027315 A1 | 3/2011 |
| WO | WO 2015/157359 A1 | 10/2015 |
| WO | WO 2018/067985 A1 | 4/2018 |
| WO | WO 2018/222667 A1 | 12/2018 |
| WO | WO 2018/237107 A1 | 12/2018 |
| WO | WO 2019/140297 A1 | 7/2019 |

OTHER PUBLICATIONS

Bowman et al., "Revised North Carolina Grade index for Flue-Cured Tobacco," Tobacco Science, 32:39-40 (1988).
Cermak et al., "Efficient Design and Assembly of Custom TALEN and Other TAL Effector-Based Constructs for DNA Targeting," Nucleic Acids Research, 39:e82 (2011).
Collins et al., "Determinatiou of Nicotine Alkaloids in Tobacco Using the Autoanalyzer," Tobacco Science 13:79-81 (1969).
Davis, D. L., and M. T. Nielsen. "World Agriculture Series: Tobacco Production." Chemistry and Technology. London: Blackwell Science (1999).
Davis, Richard E. "A combined automated procedure for the determinaton of reducing sugars and nicotine alkaloids in tobacco products using a new reducing sugar method." Tab. Sci 20(1976): 139-144.
Doyle et al., "TAL Effector-Nucleotide Targeter (TALE-NT) 2.0: Tools for TAL Effector Design and Target Prediction," Nucleic Acids Research, 40:W117-122 (2012).
Estruch, Juan J., et al. "Transgenic plants: an emerging approach to pest control." Nature biotechnology 15.2 (1997): 137-141.
Fedoroff et al., "Cloning of the Bronze Locus in Maize by a Simple Procedure Using the Transposable Controlling Element Activator (Ac)," Proc. Natl. Acad. Sci. USA, 81:3825-3829 (1984).
Gaj et al., "ZFN, TALEN, and CRISPR/Cas-based methods for genome engineering." Trends in biotechnology 31.7 (2013): 397-405.

(Continued)

*Primary Examiner* — Phuong T Bui
(74) *Attorney, Agent, or Firm* — Arnold & Porter Kaye Scholer LLP

(57) ABSTRACT

The present disclosure provides compositions and methods related to tobacco plants with altered total alkaloid and nicotine levels and commercially acceptable leaf grade, their development via breeding or transgenic approaches, and production of tobacco products from these tobacco plants.

8 Claims, 11 Drawing Sheets

Specification includes a Sequence Listing.

(56) References Cited

OTHER PUBLICATIONS

Hibi, Naruhiro, et al. "Gene expression in tobacco low-nicotine mutants." The Plant Cell 6.5 (1994): 723-735.
Hibi, Naruhiro, et al. "Putrescine N-methyltransferase in cultured roots of Hyoseyamus albus: n-butylamine as a potent inhibitor of the transferase both in vitro and in vivo." Plant physiology 100.2 (1992): 826-835.
Hildering, G. J., and K. Verkerk. "Chimeric structure of tomato plants after seed treatment with EMS and X-rays. The use of induced mutations in plant breeding." (1965): 317-320.
Hoekema, André, et al. "A binary plant vector strategy based on separation of vir- and T-region of the Agrobacterium tumefaciens Ti-pasmid." Nature 303.5913 (1983): 179-180.
International Search Report and Written Opinion dated Oct. 10, 2019, in International Patent Application No. PCT/US2019/043640.
Kajikawa, Masataka, et al. "Genoric insights into the evolution of the nicotine biosynthesis pathway in tobacco." Plant physiology 174.2 (2017): 999-1011.
Legg et al., "Inheritance of Percent Total Alkaloids in Nicotiana tabacum," L. J. Hered., 60:213-217 (1969).
Lopez, Harry. "Developing Non-GMO Tobacco Cultivars with Lower Alkaloid Content Using a Reverse Genetics Strategy." (2011).
McCallum ef al., "Targeting Induced Local Lesions IN Genomes (TILLING) for Plant Functional Genomics," Nat. Biotechnol., 18:455-457 (2000).
Miller et al., "A Grade Index for Type 22 and 23 Fire-Cured Tobacco," Tobacco Intern., 192:55-57 (1990).
Morita et al., "Vacuolar Transport of Nicotine is Mediated by a Multidrug and Toxic Compound Extrusion (MATE) Transporter in Nicotiana tabacum," PNAS, 106:2447-52 (2009).
Official Standard Grades for Burley Tobacco (U.S. Type 31 and Foreign Type 93), effective Nov. 5, 1990 (55 F.R. 40645).
Official Standard Grades for Flue-Cured Tobacco (U.S. Types 11, 12, 13, 14 and Foreign Type 92), effective Mar. 27, 1989 (54 F.R. 7925).
Official Standard Grades for Georgia and Florida Shade-Grown Cigar-Wrapper Tobacco (U.S. Type 62), Effective Apr. 1971 (36 F.R. 5669).
Official Standard Grades for Ohio Cigar-Leaf Tobacco (U.S. Types 42, 43, and 44), effective Dec. 8, 1963 (28 F.R. 11719 and 28 F.R. 11926).
Official Standard Grades for Pennsylvania Seedleaf Tobacco (U.S. Type 41), effective Jan. 8, 1965 (29 F.R. 16854).
Official Standard Grades for Wisconsin Cigar-Binder Tobacco (U.S. Types 54 and 55), effective Nov. 20, 1969 (34 F.R. 17061).
Poehlman, "Breeding Field Crops," Van Nostrand Reinhold, New York (3.sup.rd ed), (1987).
Shoji et al. Clustered Transcription Factor Genes Regulate Nicotine Biosynthesis in Tobacco, The Plant Cell, 22:3390-3409 (2010).
Verkerk, "Chimerism of the Tomato Plant After Seed Irradiation wit Fast Neutrons," Neth. J. Agric. Sci., 19:197-203 (1971).
Wemsman, E. A., and Rutty, R. C., "Tobacco," Chapter 17, pp. 669-698. In: Cultivar Development. Crop Species. W. H. Fehr (ed.), MacMillan Publishing Co., Inc., New York, N.Y. (1987).
Caldwell et al., "A structured mutant population for forward and reverse genetics in Barley (*Hordeum vulgare* L.)," *The Plant Journal* 40:143-150 (2004).
Hudson, "Soybean Oil-Quality Variants Identified by Large-Scale Mutagenesis," *International Journal of Agronomy* vol. 2012 (2012).
Lu et al., "Genome-wide Targeted Mutagenesis in Rice Using the CRISPR/Cas9 System," *Molecular Plant*, 10:1242-1245 (2017).
Mohr et al., "CRISPR guide RNA design for research applications," *The FEBS Journal*, 283:3232-3238 (2016).
Sessions et al., "A High-Throughput Arabidopsis Reverse Genetics System," *The Plant Cell*, 14:2985-2984 (2002).
Tadege et al., "Large-scale insertional mutagenesis using the Tnt1 retrotransposon in the model legume *Medicago truncatula*," *The Plant Journal*, 54:335-347 (2008).

\* cited by examiner

SEQUENCE LISTING

<160> NUMBER OF SEQ ID NOS: 729

<210> SEQ ID NO 1
<211> LENGTH: 4317
<212> TYPE: DNA
<213> ORGANISM: Nicotiana tabacum

<400> SEQUENCE: 1

| | | | | | |
|---|---|---|---|---|---|
| agtctcagac | ttaatccagt | atatcccatc | ttatctcaca | ttatcccatc | aaatgtgaga | 60 |
| ttattttatc | tcatctctca | tgtggtataa | attagtcatg | aaattataat | ctcgggataa | 120 |
| tttagtccgc | gtaccaaacg | accccaagtg | ctttattgtt | ttcttattga | cagagtaagt | 180 |
| gtatgggaac | ttaccataga | aatccttcgc | tcaaaaggaa | atacttgcaa | gaactggcca | 240 |
| aacccaaaga | tgaataaact | caattacttg | attcttaaac | tcttaaaaat | gaattcaatg | 300 |
| gagaaggaaa | atatttccag | tgtaaacaca | agtgaatgaa | gagaagccaa | aataatctct | 360 |
| atcattcaag | ccttaggtgg | agattaaaaa | aattatttac | tttcttatca | agtaataggg | 420 |
| tgatcaacag | ctttcgtaaa | acgtcattag | gagaatatta | taatctcttt | tatgctgaag | 480 |
| aacccacata | aggaagatca | taaaatacat | gactttcaga | tgacttcttg | gagctttatt | 540 |
| tttaaagagt | ggctagctgg | tcagcaaaga | ggtgctcgtc | agatatcata | aaattttact | 600 |
| attatttgtt | ttaagaggga | gatggggcac | acatgcttgt | gacaaagta | agaggaagaa | 660 |
| aggagacaga | agaggaaata | gatttggggg | gggggggggg | gtttcacaat | caaagaaaat | 720 |
| ttttaaaatg | gagagagaaa | tgagcacaca | catatactaa | caaaatttta | ctaataattg | 780 |
| caccgagaca | aacttatatt | ttagttccaa | aatgtcagtc | taaccctgca | cgttgtaatg | 840 |
| aattttttaac | tattatatta | tatcgagttg | cgccctccac | tcctcggtgt | ccaaattgta | 900 |
| tttaaatgca | tagatgttta | ttgggagtgt | acagcaagct | ttcggaaaat | acaaaccata | 960 |
| atactttctc | ttcttcaatt | tgtttagttt | aattttgaaa | atggaagtca | tatctaccaa | 1020 |
| cacaaatggc | tctaccatct | tcaagaatgg | tgccattccc | atgaacggcc | accaaaatgg | 1080 |
| cacttctgaa | cacctcaacg | gctaccagaa | tggcacttcc | aaacaccaaa | acgggcacca | 1140 |
| gaatggcact | ttcgaacatc | ggaacggcca | ccagaatggg | acatccgaac | aacagaacgg | 1200 |
| gacaatcagc | catgacaatg | gcaacgagct | actgggaagc | tccgactcta | ttaagcctgg | 1260 |
| ctggttttca | gagtttagcg | cattatggcc | aggttagtac | taagaaagca | actcaaatgc | 1320 |
| atcggcctct | tgttgctact | aaatatagag | agctatcata | cttttaggga | ctaactaaaa | 1380 |
| aggaaagatt | atcacaggga | cgaagtgagc | agttaacttc | gcatattatc | agacgcatta | 1440 |
| atttgaaata | atcgaatttt | gcaggtgaag | cattctcact | taaggttgag | aagttactat | 1500 |
| tccagggaa | gtctgattac | caagatgtca | tgctctttga | ggtaattaat | attctaatac | 1560 |
| acatgcttta | atttaaagtg | atacttttaa | tttactttta | gtttattgca | tgtgcacgta | 1620 |
| cagtcagcaa | cttatgggaa | ggttctgact | ttggatggag | caattcaaca | tacagagaat | 1680 |
| ggtggatttc | catacactga | aatgattgtt | catctaccac | ttggttccat | cccaaaccca | 1740 |
| aaaaaggttt | tgatcatcgg | cggaggaatt | ggttttacat | tattcgaaat | gcttcgttat | 1800 |
| ccttcaatcg | aaaaaattga | cattgttgag | atcgatgacg | tggtagttga | tgtaagtcaa | 1860 |
| acttctttta | cccacataaa | gaaatgatt | tagattgcaa | ttcttttttat | ttttctaaaa | 1920 |
| gaataaatat | attctctttt | tttttttaaa | acaaaattct | ctttcttaca | ggtatccaga | 1980 |
| aaattttttcc | cttatctggc | agctaatttt | aacgatcctc | gtgtaaccct | agttctcgga | 2040 |
| gatggtgcgt | atatgatagt | ctcgttttat | attttatttc | acttgatttt | tacctttttt | 2100 |

```
tgtggttaat taatcatcta ccattggttc tctttacctt caggagctgc atttgtaaag    2160
gctgcacaag cgggatatta tgatgctatt atagtggact cttctgatcc cattggtacg    2220
ctattactat ttaataccaa gactattctt attaaataag ctactaagaa actaattgaa    2280
taattaataa acgtaactgt aattgatttc taaaataata tatataattt caggtccagc    2340
aaaagatttg tttgagaggc cattctttga ggcagtagcc aaagcccctta ggccaggagg    2400 agttgtatgc acacaggctg aaagcatttg gcttcatatg catattatta agcaaatcat    2460
tgctaactgt cgtcaagtct ttaagggttc tgtcaactat gcttggacaa ccgttccaac    2520
atatcccacg tattcttttt ctctctctct cttcctgtct ttttcgatgc aatgtaaatt    2580
tataaaattg gaagtccgtt ttacttttct atagacgtag atcctaaaat tgtcaagaaa    2640
tggagaattg acttacaaga aaaatcaact tcttttcatt tactattctt tttggtgaca    2700
aactttactt attatttcgt tctaaaatga aaatttattt ttatatttta aaataattta    2760
gctttaaact tttaattta cttgttatat ttttaataaa aaagatttat agtcaaataa    2820
atgttgtgac catataaaaa cctccgcatt tttaagatca taagtttcag agtcaaacga    2880
gttaatttat ttttagtatg ccggtgcgga gtcaaattat gtcataaaaa ttgaaacgga    2940
gtgagaacat ttttatttcg agtaaacttt caaggtattg tgtttaattt caagtgatac    3000
tgatcaatga tgtcttaaat attttgattt cagcggtgtg atcggttata tgctctgctc    3060
tactgaaggg ccagaagttg acttcaagaa tccagtaaat ccaattgaca agagacaac    3120 tcaagtcaag tccaaattag gacctctcaa gttctacaac tctgatgtaa cttcatatct    3180
cacaatttct ttttccgttt tactgtatgt tcttcgtcaa attttataac taactctttt    3240
catattgtct ttttttcag attcacaaag cagcattcat tttaccatct ttcgccagaa    3300
gtatgatcga gtcttaatca agtgaataat gaacactggt agtacaatca ttggaccaag    3360
atcgagtctt aatcaagtga ataataagt gaaatgcgac gtattgtagg agaattctgc    3420
agtaattatc ataatttcca attcacaatc attgtaaaat tctttctctg tggtgtttcg    3480
tactttaata taaattttcc tgctgaagtt ttgaatcgac gtttcaactc aatcctcgca    3540
aatcagttca ttaccctctt tcagtgtact atagtaaaca aatctcatag ttaccgtggt    3600
gttgtttttt gactatgaga ttttcgatct ttattaaggt tttggtctat gttttggaat    3660
tgtattgaat atatttgtaa cttactatgt atctaaatcg gctagtctct ctttttaat    3720 aaatggcgtc attgccgttg tagtttgttt actcggtact attttatcag cagtttcgat    3780
ttgtttgctc attttttaga agagggttga aatgtctttg ttgtaagata acttaccat    3840 atcttataga ttagtataga atgacccgtt ctgagccggg gccaaactta tattatttta    3900 taaaagaat ggataaattt ctttgatatg tatcagttta ttgttattaa ttagagatat    3960
agtttgagaa gctcaatgcg atgaaagaga gtaacatcgc tatattaaac taatcacaaa    4020
atagcacttt gaataagtct tcggatccca tgttgtagta ggacaaacaa taactttgtt    4080
tctatttatt tatcgttcta ttttcaccca tcaaacaaaa agtaaatttg tttctatta    4140 gtttgaatag tcgcgtagaa aattcggtag atagcagaac aaagaaaata aattcaagcc    4200
aaaaatagat catatttact gttgttcttt cagcaactac tattttgcat cagttacaag    4260
accaatatgc tttaccgtat aacaaaaata taaatgtata tgccagtaaa ttacaga     4317
```

<210> SEQ ID NO 2
<211> LENGTH: 4210
<212> TYPE: DNA

<213> ORGANISM: Nicotiana tabacum

<400> SEQUENCE: 2

```
gaattttgta aatgcttttt ttggctcagt gattttgtgg agttgggaaa atcctattg      60
gaaagtaggt cgtggttttt tcaccttttg aaccaggtat ttttcatgta aaaatacttg    120
tgttctttac ttttttgcatt tactattcca caactgtagt gtaaggaaca cgtagaagaa   180
ccatgtccta taatctgtgc acgcgaaaaa ttggacacca cgcaaatcac ccttattgtg   240
tgtcattgaa atataaaaca tcaagctcaa tcatagatta atcttttttt agtaccaaca   300
tcatatgcaa aaatcaattc aaccccccaaa acataataca accaatgtta atgcaatatc  360
tctgctgcta tcacgaaaat aattgtagct cacgaaagta ggatacatta tgtaggttac   420
atcacataga ggtaatctaa agctcccaat aataagatgt gtaatgttga ttatgtagaa   480
atttgccagg ttatttagaa taaacaagaa gaggagaaaa aaagtacaat ttacctgaac   540
tcttgaatgt atcctacaaa taacctagac ttcatggacg tcagttgtca gtttactttt   600
gttttaatgg tacatcattt gtcaaatact ttatttggat aaaaacagtt ttgcctaagg   660
agtaaacaga tccggagtaa gaaagcagac gattaaagca atttttaaaa aaggagagag  720
aaattaatga gcacacacat atactagtga aattagggta ctaatttact aataattgca   780
ccgagacaaa cttatatttt agttccaaaa tgtcagtcta accctgcacg ttgtaataaa   840
tttttaactc tattatatta tatcgagttg cgccctccac tcctcggtgt ccaaattgta   900
tttaaatgca tagatgttta atgggagtgt acagcaagct ttcggaaaat acaaaccata  960
atactttctc ttcttcaatt tgtttagttt aattttgaaa atggaagtca tatctaccaa  1020
cacaaatggc tctaccatct tcaagaatgg tgccattccc atgaacggcc accaaaatgg  1080
cacttctgaa cacctcaacg gctaccagaa tggcacttcc aaacaccaaa acgggcacca  1140
gaatggcact ttcgaacatc ggaacggcca ccagaatggg acatccgaac aacagaacgg  1200
gacaatcagc catgacaatg gcaacgagct actgggaagc tccgactcta ttaagcctgg  1260
ctggttttca gagtttagcg cattatggcc aggttagtat taagaaagaa actcaaatgc  1320
atcgtactct tgtattttgg tttgtgtata atttataata tggataaatt atgacgaagt  1380
aaactcgcat acattaattt gaaataatct aattttgcag gtgaagcatt ctcacttaag  1440
gttgagaagt tactattcca ggggaagtct gattaccaag atgtcatgct ctttgaggta  1500
attaatattc tgatacacat gctttaatct aaagtgatac ttttaattta cttttagttt  1560
attgcatgtg cacgtacagt cagcaactta tgggaaggtt ctgactttgg atggagcaat  1620
tcaacataca gagaatggtg gatttccata cactgaaatg attgttcatc taccacttgg  1680
ttccatccca aacccaaaaa aggttttgat catcggcgga ggaattggtt ttacattatt  1740
cgaaatgctt cgttatcctt caatcgaaaa aattgacatt gttgagatcg atgacgtggt  1800
agttgatgta agtcaaactt cttttaccca cataaagaaa atgatttaga ttgcaattct  1860
ttttattttt ctaaaagaat aaatatattc tctctttttt ttttaaaac aaaattctct   1920
ttcttacagg tatccagaaa attttttccct tatctggcag ctaattttaa cgatcctcgt  1980
gtaaccctag ttctcggaga tggtgcgtat atgatagtct cgttttatat tttatttcac  2040
ttgattttta ccttttttttg tggttaatta atcatctacc attggttctc tttaccttca  2100
ggagctgcat ttgtaaaggc tgcacaagcg ggatattatg atgctattat agtggactct  2160
tctgatccca ttggtacgct attactattt aataccaaga ctattcttat tatataagct  2220
actaagaaac taattgaata attaataaac gtaactgtaa ttgatttcta aaataatata  2280
```

```
tataatttca ggtccagcaa aagatttgtt tgagaggcca ttctttgagg cagtagccaa    2340
agcccttagg ccaggaggag ttgtatgcac acaggctgaa agcatttggc ttcatatgca    2400
tattattaag caaatcattg ctaactgtcg tcaagtcttt aagggttctg tcaactatgc    2460
ttggacaacc gttccaacat atcccacgta ttcttttctc tctctcttcc ctgtcttttt    2520
cgatgcaatg taaatttata aaattggaag tccgttttac ttttctatag acgtagatcc    2580
taaaattgtc aagaaatgga gaattgactt acaagaaaaa tcaacttctt ttcatttact    2640 attcttttg gtgacaaact ttacttatta tttcgttcta aaatgaaaat ttattttat     2700 atttttaaaat aatttagctt taaactttta atttttacttg ttatatttt aataaaaaag    2760 atttattgtc aaataaatgt tgtggccata caataagttt caaattatgt cacaaaaatt    2820
gaaacagagt gagcaaattt ttatttcaag taaactttca aggaattgtg tttaagtttt    2880
ctcaactgat actgatcaat gatgtcttaa atattttgat ttcagcggtg tgatcggtta    2940
tatgctctgc tctactgaag ggccagaagt tgacttcaag aatccagtaa atccaattga    3000
caaagagaca actcaagtca gtccaaattt aggacctctc aagttctaca actctgatgt    3060
aacttcatat ctcacaattt cttttttccgt tttactgtat gttcttcatc aaatttttata    3120 actaactctt ttcatattgt ctttttttttt cagattcaca aagcagcatt cattttacca    3180
tctttcgcca gaagtatgat cgagtcttaa tcaagtgaat aatgaacact ggtcgtacaa    3240
tcattggacc aagatcaagt cttaatcaag tgaataaata agtgaaatgc aacgtattgt    3300
atgagaattc tgcagtaatt atcataattt ccaattcact aattgttgta aaattctttc    3360
tctgtggtgt ttggtacttt aatataaatt ttcctgctga agttttaaaa tggacgttcc    3420
aattcgatcc tcgcaaatca gttcattatc cttctttcag tgtactaaag ccaacaaatc    3480
tcatagttac cgtggtgttg ttttactat gggatttgcg atcttattaa ggttttggtc     3540
tatgttttgg aattgtaata ttcatatttt taagttactc tgtatctaaa tcggcctagt    3600
ctctcttttt taataaatgg cgtcatcgtc gttgcagttt gtttgctcat ttttcagaag    3660
tatgatggtt tgaaatgtct ttgtttctat ggcctcttta ctgcagctta ccgatttgct    3720
tatgttggat attgcttctg attcatatgg gatatgaagt ttggtatttg ttgaatgatt    3780
aaggaaaaaa tttacaacaa taactatgcc tcaatcccaa cctaattatg atcagcgctt    3840
caaaaaaaaa aaaaagtag aactaaaatt tttaagctta gatgcaaatc cataacactg     3900
taaaaaaaag tagggatttc tgttcctttc ttttatagtt aagaaagaac tctctgcctt    3960
gtgaatctta ttgcatctct ctaattcagc aaaataattg aacaatgact aggataaaat    4020
atttcagcta agataaccct aattttctgg atggaatcac cttctccacc aagttgttat    4080
tttcttgcat tgtgagcaga ctagttcaat tacaccatta gagttttttc tcagcactat    4140
cctggcaatg atgcgctaag ctctgaaaac caattagcct aatagagtt ggagctcccc     4200 aataactctt                                                           4210

<210> SEQ ID NO 3
<211> LENGTH: 3686
<212> TYPE: DNA
<213> ORGANISM: Nicotiana tabacum

<400> SEQUENCE: 3
ttgtgagaga tttggtgtcc tctacaatga ttgttgaagt ccctatttat agctatacac       60
aggaaacaaa atcctaggat caagcccctc ttaaatgaca ataatggggt taatgatgaa      120
```

```
tatgtagcgg catgacatga atgccaaaat tctccgcaac gactatttat ttaatattga      180
ggaatatttt ttattaaata ctatctggtg acaagcattc gtttgcttcc gttgattacg      240
ttgattttgg gatctactct ataccaaccg aagccgttgt ccttgatctt cgctttcatt      300
taattcatct tccgtctgcc tccgatttca caagtcatgc acccattcaa ttatttaatg      360
gaaaccaatt ttaccctata caaatggtac atcattcgtc aaatacttta cttggatata      420
aacaattttg cccgaggagt aaacagatgc gaagaaagaa agcagacgat taaagaaatt      480
tttaaaaaag gagagagaaa tgaacacaca catgtactaa taaaattagg gtactacttt      540
actaataatt ggacagagac taaattcata ttttagttcc aaaatgtctc gggcagtcca      600
accatgcacg ttgtaatgat tttttaactc tattatatcg agttgcgccc tccactcctc      660
ggtgtccaaa ttgtatataa atgcatatgt gtctattggg agtgtacatc aagctttcat      720
aaagtacaaa tcgtaatact tgttgaaaca taatactttc tcttctccaa tttgtttagt      780
ttaattttga aaatggaagt catatctacc aacacaaatg gctctaccat cttcaagagt      840
ggtgccattc ccatgaatgg ccaccataat ggcacttcca acaccaaaaa cggccacaag      900
aatgggactt ccgaacaaca gaacgggaca atcagccttg ataatggcaa cgagctactg      960
ggaaactcca attgtattaa gcctggttgg ttttcagagt ttagcgcatt atggccaggt     1020
tagtactgag aaagaaactc aaatgcatat ttaaagttaa aattgttagg ctaatataag     1080
gagttgatat tcttttagtg attaattaaa aaggaaaaag tatcaaataa attcaaaaaa     1140
tggatagtaa cttcgcatat tactctacac attaatttga aataaatcga attttgcagg     1200
tgaagcattc tcacttaagg ttgagaagtt actgttccag gggaagtctg actaccaaga     1260
tgtcatgctc tttgaggtaa ataatatttt aatacacatg cttccattta aattgatact     1320
tttaatttac ttttacttta ttgcatgtgt acgtacagtc agcaacttat gggaaggttc     1380
tgactttgga tggagcaatt caacacacag agaatggtgg atttccatac actgaaatga     1440
ttgttcatct tccacttggt tccatcccaa acccaaaaaa ggttttgatc atcggcggag     1500
gaattggttt tacattattc gaaatgcttc gttatcctac aatcgaaaaa attgacattg     1560
ttgagatcga tgacgtggta gttgatgtaa gtcaaacttc ttttactcac ataaaaaaat     1620
ggtttagatt gcttcttgtt attttttctaa aagaatacta ttttttttaaa acaaaatttt     1680 cttttttaca ggtatctaga aaattttttcc cttatctcgc tgctaatttt aacgatcctc     1740
gtgtaaccct agtccttgga gatggtgcgt atttgataat ctcgcttttg ttttatctttt    1800 tattttatt gcatttaatt tttacctttt ggtgtgtggt taattcacct gccattggtt      1860
ctctttcatt tcagggctg catttgtaaa ggctgcacaa gcagaatatt atgatgctat     1920
tatagtggac tcttctgatc ccattggtac tctattactt cttaataccaa agactaatct    1980 tattgaataa gctactaata aacggtaatt gatttctaaa acaatataat ttcaggtcca    2040
gcaaaagatt tgtttgagag gccattcttt gaggcagtag ctaaagccct aaggccagga    2100
ggagttgtat gcacacaggc tgaaagcatt tggcttcata tgcatattat taagcaaatc    2160
attgctaact gtcgtcaagt ctttaagggc tctgtcaact atgcttggac tactgttcca    2220
acatatccaa cgtatttttc tctctctctc tcttcctata aaattggaag ttttgattct    2280
ataattgtca agaaatggag aatcagttcc aagaaaaacc aacttctttt cttttactct    2340
tcaaggtatt gtgtttaatt ttttttcaac tgatatgatc aattattttg atttcagcgg    2400
tgtgattggt tatatgctct gctctactga aggaccagaa attgacttca gaatccagt     2460 aaatccaatt gacaaagaga cagctcaagt caagtccaaa ttagcacctc tcaagttcta    2520
```

| | |
|---|---|
| caactctgat gtaacttcat atctcacaat ttctttttc ctattgtact ttatgttctt | 2580 |
| cgtcaaattt tataattaac tcttttcaaa ttgtctttt tttttcaga ttcacaaagc | 2640 |
| agcattcatt ttgccatctt tcgccagaag tatgatcgag tcttaatcaa ctgattaatg | 2700 |
| aatactggtg gtacaatcat tggaccaaga tcaataagtg aaagacgtat tgtatgagaa | 2760 |
| ttctgcagta attaattatc ataatttcca atttaccaat tattgtaaaa ttctttctct | 2820 |
| gtggtgtttg gtactttaat ataaattttc ctgcttaagt tttgaatcga cgtatcaact | 2880 |
| caatcctcgc aaatcacttc attaccctcc tttcagtgta ctaaagtaaa ctgttgcgga | 2940 |
| atatcgtggg ttaactagaa cacaatcaca cacaaatcaa atagaagaa atttattaac | 3000 |
| ggggttcggc taagcctaat cctcaggaca aaagcagaga gagttttcca ctatgaatga | 3060 |
| gaagaaaaac acaatacaat atataaaatc ctcaactaca acccctatat atgatcccaa | 3120 |
| aaggtcccaa acatatatga gaaaagtttc ccaatttgac aaagattata ggttttcctt | 3180 |
| tcccaaatct attagggcaa tgggttttct taaacctatg gggactatgg ctttcctaaa | 3240 |
| aatacaagga aataattcaa accacaaata ataaatcttc cccttggctt gaattctctt | 3300 |
| catcaacagg aacaatagct ctctaccttg ccctcaaccc tcgcaagggc tctattgatt | 3360 |
| gtcgcacaca tcaaccaagt ctaggcaacg cctaaacttg ttatgagact taatctcttc | 3420 |
| agccatagca ctaatccgtc gatttggttc tgtacccgaa atagcttttg gatagctata | 3480 |
| acactgaaac acatcagtgg tctctgcaac taccaaagca aatcccacag tattcgtata | 3540 |
| tccaagaaga tttccatcaa ctacgtttgc aaacctttgc ggtcggttga tcactctctt | 3600 |
| ctctctgtat gttgcaatgc tatatggttg ttgttgcgca ggtgcatcaa cattatcgtc | 3660 |
| ttgatcaata ttttgtacct cctcta | 3686 |

<210> SEQ ID NO 4
<211> LENGTH: 4035
<212> TYPE: DNA
<213> ORGANISM: Nicotiana tabacum

<400> SEQUENCE: 4

| | |
|---|---|
| ggaagagtgt ggtatgggag atgcctccca gggagtacct aaagctgaat actgatggaa | 60 |
| gttttaacaa acaaattggg aaagcaggga ttggagggat tctcagagat gaagagggag | 120 |
| gctttgtcat ggcttttcg atgcctataa tctataataa catcagtgaa gcagaattga | 180 |
| aagccatcaa gtatgggtgt gaatggtgca aatacaaagg aatatcaaac ttcattgtgg | 240 |
| aaactgactc gaggatgatc tatgacatac tacagaccaa aaatctaagc aacaacaagt | 300 |
| tgaaacaaga gaccgagaaa ttaatggaga ttctggacac ctgcaggaca cctgttaccc | 360 |
| attgccttcg cgaagcaaat caagtggcag actggtttgc taaagaggcc accagagcta | 420 |
| acgaaggtat cactcataca gattttagac aggtatcaaa agcggccaag ggccctttct | 480 |
| tcatggatat gtgcaggtc ccttatttta gaattagata tgaaaaatct aatttttttt | 540 |
| tgtaagttaa ttctgtgtat agtgagagga atcgtctaa tatgtatttt tgcccataga | 600 |
| ctcttcctct ccttaggtaa aaaggtagct ccgaggtaag gtttatgttc ccctcagtgt | 660 |
| aaccttttt tgtttatata atagacatgg tatgggtcca gctaaacccc caacaccaca | 720 |
| ggggatagat acctgggtga ttggtttatt ttttaaaaaa aaaaactta ctaataattg | 780 |
| cacggagaca aaactatat tttagttcca aaatgacagt ccaaccatgc acgttgtaat | 840 |
| gatttttaa ctctattata tcgagttccg ccctccactc ctcggtgtcc aaattgtatt | 900 |

-continued

```
taaatgcata gatatgttta ttgggagtgt acatcaagct ttcagaaaat acaaaccata    960
atactttctc ttctccaatt tgcttagttt aatttggaaa atggaagtca tatctaccaa   1020
cacaaatggc tctactatct tcaagaatgg tgccattccc atgaacggtt accagaatgg   1080
cacttccaaa caccaaaacg gccaccagaa tggcacttcc gaacatcgga acggccacca   1140
gaatgggatt tccgaacacc aaaacggcca ccagaatggc acttccgagc atcagaacgg   1200
ccatcagaat gggacaatca gccatgacaa cggcaacgag ctacagctac tgggaagctc   1260
caactctatt aagcctggtt ggttttcaga gtttagcgca ttatggccag gttagtacta   1320
agaaagaaac tcaaatgcat cgtactcttg tattctgctt tgcgtataat ttagatgatg   1380
gtgtttgact aagcactgag tttaaaaata aaaagtttaa agttaaattg ttactataga   1440
gagctatatc tttaggaact aactaaaaag gaaaaattat cacataaaat tgggatgaag   1500
taagcagtta acttcgcata ttattcgaca cattaatttg aaataaatcg aattttgcag   1560
gtgaagcatt ctcacttaag gttgagaagt tactattcca ggggaagtct gattaccaag   1620
atgtcatgct ctttgaggta attaattaat actaatagtc aagctcatgt atgattatat   1680
ttaaagtggt attttcgtt tatttttaat ttattgcacg tgtacgtaca gtcagcaaca   1740
tatgggaagg ttctgacttt ggatggagca attcaacaca cagagaatgg tggatttcca   1800
tacactgaaa tgattgttca tcttccactt ggttccatcc caaaccctaa aaaggttttg   1860
atcatcggcg gaggaattgg ttttacatta ttcgaaatgc ttcgttatcc tacaatcgaa   1920
aaaattgaca ttgttgagat cgatgacgtg gtagttgatg taagtcaaac ttcttttact   1980
cacataaaaa aatgatttag attcttattt ttctaaaaga attaaaacaa aattttccgt   2040
tttacaggta tctagaaaat ttttccctta tcttgctgct aatttagcg atcctcgtgt   2100
aaccctagtc cttggagatg gtgcgtattt gataatctcg ttttattt atcttttact   2160
tttattttat ttaatttta ccttttgtg tgtggttaat tcacctgcca ttggttcttt   2220
ttatttcagg ggctgcattt gtaaaggccg cacaagcagg atattatgat gctattatag   2280
tggactcttc tgatcccatt ggtactctat tactacttaa taccaagact attcttatta   2340
aataagctac taataaacgt aactctgata gttttctaaa ataatataat ttcaggtcca   2400
gcaaaagact tgtttgagag gccattcttt gaggcagtag ccaaagccct aaggccagga   2460
ggagttgtat gcacacaggc tgaaagcatt tggcttcata tgcatattat taagcaaatc   2520
attgctaact gtcgtcaagt ctttaagggc tctgtcaact atgcttggac tactgttcca   2580
acatatccaa cgtattttc tctctctctt cctataaaat tggaagtttt gattctataa   2640
ttgtcaagaa atggagaatc agttccaaga aaaaccaaat tctttctttt tactcttcaa   2700
ggtgtgttta agtttttaa actgatactg atcaattatt ttgatttcag cggtgtgatt   2760
ggttatatgc tctgttctac tgaaggacca gaagttgact tcaagaatcc agtaaatcca   2820
attgacaaag agacaactca agtcaagtcc aaattagcac ctctcaagtt ctacaactct   2880
gatgtaactt catatctcaa tttctttttt cttattgtac tttatgttct tagtcaaatt   2940
ttataattaa ctcttttcaa attgtctttt tttttcagat tcacaaagca gcattcattt   3000
tgccatcttt cgccagaagt atgatcgagt cttaatcaag tgactaatga atactggcgg   3060
tacaatcatt ggaccaagat cgagtcttaa tcaagtgaat aaataagtga atgcgacgt   3120
attgtataag aattctgcag tagttaatta tcataatttc caattcacca attactgtaa   3180
aattcttcct ctgtggtgtt tggtacttta ctataaattt tcccgcttaa gttttgaatc   3240
gacgtttcaa ctcagtcctc gcaaatcact tcattaccct tctttcggta tactaaagta   3300
```

-continued

```
aactgttgca gaatatcgtg ggttaactag aacacaatca cacacatagc aaatagagaa   3360
gaaaaatcaa cacaagaatt tattaacgag gttcggctaa gcctaatcct ccgggcaaaa   3420
gcagagagag tttttcacta tgaatgagaa gtaaaacaca atacaatcta tagaatttcc   3480
aactacaacc cctatatata gatttcaaaa ggtcccaaac atatatgaga aaggtttccc   3540
aatttgacaa ggattatagg ttttcttttc caaaatctat tagggtaatg ggttttccta   3600
aacctatgag gactatgggt ttcctaaaaa tacaaggaaa taatttaaac caaaaataac   3660
aaatcttccc cttggtttga attctcttca ttaacaggaa caacagctct ctacctttcc   3720
ctcagccctc gcaatggctc tattgattgc cgcactcatc aaccaagtct acgcaacgcc   3780
taaacttgtt aagagactta atctcttcag ccatagcact aatttgtcga tttggttctg   3840
tacccgaaat agcttttgga taactataac actcaaatgc atcagtggtc tctgcaacta   3900
ccaaagcaaa tcccacaaga ttcgtatatc caagaagatt tccatcaact acatttgcaa   3960
accttttgcgg tcggttgatc actctctctc tctctgcatg ttgcaatgct atatggttgt   4020
tgttgtgcat gtgca                                                   4035
```

<210> SEQ ID NO 5
<211> LENGTH: 4431
<212> TYPE: DNA
<213> ORGANISM: Nicotiana tabacum

<400> SEQUENCE: 5

```
acggtacaat tgaatttgtt gcgtgacttg tagacaagtg aattgatttg tccaaaatga     60
ttaataaatc aaattaaaaa taaggcttag cgttaaaatc aaaggaaatg gcaagcctga    120
ctcccggagc aatgcttctg aggacagtag taaaaacaat atcagacaaa agtaaagtt    180
atattattta gcttgaggat aaagtatgtc atcagttttg ttagagattt ggtgtcctct    240
acaatgattg ttgaagtccc tatttatagc tatacatagg aaacaagatc ctagaatcaa    300
acccttctta aatgacatta atgggagtta ttgatgaata tgtagcggca tgacatgaat    360
gccaaaattc tccgcaacgg ctatttactt aatattgagg aatatttttc attaaatact    420
atctggtgac aagtattcgt ttgcttccgt tgattgcatt gattttggga tctactatgt    480
accaaccgaa gttgttgtcc ttgatcttcg ctttcattta attcatcttt cgtcgacctc    540
tgattccaca agtcatgcac ccattcaatt atttaatgga aaccaatttt accctgtaca    600
aatggtacaa atactttcct tggataaaaa caattttgcc taaggagtaa acagatgcga    660
agtaagaaag cagacgacta aagaaaattt taaaaaagga gagagaaatg agcacacaca    720
cgtactaata aaattagggt actactttac taataattgg acagagacta aattcatatt    780
ttagttccaa aatgtctcgg gcagtccaac catgcacgtt gtaatgagtt tttaactcta    840
ttatctcgag ttgcgccctc cactcctctg tgtccaagtt gtatataaat gcatatatgt    900
ctattgggag tgtacagcga gctttcataa agtacaaatc ataatacttg ttgaaacata    960
atactttctc ttctccaatt tgtttagttt aattttgaaa atggaagtca tatctaccaa   1020
cacaaatggc tcgaccatct tcaagaatgg tgccattccc atgaatggcc accagagtgg   1080
cacttccaaa cacctcaacg gctaccagaa cggcacttcc aaacaccaaa acggccacca   1140
taatggcact tccgaacatc ggaacggcca ccagaatggg atttccgaac accaaaacgg   1200
ccaccagaat gggacttccg aacatcggaa cggccaccag aatgggattt ccgaacacca   1260
aaacggccac cagaatggga cttccgaaca ccaaaacggc caccagaatg ggacttccga   1320
```

```
acaacagaac gggacaatca gccatgacaa tggcaacgag ctactgggaa actccaactc    1380
tattaagctt ggttggtttt cagagtttag cgcattatgg ccaggttagt actgagaaag    1440
aaactcaaat tcatatttaa agttaaaatt gttaggctaa tataagaagt tgattttctt    1500
ttagtgatta attaaaaaag gaaagagtat caaataaatt ccaaaaaatg accagtaact    1560
tcgcatatta ttctacacat taatttgaaa taaatcgaat tttgcaggtg aagcattctc    1620
ccttaaggtt gagaagttac tatttcaggg gaagtctgac taccaagatg tcatgctctt    1680
tgaggtaaat aatattctaa tacacatgct ttaatatgaa taaatacttt taatttactt    1740
ttagtttatt gcacgtgtac gtacagtcag caacatatgg gaaggttttg actttggatg    1800
gagcaattca acacacagag aatggtggat ttccatacac tgaaatgatt gttcatcttc    1860
cacttggttc catcccaaac ccaaaaaagg ttttgatcat cggcggagga attggtttta    1920
cattattcga aatgcttcgt tatcctacaa tcgaaaaaat tgacattgtt gaaatcgatg    1980
acgtggtagt tgatgtaagt caaatttctt ttactcacat aaaaaaatga tttagattgc    2040
ttcttttat ttttctaaaa gaataaatat attctctctt agttttaaac aaaattctct    2100
ttcttacagg tatctagaaa atctttccct tatctcgcag ctaatttaaa tgatcctcgt    2160
gtaaccctcg ttctcggaga tggtgcgtat ttataatctc gttttgttt tatcttttat    2220
tttatttca tttaatttac cttttgtgt gtggttaatt tacccgtcat tggttctctt    2280
tcatttcagg ggctgcattt gtaaaggctg cacaagcagg atattatgat gctattatag    2340
tggactcttc tgatcccatt ggtactctat tactacttaa taccaagact aatcttattg    2400
aataagctac taataaactg taattgattt ctaaaataat ataatttcag gtccagcaaa    2460
agatttgttt gagaggccat tctttgaggc agtagccaaa gccctaaggc caggaggagt    2520
tgtatgcaca caggccgaaa gcatttggct tcatatgcat attattaagc aaatcattgc    2580
taactgtcgt caagtcttta agggctctgt caactacgct tggactactg ttccaacata    2640
tcccacgtat tttctctctc tctctcttca tctttgaaaa ttgaaaatcc tgactacttt    2700
ccttcctttg attcctcggt taaggggcg tagatcataa gattttcaag aaatagataa    2760
tgacgtccaa gaaaaactaa cttcttttca tttactattc tttttggtga caaactttat    2820
ttattatttc gttctaaaga gaaaatttat ttttatattt taaaataatt tgtttttaaa    2880
cttttatttt tacttattat atctttaata aaaaaattat agtcaaataa atattatggc    2940
cacactaaac atccaagttt ttgaaaccat aagttttaga gccaaatgag ttaatttgtt    3000
tttggtatgc gggtgcggag tcaaattatg tcacaaaaat tgtaatggag tgagcaaatt    3060
tttatttcga gtaaactttc aaggtattgt gttaaagttt tttcaactga tactaatcaa    3120
ttatgtctca accattttga tttcagtggt gtaattgggt atatgctctg ctctactgaa    3180
gggccagaag ttgacttcaa gaatccaata aatccaattg acaaagagac aactcaagtc    3240
aagtccaaat tagcacctct caagttttac aattctgatg taacttcata tctaacaatt    3300
tcttttctg ttttactgta tcttcattgt caaaatttta taattaactc ttctcaaatt    3360
atctttttt ttagattcac aaagcagcat tcattttgcc atctttcgcc agaagtatga    3420
tcgagtctta atcaagtgaa taatgaacac tggtggtgca atcattggac caagatcgag    3480
tcttaatcaa gtgaataaat aagtgaaatg ccgacgtatt gtatgagaat tctacagtaa    3540
ttaattatca taatttccaa ttcaccaatt attgtaaaat tctttctctg tggtgtttgg    3600
tacttcaata taaattttcc tgctgaagtt ttgaatcgat gttccaactc aatcctcgca    3660
aatcagttcc ttattttttct ttcagtgtac ttagtaatct tagtgggatc ggcgcttcca    3720
```

```
taaaagaatg taaacttaat attttttta agcctaaatg caaatccatc acactgtaaa      3780
acatattgat cttcagcctc tgaagatgag tagggatttc tgctcctttc atttacagtc      3840
gagaactttc tgtcttgcat ctctctaatt cagccaaatt attgataacc acgactttag      3900
ttaaacattt gtttaactaa aacaactccc ctaaccatgg taaaacacag tagttatcag      3960
tgtttaatta acctttcctt tttggtaaat atagggtgaa gtcttgctgc gaactttgtt      4020
ctcatatgtt gaagatagta atccaactca agaaacaaac atgattgatt aaatgttgtc      4080
gatgacacac tttcaactga tccaaatggt aacgttccgg ccggctattt tatgtatttg      4140
agtcccgttc tcctacttga tattttccct atgcttgttt gacgttttgt gagttgtgga      4200
gatggttggt ttggttcggg aaggttttgg aatgagtaga gacgcttcaa ctcattttga      4260
aagcttaagt tgtacgagtt gatcaaggtt tgactttggt ataaacgata tcaatttgat      4320
ggtttcagta tgttcatatg gtgattttgg aattagacgc atgttcggat atgaatttgg      4380
aggtttctag aatgttttgt ctctgagtgc caaaagctgg gaatttaaag g              4431

<210> SEQ ID NO 6
<211> LENGTH: 1128
<212> TYPE: DNA
<213> ORGANISM: Nicotiana tabacum

<400> SEQUENCE: 6
atggaagtca tatctaccaa cacaaatggc tctaccatct tcaagaatgg taccattccc        60
atgaacggcc accaaaatgg ctcttccgaa cacctcaacg gctaccagaa tggcatttcc       120
aaacaccaaa acgggcacca gaatggcact tccgaacatc ggaacggcca ccagaatggg       180
acatccgaac aacagaacgg gacaatcagc catgacaatg gcaacgagct actgggaagc       240
tccaactcta ttaagcctgg ttggttttca gagtttagcg cattatggcc aggtgaagca       300
ttctcactta aggtcgagaa gttactattc caggggaaat ctgattacca agatgtcatg       360
ctctttgagt cagcaactta tgggaaggtt ctgactttgg atggagcaat tcaacataca       420
gagaatggtg gatttccata cactgaaatg attgttcatc taccacttgg ttccatccca       480
aacccaaaaa aggttttgat catcggcgga ggaattggtt ttacattatt cgaaatgctt       540
cgttatcctt caatcgaaaa aattgacatt gttgagatcg atgacgtggt agttgatgta       600
tccagaaaat ttttcccctta tctggcagct aattttaacg atcctcgtgt aaccctagtt       660
ctcggagatg gagctgcatt tgtaaaggct gcacaagcgg gatattatga tgctattata       720
gtggactctt ctgatcccat tggtccagca aaagatttgt ttgagaggcc attctttgag       780
gcagtagcca aagcccttag gccaggagga gttgtatgca cacaggctga aagcatttgg       840
cttcatatgc atattattaa gcaaatcatt gctaactgtc gtcaagtctt taagggttct       900
gtcaactatg cttggacaac cgttccaaca tatcccaccg gtgtgattgg ttatatgctc       960
tgctctactg aagggccaga agttaacttc aagaatccag taaatccaat tgacaaagag      1020
acaactcaag tcaagtccaa attaggacct ctcaagttct acaactctga tattcacaaa      1080
gcagcattca ttttgccatc tttcgcccga agtatgatcg agtcttaa                  1128

<210> SEQ ID NO 7
<211> LENGTH: 1128
<212> TYPE: DNA
<213> ORGANISM: Nicotiana tabacum

<400> SEQUENCE: 7
```

```
atggaagtca tatctaccaa cacaaatggc tctaccatct tcaagaatgg tgccattccc      60
atgaacggcc accaaaatgg cacttctgaa cacctcaacg gctaccagaa tggcacttcc     120
aaacaccaaa acgggcacca gaatggcact ttcgaacatc ggaacggcca ccagaatggg     180
acatccgaac aacagaacgg gacaatcagc catgacaatg caacgagct  actgggaagc     240 tccgactcta ttaagcctgg ctggttttca gagtttagcg cattatggcc aggtgaagca     300
ttctcactta aggttgagaa gttactattc caggggaagt ctgattacca agatgtcatg     360
ctctttgagt cagcaactta tgggaaggtt ctgactttgg atggagcaat tcaacataca     420
gagaatggtg gatttccata cactgaaatg attgttcatc taccacttgg ttccatccca     480
aacccaaaaa aggttttgat catcggcgga ggaattggtt ttacattatt cgaaatgctt     540
cgttatcctt caatcgaaaa aattgacatt gttgagatcg atgacgtggt agttgatgta     600
tccagaaaat ttttccctta tctggcagct aattttaacg atcctcgtgt aaccctagtt     660
ctcggagatg gagctgcatt tgtaaaggct gcacaagcgg gatattatga tgctattata     720
gtggactctt ctgatcccat tggtccagca aaagatttgt ttgagaggcc attctttgag     780
gcagtagcca aagcccttag gccaggagga gttgtatgca cacaggctga agcatttgg      840 cttcatatgc atattattaa gcaaatcatt gctaactgtc gtcaagtctt taagggttct     900
gtcaactatg cttggacaac cgttccaaca tatcccaccg gtgtgatcgg ttatatgctc     960
tgctctactg aagggccaga agttgacttc aagaatccag taaatccaat tgacaaagag    1020
acaactcaag tcaagtccaa attaggacct ctcaagttct acaactctga tattcacaaa    1080
gcagcattca ttttaccatc tttcgccaga agtatgatcg agtcttaa                 1128
```

<210> SEQ ID NO 8
<211> LENGTH: 1062
<212> TYPE: DNA
<213> ORGANISM: Nicotiana tabacum

<400> SEQUENCE: 8

```
atggaagtca tatctaccaa cacaaatggc tctaccatct tcaagagtgg tgccattccc      60
atgaatggcc accataatgg cacttccaaa caccaaaacg ccacaagaa  tgggacttcc     120 gaacaacaga acgggacaat cagccttgat aatggcaacg agctactggg aaactccaat     180
tgtattaagc ctggttggtt ttcagagttt agcgcattat ggccaggtga agcattctca     240
cttaaggttg agaagttact gttccagggg aagtctgact accaagatgt catgctcttt     300
gagtcagcaa cttatgggaa ggttctgact ttggatggag caattcaaca cacagagaat     360
ggtggatttc catacactga aatgattgtt catcttccac ttggttccat cccaaaccca     420
aaaaaggttt tgatcatcgg cggaggaatt ggttttacat tattcgaaat gcttcgttat     480
cctacaatcg aaaaaattga cattgttgag atcgatgacg tggtagttga tgtatctaga     540 aaattttttcc cttatctcgc tgctaatttt aacgatcctc gtgtaaccct agtccttgga     600 gatgggctg catttgtaaa ggctgcacaa gcagaatatt atgatgctat tatagtggac     660
tcttctgatc ccattggtcc agcaaaagat ttgtttgaga ggccattctt tgaggcagta     720
gctaaagccc taaggccagg aggagttgta tgcacacagg ctgaaagcat ttggcttcat     780
atgcatatta ttaagcaaat cattgctaac tgtcgtcaag tctttaaggg ctctgtcaac     840
tatgcttgga ctactgttcc aacatatcca accggtgtga ttggttatat gctctgctct     900
actgaaggac agaaattga  cttcaagaat ccagtaaatc caattgacaa agagacagct    960
caagtcaagt ccaaattagc acctctcaag ttctacaact ctgatattca caaagcagca    1020
```

```
ttcattttgc catctttcgc cagaagtatg atcgagtctt aa                1062
```

<210> SEQ ID NO 9
<211> LENGTH: 1146
<212> TYPE: DNA
<213> ORGANISM: Nicotiana tabacum

<400> SEQUENCE: 9

```
atggaagtca tatctaccaa cacaaatggc tctactatct tcaagaatgg tgccattccc    60
atgaacggtt accagaatgg cacttccaaa caccaaaacg ccaccagaa tggcacttcc    120
gaacatcgga acggccacca gaatgggatt ccgaacacc aaaacggcca ccagaatggc    180
acttccgagc atcagaacgg ccatcagaat gggacaatca gccatgacaa cggcaacgag    240
ctacagctac tgggaagctc caactctatt aagcctggtt ggttttcaga gtttagcgca    300
ttatggccag gtgaagcatt ctcacttaag gttgagaagt tactattcca ggggaagtct    360
gattaccaag atgtcatgct ctttgagtca gcaacatatg ggaaggttct gactttggat    420
ggagcaattc aacacacaga gaatggtgga tttccataca ctgaaatgat tgttcatctt    480
ccacttggtt ccatcccaaa ccctaaaaag gttttgatca tcggcggagg aattggtttt    540
acattattcg aaatgcttcg ttatcctaca atcgaaaaaa ttgacattgt tgagatcgat    600
gacgtggtag ttgatgtatc tagaaaattt ttcccttatc ttgctgctaa ttttagcgat    660
cctcgtgtaa ccctagtcct tggagatggg gctgcatttg taaaggccgc acaagcagga    720
tattatgatg ctattatagt ggactcttct gatcccattg gtccagcaaa agacttgttt    780
gagaggccat tctttgaggc agtagccaaa gccctaaggc caggaggagt tgtatgcaca    840
caggctgaaa gcatttggct tcatatgcat attattaagc aaatcattgc taactgtcgt    900
caagtcttta agggctctgt caactatgct tggactactg ttccaacata tccaaccggt    960
gtgattggtt atatgctctg ttctactgaa ggaccagaag ttgacttcaa gaatccagta    1020
aatccaattg acaaagagac aactcaagtc aagtccaaat tagcacctct caagttctac    1080
aactctgata ttcacaaagc agcattcatt ttgccatctt cgccagaag tatgatcgag    1140
tcttaa                                                              1146
```

<210> SEQ ID NO 10
<211> LENGTH: 1260
<212> TYPE: DNA
<213> ORGANISM: Nicotiana tabacum

<400> SEQUENCE: 10

```
atggaagtca tatctaccaa cacaaatggc tcgaccatct tcaagaatgg tgccattccc    60
atgaatggcc accagagtgg cacttccaaa cacctcaacg ctaccagaa cggcacttcc    120
aaacaccaaa acggccacca taatggcact tccgaacatc ggaacggcca ccagaatggg    180
atttccgaac accaaaacgg ccaccagaat gggacttccg aacatcggaa cggccaccag    240
aatgggattt ccgaacacca aaacggccac cagaatggga cttccgaaca ccaaaacggc    300
caccagaatg ggacttccga caacagaac gggacaatca gccatgacaa cggcaacgag    360
ctactgggaa actccaactc tattaagctt ggttggtttt cagagtttag cgcattatgg    420
ccaggtgaag cattctccct taaggttgag aagttactat tcaggggaa gtctgactac    480
caagatgtca tgctctttga gtcagcaaca tatgggaagg ttttgacttt ggatggagca    540
attcaacaca cagagaatgg tggatttcca tacactgaaa tgattgttca tcttccactt    600
```

| | | |
|---|---|---|
| ggttccatcc caaacccaaa aaaggttttg atcatcggcg gaggaattgg ttttacatta | 660 | |
| ttcgaaatgc ttcgttatcc tacaatcgaa aaaattgaca ttgttgaaat cgatgacgtg | 720 | |
| gtagttgatg tatctagaaa atctttccct tatctcgcag ctaattttaa tgatcctcgt | 780 | |
| gtaaccctcg ttctcggaga tggggctgca tttgtaaagg ctgcacaagc aggatattat | 840 | |
| gatgctatta tagtggactc ttctgatccc attggtccag caaaagattt gtttgagagg | 900 | |
| ccattctttg aggcagtagc caaagcccta aggccaggag gagttgtatg cacacaggcc | 960 | |
| gaaagcattt ggcttcatat gcatattatt aagcaaatca ttgctaactg tcgtcaagtc | 1020 | |
| tttaagggct ctgtcaacta cgcttggact actgttccaa catatcccac tggtgtaatt | 1080 | |
| gggtatatgc tctgctctac tgaagggcca gaagttgact tcaagaatcc aataaatcca | 1140 | |
| attgacaaag agacaactca agtcaagtcc aaattagcac ctctcaagtt ttacaattct | 1200 | |
| gatattcaca aagcagcatt cattttgcca tctttcgcca aagtatgat cgagtcttaa | 1260 | |

<210> SEQ ID NO 11
<211> LENGTH: 375
<212> TYPE: PRT
<213> ORGANISM: Nicotiana tabacum

<400> SEQUENCE: 11

Met Glu Val Ile Ser Thr Asn Thr Asn Gly Ser Thr Ile Phe Lys Asn
1               5                   10                  15

Gly Thr Ile Pro Met Asn Gly His Gln Asn Gly Ser Ser Glu His Leu
            20                  25                  30

Asn Gly Tyr Gln Asn Gly Ile Ser Lys His Gln Asn Gly His Gln Asn
        35                  40                  45

Gly Thr Ser Glu His Arg Asn Gly His Gln Asn Gly Thr Ser Glu Gln
    50                  55                  60

Gln Asn Gly Thr Ile Ser His Asp Asn Gly Asn Glu Leu Leu Gly Ser
65                  70                  75                  80

Ser Asn Ser Ile Lys Pro Gly Trp Phe Ser Glu Phe Ser Ala Leu Trp
                85                  90                  95

Pro Gly Glu Ala Phe Ser Leu Lys Val Glu Lys Leu Leu Phe Gln Gly
            100                 105                 110

Lys Ser Asp Tyr Gln Asp Val Met Leu Phe Glu Ser Ala Thr Tyr Gly
        115                 120                 125

Lys Val Leu Thr Leu Asp Gly Ala Ile Gln His Thr Glu Asn Gly Gly
    130                 135                 140

Phe Pro Tyr Thr Glu Met Ile Val His Leu Pro Leu Gly Ser Ile Pro
145                 150                 155                 160

Asn Pro Lys Lys Val Leu Ile Ile Gly Gly Gly Ile Gly Phe Thr Leu
                165                 170                 175

Phe Glu Met Leu Arg Tyr Pro Ser Ile Glu Lys Ile Asp Ile Val Glu
            180                 185                 190

Ile Asp Asp Val Val Val Asp Val Ser Arg Lys Phe Phe Pro Tyr Leu
        195                 200                 205

Ala Ala Asn Phe Asn Asp Pro Arg Val Thr Leu Val Leu Gly Asp Gly
    210                 215                 220

Ala Ala Phe Val Lys Ala Gln Ala Gly Tyr Tyr Asp Ala Ile Ile
225                 230                 235                 240

Val Asp Ser Ser Asp Pro Ile Gly Pro Ala Lys Asp Leu Phe Glu Arg
                245                 250                 255

Pro Phe Phe Glu Ala Val Ala Lys Ala Leu Arg Pro Gly Gly Val Val

```
                    260                 265                 270
Cys Thr Gln Ala Glu Ser Ile Trp Leu His Met His Ile Ile Lys Gln
                275                 280                 285

Ile Ile Ala Asn Cys Arg Gln Val Phe Lys Gly Ser Val Asn Tyr Ala
            290                 295                 300

Trp Thr Thr Val Pro Thr Tyr Pro Thr Gly Val Ile Gly Tyr Met Leu
305                 310                 315                 320

Cys Ser Thr Glu Gly Pro Glu Val Asn Phe Lys Asn Pro Val Asn Pro
                325                 330                 335

Ile Asp Lys Glu Thr Thr Gln Val Lys Ser Lys Leu Gly Pro Leu Lys
            340                 345                 350

Phe Tyr Asn Ser Asp Ile His Lys Ala Ala Phe Ile Leu Pro Ser Phe
        355                 360                 365

Ala Arg Ser Met Ile Glu Ser
    370                 375

<210> SEQ ID NO 12
<211> LENGTH: 375
<212> TYPE: PRT
<213> ORGANISM: Nicotiana tabacum

<400> SEQUENCE: 12

Met Glu Val Ile Ser Thr Asn Thr Asn Gly Ser Thr Ile Phe Lys Asn
1               5                   10                  15

Gly Ala Ile Pro Met Asn Gly His Gln Asn Gly Thr Ser Glu His Leu
            20                  25                  30

Asn Gly Tyr Gln Asn Gly Thr Ser Lys His Gln Asn Gly His Gln Asn
        35                  40                  45

Gly Thr Phe Glu His Arg Asn Gly His Gln Asn Gly Thr Ser Glu Gln
    50                  55                  60

Gln Asn Gly Thr Ile Ser His Asp Asn Gly Asn Glu Leu Leu Gly Ser
65                  70                  75                  80

Ser Asp Ser Ile Lys Pro Gly Trp Phe Ser Glu Phe Ser Ala Leu Trp
                85                  90                  95

Pro Gly Glu Ala Phe Ser Leu Lys Val Glu Lys Leu Leu Phe Gln Gly
            100                 105                 110

Lys Ser Asp Tyr Gln Asp Val Met Leu Phe Glu Ser Ala Thr Tyr Gly
        115                 120                 125

Lys Val Leu Thr Leu Asp Gly Ala Ile Gln His Thr Glu Asn Gly Gly
    130                 135                 140

Phe Pro Tyr Thr Glu Met Ile Val His Leu Pro Leu Gly Ser Ile Pro
145                 150                 155                 160

Asn Pro Lys Lys Val Leu Ile Ile Gly Gly Gly Ile Gly Phe Thr Leu
                165                 170                 175

Phe Glu Met Leu Arg Tyr Pro Ser Ile Glu Lys Ile Asp Ile Val Glu
            180                 185                 190

Ile Asp Asp Val Val Asp Val Ser Arg Lys Phe Phe Pro Tyr Leu
        195                 200                 205

Ala Ala Asn Phe Asn Asp Pro Arg Val Thr Leu Val Leu Gly Asp Gly
    210                 215                 220

Ala Ala Phe Val Lys Ala Ala Gln Gly Tyr Tyr Asp Ala Ile Ile
225                 230                 235                 240

Val Asp Ser Ser Asp Pro Ile Gly Pro Ala Lys Asp Leu Phe Glu Arg
                245                 250                 255
```

```
Pro Phe Phe Glu Ala Val Ala Lys Ala Leu Arg Pro Gly Gly Val Val
            260                 265                 270

Cys Thr Gln Ala Glu Ser Ile Trp Leu His Met His Ile Ile Lys Gln
        275                 280                 285

Ile Ile Ala Asn Cys Arg Gln Val Phe Lys Gly Ser Val Asn Tyr Ala
    290                 295                 300

Trp Thr Thr Val Pro Thr Tyr Pro Thr Gly Val Ile Gly Tyr Met Leu
305                 310                 315                 320

Cys Ser Thr Glu Gly Pro Glu Val Asp Phe Lys Asn Pro Val Asn Pro
                325                 330                 335

Ile Asp Lys Glu Thr Thr Gln Val Lys Ser Lys Leu Gly Pro Leu Lys
            340                 345                 350

Phe Tyr Asn Ser Asp Ile His Lys Ala Ala Phe Ile Leu Pro Ser Phe
        355                 360                 365

Ala Arg Ser Met Ile Glu Ser
    370                 375

<210> SEQ ID NO 13
<211> LENGTH: 353
<212> TYPE: PRT
<213> ORGANISM: Nicotiana tabacum

<400> SEQUENCE: 13

Met Glu Val Ile Ser Thr Asn Thr Asn Gly Ser Thr Ile Phe Lys Ser
1               5                   10                  15

Gly Ala Ile Pro Met Asn Gly His His Asn Gly Thr Ser Lys His Gln
            20                  25                  30

Asn Gly His Lys Asn Gly Thr Ser Glu Gln Gln Asn Gly Thr Ile Ser
        35                  40                  45

Leu Asp Asn Gly Asn Glu Leu Leu Gly Asn Ser Asn Cys Ile Lys Pro
    50                  55                  60

Gly Trp Phe Ser Glu Phe Ser Ala Leu Trp Pro Gly Glu Ala Phe Ser
65                  70                  75                  80

Leu Lys Val Glu Lys Leu Leu Phe Gln Gly Lys Ser Asp Tyr Gln Asp
                85                  90                  95

Val Met Leu Phe Glu Ser Ala Thr Tyr Gly Lys Val Leu Thr Leu Asp
            100                 105                 110

Gly Ala Ile Gln His Thr Glu Asn Gly Gly Phe Pro Tyr Thr Glu Met
        115                 120                 125

Ile Val His Leu Pro Leu Gly Ser Ile Pro Asn Pro Lys Lys Val Leu
    130                 135                 140

Ile Ile Gly Gly Gly Ile Gly Phe Thr Leu Phe Glu Met Leu Arg Tyr
145                 150                 155                 160

Pro Thr Ile Glu Lys Ile Asp Ile Val Glu Ile Asp Asp Val Val Val
                165                 170                 175

Asp Val Ser Arg Lys Phe Phe Pro Tyr Leu Ala Ala Asn Phe Asn Asp
            180                 185                 190

Pro Arg Val Thr Leu Val Leu Gly Asp Gly Ala Ala Phe Val Lys Ala
        195                 200                 205

Ala Gln Ala Glu Tyr Tyr Asp Ala Ile Ile Val Asp Ser Ser Asp Pro
    210                 215                 220

Ile Gly Pro Ala Lys Asp Leu Phe Glu Arg Pro Phe Phe Glu Ala Val
225                 230                 235                 240

Ala Lys Ala Leu Arg Pro Gly Gly Val Val Cys Thr Gln Ala Glu Ser
                245                 250                 255
```

```
Ile Trp Leu His Met His Ile Ile Lys Gln Ile Ile Ala Asn Cys Arg
            260                 265                 270

Gln Val Phe Lys Gly Ser Val Asn Tyr Ala Trp Thr Thr Val Pro Thr
        275                 280                 285

Tyr Pro Thr Gly Val Ile Gly Tyr Met Leu Cys Ser Thr Glu Gly Pro
    290                 295                 300

Glu Ile Asp Phe Lys Asn Pro Val Asn Pro Ile Asp Lys Glu Thr Ala
305                 310                 315                 320

Gln Val Lys Ser Lys Leu Ala Pro Leu Lys Phe Tyr Asn Ser Asp Ile
                325                 330                 335

His Lys Ala Ala Phe Ile Leu Pro Ser Phe Ala Arg Ser Met Ile Glu
            340                 345                 350

Ser

<210> SEQ ID NO 14
<211> LENGTH: 381
<212> TYPE: PRT
<213> ORGANISM: Nicotiana tabacum

<400> SEQUENCE: 14

Met Glu Val Ile Ser Thr Asn Thr Asn Gly Ser Thr Ile Phe Lys Asn
1               5                   10                  15

Gly Ala Ile Pro Met Asn Gly Tyr Gln Asn Gly Thr Ser Lys His Gln
            20                  25                  30

Asn Gly His Gln Asn Gly Thr Ser Glu His Arg Asn Gly His Gln Asn
        35                  40                  45

Gly Ile Ser Glu His Gln Asn Gly His Gln Asn Gly Thr Ser Glu His
    50                  55                  60

Gln Asn Gly His Gln Asn Gly Thr Ile Ser His Asp Asn Gly Asn Glu
65                  70                  75                  80

Leu Gln Leu Leu Gly Ser Ser Asn Ser Ile Lys Pro Gly Trp Phe Ser
                85                  90                  95

Glu Phe Ser Ala Leu Trp Pro Gly Glu Ala Phe Ser Leu Lys Val Glu
            100                 105                 110

Lys Leu Leu Phe Gln Gly Lys Ser Asp Tyr Gln Asp Val Met Leu Phe
        115                 120                 125

Glu Ser Ala Thr Tyr Gly Lys Val Leu Thr Leu Asp Gly Ala Ile Gln
    130                 135                 140

His Thr Glu Asn Gly Gly Phe Pro Tyr Thr Glu Met Ile Val His Leu
145                 150                 155                 160

Pro Leu Gly Ser Ile Pro Asn Pro Lys Lys Val Leu Ile Ile Gly Gly
                165                 170                 175

Gly Ile Gly Phe Thr Leu Phe Glu Met Leu Arg Tyr Pro Thr Ile Glu
            180                 185                 190

Lys Ile Asp Ile Val Glu Ile Asp Asp Val Val Asp Val Ser Arg
        195                 200                 205

Lys Phe Phe Pro Tyr Leu Ala Ala Asn Phe Ser Asp Pro Arg Val Thr
    210                 215                 220

Leu Val Leu Gly Asp Gly Ala Ala Phe Val Lys Ala Ala Gln Ala Gly
225                 230                 235                 240

Tyr Tyr Asp Ala Ile Ile Val Asp Ser Ser Asp Pro Ile Gly Pro Ala
                245                 250                 255

Lys Asp Leu Phe Glu Arg Pro Phe Phe Glu Ala Val Ala Lys Ala Leu
            260                 265                 270
```

Arg Pro Gly Gly Val Val Cys Thr Gln Ala Glu Ser Ile Trp Leu His
                275                 280                 285

Met His Ile Ile Lys Gln Ile Ile Ala Asn Cys Arg Gln Val Phe Lys
    290                 295                 300

Gly Ser Val Asn Tyr Ala Trp Thr Thr Val Pro Thr Tyr Pro Thr Gly
305                 310                 315                 320

Val Ile Gly Tyr Met Leu Cys Ser Thr Glu Gly Pro Glu Val Asp Phe
                325                 330                 335

Lys Asn Pro Val Asn Pro Ile Asp Lys Glu Thr Thr Gln Val Lys Ser
                340                 345                 350

Lys Leu Ala Pro Leu Lys Phe Tyr Asn Ser Asp Ile His Lys Ala Ala
                355                 360                 365

Phe Ile Leu Pro Ser Phe Ala Arg Ser Met Ile Glu Ser
                370                 375                 380

<210> SEQ ID NO 15
<211> LENGTH: 419
<212> TYPE: PRT
<213> ORGANISM: Nicotiana tabacum

<400> SEQUENCE: 15

Met Glu Val Ile Ser Thr Asn Thr Asn Gly Ser Thr Ile Phe Lys Asn
1               5                   10                  15

Gly Ala Ile Pro Met Asn Gly His Gln Ser Gly Thr Ser Lys His Leu
                20                  25                  30

Asn Gly Tyr Gln Asn Gly Thr Ser Lys His Gln Asn Gly His His Asn
                35                  40                  45

Gly Thr Ser Glu His Arg Asn Gly His Gln Asn Gly Ile Ser Glu His
            50                  55                  60

Gln Asn Gly His Gln Asn Gly Thr Ser Glu His Arg Asn Gly His Gln
65                  70                  75                  80

Asn Gly Ile Ser Glu His Gln Asn Gly His Gln Asn Gly Thr Ser Glu
                85                  90                  95

His Gln Asn Gly His Gln Asn Gly Thr Ser Glu Gln Gln Asn Gly Thr
            100                 105                 110

Ile Ser His Asp Asn Gly Asn Glu Leu Leu Gly Asn Ser Asn Ser Ile
            115                 120                 125

Lys Leu Gly Trp Phe Ser Glu Phe Ser Ala Leu Trp Pro Gly Glu Ala
130                 135                 140

Phe Ser Leu Lys Val Glu Lys Leu Leu Phe Gln Gly Lys Ser Asp Tyr
145                 150                 155                 160

Gln Asp Val Met Leu Phe Glu Ser Ala Thr Tyr Gly Lys Val Leu Thr
                165                 170                 175

Leu Asp Gly Ala Ile Gln His Thr Glu Asn Gly Gly Phe Pro Tyr Thr
            180                 185                 190

Glu Met Ile Val His Leu Pro Leu Gly Ser Ile Pro Asn Pro Lys Lys
        195                 200                 205

Val Leu Ile Ile Gly Gly Gly Ile Gly Phe Thr Leu Phe Glu Met Leu
210                 215                 220

Arg Tyr Pro Thr Ile Glu Lys Ile Asp Ile Val Glu Ile Asp Asp Val
225                 230                 235                 240

Val Val Asp Val Ser Arg Lys Ser Phe Pro Tyr Leu Ala Ala Asn Phe
                245                 250                 255

Asn Asp Pro Arg Val Thr Leu Val Leu Gly Asp Gly Ala Ala Phe Val

```
            260                 265                 270
Lys Ala Ala Gln Ala Gly Tyr Tyr Asp Ala Ile Ile Val Asp Ser Ser
            275                 280                 285

Asp Pro Ile Gly Pro Ala Lys Asp Leu Phe Glu Arg Pro Phe Phe Glu
        290                 295                 300

Ala Val Ala Lys Ala Leu Arg Pro Gly Gly Val Val Cys Thr Gln Ala
305                 310                 315                 320

Glu Ser Ile Trp Leu His Met His Ile Ile Lys Gln Ile Ile Ala Asn
                325                 330                 335

Cys Arg Gln Val Phe Lys Gly Ser Val Asn Tyr Ala Trp Thr Thr Val
            340                 345                 350

Pro Thr Tyr Pro Thr Gly Val Ile Gly Tyr Met Leu Cys Ser Thr Glu
        355                 360                 365

Gly Pro Glu Val Asp Phe Lys Asn Pro Ile Asn Pro Ile Asp Lys Glu
    370                 375                 380

Thr Thr Gln Val Lys Ser Lys Leu Ala Pro Leu Lys Phe Tyr Asn Ser
385                 390                 395                 400

Asp Ile His Lys Ala Ala Phe Ile Leu Pro Ser Phe Ala Arg Ser Met
                405                 410                 415

Ile Glu Ser

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cccatgaacg gccaccaaaa                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcacttcca aacaccaaaa                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gttgttcgga tgtcccattc                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 19
ctaaactctg aaaaccaacc                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tttcagagtt tagcgcatta                                            20

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatggagcaa ttcaacatac aga                                        23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gatggagcaa ttcaacacac aga                                        23

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tggcatttcc aaacaccaaa cgggcaccag aatggcactt                      40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccaactctat taagcctggt ggttttcaga gtttagcgca                      40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 ttctgactttggatggagcaatacagagaatggtggatttt    40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctgactttgg atggagcaat gagaatggtg gatttccata    40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgactttgga tggagcaatt cagagaatgg tggatttcca    40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgactttgga tggagcaatt agaatggtgg atttccatac    40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gactttggat ggagcaattc agagaatggt ggatttccat    40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gactttggat ggagcaattc gagaatggtg gatttccata    40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gactttggat ggagcaattc agaatggtgg atttccatac       40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gactttggat ggagcaattc tggatttcca tacactgaaa       40

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
actttggatg gagcaattca tacagagaat ggtggatttc c       41

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
actttggatg gagcaattca cagagaatgg tggatttcca       40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
actttggatg gagcaattca agagaatggt ggatttccat       40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
actttggatg gagcaattca gagaatggtg gatttccata       40

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
actttggatg gagcaattca atacactgaa atgattgttc       40

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctttggatgg agcaattcaa tacagagaat ggtggatttc                            40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctttggatgg agcaattcaa cagagaatgg tggatttcca                            40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctttggatgg agcaattcaa gagaatggtg gatttccata                            40

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctttggatgg agcaattcaa agaatggtgg atttccatac                            40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tttggatgga gcaattcaac tacagagaat ggtggatttc                            40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tttggatgga gcaattcaac cagagaatgg tggatttcca                            40

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tttggatgga gcaattcaac agagaatggt ggatttccat         40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tttggatgga gcaattcaac gagaatggtg gatttccata         40

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tttggatgga gcaattcaac agaatggtgg atttccatac         40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tttggatgga gcaattcaac aatggtggat ttccatacac         40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttggatggag caattcaaca cagagaatgg tggatttcca         40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttggatggag caattcaaca gagaatggtg gatttccata         40

```
<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tggatggagc aattcaacat agagaatggt ggatttccat                    40

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tggatggagc aattcaacat gagaatggtg gatttccata                    40

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tggatggagc aattcaacat agaatggtgg atttccatac                    40

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tggatggagc aattcaacat aatggtggat ttccatacac                    40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggatggagca attcaacata gagaatggtg gatttccata                    40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
caattcaaca tacagagaat gtggatttcc atacactgaa                    40

<210> SEQ ID NO 56
```

```
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gcacttccaa acaccaaaac agggcaccag aatggcactt t                        41

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ttctgacttt ggatggagca atacagagaa tggtggattt                          40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttctgacttt ggatggagca gagaatggtg gatttccata                          40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctgactttgg atggagcaat acagagaatg gtggatttcc                          40

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctgactttgg atggagcaat gagaatggtg gatttccata                          40

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgactttgga tggagcaatt cagagaatgg tggatttcca                          40

<210> SEQ ID NO 62
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tgactttgga tggagcaatt agaatggtgg atttccatac                             40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gactttggat ggagcaattc agagaatggt ggatttccat                             40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gactttggat ggagcaattc gagaatggtg gatttccata                             40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gactttggat ggagcaattc agaatggtgg atttccatac                             40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gactttggat ggagcaattc gaatggtgga tttccataca                             40

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gactttggat ggagcaattc tggatttcca tacactgaaa                             40

<210> SEQ ID NO 68
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 68
actttggatg gagcaattca atacagagaa tggtggattt                             40

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
actttggatg gagcaattca acagagaatg gtggatttcc                             40

<210> SEQ ID NO 70
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
actttggatg gagcaattca agagaatggt ggatttccat                             40

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
actttggatg gagcaattca gagaatggtg gatttccata                             40

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
actttggatg gagcaattca agaatggtgg atttccatac                             40

<210> SEQ ID NO 73
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
actttggatg gagcaattca aatggtggat ttccatacac                             40

<210> SEQ ID NO 74
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 74
ctttggatgg agcaattcaa atacagagaa tggtggattt                             40

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctttggatgg agcaattcaa tacagagaat ggtggatttc                             40

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ctttggatgg agcaattcaa cagagaatgg tggatttcca                             40

<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ctttggatgg agcaattcaa agagaatggt ggatttccat                             40

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctttggatgg agcaattcaa agaatggtgg atttccatac                             40

<210> SEQ ID NO 79
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tttggatgga gcaattcaac tacagagaat ggtggatttc c                           41

<210> SEQ ID NO 80
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 80
tttggatgga gcaattcaac agagaatggt ggatttccat                          40

<210> SEQ ID NO 81
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tttggatgga gcaattcaac gagaatggtg gatttccata                          40

<210> SEQ ID NO 82
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tttggatgga gcaattcaac agaatggtgg atttccatac                          40

<210> SEQ ID NO 83
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tttggatgga gcaattcaac gaatggtgga tttccataca                          40

<210> SEQ ID NO 84
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tttggatgga gcaattcaac ggatttccat acactgaaat                          40

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttggatggag caattcaaca acagagaatg gtggatttcc                          40

<210> SEQ ID NO 86
<211> LENGTH: 40
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 86
ttggatggag caattcaaca cagagaatgg tggatttcca                          40

<210> SEQ ID NO 87
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ttggatggag caattcaaca agagaatggt ggatttccat                          40

<210> SEQ ID NO 88
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ttggatggag caattcaaca gagaatggtg gatttccata                          40

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ttggatggag caattcaaca agaatggtgg atttccatac                          40

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ttggatggag caattcaaca gaatggtgga tttccataca                          40

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ttggatggag caattcaaca aatggtggat ttccatacac                          40

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tggatggagc aattcaacat agagaatggt ggatttccat                    40

<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tggatggagc aattcaacat agaatggtgg atttccatac                    40

<210> SEQ ID NO 94
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tggatggagc aattcaacat atggtggatt tccatacact                    40

<210> SEQ ID NO 95
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ggatggagca attcaacata gagaatggtg gatttccata                    40

<210> SEQ ID NO 96
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggatggagca attcaacata agaatggtgg atttccatac                    40

<210> SEQ ID NO 97
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gagcaattca acatacagag tggtggattt ccatacactg                    40

<210> SEQ ID NO 98
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tggcacttcc aaacaccaaa cggccacaag aatgggactt                     40

<210> SEQ ID NO 99
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ccaattgtat taagcctggt ggttttcaga gtttagcgca                     40

<210> SEQ ID NO 100
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tgactttgga tggagcaatt cacagagaat ggtggatttc                     40

<210> SEQ ID NO 101
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgactttgga tggagcaatt cagagaatgg tggatttcca                     40

<210> SEQ ID NO 102
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tgactttgga tggagcaatt agaatggtgg atttccatac                     40

<210> SEQ ID NO 103
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gactttggat ggagcaattc gagaatggtg gatttccata                     40

<210> SEQ ID NO 104
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gactttggat ggagcaattc aatggtggat ttccatacac        40

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
actttggatg gagcaattca acacagagaa tggtggattt        40

<210> SEQ ID NO 106
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
actttggatg gagcaattca acagagaatg gtggatttcc        40

<210> SEQ ID NO 107
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
actttggatg gagcaattca cagagaatgg tggatttcca        40

<210> SEQ ID NO 108
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
actttggatg gagcaattca agagaatggt ggatttccat        40

<210> SEQ ID NO 109
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
actttggatg gagcaattca gagaatggtg gatttccata        40

<210> SEQ ID NO 110
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
actttggatg gagcaattca agaatggtgg atttccatac					40

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
actttggatg gagcaattca aatggtggat ttccatacac					40

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ctttggatgg agcaattcaa acacagagaa tggtggattt					40

<210> SEQ ID NO 113
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ctttggatgg agcaattcaa cacagagaat ggtggatttc					40

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctttggatgg agcaattcaa cagagaatgg tggatttcca					40

<210> SEQ ID NO 115
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ctttggatgg agcaattcaa agaatggtgg atttccatac					40

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tttggatgga gcaattcaac acagagaatg gtggatttcc					40

<210> SEQ ID NO 117
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tttggatgga gcaattcaac agagaatggt ggatttccat                   40

<210> SEQ ID NO 118
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tttggatgga gcaattcaac gagaatggtg gatttccata                   40

<210> SEQ ID NO 119
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tttggatgga gcaattcaac agaatggtgg atttccatac                   40

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tttggatgga gcaattcaac aatggtggat ttccatacac                   40

<210> SEQ ID NO 121
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tttggatgga gcaattcaac ggatttccat acactgaaat                   40

<210> SEQ ID NO 122
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ttggatggag caattcaaca cagagaatgg tggatttcca                   40

<210> SEQ ID NO 123
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
ttggatggag caattcaaca gagaatggtg gatttccata          40

<210> SEQ ID NO 124
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
ttggatggag caattcaaca gaatggtgga tttccataca          40

<210> SEQ ID NO 125
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
ttggatggag caattcaaca aatggtggat ttccatacac          40

<210> SEQ ID NO 126
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
ttggatggag caattcaaca tggatttcca tacactgaaa          40

<210> SEQ ID NO 127
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 127
tggatggagc aattcaacac gagaatggtg gatttccata          40

<210> SEQ ID NO 128
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128
tggatggagc aattcaacac agaatggtgg atttccatac          40

```
<210> SEQ ID NO 129
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggatggagca attcaacaca gagaatggtg gatttccata                          40

<210> SEQ ID NO 130
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggatggagca attcaacaca gaatggtgga tttccataca                          40

<210> SEQ ID NO 131
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggatggagca attcaacaca gtggatttcc atacactgaa                          40

<210> SEQ ID NO 132
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gatggagcaa ttcaacacac tggtggattt ccatacactg                          40

<210> SEQ ID NO 133
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tggcacttcc aaacaccaaa cggccaccag aatggcactt                          40

<210> SEQ ID NO 134
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ccaactctat taagcctggt ggttttcaga gtttagcgca                          40

<210> SEQ ID NO 135
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aacatatggg aaggttctga ttggatggag caattcaaca                              40

<210> SEQ ID NO 136
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
atgggaaggt tctgactttg tggagcaatt caacacacag                              40

<210> SEQ ID NO 137
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gttctgactt tggatggagc ttcaacacac agagaatggt                              40

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ctgactttgg atggagcaat acagagaatg gtggatttcc                              40

<210> SEQ ID NO 139
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ctgactttgg atggagcaat gagaatggtg gatttccata                              40

<210> SEQ ID NO 140
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ctgactttgg atggagcaat agaatggtgg atttccatac                              40

<210> SEQ ID NO 141
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tgactttgga tggagcaatt cagagaatgg tggatttcca                            40

<210> SEQ ID NO 142
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gactttggat ggagcaattc acacacagag aatggtggat                            40

<210> SEQ ID NO 143
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gactttggat ggagcaattc cacacagaga atggtggatt                            40

<210> SEQ ID NO 144
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gactttggat ggagcaattc gagaatggtg gatttccata                            40

<210> SEQ ID NO 145
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gactttggat ggagcaattc aatggtggat ttccatacac                            40

<210> SEQ ID NO 146
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
actttggatg gagcaattca acacagagaa tggtggattt                            40

<210> SEQ ID NO 147
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 147
actttggatg gagcaattca acagagaatg gtggatttcc                          40

<210> SEQ ID NO 148
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
actttggatg gagcaattca agagaatggt ggatttccat                          40

<210> SEQ ID NO 149
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
actttggatg gagcaattca agaatggtgg atttccatac                          40

<210> SEQ ID NO 150
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
actttggatg gagcaattca aatggtggat ttccatacac                          40

<210> SEQ ID NO 151
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
actttggatg gagcaattca tggatttcca tacactgaaa                          40

<210> SEQ ID NO 152
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
actttggatg gagcaattca gatttccata cactgaaatg                          40

<210> SEQ ID NO 153
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 153
ctttggatgg agcaattcaa acacagagaa tggtggattt                              40

<210> SEQ ID NO 154
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ctttggatgg agcaattcaa cagagaatgg tggatttcca                              40

<210> SEQ ID NO 155
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ctttggatgg agcaattcaa agagaatggt ggatttccat                              40

<210> SEQ ID NO 156
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ctttggatgg agcaattcaa agaatggtgg atttccatac                              40

<210> SEQ ID NO 157
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tttggatgga gcaattcaac acagagaatg gtggatttcc                              40

<210> SEQ ID NO 158
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tttggatgga gcaattcaac agagaatggt ggatttccat                              40

<210> SEQ ID NO 159
<211> LENGTH: 40
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 159
tttggatgga gcaattcaac gagaatggtg gatttccata                           40

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 160
ttggatggag caattcaaca cagagaatgg tggatttcca                           40

<210> SEQ ID NO 161
<211> LENGTH: 40
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 161
ttggatggag caattcaaca gagaatggtg gatttccata                           40

<210> SEQ ID NO 162
<211> LENGTH: 40
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 162
ttggatggag caattcaaca agaatggtgg atttccatac                           40

<210> SEQ ID NO 163
<211> LENGTH: 40
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 163
ttggatggag caattcaaca ggatttccat acactgaaat                           40

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 164
tggatggagc aattcaacac agagaatggt ggatttccat                           40

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
tggatggagc aattcaacac agaatggtgg atttccatac                40

<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tggatggagc aattcaacac tggtggattt ccatacactg                40

<210> SEQ ID NO 167
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggatggagca attcaacaca gagaatggtg gatttccata                40

<210> SEQ ID NO 168
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tggagcaatt caacacacag atggtggatt tccatacact                40

<210> SEQ ID NO 169
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tggagcaatt caacacacag tggtggattt ccatacactg                40

<210> SEQ ID NO 170
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ggagcaattc aacacacaga atggtggat ttccatacac                40

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
caattcaaca cacagagaat atttccatac actgaaatga                                40

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
aacacacaga gaatggtgga aaatgattgt tcatcttcca                                40

<210> SEQ ID NO 173
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cggcacttcc aaacaccaaa cggccaccat aatggcactt                                40

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174 ttttgactttt ggatggagca agagaatggt ggatttccat                               40

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ttgactttgg atggagcaat gaatggtgga tttccataca                                40

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tgactttgga tggagcaatt cagagaatgg tggatttcca                                40

<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tgactttgga tggagcaatt agaatggtgg atttccatac        40

<210> SEQ ID NO 178
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gactttggat ggagcaattc aatggtggat ttccatacac        40

<210> SEQ ID NO 179
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gactttggat ggagcaattc tggtggattt ccatacactg        40

<210> SEQ ID NO 180
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
actttggatg gagcaattca acacagagaa tggtggattt        40

<210> SEQ ID NO 181
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
actttggatg gagcaattca acagagaatg gtggatttcc        40

<210> SEQ ID NO 182
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
actttggatg gagcaattca agagaatggt ggatttccat        40

<210> SEQ ID NO 183
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
actttggatg gagcaattca gagaatggtg gatttccata                    40

<210> SEQ ID NO 184
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
actttggatg gagcaattca agaatggtgg atttccatac                    40

<210> SEQ ID NO 185
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ctttggatgg agcaattcaa cagagaatgg tggatttcca                    40

<210> SEQ ID NO 186
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ctttggatgg agcaattcaa agagaatggt ggatttccat                    40

<210> SEQ ID NO 187
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tttggatgga gcaattcaac acagagaatg gtggatttcc                    40

<210> SEQ ID NO 188
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tttggatgga gcaattcaac agagaatggt ggatttccat                    40

<210> SEQ ID NO 189
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tttggatgga gcaattcaac gagaatggtg gatttccata         40

<210> SEQ ID NO 190
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ttggatggag caattcaaca gagaatggtg gatttccata         40

<210> SEQ ID NO 191
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ttggatggag caattcaaca agaatggtgg atttccatac         40

<210> SEQ ID NO 192
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tggatggagc aattcaacac agagaatggt ggatttccat         40

<210> SEQ ID NO 193
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tggatggagc aattcaacac gagaatggtg gatttccata         40

<210> SEQ ID NO 194
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tggatggagc aattcaacac agaatggtgg atttccatac         40

<210> SEQ ID NO 195
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tggatggagc aattcaacac atggtggatt tccatacact         40

<210> SEQ ID NO 196
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ggatggagca attcaacaca gagaatggtg gatttccata                                40

<210> SEQ ID NO 197
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tggagcaatt caacacacag gaatggtgga tttccataca                                40

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gcaattcaac acacagagaa atttccatac actgaaatga                                40

<210> SEQ ID NO 199
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
aacacacaga gaatggtgga tccatacact gaaatgattg                                40

<210> SEQ ID NO 200
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cacagagaat ggtggatttc cactgaaatg attgttcatc                                40

<210> SEQ ID NO 201
<211> LENGTH: 41
<212> TYPE: DNA
<213> ORGANISM: Nicotiana tabacum

<400> SEQUENCE: 201
tggcatttcc aaacaccaaa acgggcacca gaatggcact t                              41

<210> SEQ ID NO 202
<211> LENGTH: 41

<212> TYPE: DNA
<213> ORGANISM: Nicotiana tabacum

<400> SEQUENCE: 202
ccaactctat taagcctggt tggttttcag agtttagcgc a    41

<210> SEQ ID NO 203
<211> LENGTH: 47
<212> TYPE: DNA
<213> ORGANISM: Nicotiana tabacum

<400> SEQUENCE: 203
ttctgacttt ggatggagca attcaacata cagagaatgg tggattt    47

<210> SEQ ID NO 204
<211> LENGTH: 50
<212> TYPE: DNA
<213> ORGANISM: Nicotiana tabacum

<400> SEQUENCE: 204
ctgactttgg atggagcaat tcaacataca gagaatggtg gatttccata    50

<210> SEQ ID NO 205
<211> LENGTH: 47
<212> TYPE: DNA
<213> ORGANISM: Nicotiana tabacum

<400> SEQUENCE: 205
tgactttgga tggagcaatt caacatacag agaatggtgg atttcca    47

<210> SEQ ID NO 206
<211> LENGTH: 50
<212> TYPE: DNA
<213> ORGANISM: Nicotiana tabacum

<400> SEQUENCE: 206
tgactttgga tggagcaatt caacatacag agaatggtgg atttccatac    50

<210> SEQ ID NO 207
<211> LENGTH: 47
<212> TYPE: DNA
<213> ORGANISM: Nicotiana tabacum

<400> SEQUENCE: 207
gactttggat ggagcaattc aacatacaga gaatggtgga tttccat    47

<210> SEQ ID NO 208
<211> LENGTH: 48
<212> TYPE: DNA
<213> ORGANISM: Nicotiana tabacum

<400> SEQUENCE: 208
gactttggat ggagcaattc aacatacaga gaatggtgga tttccata    48

<210> SEQ ID NO 209
<211> LENGTH: 49
<212> TYPE: DNA
<213> ORGANISM: Nicotiana tabacum

<400> SEQUENCE: 209
gactttggat ggagcaattc aacatacaga gaatggtgga tttccatac    49

<210> SEQ ID NO 210

```
<211> LENGTH: 56
<212> TYPE: DNA
<213> ORGANISM: Nicotiana tabacum

<400> SEQUENCE: 210
gactttggat ggagcaattc aacatacaga gaatggtgga tttccataca ctgaaa          56

<210> SEQ ID NO 211
<211> LENGTH: 44
<212> TYPE: DNA
<213> ORGANISM: Nicotiana tabacum

<400> SEQUENCE: 211
actttggatg gagcaattca acatacagag aatggtggat ttcc                       44

<210> SEQ ID NO 212
<211> LENGTH: 45
<212> TYPE: DNA
<213> ORGANISM: Nicotiana tabacum

<400> SEQUENCE: 212
actttggatg gagcaattca acatacagag aatggtggat ttcca                      45

<210> SEQ ID NO 213
<211> LENGTH: 46
<212> TYPE: DNA
<213> ORGANISM: Nicotiana tabacum

<400> SEQUENCE: 213
actttggatg gagcaattca acatacagag aatggtggat ttccat                     46

<210> SEQ ID NO 214
<211> LENGTH: 47
<212> TYPE: DNA
<213> ORGANISM: Nicotiana tabacum

<400> SEQUENCE: 214
actttggatg gagcaattca acatacagag aatggtggat ttccata                    47

<210> SEQ ID NO 215
<211> LENGTH: 64
<212> TYPE: DNA
<213> ORGANISM: Nicotiana tabacum

<400> SEQUENCE: 215
actttggatg gagcaattca acatacagag aatggtggat ttccatacac tgaaatgatt      60
gttc                                                                   64

<210> SEQ ID NO 216
<211> LENGTH: 42
<212> TYPE: DNA
<213> ORGANISM: Nicotiana tabacum

<400> SEQUENCE: 216
ctttggatgg agcaattcaa catacagaga atggtggatt tc                         42

<210> SEQ ID NO 217
<211> LENGTH: 44
<212> TYPE: DNA
<213> ORGANISM: Nicotiana tabacum

<400> SEQUENCE: 217
ctttggatgg agcaattcaa catacagaga atggtggatt tcca                       44
```

<210> SEQ ID NO 218
<211> LENGTH: 46
<212> TYPE: DNA
<213> ORGANISM: Nicotiana tabacum

<400> SEQUENCE: 218
ctttggatgg agcaattcaa catacagaga atggtggatt tccata           46

<210> SEQ ID NO 219
<211> LENGTH: 47
<212> TYPE: DNA
<213> ORGANISM: Nicotiana tabacum

<400> SEQUENCE: 219
ctttggatgg agcaattcaa catacagaga atggtggatt tccatac          47

<210> SEQ ID NO 220
<211> LENGTH: 41
<212> TYPE: DNA
<213> ORGANISM: Nicotiana tabacum

<400> SEQUENCE: 220
tttggatgga gcaattcaac atacagagaa tggtggattt c                41

<210> SEQ ID NO 221
<211> LENGTH: 43
<212> TYPE: DNA
<213> ORGANISM: Nicotiana tabacum

<400> SEQUENCE: 221
tttggatgga gcaattcaac atacagagaa tggtggattt cca              43

<210> SEQ ID NO 222
<211> LENGTH: 44
<212> TYPE: DNA
<213> ORGANISM: Nicotiana tabacum

<400> SEQUENCE: 222
tttggatgga gcaattcaac atacagagaa tggtggattt ccat             44

<210> SEQ ID NO 223
<211> LENGTH: 45
<212> TYPE: DNA
<213> ORGANISM: Nicotiana tabacum

<400> SEQUENCE: 223
tttggatgga gcaattcaac atacagagaa tggtggattt ccata            45

<210> SEQ ID NO 224
<211> LENGTH: 46
<212> TYPE: DNA
<213> ORGANISM: Nicotiana tabacum

<400> SEQUENCE: 224
tttggatgga gcaattcaac atacagagaa tggtggattt ccatac           46

<210> SEQ ID NO 225
<211> LENGTH: 48
<212> TYPE: DNA
<213> ORGANISM: Nicotiana tabacum

<400> SEQUENCE: 225
tttggatgga gcaattcaac atacagagaa tggtggattt ccatacac          48

<210> SEQ ID NO 226
<211> LENGTH: 42
<212> TYPE: DNA
<213> ORGANISM: Nicotiana tabacum

<400> SEQUENCE: 226
ttggatggag caattcaaca tacagagaat ggtggatttc ca                42

<210> SEQ ID NO 227
<211> LENGTH: 44
<212> TYPE: DNA
<213> ORGANISM: Nicotiana tabacum

<400> SEQUENCE: 227
ttggatggag caattcaaca tacagagaat ggtggatttc cata              44

<210> SEQ ID NO 228
<211> LENGTH: 42
<212> TYPE: DNA
<213> ORGANISM: Nicotiana tabacum

<400> SEQUENCE: 228
tggatggagc aattcaacat acagagaatg gtggatttcc at                42

<210> SEQ ID NO 229
<211> LENGTH: 43
<212> TYPE: DNA
<213> ORGANISM: Nicotiana tabacum

<400> SEQUENCE: 229
tggatggagc aattcaacat acagagaatg gtggatttcc ata               43

<210> SEQ ID NO 230
<211> LENGTH: 44
<212> TYPE: DNA
<213> ORGANISM: Nicotiana tabacum

<400> SEQUENCE: 230
tggatggagc aattcaacat acagagaatg gtggatttcc atac              44

<210> SEQ ID NO 231
<211> LENGTH: 46
<212> TYPE: DNA
<213> ORGANISM: Nicotiana tabacum

<400> SEQUENCE: 231
tggatggagc aattcaacat acagagaatg gtggatttcc atacac            46

<210> SEQ ID NO 232
<211> LENGTH: 42
<212> TYPE: DNA
<213> ORGANISM: Nicotiana tabacum

<400> SEQUENCE: 232
ggatggagca attcaacata cagagaatgg tggatttcca ta                42

<210> SEQ ID NO 233
<211> LENGTH: 41
<212> TYPE: DNA
<213> ORGANISM: Nicotiana tabacum

<400> SEQUENCE: 233

```
caattcaaca tacagagaat ggtggatttc catacactga a                         41

<210> SEQ ID NO 234
<211> LENGTH: 40
<212> TYPE: DNA
<213> ORGANISM: Nicotiana tabacum

<400> SEQUENCE: 234
gcacttccaa acaccaaaac gggcaccaga atggcacttt                           40

<210> SEQ ID NO 235
<211> LENGTH: 47
<212> TYPE: DNA
<213> ORGANISM: Nicotiana tabacum

<400> SEQUENCE: 235
ttctgacttt ggatggagca attcaacata cagagaatgg tggattt                   47

<210> SEQ ID NO 236
<211> LENGTH: 52
<212> TYPE: DNA
<213> ORGANISM: Nicotiana tabacum

<400> SEQUENCE: 236
ttctgacttt ggatggagca attcaacata cagagaatgg tggatttcca ta             52

<210> SEQ ID NO 237
<211> LENGTH: 47
<212> TYPE: DNA
<213> ORGANISM: Nicotiana tabacum

<400> SEQUENCE: 237
ctgactttgg atggagcaat tcaacataca gagaatggtg gatttcc                   47

<210> SEQ ID NO 238
<211> LENGTH: 50
<212> TYPE: DNA
<213> ORGANISM: Nicotiana tabacum

<400> SEQUENCE: 238
ctgactttgg atggagcaat tcaacataca gagaatggtg gatttccata               50

<210> SEQ ID NO 239
<211> LENGTH: 47
<212> TYPE: DNA
<213> ORGANISM: Nicotiana tabacum

<400> SEQUENCE: 239
tgactttgga tggagcaatt caacatacag agaatggtgg atttcca                   47

<210> SEQ ID NO 240
<211> LENGTH: 50
<212> TYPE: DNA
<213> ORGANISM: Nicotiana tabacum

<400> SEQUENCE: 240
tgactttgga tggagcaatt caacatacag agaatggtgg atttccatac               50

<210> SEQ ID NO 241
<211> LENGTH: 47
<212> TYPE: DNA
<213> ORGANISM: Nicotiana tabacum
```

```
<400> SEQUENCE: 241
gactttggat ggagcaattc aacatacaga gaatggtgga tttccat          47

<210> SEQ ID NO 242
<211> LENGTH: 48
<212> TYPE: DNA
<213> ORGANISM: Nicotiana tabacum

<400> SEQUENCE: 242
gactttggat ggagcaattc aacatacaga gaatggtgga tttccata         48

<210> SEQ ID NO 243
<211> LENGTH: 49
<212> TYPE: DNA
<213> ORGANISM: Nicotiana tabacum

<400> SEQUENCE: 243
gactttggat ggagcaattc aacatacaga gaatggtgga tttccatac        49

<210> SEQ ID NO 244
<211> LENGTH: 50
<212> TYPE: DNA
<213> ORGANISM: Nicotiana tabacum

<400> SEQUENCE: 244
gactttggat ggagcaattc aacatacaga gaatggtgga tttccataca       50

<210> SEQ ID NO 245
<211> LENGTH: 56
<212> TYPE: DNA
<213> ORGANISM: Nicotiana tabacum

<400> SEQUENCE: 245
gactttggat ggagcaattc aacatacaga gaatggtgga tttccataca ctgaaa    56

<210> SEQ ID NO 246
<211> LENGTH: 42
<212> TYPE: DNA
<213> ORGANISM: Nicotiana tabacum

<400> SEQUENCE: 246
actttggatg gagcaattca acatacagag aatggtggat tt               42

<210> SEQ ID NO 247
<211> LENGTH: 44
<212> TYPE: DNA
<213> ORGANISM: Nicotiana tabacum

<400> SEQUENCE: 247
actttggatg gagcaattca acatacagag aatggtggat ttcc             44

<210> SEQ ID NO 248
<211> LENGTH: 46
<212> TYPE: DNA
<213> ORGANISM: Nicotiana tabacum

<400> SEQUENCE: 248
actttggatg gagcaattca acatacagag aatggtggat ttccat           46

<210> SEQ ID NO 249
<211> LENGTH: 47
<212> TYPE: DNA
<213> ORGANISM: Nicotiana tabacum
```

```
<400> SEQUENCE: 249
actttggatg gagcaattca acatacagag aatggtggat ttccata          47

<210> SEQ ID NO 250
<211> LENGTH: 48
<212> TYPE: DNA
<213> ORGANISM: Nicotiana tabacum

<400> SEQUENCE: 250
actttggatg gagcaattca acatacagag aatggtggat ttccatac         48

<210> SEQ ID NO 251
<211> LENGTH: 50
<212> TYPE: DNA
<213> ORGANISM: Nicotiana tabacum

<400> SEQUENCE: 251
actttggatg gagcaattca acatacagag aatggtggat ttccatacac       50

<210> SEQ ID NO 252
<211> LENGTH: 41
<212> TYPE: DNA
<213> ORGANISM: Nicotiana tabacum

<400> SEQUENCE: 252
ctttggatgg agcaattcaa catacagaga atggtggatt t                41

<210> SEQ ID NO 253
<211> LENGTH: 42
<212> TYPE: DNA
<213> ORGANISM: Nicotiana tabacum

<400> SEQUENCE: 253
ctttggatgg agcaattcaa catacagaga atggtggatt tc               42

<210> SEQ ID NO 254
<211> LENGTH: 44
<212> TYPE: DNA
<213> ORGANISM: Nicotiana tabacum

<400> SEQUENCE: 254
ctttggatgg agcaattcaa catacagaga atggtggatt tcca             44

<210> SEQ ID NO 255
<211> LENGTH: 45
<212> TYPE: DNA
<213> ORGANISM: Nicotiana tabacum

<400> SEQUENCE: 255
ctttggatgg agcaattcaa catacagaga atggtggatt tccat            45

<210> SEQ ID NO 256
<211> LENGTH: 47
<212> TYPE: DNA
<213> ORGANISM: Nicotiana tabacum

<400> SEQUENCE: 256
ctttggatgg agcaattcaa catacagaga atggtggatt tccatac          47

<210> SEQ ID NO 257
<211> LENGTH: 42
<212> TYPE: DNA
```

<213> ORGANISM: Nicotiana tabacum

<400> SEQUENCE: 257
tttggatgga gcaattcaac atacagagaa tggtggattt cc                42

<210> SEQ ID NO 258
<211> LENGTH: 44
<212> TYPE: DNA
<213> ORGANISM: Nicotiana tabacum

<400> SEQUENCE: 258
tttggatgga gcaattcaac atacagagaa tggtggattt ccat              44

<210> SEQ ID NO 259
<211> LENGTH: 45
<212> TYPE: DNA
<213> ORGANISM: Nicotiana tabacum

<400> SEQUENCE: 259
tttggatgga gcaattcaac atacagagaa tggtggattt ccata             45

<210> SEQ ID NO 260
<211> LENGTH: 46
<212> TYPE: DNA
<213> ORGANISM: Nicotiana tabacum

<400> SEQUENCE: 260
tttggatgga gcaattcaac atacagagaa tggtggattt ccatac            46

<210> SEQ ID NO 261
<211> LENGTH: 47
<212> TYPE: DNA
<213> ORGANISM: Nicotiana tabacum

<400> SEQUENCE: 261
tttggatgga gcaattcaac atacagagaa tggtggattt ccataca           47

<210> SEQ ID NO 262
<211> LENGTH: 54
<212> TYPE: DNA
<213> ORGANISM: Nicotiana tabacum

<400> SEQUENCE: 262
tttggatgga gcaattcaac atacagagaa tggtggattt ccatacactg aaat   54

<210> SEQ ID NO 263
<211> LENGTH: 41
<212> TYPE: DNA
<213> ORGANISM: Nicotiana tabacum

<400> SEQUENCE: 263
ttggatggag caattcaaca tacagagaat ggtggatttc c                 41

<210> SEQ ID NO 264
<211> LENGTH: 42
<212> TYPE: DNA
<213> ORGANISM: Nicotiana tabacum

<400> SEQUENCE: 264
ttggatggag caattcaaca tacagagaat ggtggatttc ca                42

<210> SEQ ID NO 265
<211> LENGTH: 43

```
<212> TYPE: DNA
<213> ORGANISM: Nicotiana tabacum

<400> SEQUENCE: 265
ttggatggag caattcaaca tacagagaat ggtggatttc cat            43

<210> SEQ ID NO 266
<211> LENGTH: 44
<212> TYPE: DNA
<213> ORGANISM: Nicotiana tabacum

<400> SEQUENCE: 266
ttggatggag caattcaaca tacagagaat ggtggatttc cata           44

<210> SEQ ID NO 267
<211> LENGTH: 45
<212> TYPE: DNA
<213> ORGANISM: Nicotiana tabacum

<400> SEQUENCE: 267
ttggatggag caattcaaca tacagagaat ggtggatttc catac          45

<210> SEQ ID NO 268
<211> LENGTH: 46
<212> TYPE: DNA
<213> ORGANISM: Nicotiana tabacum

<400> SEQUENCE: 268
ttggatggag caattcaaca tacagagaat ggtggatttc cataca         46

<210> SEQ ID NO 269
<211> LENGTH: 47
<212> TYPE: DNA
<213> ORGANISM: Nicotiana tabacum

<400> SEQUENCE: 269
ttggatggag caattcaaca tacagagaat ggtggatttc catacac        47

<210> SEQ ID NO 270
<211> LENGTH: 42
<212> TYPE: DNA
<213> ORGANISM: Nicotiana tabacum

<400> SEQUENCE: 270
tggatggagc aattcaacat acagagaatg gtggatttcc at             42

<210> SEQ ID NO 271
<211> LENGTH: 44
<212> TYPE: DNA
<213> ORGANISM: Nicotiana tabacum

<400> SEQUENCE: 271
tggatggagc aattcaacat acagagaatg gtggatttcc atac           44

<210> SEQ ID NO 272
<211> LENGTH: 47
<212> TYPE: DNA
<213> ORGANISM: Nicotiana tabacum

<400> SEQUENCE: 272
tggatggagc aattcaacat acagagaatg gtggatttcc atacact        47

<210> SEQ ID NO 273
```

```
<211> LENGTH: 42
<212> TYPE: DNA
<213> ORGANISM: Nicotiana tabacum

<400> SEQUENCE: 273
ggatggagca attcaacata cagagaatgg tggatttcca ta                    42

<210> SEQ ID NO 274
<211> LENGTH: 43
<212> TYPE: DNA
<213> ORGANISM: Nicotiana tabacum

<400> SEQUENCE: 274
ggatggagca attcaacata cagagaatgg tggatttcca tac                   43

<210> SEQ ID NO 275
<211> LENGTH: 42
<212> TYPE: DNA
<213> ORGANISM: Nicotiana tabacum

<400> SEQUENCE: 275
gagcaattca acatacagag aatggtggat tccatacac tg                     42

<210> SEQ ID NO 276
<211> LENGTH: 41
<212> TYPE: DNA
<213> ORGANISM: Nicotiana tabacum

<400> SEQUENCE: 276
tggcacttcc aaacaccaaa acggccacaa gaatgggact t                     41

<210> SEQ ID NO 277
<211> LENGTH: 41
<212> TYPE: DNA
<213> ORGANISM: Nicotiana tabacum

<400> SEQUENCE: 277
ccaattgtat taagcctggt tggttttcag agtttagcgc a                     41

<210> SEQ ID NO 278
<211> LENGTH: 45
<212> TYPE: DNA
<213> ORGANISM: Nicotiana tabacum

<400> SEQUENCE: 278
tgactttgga tggagcaatt caacacacag agaatggtgg atttc                 45

<210> SEQ ID NO 279
<211> LENGTH: 47
<212> TYPE: DNA
<213> ORGANISM: Nicotiana tabacum

<400> SEQUENCE: 279
tgactttgga tggagcaatt caacacacag agaatggtgg atttcca               47

<210> SEQ ID NO 280
<211> LENGTH: 50
<212> TYPE: DNA
<213> ORGANISM: Nicotiana tabacum

<400> SEQUENCE: 280
tgactttgga tggagcaatt caacacacag agaatggtgg atttccatac            50
```

```
<210> SEQ ID NO 281
<211> LENGTH: 48
<212> TYPE: DNA
<213> ORGANISM: Nicotiana tabacum

<400> SEQUENCE: 281
gactttggat ggagcaattc aacacacaga gaatggtgga tttccata            48

<210> SEQ ID NO 282
<211> LENGTH: 51
<212> TYPE: DNA
<213> ORGANISM: Nicotiana tabacum

<400> SEQUENCE: 282
gactttggat ggagcaattc aacacacaga gaatggtgga tttccataca c         51

<210> SEQ ID NO 283
<211> LENGTH: 42
<212> TYPE: DNA
<213> ORGANISM: Nicotiana tabacum

<400> SEQUENCE: 283
actttggatg gagcaattca acacacagag aatggtggat tt                   42

<210> SEQ ID NO 284
<211> LENGTH: 44
<212> TYPE: DNA
<213> ORGANISM: Nicotiana tabacum

<400> SEQUENCE: 284
actttggatg gagcaattca acacacagag aatggtggat ttcc                 44

<210> SEQ ID NO 285
<211> LENGTH: 45
<212> TYPE: DNA
<213> ORGANISM: Nicotiana tabacum

<400> SEQUENCE: 285
actttggatg gagcaattca acacacagag aatggtggat ttcca                45

<210> SEQ ID NO 286
<211> LENGTH: 46
<212> TYPE: DNA
<213> ORGANISM: Nicotiana tabacum

<400> SEQUENCE: 286
actttggatg gagcaattca acacacagag aatggtggat ttccat               46

<210> SEQ ID NO 287
<211> LENGTH: 47
<212> TYPE: DNA
<213> ORGANISM: Nicotiana tabacum

<400> SEQUENCE: 287
actttggatg gagcaattca acacacagag aatggtggat ttccata              47

<210> SEQ ID NO 288
<211> LENGTH: 48
<212> TYPE: DNA
<213> ORGANISM: Nicotiana tabacum

<400> SEQUENCE: 288
actttggatg gagcaattca acacacagag aatggtggat ttccatac             48
```

<210> SEQ ID NO 289
<211> LENGTH: 50
<212> TYPE: DNA
<213> ORGANISM: Nicotiana tabacum

<400> SEQUENCE: 289
actttggatg gagcaattca acacacagag aatggtggat ttccatacac         50

<210> SEQ ID NO 290
<211> LENGTH: 41
<212> TYPE: DNA
<213> ORGANISM: Nicotiana tabacum

<400> SEQUENCE: 290
ctttggatgg agcaattcaa cacacagaga atggtggatt t                  41

<210> SEQ ID NO 291
<211> LENGTH: 42
<212> TYPE: DNA
<213> ORGANISM: Nicotiana tabacum

<400> SEQUENCE: 291
ctttggatgg agcaattcaa cacacagaga atggtggatt tc                 42

<210> SEQ ID NO 292
<211> LENGTH: 44
<212> TYPE: DNA
<213> ORGANISM: Nicotiana tabacum

<400> SEQUENCE: 292
ctttggatgg agcaattcaa cacacagaga atggtggatt tcca               44

<210> SEQ ID NO 293
<211> LENGTH: 47
<212> TYPE: DNA
<213> ORGANISM: Nicotiana tabacum

<400> SEQUENCE: 293
ctttggatgg agcaattcaa cacacagaga atggtggatt tccatac            47

<210> SEQ ID NO 294
<211> LENGTH: 42
<212> TYPE: DNA
<213> ORGANISM: Nicotiana tabacum

<400> SEQUENCE: 294
tttggatgga gcaattcaac acacagagaa tggtggattt cc                 42

<210> SEQ ID NO 295
<211> LENGTH: 44
<212> TYPE: DNA
<213> ORGANISM: Nicotiana tabacum

<400> SEQUENCE: 295
tttggatgga gcaattcaac acacagagaa tggtggattt ccat               44

<210> SEQ ID NO 296
<211> LENGTH: 45
<212> TYPE: DNA
<213> ORGANISM: Nicotiana tabacum

<400> SEQUENCE: 296
tttggatgga gcaattcaac acacagagaa tggtggattt ccata              45

<210> SEQ ID NO 297
<211> LENGTH: 46
<212> TYPE: DNA
<213> ORGANISM: Nicotiana tabacum

<400> SEQUENCE: 297
tttggatgga gcaattcaac acacagagaa tggtggattt ccatac        46

<210> SEQ ID NO 298
<211> LENGTH: 48
<212> TYPE: DNA
<213> ORGANISM: Nicotiana tabacum

<400> SEQUENCE: 298
tttggatgga gcaattcaac acacagagaa tggtggattt ccatacac      48

<210> SEQ ID NO 299
<211> LENGTH: 54
<212> TYPE: DNA
<213> ORGANISM: Nicotiana tabacum

<400> SEQUENCE: 299
tttggatgga gcaattcaac acacagagaa tggtggattt ccatacactg aaat    54

<210> SEQ ID NO 300
<211> LENGTH: 42
<212> TYPE: DNA
<213> ORGANISM: Nicotiana tabacum

<400> SEQUENCE: 300
ttggatggag caattcaaca cacagagaat ggtggatttc ca            42

<210> SEQ ID NO 301
<211> LENGTH: 44
<212> TYPE: DNA
<213> ORGANISM: Nicotiana tabacum

<400> SEQUENCE: 301
ttggatggag caattcaaca cacagagaat ggtggatttc cata          44

<210> SEQ ID NO 302
<211> LENGTH: 46
<212> TYPE: DNA
<213> ORGANISM: Nicotiana tabacum

<400> SEQUENCE: 302
ttggatggag caattcaaca cacagagaat ggtggatttc cataca        46

<210> SEQ ID NO 303
<211> LENGTH: 47
<212> TYPE: DNA
<213> ORGANISM: Nicotiana tabacum

<400> SEQUENCE: 303
ttggatggag caattcaaca cacagagaat ggtggatttc catacac       47

<210> SEQ ID NO 304
<211> LENGTH: 52
<212> TYPE: DNA
<213> ORGANISM: Nicotiana tabacum

<400> SEQUENCE: 304
ttggatggag caattcaaca cacagagaat ggtggatttc catacactga aa        52

<210> SEQ ID NO 305
<211> LENGTH: 43
<212> TYPE: DNA
<213> ORGANISM: Nicotiana tabacum

<400> SEQUENCE: 305
tggatggagc aattcaacac acagagaatg gtggatttcc ata                  43

<210> SEQ ID NO 306
<211> LENGTH: 44
<212> TYPE: DNA
<213> ORGANISM: Nicotiana tabacum

<400> SEQUENCE: 306
tggatggagc aattcaacac acagagaatg gtggatttcc atac                 44

<210> SEQ ID NO 307
<211> LENGTH: 42
<212> TYPE: DNA
<213> ORGANISM: Nicotiana tabacum

<400> SEQUENCE: 307
ggatggagca attcaacaca cagagaatgg tggatttcca ta                   42

<210> SEQ ID NO 308
<211> LENGTH: 44
<212> TYPE: DNA
<213> ORGANISM: Nicotiana tabacum

<400> SEQUENCE: 308
ggatggagca attcaacaca cagagaatgg tggatttcca taca                 44

<210> SEQ ID NO 309
<211> LENGTH: 49
<212> TYPE: DNA
<213> ORGANISM: Nicotiana tabacum

<400> SEQUENCE: 309
ggatggagca attcaacaca cagagaatgg tggatttcca tacactgaa            49

<210> SEQ ID NO 310
<211> LENGTH: 46
<212> TYPE: DNA
<213> ORGANISM: Nicotiana tabacum

<400> SEQUENCE: 310
gatggagcaa ttcaacacac agagaatggt ggatttccat acactg               46

<210> SEQ ID NO 311
<211> LENGTH: 41
<212> TYPE: DNA
<213> ORGANISM: Nicotiana tabacum

<400> SEQUENCE: 311
tggcacttcc aaacaccaaa acggccacca gaatggcact t                    41

<210> SEQ ID NO 312
<211> LENGTH: 41
<212> TYPE: DNA
<213> ORGANISM: Nicotiana tabacum

<400> SEQUENCE: 312
ccaactctat taagcctggt tggttttcag agtttagcgc a                               41

<210> SEQ ID NO 313
<211> LENGTH: 42
<212> TYPE: DNA
<213> ORGANISM: Nicotiana tabacum

<400> SEQUENCE: 313
aacatatggg aaggttctga ctttggatgg agcaattcaa ca                              42

<210> SEQ ID NO 314
<211> LENGTH: 42
<212> TYPE: DNA
<213> ORGANISM: Nicotiana tabacum

<400> SEQUENCE: 314
atgggaaggt tctgactttg gatggagcaa ttcaacacac ag                              42

<210> SEQ ID NO 315
<211> LENGTH: 42
<212> TYPE: DNA
<213> ORGANISM: Nicotiana tabacum

<400> SEQUENCE: 315
gttctgactt tggatggagc aattcaacac acagagaatg gt                              42

<210> SEQ ID NO 316
<211> LENGTH: 47
<212> TYPE: DNA
<213> ORGANISM: Nicotiana tabacum

<400> SEQUENCE: 316
ctgactttgg atggagcaat tcaacacaca gagaatggtg gatttcc                         47

<210> SEQ ID NO 317
<211> LENGTH: 50
<212> TYPE: DNA
<213> ORGANISM: Nicotiana tabacum

<400> SEQUENCE: 317
ctgactttgg atggagcaat tcaacacaca gagaatggtg gatttccata                      50

<210> SEQ ID NO 318
<211> LENGTH: 51
<212> TYPE: DNA
<213> ORGANISM: Nicotiana tabacum

<400> SEQUENCE: 318
ctgactttgg atggagcaat tcaacacaca gagaatggtg gatttccata c                    51

<210> SEQ ID NO 319
<211> LENGTH: 47
<212> TYPE: DNA
<213> ORGANISM: Nicotiana tabacum

<400> SEQUENCE: 319
tgactttgga tggagcaatt caacacacag agaatggtgg atttcca                         47

<210> SEQ ID NO 320
<211> LENGTH: 41
<212> TYPE: DNA
<213> ORGANISM: Nicotiana tabacum

```
<400> SEQUENCE: 320
gactttggat ggagcaattc aacacacaga gaatggtgga t                    41

<210> SEQ ID NO 321
<211> LENGTH: 42
<212> TYPE: DNA
<213> ORGANISM: Nicotiana tabacum

<400> SEQUENCE: 321
gactttggat ggagcaattc aacacacaga gaatggtgga tt                   42

<210> SEQ ID NO 322
<211> LENGTH: 48
<212> TYPE: DNA
<213> ORGANISM: Nicotiana tabacum

<400> SEQUENCE: 322
gactttggat ggagcaattc aacacacaga gaatggtgga tttccata             48

<210> SEQ ID NO 323
<211> LENGTH: 51
<212> TYPE: DNA
<213> ORGANISM: Nicotiana tabacum

<400> SEQUENCE: 323
gactttggat ggagcaattc aacacacaga gaatggtgga tttccataca c         51

<210> SEQ ID NO 324
<211> LENGTH: 42
<212> TYPE: DNA
<213> ORGANISM: Nicotiana tabacum

<400> SEQUENCE: 324
actttggatg gagcaattca acacacagag aatggtggat tt                   42

<210> SEQ ID NO 325
<211> LENGTH: 44
<212> TYPE: DNA
<213> ORGANISM: Nicotiana tabacum

<400> SEQUENCE: 325
actttggatg gagcaattca acacacagag aatggtggat ttcc                 44

<210> SEQ ID NO 326
<211> LENGTH: 46
<212> TYPE: DNA
<213> ORGANISM: Nicotiana tabacum

<400> SEQUENCE: 326
actttggatg gagcaattca acacacagag aatggtggat ttccat               46

<210> SEQ ID NO 327
<211> LENGTH: 48
<212> TYPE: DNA
<213> ORGANISM: Nicotiana tabacum

<400> SEQUENCE: 327
actttggatg gagcaattca acacacagag aatggtggat ttccatac             48

<210> SEQ ID NO 328
<211> LENGTH: 50
<212> TYPE: DNA
<213> ORGANISM: Nicotiana tabacum
```

-continued

<400> SEQUENCE: 328
actttggatg gagcaattca acacacagag aatggtggat ttccatacac    50

<210> SEQ ID NO 329
<211> LENGTH: 55
<212> TYPE: DNA
<213> ORGANISM: Nicotiana tabacum

<400> SEQUENCE: 329
actttggatg gagcaattca acacacagag aatggtggat ttccatacac tgaaa    55

<210> SEQ ID NO 330
<211> LENGTH: 57
<212> TYPE: DNA
<213> ORGANISM: Nicotiana tabacum

<400> SEQUENCE: 330
actttggatg gagcaattca acacacagag aatggtggat ttccatacac tgaaatg    57

<210> SEQ ID NO 331
<211> LENGTH: 41
<212> TYPE: DNA
<213> ORGANISM: Nicotiana tabacum

<400> SEQUENCE: 331
ctttggatgg agcaattcaa cacacagaga atggtggatt t    41

<210> SEQ ID NO 332
<211> LENGTH: 44
<212> TYPE: DNA
<213> ORGANISM: Nicotiana tabacum

<400> SEQUENCE: 332
ctttggatgg agcaattcaa cacacagaga atggtggatt tcca    44

<210> SEQ ID NO 333
<211> LENGTH: 45
<212> TYPE: DNA
<213> ORGANISM: Nicotiana tabacum

<400> SEQUENCE: 333
ctttggatgg agcaattcaa cacacagaga atggtggatt tccat    45

<210> SEQ ID NO 334
<211> LENGTH: 47
<212> TYPE: DNA
<213> ORGANISM: Nicotiana tabacum

<400> SEQUENCE: 334
ctttggatgg agcaattcaa cacacagaga atggtggatt tccatac    47

<210> SEQ ID NO 335
<211> LENGTH: 42
<212> TYPE: DNA
<213> ORGANISM: Nicotiana tabacum

<400> SEQUENCE: 335
tttggatgga gcaattcaac acacagagaa tggtggattt cc    42

<210> SEQ ID NO 336
<211> LENGTH: 44
<212> TYPE: DNA

<213> ORGANISM: Nicotiana tabacum

<400> SEQUENCE: 336
tttggatgga gcaattcaac acacagagaa tggtggattt ccat    44

<210> SEQ ID NO 337
<211> LENGTH: 45
<212> TYPE: DNA
<213> ORGANISM: Nicotiana tabacum

<400> SEQUENCE: 337
tttggatgga gcaattcaac acacagagaa tggtggattt ccata    45

<210> SEQ ID NO 338
<211> LENGTH: 42
<212> TYPE: DNA
<213> ORGANISM: Nicotiana tabacum

<400> SEQUENCE: 338
ttggatggag caattcaaca cacagagaat ggtggatttc ca    42

<210> SEQ ID NO 339
<211> LENGTH: 44
<212> TYPE: DNA
<213> ORGANISM: Nicotiana tabacum

<400> SEQUENCE: 339
ttggatggag caattcaaca cacagagaat ggtggatttc cata    44

<210> SEQ ID NO 340
<211> LENGTH: 45
<212> TYPE: DNA
<213> ORGANISM: Nicotiana tabacum

<400> SEQUENCE: 340
ttggatggag caattcaaca cacagagaat ggtggatttc catac    45

<210> SEQ ID NO 341
<211> LENGTH: 53
<212> TYPE: DNA
<213> ORGANISM: Nicotiana tabacum

<400> SEQUENCE: 341
ttggatggag caattcaaca cacagagaat ggtggatttc catacactga aat    53

<210> SEQ ID NO 342
<211> LENGTH: 42
<212> TYPE: DNA
<213> ORGANISM: Nicotiana tabacum

<400> SEQUENCE: 342
tggatggagc aattcaacac acagagaatg gtggatttcc at    42

<210> SEQ ID NO 343
<211> LENGTH: 44
<212> TYPE: DNA
<213> ORGANISM: Nicotiana tabacum

<400> SEQUENCE: 343
tggatggagc aattcaacac acagagaatg gtggatttcc atac    44

<210> SEQ ID NO 344
<211> LENGTH: 48

```
<212> TYPE: DNA
<213> ORGANISM: Nicotiana tabacum

<400> SEQUENCE: 344
tggatggagc aattcaacac acagagaatg gtggatttcc atacactg        48

<210> SEQ ID NO 345
<211> LENGTH: 42
<212> TYPE: DNA
<213> ORGANISM: Nicotiana tabacum

<400> SEQUENCE: 345
ggatggagca attcaacaca cagagaatgg tggatttcca ta              42

<210> SEQ ID NO 346
<211> LENGTH: 43
<212> TYPE: DNA
<213> ORGANISM: Nicotiana tabacum

<400> SEQUENCE: 346
tggagcaatt caacacacag agaatggtgg atttccatac act             43

<210> SEQ ID NO 347
<211> LENGTH: 44
<212> TYPE: DNA
<213> ORGANISM: Nicotiana tabacum

<400> SEQUENCE: 347
tggagcaatt caacacacag agaatggtgg atttccatac actg            44

<210> SEQ ID NO 348
<211> LENGTH: 41
<212> TYPE: DNA
<213> ORGANISM: Nicotiana tabacum

<400> SEQUENCE: 348
ggagcaattc aacacacaga gaatggtgga tttccataca c               41

<210> SEQ ID NO 349
<211> LENGTH: 45
<212> TYPE: DNA
<213> ORGANISM: Nicotiana tabacum

<400> SEQUENCE: 349
caattcaaca cacagagaat ggtggatttc catacactga aatga           45

<210> SEQ ID NO 350
<211> LENGTH: 53
<212> TYPE: DNA
<213> ORGANISM: Nicotiana tabacum

<400> SEQUENCE: 350
aacacacaga gaatggtgga tttccataca ctgaaatgat tgttcatctt cca  53

<210> SEQ ID NO 351
<211> LENGTH: 41
<212> TYPE: DNA
<213> ORGANISM: Nicotiana tabacum

<400> SEQUENCE: 351
cggcacttcc aaaacaccaaa acggccacca taatggcact t              41

<210> SEQ ID NO 352
```

```
<211> LENGTH: 51
<212> TYPE: DNA
<213> ORGANISM: Nicotiana tabacum

<400> SEQUENCE: 352
ttttgacttt ggatggagca attcaacaca cagagaatgg tggatttcca t          51

<210> SEQ ID NO 353
<211> LENGTH: 52
<212> TYPE: DNA
<213> ORGANISM: Nicotiana tabacum

<400> SEQUENCE: 353
ttgactttgg atggagcaat tcaacacaca gagaatggtg gatttccata ca         52

<210> SEQ ID NO 354
<211> LENGTH: 47
<212> TYPE: DNA
<213> ORGANISM: Nicotiana tabacum

<400> SEQUENCE: 354
tgactttgga tggagcaatt caacacacag agaatggtgg atttcca              47

<210> SEQ ID NO 355
<211> LENGTH: 50
<212> TYPE: DNA
<213> ORGANISM: Nicotiana tabacum

<400> SEQUENCE: 355
tgactttgga tggagcaatt caacacacag agaatggtgg atttccatac           50

<210> SEQ ID NO 356
<211> LENGTH: 51
<212> TYPE: DNA
<213> ORGANISM: Nicotiana tabacum

<400> SEQUENCE: 356
gactttggat ggagcaattc aacacacaga gaatggtgga tttccataca c          51

<210> SEQ ID NO 357
<211> LENGTH: 53
<212> TYPE: DNA
<213> ORGANISM: Nicotiana tabacum

<400> SEQUENCE: 357
gactttggat ggagcaattc aacacacaga gaatggtgga tttccataca ctg        53

<210> SEQ ID NO 358
<211> LENGTH: 42
<212> TYPE: DNA
<213> ORGANISM: Nicotiana tabacum

<400> SEQUENCE: 358
actttggatg gagcaattca acacacagag aatggtggat tt                   42

<210> SEQ ID NO 359
<211> LENGTH: 44
<212> TYPE: DNA
<213> ORGANISM: Nicotiana tabacum

<400> SEQUENCE: 359
actttggatg gagcaattca acacacagag aatggtggat ttcc                 44
```

```
<210> SEQ ID NO 360
<211> LENGTH: 46
<212> TYPE: DNA
<213> ORGANISM: Nicotiana tabacum

<400> SEQUENCE: 360
actttggatg gagcaattca acacacagag aatggtggat ttccat            46

<210> SEQ ID NO 361
<211> LENGTH: 47
<212> TYPE: DNA
<213> ORGANISM: Nicotiana tabacum

<400> SEQUENCE: 361
actttggatg gagcaattca acacacagag aatggtggat ttccata           47

<210> SEQ ID NO 362
<211> LENGTH: 48
<212> TYPE: DNA
<213> ORGANISM: Nicotiana tabacum

<400> SEQUENCE: 362
actttggatg gagcaattca acacacagag aatggtggat ttccatac          48

<210> SEQ ID NO 363
<211> LENGTH: 44
<212> TYPE: DNA
<213> ORGANISM: Nicotiana tabacum

<400> SEQUENCE: 363
ctttggatgg agcaattcaa cacacagaga atggtggatt tcca              44

<210> SEQ ID NO 364
<211> LENGTH: 45
<212> TYPE: DNA
<213> ORGANISM: Nicotiana tabacum

<400> SEQUENCE: 364
ctttggatgg agcaattcaa cacacagaga atggtggatt tccat             45

<210> SEQ ID NO 365
<211> LENGTH: 42
<212> TYPE: DNA
<213> ORGANISM: Nicotiana tabacum

<400> SEQUENCE: 365
tttggatgga gcaattcaac acacagagaa tggtggattt cc                42

<210> SEQ ID NO 366
<211> LENGTH: 44
<212> TYPE: DNA
<213> ORGANISM: Nicotiana tabacum

<400> SEQUENCE: 366
tttggatgga gcaattcaac acacagagaa tggtggattt ccat              44

<210> SEQ ID NO 367
<211> LENGTH: 45
<212> TYPE: DNA
<213> ORGANISM: Nicotiana tabacum

<400> SEQUENCE: 367
tttggatgga gcaattcaac acacagagaa tggtggattt ccata             45
```

<210> SEQ ID NO 368
<211> LENGTH: 44
<212> TYPE: DNA
<213> ORGANISM: Nicotiana tabacum

<400> SEQUENCE: 368
ttggatggag caattcaaca cacagagaat ggtggatttc cata            44

<210> SEQ ID NO 369
<211> LENGTH: 45
<212> TYPE: DNA
<213> ORGANISM: Nicotiana tabacum

<400> SEQUENCE: 369
ttggatggag caattcaaca cacagagaat ggtggatttc catac           45

<210> SEQ ID NO 370
<211> LENGTH: 42
<212> TYPE: DNA
<213> ORGANISM: Nicotiana tabacum

<400> SEQUENCE: 370
tggatggagc aattcaacac acagagaatg gtggatttcc at              42

<210> SEQ ID NO 371
<211> LENGTH: 43
<212> TYPE: DNA
<213> ORGANISM: Nicotiana tabacum

<400> SEQUENCE: 371
tggatggagc aattcaacac acagagaatg gtggatttcc ata             43

<210> SEQ ID NO 372
<211> LENGTH: 44
<212> TYPE: DNA
<213> ORGANISM: Nicotiana tabacum

<400> SEQUENCE: 372
tggatggagc aattcaacac acagagaatg gtggatttcc atac            44

<210> SEQ ID NO 373
<211> LENGTH: 47
<212> TYPE: DNA
<213> ORGANISM: Nicotiana tabacum

<400> SEQUENCE: 373
tggatggagc aattcaacac acagagaatg gtggatttcc atacact         47

<210> SEQ ID NO 374
<211> LENGTH: 42
<212> TYPE: DNA
<213> ORGANISM: Nicotiana tabacum

<400> SEQUENCE: 374
ggatggagca attcaacaca cagagaatgg tggatttcca ta              42

<210> SEQ ID NO 375
<211> LENGTH: 41
<212> TYPE: DNA
<213> ORGANISM: Nicotiana tabacum

<400> SEQUENCE: 375
tggagcaatt caacacacag agaatggtgg atttccatac a               41

```
<210> SEQ ID NO 376
<211> LENGTH: 46
<212> TYPE: DNA
<213> ORGANISM: Nicotiana tabacum

<400> SEQUENCE: 376
gcaattcaac acacagagaa tggtggattt ccatacactg aaatga          46

<210> SEQ ID NO 377
<211> LENGTH: 42
<212> TYPE: DNA
<213> ORGANISM: Nicotiana tabacum

<400> SEQUENCE: 377
aacacacaga gaatggtgga tttccataca ctgaaatgat tg              42

<210> SEQ ID NO 378
<211> LENGTH: 44
<212> TYPE: DNA
<213> ORGANISM: Nicotiana tabacum

<400> SEQUENCE: 378
cacagagaat ggtggatttc catacactga atgattgtt catc             44

<210> SEQ ID NO 379
<211> LENGTH: 10
<212> TYPE: DNA
<213> ORGANISM: Nicotiana tabacum

<400> SEQUENCE: 379
tcaacataca                                                  10

<210> SEQ ID NO 380
<211> LENGTH: 10
<212> TYPE: DNA
<213> ORGANISM: Nicotiana tabacum

<400> SEQUENCE: 380
caacatacag                                                  10

<210> SEQ ID NO 381
<211> LENGTH: 16
<212> TYPE: DNA
<213> ORGANISM: Nicotiana tabacum

<400> SEQUENCE: 381
aacatacaga gaatgg                                           16

<210> SEQ ID NO 382
<211> LENGTH: 24
<212> TYPE: DNA
<213> ORGANISM: Nicotiana tabacum

<400> SEQUENCE: 382
acatacagag aatggtggat ttcc                                  24

<210> SEQ ID NO 383
<211> LENGTH: 12
<212> TYPE: DNA
<213> ORGANISM: Nicotiana tabacum

<400> SEQUENCE: 383
```

```
attcaacata ca                                                    12

<210> SEQ ID NO 384
<211> LENGTH: 10
<212> TYPE: DNA
<213> ORGANISM: Nicotiana tabacum

<400> SEQUENCE: 384
tcaacataca                                                       10

<210> SEQ ID NO 385
<211> LENGTH: 10
<212> TYPE: DNA
<213> ORGANISM: Nicotiana tabacum

<400> SEQUENCE: 385
caacatacag                                                       10

<210> SEQ ID NO 386
<211> LENGTH: 10
<212> TYPE: DNA
<213> ORGANISM: Nicotiana tabacum

<400> SEQUENCE: 386
aacatacaga                                                       10

<210> SEQ ID NO 387
<211> LENGTH: 16
<212> TYPE: DNA
<213> ORGANISM: Nicotiana tabacum

<400> SEQUENCE: 387
aacatacaga gaatgg                                                16

<210> SEQ ID NO 388
<211> LENGTH: 10
<212> TYPE: DNA
<213> ORGANISM: Nicotiana tabacum

<400> SEQUENCE: 388
acatacagag                                                       10

<210> SEQ ID NO 389
<211> LENGTH: 14
<212> TYPE: DNA
<213> ORGANISM: Nicotiana tabacum

<400> SEQUENCE: 389
atacagagaa tggt                                                  14

<210> SEQ ID NO 390
<211> LENGTH: 10
<212> TYPE: DNA
<213> ORGANISM: Nicotiana tabacum

<400> SEQUENCE: 390
caacacacag                                                       10

<210> SEQ ID NO 391
<211> LENGTH: 11
<212> TYPE: DNA
<213> ORGANISM: Nicotiana tabacum

<400> SEQUENCE: 391
```

```
aacacacaga g                                                    11

<210> SEQ ID NO 392
<211> LENGTH: 10
<212> TYPE: DNA
<213> ORGANISM: Nicotiana tabacum

<400> SEQUENCE: 392
acacacagag                                                      10

<210> SEQ ID NO 393
<211> LENGTH: 14
<212> TYPE: DNA
<213> ORGANISM: Nicotiana tabacum

<400> SEQUENCE: 393
acacagagaa tggt                                                 14

<210> SEQ ID NO 394
<211> LENGTH: 12
<212> TYPE: DNA
<213> ORGANISM: Nicotiana tabacum

<400> SEQUENCE: 394
cacagagaat gg                                                   12

<210> SEQ ID NO 395
<211> LENGTH: 10
<212> TYPE: DNA
<213> ORGANISM: Nicotiana tabacum

<400> SEQUENCE: 395
tcaacacaca                                                      10

<210> SEQ ID NO 396
<211> LENGTH: 11
<212> TYPE: DNA
<213> ORGANISM: Nicotiana tabacum

<400> SEQUENCE: 396
tcaacacaca g                                                    11

<210> SEQ ID NO 397
<211> LENGTH: 11
<212> TYPE: DNA
<213> ORGANISM: Nicotiana tabacum

<400> SEQUENCE: 397
aacacacaga g                                                    11

<210> SEQ ID NO 398
<211> LENGTH: 10
<212> TYPE: DNA
<213> ORGANISM: Nicotiana tabacum

<400> SEQUENCE: 398
acacacagag                                                      10

<210> SEQ ID NO 399
<211> LENGTH: 15
<212> TYPE: DNA
<213> ORGANISM: Nicotiana tabacum
```

```
<400> SEQUENCE: 399
acacacagag aatgg                                              15

<210> SEQ ID NO 400
<211> LENGTH: 17
<212> TYPE: DNA
<213> ORGANISM: Nicotiana tabacum

<400> SEQUENCE: 400
acacacagag aatggtg                                            17

<210> SEQ ID NO 401
<211> LENGTH: 13
<212> TYPE: DNA
<213> ORGANISM: Nicotiana tabacum

<400> SEQUENCE: 401
cacagagaat ggt                                                13

<210> SEQ ID NO 402
<211> LENGTH: 13
<212> TYPE: DNA
<213> ORGANISM: Nicotiana tabacum

<400> SEQUENCE: 402
tttccataca ctg                                                13

<210> SEQ ID NO 403
<211> LENGTH: 11
<212> TYPE: DNA
<213> ORGANISM: Nicotiana tabacum

<400> SEQUENCE: 403
attcaacaca c                                                  11

<210> SEQ ID NO 404
<211> LENGTH: 12
<212> TYPE: DNA
<213> ORGANISM: Nicotiana tabacum

<400> SEQUENCE: 404
tcaacacaca ga                                                 12

<210> SEQ ID NO 405
<211> LENGTH: 10
<212> TYPE: DNA
<213> ORGANISM: Nicotiana tabacum

<400> SEQUENCE: 405
caacacacag                                                    10

<210> SEQ ID NO 406
<211> LENGTH: 11
<212> TYPE: DNA
<213> ORGANISM: Nicotiana tabacum

<400> SEQUENCE: 406
aacacacaga g                                                  11

<210> SEQ ID NO 407
<211> LENGTH: 13
<212> TYPE: DNA
<213> ORGANISM: Nicotiana tabacum
```

```
<400> SEQUENCE: 407
aacacacaga gaa                                                        13

<210> SEQ ID NO 408
<211> LENGTH: 19
<212> TYPE: DNA
<213> ORGANISM: Nicotiana tabacum

<400> SEQUENCE: 408
gagcaattca acatacaga                                                  19

<210> SEQ ID NO 409
<211> LENGTH: 13
<212> TYPE: DNA
<213> ORGANISM: Nicotiana tabacum

<400> SEQUENCE: 409
ggagcaattc aac                                                        13

<210> SEQ ID NO 410
<211> LENGTH: 86
<212> TYPE: DNA
<213> ORGANISM: Nicotiana tabacum

<400> SEQUENCE: 410
tcagcaactt atgggaaggt tctgactttg gatggagcaa ttcagagaat ggtggatttc     60
catacactga aatgattgtt catcta                                          86

<210> SEQ ID NO 411
<211> LENGTH: 89
<212> TYPE: DNA
<213> ORGANISM: Nicotiana tabacum

<400> SEQUENCE: 411
tcagcaactt atgggaaggt tctgactttg gatggagcaa ttcaacagag aatggtggat     60
ttccatacac tgaaatgatt gttcatcta                                       89

<210> SEQ ID NO 412
<211> LENGTH: 83
<212> TYPE: DNA
<213> ORGANISM: Nicotiana tabacum

<400> SEQUENCE: 412
tcagcaactt atgggaaggt tctgactttg gatggagcaa tgagaatggt ggatttccat     60
acactgaaat gattgttcat cta                                             83

<210> SEQ ID NO 413
<211> LENGTH: 89
<212> TYPE: DNA
<213> ORGANISM: Nicotiana tabacum

<400> SEQUENCE: 413
tcagcaactt atgggaaggt tctgactttg gatggagcaa ttcaacagag aatggtggat     60
ttccatacac tgaaatgatt gttcatcta                                       89

<210> SEQ ID NO 414
<211> LENGTH: 89
<212> TYPE: DNA
<213> ORGANISM: Nicotiana tabacum
```

<400> SEQUENCE: 414
tcagcaactt atgggaaggt tctgactttg gatggagcaa ttcaacagag aatggtggat     60
ttccatacac tgaaatgatt gttcatcta     89

<210> SEQ ID NO 415
<211> LENGTH: 86
<212> TYPE: DNA
<213> ORGANISM: Nicotiana tabacum

<400> SEQUENCE: 415
tcagcaactt atgggaaggt tctgactttg gatggagcaa ttcaaagaat ggtggatttc     60
catacactga aatgattgtt catcta     86

<210> SEQ ID NO 416
<211> LENGTH: 86
<212> TYPE: DNA
<213> ORGANISM: Nicotiana tabacum

<400> SEQUENCE: 416
tcagcaactt atgggaaggt tctgactttg gatggagcaa ttcaaagaat ggtggatttc     60
catacactga aatgattgtt catcta     86

<210> SEQ ID NO 417
<211> LENGTH: 89
<212> TYPE: DNA
<213> ORGANISM: Nicotiana tabacum

<400> SEQUENCE: 417
tcagcaactt atgggaaggt tctgactttg gatggagcaa ttcaacagag aatggtggat     60
ttccatacac tgaaatgatt gttcatcta     89

<210> SEQ ID NO 418
<211> LENGTH: 91
<212> TYPE: DNA
<213> ORGANISM: Nicotiana tabacum

<400> SEQUENCE: 418
tcagcaactt atgggaaggt tctgactttg gatggagcaa ttcaacacag agaatggtgg     60
atttccatac actgaaatga ttgttcatct a     91

<210> SEQ ID NO 419
<211> LENGTH: 89
<212> TYPE: DNA
<213> ORGANISM: Nicotiana tabacum

<400> SEQUENCE: 419
tcagcaactt atgggaaggt tctgactttg gatggagcaa ttcaacagag aatggtggat     60
ttccatacac tgaaatgatt gttcatcta     89

<210> SEQ ID NO 420
<211> LENGTH: 74
<212> TYPE: DNA
<213> ORGANISM: Nicotiana tabacum

<400> SEQUENCE: 420
tcagcaactt atgggaaggt tctgactttg gatggaatgg tggatttcca tacactgaaa     60
tgattgttca tcta     74

```
<210> SEQ ID NO 421
<211> LENGTH: 89
<212> TYPE: DNA
<213> ORGANISM: Nicotiana tabacum

<400> SEQUENCE: 421
tcagcaactt atgggaaggt tctgactttg gatggagcaa ttcaacagag aatggtggat      60
ttccatacac tgaaatgatt gttcatcta                                        89

<210> SEQ ID NO 422
<211> LENGTH: 91
<212> TYPE: DNA
<213> ORGANISM: Nicotiana tabacum

<400> SEQUENCE: 422
tcagcaactt atgggaaggt tctgactttg gatggagcaa ttcaacacag agaatggtgg      60
atttccatac actgaaatga ttgttcatct a                                     91

<210> SEQ ID NO 423
<211> LENGTH: 91
<212> TYPE: DNA
<213> ORGANISM: Nicotiana tabacum

<400> SEQUENCE: 423
tcagcaactt atgggaaggt tctgactttg gatggagcaa ttcaacacag agaatggtgg      60
atttccatac actgaaatga ttgttcatct a                                     91

<210> SEQ ID NO 424
<211> LENGTH: 89
<212> TYPE: DNA
<213> ORGANISM: Nicotiana tabacum

<400> SEQUENCE: 424
tcagcaactt atgggaaggt tctgactttg gatggagcaa ttcaacagag aatggtggat      60
ttccatacac tgaaatgatt gttcatcta                                        89

<210> SEQ ID NO 425
<211> LENGTH: 89
<212> TYPE: DNA
<213> ORGANISM: Nicotiana tabacum

<400> SEQUENCE: 425
tcagcaactt atgggaaggt tctgactttg gatggagcaa ttcaacagag aatggtggat      60
ttccatacac tgaaatgatt gttcatcta                                        89

<210> SEQ ID NO 426
<211> LENGTH: 91
<212> TYPE: DNA
<213> ORGANISM: Nicotiana tabacum

<400> SEQUENCE: 426
tcagcaactt atgggaaggt tctgactttg gatggagcaa ttcaacatag agaatggtgg      60
atttccatac actgaaatga ttgttcatct a                                     91

<210> SEQ ID NO 427
<211> LENGTH: 86
<212> TYPE: DNA
<213> ORGANISM: Nicotiana tabacum

<400> SEQUENCE: 427
```

```
tcagcaactt atgggaaggt tctgactttg gatggagcaa ttcagagaat ggtggatttc    60
catacactga aatgattgtt catcta                                         86

<210> SEQ ID NO 428
<211> LENGTH: 89
<212> TYPE: DNA
<213> ORGANISM: Nicotiana tabacum

<400> SEQUENCE: 428
tcagcaactt atgggaaggt tctgactttg gatggagcaa ttcaacagag aatggtggat    60
ttccatacac tgaaatgatt gttcatcta                                      89

<210> SEQ ID NO 429
<211> LENGTH: 91
<212> TYPE: DNA
<213> ORGANISM: Nicotiana tabacum

<400> SEQUENCE: 429
tcagcaactt atgggaaggt tctgactttg gatggagcaa ttcaacatag agaatggtgg    60
atttccatac actgaaatga ttgttcatct a                                   91

<210> SEQ ID NO 430
<211> LENGTH: 86
<212> TYPE: DNA
<213> ORGANISM: Nicotiana tabacum

<400> SEQUENCE: 430
tcagcaactt atgggaaggt tctgactttg gatggagcaa ttcaacaaat ggtggatttc    60
catacactga aatgattgtt catcta                                         86

<210> SEQ ID NO 431
<211> LENGTH: 91
<212> TYPE: DNA
<213> ORGANISM: Nicotiana tabacum

<400> SEQUENCE: 431
tcagcaactt atgggaaggt tctgactttg gatggagcaa ttcaacatag agaatggtgg    60
atttccatac actgaaatga ttgttcatct a                                   91

<210> SEQ ID NO 432
<211> LENGTH: 89
<212> TYPE: DNA
<213> ORGANISM: Nicotiana tabacum

<400> SEQUENCE: 432
tcagcaactt atgggaaggt tctgactttg gatggagcaa ttcaacagag aatggtggat    60
ttccatacac tgaaatgatt gttcatcta                                      89

<210> SEQ ID NO 433
<211> LENGTH: 89
<212> TYPE: DNA
<213> ORGANISM: Nicotiana tabacum

<400> SEQUENCE: 433
tcagcaactt atgggaaggt tctgactttg gatggagcaa ttcaacagag aatggtggat    60
ttccatacac tgaaatgatt gttcatcta                                      89

<210> SEQ ID NO 434
<211> LENGTH: 89
```

-continued

```
<212> TYPE: DNA
<213> ORGANISM: Nicotiana tabacum

<400> SEQUENCE: 434
tcagcaactt atgggaaggt tctgactttg gatggagcaa ttcaacagag aatggtggat    60
ttccatacac tgaaatgatt gttcatcta                                      89

<210> SEQ ID NO 435
<211> LENGTH: 89
<212> TYPE: DNA
<213> ORGANISM: Nicotiana tabacum

<400> SEQUENCE: 435
tcagcaactt atgggaaggt tctgactttg gatggagcaa ttcaacagag aatggtggat    60
ttccatacac tgaaatgatt gttcatcta                                      89

<210> SEQ ID NO 436
<211> LENGTH: 89
<212> TYPE: DNA
<213> ORGANISM: Nicotiana tabacum

<400> SEQUENCE: 436
tcagcaactt atgggaaggt tctgactttg gatggagcaa ttcaacagag aatggtggat    60
ttccatacac tgaaatgatt gttcatcta                                      89

<210> SEQ ID NO 437
<211> LENGTH: 89
<212> TYPE: DNA
<213> ORGANISM: Nicotiana tabacum

<400> SEQUENCE: 437
tcagcaactt atgggaaggt tctgactttg gatggagcaa ttcaacagag aatggtggat    60
ttccatacac tgaaatgatt gttcatcta                                      89

<210> SEQ ID NO 438
<211> LENGTH: 80
<212> TYPE: DNA
<213> ORGANISM: Nicotiana tabacum

<400> SEQUENCE: 438
tcagcaactt atgggaaggt tctgactttg gatatacaga gaatggtgga tttccataca    60
ctgaaatgat tgttcatcta                                                80

<210> SEQ ID NO 439
<211> LENGTH: 89
<212> TYPE: DNA
<213> ORGANISM: Nicotiana tabacum

<400> SEQUENCE: 439
tcagcaactt atgggaaggt tctgactttg gatggagcaa ttcaacagag aatggtggat    60
ttccatacac tgaaatgatt gttcatcta                                      89

<210> SEQ ID NO 440
<211> LENGTH: 91
<212> TYPE: DNA
<213> ORGANISM: Nicotiana tabacum

<400> SEQUENCE: 440
tcagcaactt atgggaaggt tctgactttg gatggagcaa ttcaatacag agaatggtgg    60
```

```
atttccatac actgaaatga ttgttcatct a                                    91

<210> SEQ ID NO 441
<211> LENGTH: 86
<212> TYPE: DNA
<213> ORGANISM: Nicotiana tabacum

<400> SEQUENCE: 441
tcagcaactt atgggaaggt tctgactttg gatggagcaa ttcagagaat ggtggatttc     60
catacactga aatgattgtt catcta                                          86

<210> SEQ ID NO 442
<211> LENGTH: 93
<212> TYPE: DNA
<213> ORGANISM: Nicotiana tabacum

<400> SEQUENCE: 442
tcagcaactt atgggaaggt tctgactttg gatggagcaa ttcaacatac agagaatggt     60
ggatttccat acactgaaat gattgttcat cta                                  93

<210> SEQ ID NO 443
<211> LENGTH: 93
<212> TYPE: DNA
<213> ORGANISM: Nicotiana tabacum

<400> SEQUENCE: 443
tcagcaactt atgggaaggt tctgactttg gatggagcaa ttcaacatac agagaatggt     60
ggatttccat acactgaaat gattgttcat cta                                  93

<210> SEQ ID NO 444
<211> LENGTH: 93
<212> TYPE: DNA
<213> ORGANISM: Nicotiana tabacum

<400> SEQUENCE: 444
tcagcaactt atgggaaggt tctgactttg gatggagcaa ttcaacatac agagaatggt     60
ggatttccat acactgaaat gattgttcat cta                                  93

<210> SEQ ID NO 445
<211> LENGTH: 93
<212> TYPE: DNA
<213> ORGANISM: Nicotiana tabacum

<400> SEQUENCE: 445
tcagcaactt atgggaaggt tctgactttg gatggagcaa ttcaacatac agagaatggt     60
ggatttccat acactgaaat gattgttcat cta                                  93

<210> SEQ ID NO 446
<211> LENGTH: 93
<212> TYPE: DNA
<213> ORGANISM: Nicotiana tabacum

<400> SEQUENCE: 446
tcagcaactt atgggaaggt tctgactttg gatggagcaa ttcaacatac agagaatggt     60
ggatttccat acactgaaat gattgttcat cta                                  93

<210> SEQ ID NO 447
<211> LENGTH: 104
<212> TYPE: DNA
<213> ORGANISM: Nicotiana tabacum
```

```
<400> SEQUENCE: 447
tcagcaactt atgggaaggt tctgactttg gatggagcaa ttcaacatac agagaatggt      60
ggatttccat acactgaaat gattgttcat ctatcaaaga atgg                      104

<210> SEQ ID NO 448
<211> LENGTH: 104
<212> TYPE: DNA
<213> ORGANISM: Nicotiana tabacum

<400> SEQUENCE: 448
tcagcaactt atgggaaggt tctgactttg gatggagcaa ttcaacatac agagaatggt      60
ggatttccat acactgaaat gattgttcat ctatcaaaga atgg                      104

<210> SEQ ID NO 449
<211> LENGTH: 93
<212> TYPE: DNA
<213> ORGANISM: Nicotiana tabacum

<400> SEQUENCE: 449
tcagcaactt atgggaaggt tctgactttg gatggagcaa ttcaacatac agagaatggt      60
ggatttccat acactgaaat gattgttcat cta                                  93

<210> SEQ ID NO 450
<211> LENGTH: 93
<212> TYPE: DNA
<213> ORGANISM: Nicotiana tabacum

<400> SEQUENCE: 450
tcagcaactt atgggaaggt tctgactttg gatggagcaa ttcaacatac agagaatggt      60
ggatttccat acactgaaat gattgttcat cta                                  93

<210> SEQ ID NO 451
<211> LENGTH: 93
<212> TYPE: DNA
<213> ORGANISM: Nicotiana tabacum

<400> SEQUENCE: 451
tcagcaactt atgggaaggt tctgactttg gatggagcaa ttcaacatac agagaatggt      60
ggatttccat acactgaaat gattgttcat cta                                  93

<210> SEQ ID NO 452
<211> LENGTH: 93
<212> TYPE: DNA
<213> ORGANISM: Nicotiana tabacum

<400> SEQUENCE: 452
tcagcaactt atgggaaggt tctgactttg gatggagcaa ttcaacatac agagaatggt      60
ggatttccat acactgaaat gattgttcat cta                                  93

<210> SEQ ID NO 453
<211> LENGTH: 93
<212> TYPE: DNA
<213> ORGANISM: Nicotiana tabacum

<400> SEQUENCE: 453
tcagcaactt atgggaaggt tctgactttg gatggagcaa ttcaacatac agagaatggt      60
ggatttccat acactgaaat gattgttcat cta                                  93
```

```
<210> SEQ ID NO 454
<211> LENGTH: 93
<212> TYPE: DNA
<213> ORGANISM: Nicotiana tabacum

<400> SEQUENCE: 454
tcagcaactt atgggaaggt tctgactttg gatggagcaa ttcaacatac agagaatggt    60
ggatttccat acactgaaat gattgttcat cta                                 93

<210> SEQ ID NO 455
<211> LENGTH: 93
<212> TYPE: DNA
<213> ORGANISM: Nicotiana tabacum

<400> SEQUENCE: 455
tcagcaactt atgggaaggt tctgactttg gatggagcaa ttcaacatac agagaatggt    60
ggatttccat acactgaaat gattgttcat cta                                 93

<210> SEQ ID NO 456
<211> LENGTH: 93
<212> TYPE: DNA
<213> ORGANISM: Nicotiana tabacum

<400> SEQUENCE: 456
tcagcaactt atgggaaggt tctgactttg gatggagcaa ttcaacatac agagaatggt    60
ggatttccat acactgaaat gattgttcat cta                                 93

<210> SEQ ID NO 457
<211> LENGTH: 93
<212> TYPE: DNA
<213> ORGANISM: Nicotiana tabacum

<400> SEQUENCE: 457
tcagcaactt atgggaaggt tctgactttg gatggagcaa ttcaacatac agagaatggt    60
ggatttccat acactgaaat gattgttcat cta                                 93

<210> SEQ ID NO 458
<211> LENGTH: 93
<212> TYPE: DNA
<213> ORGANISM: Nicotiana tabacum

<400> SEQUENCE: 458
tcagcaactt atgggaaggt tctgactttg gatggagcaa ttcaacatac agagaatggt    60
ggatttccat acactgaaat gattgttcat cta                                 93

<210> SEQ ID NO 459
<211> LENGTH: 93
<212> TYPE: DNA
<213> ORGANISM: Nicotiana tabacum

<400> SEQUENCE: 459
tcagcaactt atgggaaggt tctgactttg gatggagcaa ttcaacatac agagaatggt    60
ggatttccat acactgaaat gattgttcat cta                                 93

<210> SEQ ID NO 460
<211> LENGTH: 93
<212> TYPE: DNA
<213> ORGANISM: Nicotiana tabacum

<400> SEQUENCE: 460
```

```
tcagcaactt atgggaaggt tctgactttg gatggagcaa ttcaacatac agagaatggt    60
ggatttccat acactgaaat gattgttcat cta                                 93

<210> SEQ ID NO 461
<211> LENGTH: 93
<212> TYPE: DNA
<213> ORGANISM: Nicotiana tabacum

<400> SEQUENCE: 461
tcagcaactt atgggaaggt tctgactttg gatggagcaa ttcaacatac agagaatggt    60
ggatttccat acactgaaat gattgttcat cta                                 93

<210> SEQ ID NO 462
<211> LENGTH: 93
<212> TYPE: DNA
<213> ORGANISM: Nicotiana tabacum

<400> SEQUENCE: 462
tcagcaactt atgggaaggt tctgactttg gatggagcaa ttcaacatac agagaatggt    60
ggatttccat acactgaaat gattgttcat cta                                 93

<210> SEQ ID NO 463
<211> LENGTH: 93
<212> TYPE: DNA
<213> ORGANISM: Nicotiana tabacum

<400> SEQUENCE: 463
tcagcaactt atgggaaggt tctgactttg gatggagcaa ttcaacatac agagaatggt    60
ggatttccat acactgaaat gattgttcat cta                                 93

<210> SEQ ID NO 464
<211> LENGTH: 93
<212> TYPE: DNA
<213> ORGANISM: Nicotiana tabacum

<400> SEQUENCE: 464
tcagcaactt atgggaaggt tctgactttg gatggagcaa ttcaacatac agagaatggt    60
ggatttccat acactgaaat gattgttcat cta                                 93

<210> SEQ ID NO 465
<211> LENGTH: 93
<212> TYPE: DNA
<213> ORGANISM: Nicotiana tabacum

<400> SEQUENCE: 465
tcagcaactt atgggaaggt tctgactttg gatggagcaa ttcaacatac agagaatggt    60
ggatttccat acactgaaat gattgttcat cta                                 93

<210> SEQ ID NO 466
<211> LENGTH: 93
<212> TYPE: DNA
<213> ORGANISM: Nicotiana tabacum

<400> SEQUENCE: 466
tcagcaactt atgggaaggt tctgactttg gatggagcaa ttcaacatac agagaatggt    60
ggatttccat acactgaaat gattgttcat cta                                 93

<210> SEQ ID NO 467
```

```
<211> LENGTH: 93
<212> TYPE: DNA
<213> ORGANISM: Nicotiana tabacum

<400> SEQUENCE: 467
tcagcaactt atgggaaggt tctgactttg gatggagcaa ttcaacatac agagaatggt      60
ggatttccat acactgaaat gattgttcat cta                                  93

<210> SEQ ID NO 468
<211> LENGTH: 93
<212> TYPE: DNA
<213> ORGANISM: Nicotiana tabacum

<400> SEQUENCE: 468
tcagcaactt atgggaaggt tctgactttg gatggagcaa ttcaacatac agagaatggt      60
ggatttccat acactgaaat gattgttcat cta                                  93

<210> SEQ ID NO 469
<211> LENGTH: 93
<212> TYPE: DNA
<213> ORGANISM: Nicotiana tabacum

<400> SEQUENCE: 469
tcagcaactt atgggaaggt tctgactttg gatggagcaa ttcaacatac agagaatggt      60
ggatttccat acactgaaat gattgttcat cta                                  93

<210> SEQ ID NO 470
<211> LENGTH: 93
<212> TYPE: DNA
<213> ORGANISM: Nicotiana tabacum

<400> SEQUENCE: 470
tcagcaactt atgggaaggt tctgactttg gatggagcaa ttcaacatac agagaatggt      60
ggatttccat acactgaaat gattgttcat cta                                  93

<210> SEQ ID NO 471
<211> LENGTH: 93
<212> TYPE: DNA
<213> ORGANISM: Nicotiana tabacum

<400> SEQUENCE: 471
tcagcaactt atgggaaggt tctgactttg gatggagcaa ttcaacatac agagaatggt      60
ggatttccat acactgaaat gattgttcat cta                                  93

<210> SEQ ID NO 472
<211> LENGTH: 93
<212> TYPE: DNA
<213> ORGANISM: Nicotiana tabacum

<400> SEQUENCE: 472
tcagcaactt atgggaaggt tctgactttg gatggagcaa ttcaacatac agagaatggt      60
ggatttccat acactgaaat gattgttcat cta                                  93

<210> SEQ ID NO 473
<211> LENGTH: 93
<212> TYPE: DNA
<213> ORGANISM: Nicotiana tabacum

<400> SEQUENCE: 473
tcagcaactt atgggaaggt tctgactttg gatggagcaa ttcaacatac agagaatggt      60
```

```
ggatttccat acactgaaat gattgttcat cta                            93
```

<210> SEQ ID NO 474
<211> LENGTH: 89
<212> TYPE: DNA
<213> ORGANISM: Nicotiana tabacum

<400> SEQUENCE: 474

```
tcagcaactt atgggaaggt tctgactttg gatggagcaa ttcaacagag aatggtggat   60
ttccatacac tgaaatgatt gttcatcta                                     89
```

<210> SEQ ID NO 475
<211> LENGTH: 89
<212> TYPE: DNA
<213> ORGANISM: Nicotiana tabacum

<400> SEQUENCE: 475

```
tcagcaactt atgggaaggt tctgactttg gatggagcaa ttcaacagag aatggtggat   60
ttccatacac tgaaatgatt gttcatcta                                     89
```

<210> SEQ ID NO 476
<211> LENGTH: 89
<212> TYPE: DNA
<213> ORGANISM: Nicotiana tabacum

<400> SEQUENCE: 476

```
tcagcaactt atgggaaggt tctgactttg gatggagcaa ttcaacagag aatggtggat   60
ttccatacac tgaaatgatt gttcatcta                                     89
```

<210> SEQ ID NO 477
<211> LENGTH: 89
<212> TYPE: DNA
<213> ORGANISM: Nicotiana tabacum

<400> SEQUENCE: 477

```
tcagcaactt atgggaaggt tctgactttg gatggagcaa ttcaacagag aatggtggat   60
ttccatacac tgaaatgatt gttcatcta                                     89
```

<210> SEQ ID NO 478
<211> LENGTH: 89
<212> TYPE: DNA
<213> ORGANISM: Nicotiana tabacum

<400> SEQUENCE: 478

```
tcagcaactt atgggaaggt tctgactttg gatggagcaa ttcaacagag aatggtggat   60
ttccatacac tgaaatgatt gttcatcta                                     89
```

<210> SEQ ID NO 479
<211> LENGTH: 91
<212> TYPE: DNA
<213> ORGANISM: Nicotiana tabacum

<400> SEQUENCE: 479

```
tcagcaactt atgggaaggt tctgactttg gatggagcaa ttcaacatag agaatggtgg   60
atttccatac actgaaatga ttgttcatct a                                  91
```

<210> SEQ ID NO 480
<211> LENGTH: 91
<212> TYPE: DNA

<213> ORGANISM: Nicotiana tabacum

<400> SEQUENCE: 480
tcagcaactt atgggaaggt tctgactttg gatggagcaa ttcaacatag agaatggtgg    60
atttccatac actgaaatga ttgttcatct a    91

<210> SEQ ID NO 481
<211> LENGTH: 89
<212> TYPE: DNA
<213> ORGANISM: Nicotiana tabacum

<400> SEQUENCE: 481
tcagcaactt atgggaaggt tctgactttg gatggagcaa ttcaacagag aatggtggat    60
ttccatacac tgaaatgatt gttcatcta    89

<210> SEQ ID NO 482
<211> LENGTH: 86
<212> TYPE: DNA
<213> ORGANISM: Nicotiana tabacum

<400> SEQUENCE: 482
tcagcaactt atgggaaggt tctgactttg gatggagcaa ttcagagaat ggtggatttc    60
catacactga aatgattgtt catcta    86

<210> SEQ ID NO 483
<211> LENGTH: 91
<212> TYPE: DNA
<213> ORGANISM: Nicotiana tabacum

<400> SEQUENCE: 483
tcagcaactt atgggaaggt tctgactttg gatggagcaa ttcaacacag agaatggtgg    60
atttccatac actgaaatga ttgttcatct a    91

<210> SEQ ID NO 484
<211> LENGTH: 89
<212> TYPE: DNA
<213> ORGANISM: Nicotiana tabacum

<400> SEQUENCE: 484
tcagcaactt atgggaaggt tctgactttg gatggagcaa ttcaacagag aatggtggat    60
ttccatacac tgaaatgatt gttcatcta    89

<210> SEQ ID NO 485
<211> LENGTH: 86
<212> TYPE: DNA
<213> ORGANISM: Nicotiana tabacum

<400> SEQUENCE: 485
tcagcaactt atgggaaggt tctgactttg gatggagcaa ttcagagaat ggtggatttc    60
catacactga aatgattgtt catcta    86

<210> SEQ ID NO 486
<211> LENGTH: 89
<212> TYPE: DNA
<213> ORGANISM: Nicotiana tabacum

<400> SEQUENCE: 486
tcagcaactt atgggaaggt tctgactttg gatggagcaa ttcaacagag aatggtggat    60
ttccatacac tgaaatgatt gttcatcta    89

<210> SEQ ID NO 487
<211> LENGTH: 89
<212> TYPE: DNA
<213> ORGANISM: Nicotiana tabacum

<400> SEQUENCE: 487
tcagcaactt atgggaaggt tctgactttg gatggagcaa ttcaacagag aatggtggat    60
ttccatacac tgaaatgatt gttcatcta                                      89

<210> SEQ ID NO 488
<211> LENGTH: 89
<212> TYPE: DNA
<213> ORGANISM: Nicotiana tabacum

<400> SEQUENCE: 488
tcagcaactt atgggaaggt tctgactttg gatggagcaa ttcaacagag aatggtggat    60
ttccatacac tgaaatgatt gttcatcta                                      89

<210> SEQ ID NO 489
<211> LENGTH: 89
<212> TYPE: DNA
<213> ORGANISM: Nicotiana tabacum

<400> SEQUENCE: 489
tcagcaactt atgggaaggt tctgactttg gatggagcaa ttcaacagag aatggtggat    60
ttccatacac tgaaatgatt gttcatcta                                      89

<210> SEQ ID NO 490
<211> LENGTH: 89
<212> TYPE: DNA
<213> ORGANISM: Nicotiana tabacum

<400> SEQUENCE: 490
tcagcaactt atgggaaggt tctgactttg gatggagcaa ttcaacagag aatggtggat    60
ttccatacac tgaaatgatt gttcatcta                                      89

<210> SEQ ID NO 491
<211> LENGTH: 91
<212> TYPE: DNA
<213> ORGANISM: Nicotiana tabacum

<400> SEQUENCE: 491
tcagcaactt atgggaaggt tctgactttg gatggagcaa ttcaatacag agaatggtgg    60
atttccatac actgaaatga ttgttcatct a                                   91

<210> SEQ ID NO 492
<211> LENGTH: 88
<212> TYPE: DNA
<213> ORGANISM: Nicotiana tabacum

<400> SEQUENCE: 492
tcagcaactt atgggaaggt tctgactttg gatggagcaa ttcacagaga atggtggatt    60
tccatacact gaaatgattg ttcatcta                                       88

<210> SEQ ID NO 493
<211> LENGTH: 86
<212> TYPE: DNA
<213> ORGANISM: Nicotiana tabacum

```
<400> SEQUENCE: 493
tcagcaactt atgggaaggt tctgactttg gatggagcaa ttcagagaat ggtggatttc      60
catacactga aatgattgtt catcta                                          86

<210> SEQ ID NO 494
<211> LENGTH: 89
<212> TYPE: DNA
<213> ORGANISM: Nicotiana tabacum

<400> SEQUENCE: 494
tcagcaactt atgggaaggt tctgactttg gatggagcaa ttcaacagag aatggtggat      60
ttccatacac tgaaatgatt gttcatcta                                       89

<210> SEQ ID NO 495
<211> LENGTH: 89
<212> TYPE: DNA
<213> ORGANISM: Nicotiana tabacum

<400> SEQUENCE: 495
tcagcaactt atgggaaggt tctgactttg gatggagcaa ttcaacagag aatggtggat      60
ttccatacac tgaaatgatt gttcatcta                                       89

<210> SEQ ID NO 496
<211> LENGTH: 89
<212> TYPE: DNA
<213> ORGANISM: Nicotiana tabacum

<400> SEQUENCE: 496
tcagcaactt atgggaaggt tctgactttg gatggagcaa ttcaacatag aatggtggat      60
ttccatacac tgaaatgatt gttcatcta                                       89

<210> SEQ ID NO 497
<211> LENGTH: 89
<212> TYPE: DNA
<213> ORGANISM: Nicotiana tabacum

<400> SEQUENCE: 497
tcagcaactt atgggaaggt tctgactttg gatggagcaa ttcaacagag aatggtggat      60
ttccatacac tgaaatgatt gttcatcta                                       89

<210> SEQ ID NO 498
<211> LENGTH: 88
<212> TYPE: DNA
<213> ORGANISM: Nicotiana tabacum

<400> SEQUENCE: 498
tcagcaactt atgggaaggt tctgactttg gatggagcaa ttcacagaga atggtggatt      60
tccatacact gaaatgattg ttcatcta                                        88

<210> SEQ ID NO 499
<211> LENGTH: 89
<212> TYPE: DNA
<213> ORGANISM: Nicotiana tabacum

<400> SEQUENCE: 499
tcagcaactt atgggaaggt tctgactttg gatggagcaa ttcaacagag aatggtggat      60
ttccatacac tgaaatgatt gttcatcta                                       89
```

```
<210> SEQ ID NO 500
<211> LENGTH: 89
<212> TYPE: DNA
<213> ORGANISM: Nicotiana tabacum

<400> SEQUENCE: 500
tcagcaactt atgggaaggt tctgactttg gatggagcaa ttcaacagag aatggtggat      60
ttccatacac tgaaatgatt gttcatcta                                       89

<210> SEQ ID NO 501
<211> LENGTH: 89
<212> TYPE: DNA
<213> ORGANISM: Nicotiana tabacum

<400> SEQUENCE: 501
tcagcaactt atgggaaggt tctgactttg gatggagcaa ttcaacagag aatggtggat      60
ttccatacac tgaaatgatt gttcatcta                                       89

<210> SEQ ID NO 502
<211> LENGTH: 83
<212> TYPE: DNA
<213> ORGANISM: Nicotiana tabacum

<400> SEQUENCE: 502
tcagcaactt atgggaaggt tctgactttg gatggagcaa ttagaatggt ggatttccat      60
acactgaaat gattgttcat cta                                             83

<210> SEQ ID NO 503
<211> LENGTH: 89
<212> TYPE: DNA
<213> ORGANISM: Nicotiana tabacum

<400> SEQUENCE: 503
tcagcaactt atgggaaggt tctgactttg gatggagcaa ttcaacatag aatggtggat      60
ttccatacac tgaaatgatt gttcatcta                                       89

<210> SEQ ID NO 504
<211> LENGTH: 89
<212> TYPE: DNA
<213> ORGANISM: Nicotiana tabacum

<400> SEQUENCE: 504
tcagcaactt atgggaaggt tctgactttg gatggagcaa ttcaacagag aatggtggat      60
ttccatacac tgaaatgatt gttcatcta                                       89

<210> SEQ ID NO 505
<211> LENGTH: 85
<212> TYPE: DNA
<213> ORGANISM: Nicotiana tabacum

<400> SEQUENCE: 505
tcagcaactt atgggaaggt tctgactttg gatggagcaa ttcaacactg gtggatttcc      60
atacactgaa atgattgttc atcta                                           85

<210> SEQ ID NO 506
<211> LENGTH: 93
<212> TYPE: DNA
<213> ORGANISM: Nicotiana tabacum

<400> SEQUENCE: 506
```

```
tcagcaactt atgggaaggt tctgactttg gatggagcaa ttcaacatac agagaatggt    60
ggatttccat acactgaaat gattgttcat cta                                 93

<210> SEQ ID NO 507
<211> LENGTH: 93
<212> TYPE: DNA
<213> ORGANISM: Nicotiana tabacum

<400> SEQUENCE: 507
tcagcaactt atgggaaggt tctgactttg gatggagcaa ttcaacatac agagaatggt    60
ggatttccat acactgaaat gattgttcat cta                                 93

<210> SEQ ID NO 508
<211> LENGTH: 93
<212> TYPE: DNA
<213> ORGANISM: Nicotiana tabacum

<400> SEQUENCE: 508
tcagcaactt atgggaaggt tctgactttg gatggagcaa ttcaacatac agagaatggt    60
ggatttccat acactgaaat gattgttcat cta                                 93

<210> SEQ ID NO 509
<211> LENGTH: 93
<212> TYPE: DNA
<213> ORGANISM: Nicotiana tabacum

<400> SEQUENCE: 509
tcagcaactt atgggaaggt tctgactttg gatggagcaa ttcaacatac agagaatggt    60
ggatttccat acactgaaat gattgttcat cta                                 93

<210> SEQ ID NO 510
<211> LENGTH: 93
<212> TYPE: DNA
<213> ORGANISM: Nicotiana tabacum

<400> SEQUENCE: 510
tcagcaactt atgggaaggt tctgactttg gatggagcaa ttcaacatac agagaatggt    60
ggatttccat acactgaaat gattgttcat cta                                 93

<210> SEQ ID NO 511
<211> LENGTH: 93
<212> TYPE: DNA
<213> ORGANISM: Nicotiana tabacum

<400> SEQUENCE: 511
tcagcaactt atgggaaggt tctgactttg gatggagcaa ttcaacatac agagaatggt    60
ggatttccat acactgaaat gattgttcat cta                                 93

<210> SEQ ID NO 512
<211> LENGTH: 93
<212> TYPE: DNA
<213> ORGANISM: Nicotiana tabacum

<400> SEQUENCE: 512
tcagcaactt atgggaaggt tctgactttg gatggagcaa ttcaacatac agagaatggt    60
ggatttccat acactgaaat gattgttcat cta                                 93

<210> SEQ ID NO 513
<211> LENGTH: 93
```

<212> TYPE: DNA
<213> ORGANISM: Nicotiana tabacum

<400> SEQUENCE: 513
tcagcaactt atgggaaggt tctgactttg gatggagcaa ttcaacatac agagaatggt    60
ggatttccat acactgaaat gattgttcat cta                                 93

<210> SEQ ID NO 514
<211> LENGTH: 93
<212> TYPE: DNA
<213> ORGANISM: Nicotiana tabacum

<400> SEQUENCE: 514
tcagcaactt atgggaaggt tctgactttg gatggagcaa ttcaacatac agagaatggt    60
ggatttccat acactgaaat gattgttcat cta                                 93

<210> SEQ ID NO 515
<211> LENGTH: 93
<212> TYPE: DNA
<213> ORGANISM: Nicotiana tabacum

<400> SEQUENCE: 515
tcagcaactt atgggaaggt tctgactttg gatggagcaa ttcaacatac agagaatggt    60
ggatttccat acactgaaat gattgttcat cta                                 93

<210> SEQ ID NO 516
<211> LENGTH: 93
<212> TYPE: DNA
<213> ORGANISM: Nicotiana tabacum

<400> SEQUENCE: 516
tcagcaactt atgggaaggt tctgactttg gatggagcaa ttcaacatac agagaatggt    60
ggatttccat acactgaaat gattgttcat cta                                 93

<210> SEQ ID NO 517
<211> LENGTH: 93
<212> TYPE: DNA
<213> ORGANISM: Nicotiana tabacum

<400> SEQUENCE: 517
tcagcaactt atgggaaggt tctgactttg gatggagcaa ttcaacatac agagaatggt    60
ggatttccat acactgaaat gattgttcat cta                                 93

<210> SEQ ID NO 518
<211> LENGTH: 93
<212> TYPE: DNA
<213> ORGANISM: Nicotiana tabacum

<400> SEQUENCE: 518
tcagcaactt atgggaaggt tctgactttg gatggagcaa ttcaacatac agagaatggt    60
ggatttccat acactgaaat gattgttcat cta                                 93

<210> SEQ ID NO 519
<211> LENGTH: 93
<212> TYPE: DNA
<213> ORGANISM: Nicotiana tabacum

<400> SEQUENCE: 519
tcagcaactt atgggaaggt tctgactttg gatggagcaa ttcaacatac agagaatggt    60

```
ggatttccat acactgaaat gattgttcat cta                                    93

<210> SEQ ID NO 520
<211> LENGTH: 93
<212> TYPE: DNA
<213> ORGANISM: Nicotiana tabacum

<400> SEQUENCE: 520
tcagcaactt atgggaaggt tctgactttg gatggagcaa ttcaacatac agagaatggt       60
ggatttccat acactgaaat gattgttcat cta                                    93

<210> SEQ ID NO 521
<211> LENGTH: 93
<212> TYPE: DNA
<213> ORGANISM: Nicotiana tabacum

<400> SEQUENCE: 521
tcagcaactt atgggaaggt tctgactttg gatggagcaa ttcaacatac agagaatggt       60
ggatttccat acactgaaat gattgttcat cta                                    93

<210> SEQ ID NO 522
<211> LENGTH: 93
<212> TYPE: DNA
<213> ORGANISM: Nicotiana tabacum

<400> SEQUENCE: 522
tcagcaactt atgggaaggt tctgactttg gatggagcaa ttcaacatac agagaatggt       60
ggatttccat acactgaaat gattgttcat cta                                    93

<210> SEQ ID NO 523
<211> LENGTH: 93
<212> TYPE: DNA
<213> ORGANISM: Nicotiana tabacum

<400> SEQUENCE: 523
tcagcaactt atgggaaggt tctgactttg gatggagcaa ttcaacatac agagaatggt       60
ggatttccat acactgaaat gattgttcat cta                                    93

<210> SEQ ID NO 524
<211> LENGTH: 93
<212> TYPE: DNA
<213> ORGANISM: Nicotiana tabacum

<400> SEQUENCE: 524
tcagcaactt atgggaaggt tctgactttg gatggagcaa ttcaacatac agagaatggt       60
ggatttccat acactgaaat gattgttcat cta                                    93

<210> SEQ ID NO 525
<211> LENGTH: 93
<212> TYPE: DNA
<213> ORGANISM: Nicotiana tabacum

<400> SEQUENCE: 525
tcagcaactt atgggaaggt tctgactttg gatggagcaa ttcaacatac agagaatggt       60
ggatttccat acactgaaat gattgttcat cta                                    93

<210> SEQ ID NO 526
<211> LENGTH: 93
<212> TYPE: DNA
<213> ORGANISM: Nicotiana tabacum
```

<400> SEQUENCE: 526
tcagcaactt atgggaaggt tctgactttg gatggagcaa ttcaacatac agagaatggt    60
ggatttccat acactgaaat gattgttcat cta                                 93

<210> SEQ ID NO 527
<211> LENGTH: 93
<212> TYPE: DNA
<213> ORGANISM: Nicotiana tabacum

<400> SEQUENCE: 527
tcagcaactt atgggaaggt tctgactttg gatggagcaa ttcaacatac agagaatggt    60
ggatttccat acactgaaat gattgttcat cta                                 93

<210> SEQ ID NO 528
<211> LENGTH: 93
<212> TYPE: DNA
<213> ORGANISM: Nicotiana tabacum

<400> SEQUENCE: 528
tcagcaactt atgggaaggt tctgactttg gatggagcaa ttcaacatac agagaatggt    60
ggatttccat acactgaaat gattgttcat cta                                 93

<210> SEQ ID NO 529
<211> LENGTH: 93
<212> TYPE: DNA
<213> ORGANISM: Nicotiana tabacum

<400> SEQUENCE: 529
tcagcaactt atgggaaggt tctgactttg gatggagcaa ttcaacatac agagaatggt    60
ggatttccat acactgaaat gattgttcat cta                                 93

<210> SEQ ID NO 530
<211> LENGTH: 93
<212> TYPE: DNA
<213> ORGANISM: Nicotiana tabacum

<400> SEQUENCE: 530
tcagcaactt atgggaaggt tctgactttg gatggagcaa ttcaacatac agagaatggt    60
ggatttccat acactgaaat gattgttcat cta                                 93

<210> SEQ ID NO 531
<211> LENGTH: 93
<212> TYPE: DNA
<213> ORGANISM: Nicotiana tabacum

<400> SEQUENCE: 531
tcagcaactt atgggaaggt tctgactttg gatggagcaa ttcaacatac agagaatggt    60
ggatttccat acactgaaat gattgttcat cta                                 93

<210> SEQ ID NO 532
<211> LENGTH: 93
<212> TYPE: DNA
<213> ORGANISM: Nicotiana tabacum

<400> SEQUENCE: 532
tcagcaactt atgggaaggt tctgactttg gatggagcaa ttcaacatac agagaatggt    60
ggatttccat acactgaaat gattgttcat cta                                 93

<210> SEQ ID NO 533
<211> LENGTH: 93
<212> TYPE: DNA
<213> ORGANISM: Nicotiana tabacum

<400> SEQUENCE: 533
tcagcaactt atgggaaggt tctgactttg gatggagcaa ttcaacatac agagaatggt      60
ggatttccat acactgaaat gattgttcat cta                                   93

<210> SEQ ID NO 534
<211> LENGTH: 93
<212> TYPE: DNA
<213> ORGANISM: Nicotiana tabacum

<400> SEQUENCE: 534
tcagcaactt atgggaaggt tctgactttg gatggagcaa ttcaacatac agagaatggt      60
ggatttccat acactgaaat gattgttcat cta                                   93

<210> SEQ ID NO 535
<211> LENGTH: 93
<212> TYPE: DNA
<213> ORGANISM: Nicotiana tabacum

<400> SEQUENCE: 535
tcagcaactt atgggaaggt tctgactttg gatggagcaa ttcaacatac agagaatggt      60
ggatttccat acactgaaat gattgttcat cta                                   93

<210> SEQ ID NO 536
<211> LENGTH: 93
<212> TYPE: DNA
<213> ORGANISM: Nicotiana tabacum

<400> SEQUENCE: 536
tcagcaactt atgggaaggt tctgactttg gatggagcaa ttcaacatac agagaatggt      60
ggatttccat acactgaaat gattgttcat cta                                   93

<210> SEQ ID NO 537
<211> LENGTH: 93
<212> TYPE: DNA
<213> ORGANISM: Nicotiana tabacum

<400> SEQUENCE: 537
tcagcaactt atgggaaggt tctgactttg gatggagcaa ttcaacatac agagactggt      60
ggatttccat acactgaaat gattgttcat cta                                   93

<210> SEQ ID NO 538
<211> LENGTH: 91
<212> TYPE: DNA
<213> ORGANISM: Nicotiana tabacum

<400> SEQUENCE: 538
tcagcaactt atgggaaggt tctgactttg gatggagcaa ttcaacacag agaatggtgg      60
atttccatac actgaaatga ttgttcatct t                                     91

<210> SEQ ID NO 539
<211> LENGTH: 91
<212> TYPE: DNA
<213> ORGANISM: Nicotiana tabacum

<400> SEQUENCE: 539

```
tcagcaactt atgggaaggt tctgactttg gatggagcaa ttcaacacag agaatggtgg    60
atttccatac actgaaatga ttgttcatct t                                   91

<210> SEQ ID NO 540
<211> LENGTH: 91
<212> TYPE: DNA
<213> ORGANISM: Nicotiana tabacum

<400> SEQUENCE: 540
tcagcaactt atgggaaggt tctgactttg gatggagcaa ttcaacacag agaatggtgg    60
atttccatac actgaaatga ttgttcatct t                                   91

<210> SEQ ID NO 541
<211> LENGTH: 85
<212> TYPE: DNA
<213> ORGANISM: Nicotiana tabacum

<400> SEQUENCE: 541
tcagcaactt atgggaaggt tctgactttg gatggagcaa ttcaagaatg gtggatttcc    60
atacactgaa atgattgttc atctt                                          85

<210> SEQ ID NO 542
<211> LENGTH: 91
<212> TYPE: DNA
<213> ORGANISM: Nicotiana tabacum

<400> SEQUENCE: 542
tcagcaactt atgggaaggt tctgactttg gatggagcaa ttcaacacag agaatggtgg    60
atttccatac actgaaatga ttgttcatct t                                   91

<210> SEQ ID NO 543
<211> LENGTH: 91
<212> TYPE: DNA
<213> ORGANISM: Nicotiana tabacum

<400> SEQUENCE: 543
tcagcaactt atgggaaggt tctgactttg gatggagcaa ttcaacacag agaatggtgg    60
atttccatac actgaaatga ttgttcatct t                                   91

<210> SEQ ID NO 544
<211> LENGTH: 91
<212> TYPE: DNA
<213> ORGANISM: Nicotiana tabacum

<400> SEQUENCE: 544
tcagcaactt atgggaaggt tctgactttg gatggagcaa ttcaacacag agaatggtgg    60
atttccatac actgaaatga ttgttcatct t                                   91

<210> SEQ ID NO 545
<211> LENGTH: 89
<212> TYPE: DNA
<213> ORGANISM: Nicotiana tabacum

<400> SEQUENCE: 545
tcagcaactt atgggaaggt tctgactttg gatggagcaa ttcaacagag aatggtggat    60
ttccatacac tgaaatgatt gttcatctt                                      89

<210> SEQ ID NO 546
```

```
<211> LENGTH: 91
<212> TYPE: DNA
<213> ORGANISM: Nicotiana tabacum

<400> SEQUENCE: 546
tcagcaactt atgggaaggt tctgactttg gatggagcaa ttcaacacag agaatggtgg      60
atttccatac actgaaatga ttgttcatct t                                    91

<210> SEQ ID NO 547
<211> LENGTH: 91
<212> TYPE: DNA
<213> ORGANISM: Nicotiana tabacum

<400> SEQUENCE: 547
tcagcaactt atgggaaggt tctgactttg gatggagcaa ttcaacacag agaatggtgg      60
atttccatac actgaaatga ttgttcatct t                                    91

<210> SEQ ID NO 548
<211> LENGTH: 91
<212> TYPE: DNA
<213> ORGANISM: Nicotiana tabacum

<400> SEQUENCE: 548
tcagcaactt atgggaaggt tctgactttg gatggagcaa ttcaacacag agaatggtgg      60
atttccatac actgaaatga ttgttcatct t                                    91

<210> SEQ ID NO 549
<211> LENGTH: 91
<212> TYPE: DNA
<213> ORGANISM: Nicotiana tabacum

<400> SEQUENCE: 549
tcagcaactt atgggaaggt tctgactttg gatggagcaa ttcaacacag agaatggtgg      60
atttccatac actgaaatga ttgttcatct t                                    91

<210> SEQ ID NO 550
<211> LENGTH: 91
<212> TYPE: DNA
<213> ORGANISM: Nicotiana tabacum

<400> SEQUENCE: 550
tcagcaactt atgggaaggt tctgactttg gatggagcaa ttcaacacag agaatggtgg      60
atttccatac actgaaatga ttgttcatct t                                    91

<210> SEQ ID NO 551
<211> LENGTH: 91
<212> TYPE: DNA
<213> ORGANISM: Nicotiana tabacum

<400> SEQUENCE: 551
tcagcaactt atgggaaggt tctgactttg gatggagcaa ttcaacacag agaatggtgg      60
atttccatac actgaaatga ttgttcatct t                                    91

<210> SEQ ID NO 552
<211> LENGTH: 91
<212> TYPE: DNA
<213> ORGANISM: Nicotiana tabacum

<400> SEQUENCE: 552
tcagcaactt atgggaaggt tctgactttg gatggagcaa ttcaacacag agaatggtgg      60
```
atttccatac actgaaatga ttgttcatct t              91

<210> SEQ ID NO 553
<211> LENGTH: 91
<212> TYPE: DNA
<213> ORGANISM: Nicotiana tabacum

<400> SEQUENCE: 553
tcagcaactt atgggaaggt tctgactttg gatggagcaa ttcaacacag agaatggtgg    60
atttccatac actgaaatga ttgttcatct t              91

<210> SEQ ID NO 554
<211> LENGTH: 91
<212> TYPE: DNA
<213> ORGANISM: Nicotiana tabacum

<400> SEQUENCE: 554
tcagcaactt atgggaaggt tctgactttg gatggagcaa ttcaacacag agaatggtgg    60
atttccatac actgaaatga ttgttcatct t              91

<210> SEQ ID NO 555
<211> LENGTH: 91
<212> TYPE: DNA
<213> ORGANISM: Nicotiana tabacum

<400> SEQUENCE: 555
tcagcaactt atgggaaggt tctgactttg gatggagcaa ttcaacacag agaatggtgg    60
atttccatac actgaaatga ttgttcatct t              91

<210> SEQ ID NO 556
<211> LENGTH: 85
<212> TYPE: DNA
<213> ORGANISM: Nicotiana tabacum

<400> SEQUENCE: 556
tcagcaactt atgggaaggt tctgactttg gatggagcaa ttcaagaatg gtggatttcc    60
atacactgaa atgattgttc atctt                     85

<210> SEQ ID NO 557
<211> LENGTH: 85
<212> TYPE: DNA
<213> ORGANISM: Nicotiana tabacum

<400> SEQUENCE: 557
tcagcaactt atgggaaggt tctgactttg gatggagcaa ttcaagaatg gtggatttcc    60
atacactgaa atgattgttc atctt                     85

<210> SEQ ID NO 558
<211> LENGTH: 91
<212> TYPE: DNA
<213> ORGANISM: Nicotiana tabacum

<400> SEQUENCE: 558
tcagcaactt atgggaaggt tctgactttg gatggagcaa ttcaacacag agaatggtgg    60
atttccatac actgaaatga ttgttcatct t              91

<210> SEQ ID NO 559
<211> LENGTH: 89
<212> TYPE: DNA

```
<213> ORGANISM: Nicotiana tabacum

<400> SEQUENCE: 559
tcagcaactt atgggaaggt tctgactttg gatggagcaa ttcaacagag aatggtggat    60
ttccatacac tgaaatgatt gttcatctt                                      89

<210> SEQ ID NO 560
<211> LENGTH: 89
<212> TYPE: DNA
<213> ORGANISM: Nicotiana tabacum

<400> SEQUENCE: 560
tcagcaactt atgggaaggt tctgactttg gatggagcaa ttcaacagag aatggtggat    60
ttccatacac tgaaatgatt gttcatctt                                      89

<210> SEQ ID NO 561
<211> LENGTH: 91
<212> TYPE: DNA
<213> ORGANISM: Nicotiana tabacum

<400> SEQUENCE: 561
tcagcaactt atgggaaggt tctgactttg gatggagcaa ttcaacacag agaatggtgg    60
atttccatac actgaaatga ttgttcatct t                                   91

<210> SEQ ID NO 562
<211> LENGTH: 91
<212> TYPE: DNA
<213> ORGANISM: Nicotiana tabacum

<400> SEQUENCE: 562
tcagcaactt atgggaaggt tctgactttg gatggagcaa ttcaacacag agaatggtgg    60
atttccatac actgaaatga ttgttcatct t                                   91

<210> SEQ ID NO 563
<211> LENGTH: 91
<212> TYPE: DNA
<213> ORGANISM: Nicotiana tabacum

<400> SEQUENCE: 563
tcagcaactt atgggaaggt tctgactttg gatggagcaa ttcaacacag agaatggtgg    60
atttccatac actgaaatga ttgttcatct t                                   91

<210> SEQ ID NO 564
<211> LENGTH: 89
<212> TYPE: DNA
<213> ORGANISM: Nicotiana tabacum

<400> SEQUENCE: 564
tcagcaactt atgggaaggt tctgactttg gatggagcaa ttcaacagag aatggtggat    60
ttccatacac tgaaatgatt gttcatctt                                      89

<210> SEQ ID NO 565
<211> LENGTH: 89
<212> TYPE: DNA
<213> ORGANISM: Nicotiana tabacum

<400> SEQUENCE: 565
tcagcaactt atgggaaggt tctgactttg gatggagcaa ttcaacagag aatggtggat    60
ttccatacac tgaaatgatt gttcatctt                                      89
```

<210> SEQ ID NO 566
<211> LENGTH: 89
<212> TYPE: DNA
<213> ORGANISM: Nicotiana tabacum

<400> SEQUENCE: 566
tcagcaactt atgggaaggt tctgactttg gatggagcaa ttcaacagag aatggtggat    60
ttccatacac tgaaatgatt gttcatctt                                      89

<210> SEQ ID NO 567
<211> LENGTH: 89
<212> TYPE: DNA
<213> ORGANISM: Nicotiana tabacum

<400> SEQUENCE: 567
tcagcaactt atgggaaggt tctgactttg gatggagcaa ttcaacagag aatggtggat    60
ttccatacac tgaaatgatt gttcatctt                                      89

<210> SEQ ID NO 568
<211> LENGTH: 89
<212> TYPE: DNA
<213> ORGANISM: Nicotiana tabacum

<400> SEQUENCE: 568
tcagcaactt atgggaaggt tctgactttg gatggagcaa ttcaacagag aatggtggat    60
ttccatacac tgaaatgatt gttcatctt                                      89

<210> SEQ ID NO 569
<211> LENGTH: 89
<212> TYPE: DNA
<213> ORGANISM: Nicotiana tabacum

<400> SEQUENCE: 569
tcagcaactt atgggaaggt tctgactttg gatggagcaa ttcaacagag aatggtggat    60
ttccatacac tgaaatgatt gttcatctt                                      89

<210> SEQ ID NO 570
<211> LENGTH: 93
<212> TYPE: DNA
<213> ORGANISM: Nicotiana tabacum

<400> SEQUENCE: 570
tcagcaactt atgggaaggt tctgactttg gatggagcaa ttcaacacac agagaatggt    60
ggatttccat acactgaaat gattgttcat ctt                                  93

<210> SEQ ID NO 571
<211> LENGTH: 93
<212> TYPE: DNA
<213> ORGANISM: Nicotiana tabacum

<400> SEQUENCE: 571
tcagcaactt atgggaaggt tctgactttg gatggagcaa ttcaacacac agagaatggt    60
ggatttccat acactgaaat gattgttcat ctt                                  93

<210> SEQ ID NO 572
<211> LENGTH: 93
<212> TYPE: DNA
<213> ORGANISM: Nicotiana tabacum

<400> SEQUENCE: 572
tcagcaactt atgggaaggt tctgactttg gatggagcaa ttcaacacac agagaatggt    60
ggatttccat acactgaaat gattgttcat ctt                                 93

<210> SEQ ID NO 573
<211> LENGTH: 93
<212> TYPE: DNA
<213> ORGANISM: Nicotiana tabacum

<400> SEQUENCE: 573
tcagcaactt atgggaaggt tctgactttg gatggagcaa ttcaacacac agagaatggt    60
ggatttccat acactgaaat gattgttcat ctt                                 93

<210> SEQ ID NO 574
<211> LENGTH: 93
<212> TYPE: DNA
<213> ORGANISM: Nicotiana tabacum

<400> SEQUENCE: 574
tcagcaactt atgggaaggt tctgactttg gatggagcaa ttcaacacac agagaatggt    60
ggatttccat acactgaaat gattgttcat ctt                                 93

<210> SEQ ID NO 575
<211> LENGTH: 93
<212> TYPE: DNA
<213> ORGANISM: Nicotiana tabacum

<400> SEQUENCE: 575
tcagcaactt atgggaaggt tctgactttg gatggagcaa ttcaacacac agagaatggt    60
ggatttccat acactgaaat gattgttcat ctt                                 93

<210> SEQ ID NO 576
<211> LENGTH: 93
<212> TYPE: DNA
<213> ORGANISM: Nicotiana tabacum

<400> SEQUENCE: 576
tcagcaactt atgggaaggt tctgactttg gatggagcaa ttcaacacac agagaatggt    60
ggatttccat acactgaaat gattgttcat ctt                                 93

<210> SEQ ID NO 577
<211> LENGTH: 93
<212> TYPE: DNA
<213> ORGANISM: Nicotiana tabacum

<400> SEQUENCE: 577
tcagcaactt atgggaaggt tctgactttg gatggagcaa ttcaacacac agagaatggt    60
ggatttccat acactgaaat gattgttcat ctt                                 93

<210> SEQ ID NO 578
<211> LENGTH: 93
<212> TYPE: DNA
<213> ORGANISM: Nicotiana tabacum

<400> SEQUENCE: 578
tcagcaactt atgggaaggt tctgactttg gatggagcaa ttcaacacac agagaatggt    60
ggatttccat acactgaaat gattgttcat ctt                                 93

```
<210> SEQ ID NO 579
<211> LENGTH: 93
<212> TYPE: DNA
<213> ORGANISM: Nicotiana tabacum

<400> SEQUENCE: 579
tcagcaactt atgggaaggt tctgactttg gatggagcaa ttcaacacac agagaatggt      60
ggatttccat acactgaaat gattgttcat ctt                                  93

<210> SEQ ID NO 580
<211> LENGTH: 93
<212> TYPE: DNA
<213> ORGANISM: Nicotiana tabacum

<400> SEQUENCE: 580
tcagcaactt atgggaaggt tctgactttg gatggagcaa ttcaacacac agagaatggt      60
ggatttccat acactgaaat gattgttcat ctt                                  93

<210> SEQ ID NO 581
<211> LENGTH: 93
<212> TYPE: DNA
<213> ORGANISM: Nicotiana tabacum

<400> SEQUENCE: 581
tcagcaactt atgggaaggt tctgactttg gatggagcaa ttcaacacac agagaatggt      60
ggatttccat acactgaaat gattgttcat ctt                                  93

<210> SEQ ID NO 582
<211> LENGTH: 93
<212> TYPE: DNA
<213> ORGANISM: Nicotiana tabacum

<400> SEQUENCE: 582
tcagcaactt atgggaaggt tctgactttg gatggagcaa ttcaacacac agagaatggt      60
ggatttccat acactgaaat gattgttcat ctt                                  93

<210> SEQ ID NO 583
<211> LENGTH: 93
<212> TYPE: DNA
<213> ORGANISM: Nicotiana tabacum

<400> SEQUENCE: 583
tcagcaactt atgggaaggt tctgactttg gatggagcaa ttcaacacac agagaatggt      60
ggatttccat acactgaaat gattgttcat ctt                                  93

<210> SEQ ID NO 584
<211> LENGTH: 93
<212> TYPE: DNA
<213> ORGANISM: Nicotiana tabacum

<400> SEQUENCE: 584
tcagcaactt atgggaaggt tctgactttg gatggagcaa ttcaacacac agagaatggt      60
ggatttccat acactgaaat gattgttcat ctt                                  93

<210> SEQ ID NO 585
<211> LENGTH: 93
<212> TYPE: DNA
<213> ORGANISM: Nicotiana tabacum

<400> SEQUENCE: 585
```

```
<210> SEQ ID NO 586
<211> LENGTH: 93
<212> TYPE: DNA
<213> ORGANISM: Nicotiana tabacum

<400> SEQUENCE: 586
tcagcaactt atgggaaggt tctgactttg gatggagcaa ttcaacacac agagaatggt    60
ggatttccat acactgaaat gattgttcat ctt                                93

<210> SEQ ID NO 587
<211> LENGTH: 93
<212> TYPE: DNA
<213> ORGANISM: Nicotiana tabacum

<400> SEQUENCE: 587
tcagcaactt atgggaaggt tctgactttg gatggagcaa ttcaacacac agagaatggt    60
ggatttccat acactgaaat gattgttcat ctt                                93

<210> SEQ ID NO 588
<211> LENGTH: 93
<212> TYPE: DNA
<213> ORGANISM: Nicotiana tabacum

<400> SEQUENCE: 588
tcagcaactt atgggaaggt tctgactttg gatggagcaa ttcaacacac agagaatggt    60
ggatttccat acactgaaat gattgttcat ctt                                93

<210> SEQ ID NO 589
<211> LENGTH: 93
<212> TYPE: DNA
<213> ORGANISM: Nicotiana tabacum

<400> SEQUENCE: 589
tcagcaactt atgggaaggt tctgactttg gatggagcaa ttcaacacac agagaatggt    60
ggatttccat acactgaaat gattgttcat ctt                                93

<210> SEQ ID NO 590
<211> LENGTH: 93
<212> TYPE: DNA
<213> ORGANISM: Nicotiana tabacum

<400> SEQUENCE: 590
tcagcaactt atgggaaggt tctgactttg gatggagcaa ttcaacacac agagaatggt    60
ggatttccat acactgaaat gattgttcat ctt                                93

<210> SEQ ID NO 591
<211> LENGTH: 93
<212> TYPE: DNA
<213> ORGANISM: Nicotiana tabacum

<400> SEQUENCE: 591
tcagcaactt atgggaaggt tctgactttg gatggagcaa ttcaacacac agagaatggt    60
ggatttccat acactgaaat gattgttcat ctt                                93

<210> SEQ ID NO 592
<211> LENGTH: 93
```

```
<212> TYPE: DNA
<213> ORGANISM: Nicotiana tabacum

<400> SEQUENCE: 592
tcagcaactt atgggaaggt tctgactttg gatggagcaa ttcaacacac agagaatggt    60
ggatttccat acactgaaat gattgttcat ctt                                 93

<210> SEQ ID NO 593
<211> LENGTH: 93
<212> TYPE: DNA
<213> ORGANISM: Nicotiana tabacum

<400> SEQUENCE: 593
tcagcaactt atgggaaggt tctgactttg gatggagcaa ttcaacacac agagaatggt    60
ggatttccat acactgaaat gattgttcat ctt                                 93

<210> SEQ ID NO 594
<211> LENGTH: 93
<212> TYPE: DNA
<213> ORGANISM: Nicotiana tabacum

<400> SEQUENCE: 594
tcagcaactt atgggaaggt tctgactttg gatggagcaa ttcaacacac agagaatggt    60
ggatttccat acactgaaat gattgttcat ctt                                 93

<210> SEQ ID NO 595
<211> LENGTH: 93
<212> TYPE: DNA
<213> ORGANISM: Nicotiana tabacum

<400> SEQUENCE: 595
tcagcaactt atgggaaggt tctgactttg gatggagcaa ttcaacacac agagaatggt    60
ggatttccat acactgaaat gattgttcat ctt                                 93

<210> SEQ ID NO 596
<211> LENGTH: 93
<212> TYPE: DNA
<213> ORGANISM: Nicotiana tabacum

<400> SEQUENCE: 596
tcagcaactt atgggaaggt tctgactttg gatggagcaa ttcaacacac agagaatggt    60
ggatttccat acactgaaat gattgttcat ctt                                 93

<210> SEQ ID NO 597
<211> LENGTH: 93
<212> TYPE: DNA
<213> ORGANISM: Nicotiana tabacum

<400> SEQUENCE: 597
tcagcaactt atgggaaggt tctgactttg gatggagcaa ttcaacacac agagaatggt    60
ggatttccat acactgaaat gattgttcat ctt                                 93

<210> SEQ ID NO 598
<211> LENGTH: 93
<212> TYPE: DNA
<213> ORGANISM: Nicotiana tabacum

<400> SEQUENCE: 598
tcagcaactt atgggaaggt tctgactttg gatggagcaa ttcaacacac agagaatggt    60
```

```
ggatttccat acactgaaat gattgttcat ctt                           93

<210> SEQ ID NO 599
<211> LENGTH: 93
<212> TYPE: DNA
<213> ORGANISM: Nicotiana tabacum

<400> SEQUENCE: 599
tcagcaactt atgggaaggt tctgactttg gatggagcaa ttcaacacac agagaatggt   60
ggatttccat acactgaaat gattgttcat ctt                               93

<210> SEQ ID NO 600
<211> LENGTH: 93
<212> TYPE: DNA
<213> ORGANISM: Nicotiana tabacum

<400> SEQUENCE: 600
tcagcaactt atgggaaggt tctgactttg gatggagcaa ttcaacacac agagaatggt   60
ggatttccat acactgaaat gattgttcat ctt                               93

<210> SEQ ID NO 601
<211> LENGTH: 93
<212> TYPE: DNA
<213> ORGANISM: Nicotiana tabacum

<400> SEQUENCE: 601
tcagcaactt atgggaaggt tctgactttg gatggagcaa ttcaacacac agagaatggt   60
ggatttccat acactgaaat gattgttcat ctt                               93

<210> SEQ ID NO 602
<211> LENGTH: 89
<212> TYPE: DNA
<213> ORGANISM: Nicotiana tabacum

<400> SEQUENCE: 602
tcagcaacat atgggaaggt tctgactttg gatggagcaa ttcaacagag aatggtggat   60
ttccatacac tgaaatgatt gttcatctt                                    89

<210> SEQ ID NO 603
<211> LENGTH: 89
<212> TYPE: DNA
<213> ORGANISM: Nicotiana tabacum

<400> SEQUENCE: 603
tcagcaacat atgggaaggt tctgactttg gatggagcaa ttcaacagag aatggtggat   60
ttccatacac tgaaatgatt gttcatctt                                    89

<210> SEQ ID NO 604
<211> LENGTH: 88
<212> TYPE: DNA
<213> ORGANISM: Nicotiana tabacum

<400> SEQUENCE: 604
tcagcaacat atgggaaggt tctgactttg gatggagcaa ttcaaagaga atggtggatt   60
tccatacact gaaatgattg ttcatctt                                     88

<210> SEQ ID NO 605
<211> LENGTH: 91
<212> TYPE: DNA
<213> ORGANISM: Nicotiana tabacum
```

<400> SEQUENCE: 605
tcagcaacat atgggaaggt tctgactttg gatggagcaa ttcaacacag agaatggtgg    60
atttccatac actgaaatga ttgttcatct t                                  91

<210> SEQ ID NO 606
<211> LENGTH: 89
<212> TYPE: DNA
<213> ORGANISM: Nicotiana tabacum

<400> SEQUENCE: 606
tcagcaacat atgggaaggt tctgactttg gatggagcaa ttcaacagag aatggtggat    60
ttccatacac tgaaatgatt gttcatctt                                     89

<210> SEQ ID NO 607
<211> LENGTH: 89
<212> TYPE: DNA
<213> ORGANISM: Nicotiana tabacum

<400> SEQUENCE: 607
tcagcaacat atgggaaggt tctgactttg gatggagcaa ttcaacagag aatggtggat    60
ttccatacac tgaaatgatt gttcatctt                                     89

<210> SEQ ID NO 608
<211> LENGTH: 89
<212> TYPE: DNA
<213> ORGANISM: Nicotiana tabacum

<400> SEQUENCE: 608
tcagcaacat atgggaaggt tctgactttg gatggagcaa ttcaacagag aatggtggat    60
ttccatacac tgaaatgatt gttcatctt                                     89

<210> SEQ ID NO 609
<211> LENGTH: 84
<212> TYPE: DNA
<213> ORGANISM: Nicotiana tabacum

<400> SEQUENCE: 609
tcagcaacat atgggaaggt tctgactttg gatggagcaa ttcagaatgg tggatttcca    60
tacactgaaa tgattgttca tctt                                          84

<210> SEQ ID NO 610
<211> LENGTH: 89
<212> TYPE: DNA
<213> ORGANISM: Nicotiana tabacum

<400> SEQUENCE: 610
tcagcaacat atgggaaggt tctgactttg gatggagcaa ttcaacagag aatggtggat    60
ttccatacac tgaaatgatt gttcatctt                                     89

<210> SEQ ID NO 611
<211> LENGTH: 89
<212> TYPE: DNA
<213> ORGANISM: Nicotiana tabacum

<400> SEQUENCE: 611
tcagcaacat atgggaaggt tctgactttg gatggagcaa ttcaacagag aatggtggat    60
ttccatacac tgaaatgatt gttcatctt                                     89

```
<210> SEQ ID NO 612
<211> LENGTH: 86
<212> TYPE: DNA
<213> ORGANISM: Nicotiana tabacum

<400> SEQUENCE: 612
tcagcaacat atgggaaggt tctgactttg gatggagcaa ttcagagaat ggtggatttc      60
catacactga aatgattgtt catctt                                          86

<210> SEQ ID NO 613
<211> LENGTH: 86
<212> TYPE: DNA
<213> ORGANISM: Nicotiana tabacum

<400> SEQUENCE: 613
tcagcaacat atgggaaggt tctgactttg gatggagcaa ttcagagaat ggtggatttc      60
catacactga aatgattgtt catctt                                          86

<210> SEQ ID NO 614
<211> LENGTH: 86
<212> TYPE: DNA
<213> ORGANISM: Nicotiana tabacum

<400> SEQUENCE: 614
tcagcaacat atgggaaggt tctgactttg gatggagcaa ttcaaagaat ggtggatttc      60
catacactga aatgattgtt catctt                                          86

<210> SEQ ID NO 615
<211> LENGTH: 89
<212> TYPE: DNA
<213> ORGANISM: Nicotiana tabacum

<400> SEQUENCE: 615
tcagcaacat atgggaaggt tctgactttg gatggagcaa ttcaacagag aatggtggat      60
ttccatacac tgaaatgatt gttcatctt                                       89

<210> SEQ ID NO 616
<211> LENGTH: 86
<212> TYPE: DNA
<213> ORGANISM: Nicotiana tabacum

<400> SEQUENCE: 616
tcagcaacat atgggaaggt tctgactttg gatggagcaa ttcaaagaat ggtggatttc      60
catacactga aatgattgtt catctt                                          86

<210> SEQ ID NO 617
<211> LENGTH: 89
<212> TYPE: DNA
<213> ORGANISM: Nicotiana tabacum

<400> SEQUENCE: 617
tcagcaacat atgggaaggt tctgactttg gatggagcaa ttcaacagag aatggtggat      60
ttccatacac tgaaatgatt gttcatctt                                       89

<210> SEQ ID NO 618
<211> LENGTH: 89
<212> TYPE: DNA
<213> ORGANISM: Nicotiana tabacum

<400> SEQUENCE: 618
```

```
tcagcaacat atgggaaggt tctgactttg gatggagcaa ttcaacagag aatggtggat    60
ttccatacac tgaaatgatt gttcatctt                                      89

<210> SEQ ID NO 619
<211> LENGTH: 89
<212> TYPE: DNA
<213> ORGANISM: Nicotiana tabacum

<400> SEQUENCE: 619
tcagcaacat atgggaaggt tctgactttg gatggagcaa ttcaacagag aatggtggat    60
ttccatacac tgaaatgatt gttcatctt                                      89

<210> SEQ ID NO 620
<211> LENGTH: 91
<212> TYPE: DNA
<213> ORGANISM: Nicotiana tabacum

<400> SEQUENCE: 620
tcagcaacat atgggaaggt tctgactttg gatggagcaa ttcaacacag agaatggtgg    60
atttccatac actgaaatga ttgttcatct t                                   91

<210> SEQ ID NO 621
<211> LENGTH: 91
<212> TYPE: DNA
<213> ORGANISM: Nicotiana tabacum

<400> SEQUENCE: 621
tcagcaacat atgggaaggt tctgactttg gatggagcaa ttcaacacag agaatggtgg    60
atttccatac actgaaatga ttgttcatct t                                   91

<210> SEQ ID NO 622
<211> LENGTH: 91
<212> TYPE: DNA
<213> ORGANISM: Nicotiana tabacum

<400> SEQUENCE: 622
tcagcaacat atgggaaggt tctgactttg gatggagcaa ttcaacacag agaatggtgg    60
atttccatac actgaaatga ttgttcatct t                                   91

<210> SEQ ID NO 623
<211> LENGTH: 89
<212> TYPE: DNA
<213> ORGANISM: Nicotiana tabacum

<400> SEQUENCE: 623
tcagcaacat atgggaaggt tctgactttg gatggagcaa ttcaacagag aatggtggat    60
ttccatacac tgaaatgatt gttcatctt                                      89

<210> SEQ ID NO 624
<211> LENGTH: 91
<212> TYPE: DNA
<213> ORGANISM: Nicotiana tabacum

<400> SEQUENCE: 624
tcagcaacat atgggaaggt tctgactttg gatggagcaa ttcaacacag agaatggtgg    60
atttccatac actgaaatga ttgttcatct t                                   91

<210> SEQ ID NO 625
```

```
<211> LENGTH: 89
<212> TYPE: DNA
<213> ORGANISM: Nicotiana tabacum

<400> SEQUENCE: 625
tcagcaacat atgggaaggt tctgactttg gatggagcaa ttcaacacag aatggtggat      60
ttccatacac tgaaatgatt gttcatctt                                       89

<210> SEQ ID NO 626
<211> LENGTH: 91
<212> TYPE: DNA
<213> ORGANISM: Nicotiana tabacum

<400> SEQUENCE: 626
tcagcaacat atgggaaggt tctgactttg gatggagcaa ttcaacacag agaatggtgg      60
atttccatac actgaaatga ttgttcatct t                                    91

<210> SEQ ID NO 627
<211> LENGTH: 91
<212> TYPE: DNA
<213> ORGANISM: Nicotiana tabacum

<400> SEQUENCE: 627
tcagcaacat atgggaaggt tctgactttg gatggagcaa ttcaacacag agaatggtgg      60
atttccatac actgaaatga ttgttcatct t                                    91

<210> SEQ ID NO 628
<211> LENGTH: 86
<212> TYPE: DNA
<213> ORGANISM: Nicotiana tabacum

<400> SEQUENCE: 628
tcagcaacat atgggaaggt tctgactttg gatggagcaa ttcagagaat ggtggatttc      60
catacactga aatgattgtt catctt                                          86

<210> SEQ ID NO 629
<211> LENGTH: 89
<212> TYPE: DNA
<213> ORGANISM: Nicotiana tabacum

<400> SEQUENCE: 629
tcagcaacat atgggaaggt tctgactttg gatggagcaa ttcaacagag aatggtggat      60
ttccatacac tgaaatgatt gttcatctt                                       89

<210> SEQ ID NO 630
<211> LENGTH: 91
<212> TYPE: DNA
<213> ORGANISM: Nicotiana tabacum

<400> SEQUENCE: 630
tcagcaacat atgggaaggt tctgactttg gatggagcaa ttcaacacag agaatggtgg      60
atttccatac actgaaatga ttgttcatct t                                    91

<210> SEQ ID NO 631
<211> LENGTH: 91
<212> TYPE: DNA
<213> ORGANISM: Nicotiana tabacum

<400> SEQUENCE: 631
tcagcaacat atgggaaggt tctgactttg gatggagcaa ttcaacacag agaatggtgg      60
```
atttccatac actgaaatga ttgttcatct t     91

<210> SEQ ID NO 632
<211> LENGTH: 91
<212> TYPE: DNA
<213> ORGANISM: Nicotiana tabacum

<400> SEQUENCE: 632
tcagcaacat atgggaaggt tctgactttg gatggagcaa ttcaacacag agaatggtgg     60
atttccatac actgaaatga ttgttcatct t     91

<210> SEQ ID NO 633
<211> LENGTH: 89
<212> TYPE: DNA
<213> ORGANISM: Nicotiana tabacum

<400> SEQUENCE: 633
tcagcaacat atgggaaggt tctgactttg gatggagcaa ttcaacagag aatggtggat     60
ttccatacac tgaaatgatt gttcatctt     89

<210> SEQ ID NO 634
<211> LENGTH: 93
<212> TYPE: DNA
<213> ORGANISM: Nicotiana tabacum

<400> SEQUENCE: 634
tcagcaacat atgggaaggt tctgactttg gatggagcaa ttcaacacac agagaatggt     60
ggatttccat acactgaaat gattgttcat ctt     93

<210> SEQ ID NO 635
<211> LENGTH: 93
<212> TYPE: DNA
<213> ORGANISM: Nicotiana tabacum

<400> SEQUENCE: 635
tcagcaacat atgggaaggt tctgactttg gatggagcaa ttcaacacac agagaatggt     60
ggatttccat acactgaaat gattgttcat ctt     93

<210> SEQ ID NO 636
<211> LENGTH: 93
<212> TYPE: DNA
<213> ORGANISM: Nicotiana tabacum

<400> SEQUENCE: 636
tcagcaacat atgggaaggt tctgactttg gatggagcaa ttcaacacac agagaatggt     60
ggatttccat acactgaaat gattgttcat ctt     93

<210> SEQ ID NO 637
<211> LENGTH: 93
<212> TYPE: DNA
<213> ORGANISM: Nicotiana tabacum

<400> SEQUENCE: 637
tcagcaacat atgggaaggt tctgactttg gatggagcaa ttcaacacac agagaatggt     60
ggatttccat acactgaaat gattgttcat ctt     93

<210> SEQ ID NO 638
<211> LENGTH: 93
<212> TYPE: DNA

<213> ORGANISM: Nicotiana tabacum

<400> SEQUENCE: 638
tcagcaacat atgggaaggt tctgactttg gatggagcaa ttcaacacac agagaatggt    60
ggatttccat acactgaaat gattgttcat ctt                                 93

<210> SEQ ID NO 639
<211> LENGTH: 93
<212> TYPE: DNA
<213> ORGANISM: Nicotiana tabacum

<400> SEQUENCE: 639
tcagcaacat atgggaaggt tctgactttg gatggagcaa ttcaacacac agagaatggt    60
ggatttccat acactgaaat gattgttcat ctt                                 93

<210> SEQ ID NO 640
<211> LENGTH: 93
<212> TYPE: DNA
<213> ORGANISM: Nicotiana tabacum

<400> SEQUENCE: 640
tcagcaacat atgggaaggt tctgactttg gatggagcaa ttcaacacac agagaatggt    60
ggatttccat acactgaaat gattgttcat ctt                                 93

<210> SEQ ID NO 641
<211> LENGTH: 93
<212> TYPE: DNA
<213> ORGANISM: Nicotiana tabacum

<400> SEQUENCE: 641
tcagcaacat atgggaaggt tctgactttg gatggagcaa ttcaacacac agagaatggt    60
ggatttccat acactgaaat gattgttcat ctt                                 93

<210> SEQ ID NO 642
<211> LENGTH: 93
<212> TYPE: DNA
<213> ORGANISM: Nicotiana tabacum

<400> SEQUENCE: 642
tcagcaacat atgggaaggt tctgactttg gatggagcaa ttcaacacac agagaatggt    60
ggatttccat acactgaaat gattgttcat ctt                                 93

<210> SEQ ID NO 643
<211> LENGTH: 93
<212> TYPE: DNA
<213> ORGANISM: Nicotiana tabacum

<400> SEQUENCE: 643
tcagcaacat atgggaaggt tctgactttg gatggagcaa ttcaacacac agagaatggt    60
ggatttccat acactgaaat gattgttcat ctt                                 93

<210> SEQ ID NO 644
<211> LENGTH: 93
<212> TYPE: DNA
<213> ORGANISM: Nicotiana tabacum

<400> SEQUENCE: 644
tcagcaacat atgggaaggt tctgactttg gatggagcaa ttcaacacac agagaatggt    60
ggatttccat acactgaaat gattgttcat ctt                                 93

<210> SEQ ID NO 645
<211> LENGTH: 93
<212> TYPE: DNA
<213> ORGANISM: Nicotiana tabacum

<400> SEQUENCE: 645
tcagcaacat atgggaaggt tctgactttg gatggagcaa ttcaacacac agagaatggt    60
ggatttccat acactgaaat gattgttcat ctt                                93

<210> SEQ ID NO 646
<211> LENGTH: 93
<212> TYPE: DNA
<213> ORGANISM: Nicotiana tabacum

<400> SEQUENCE: 646
tcagcaacat atgggaaggt tctgactttg gatggagcaa ttcaacacac agagaatggt    60
ggatttccat acactgaaat gattgttcat ctt                                93

<210> SEQ ID NO 647
<211> LENGTH: 93
<212> TYPE: DNA
<213> ORGANISM: Nicotiana tabacum

<400> SEQUENCE: 647
tcagcaacat atgggaaggt tctgactttg gatggagcaa ttcaacacac agagaatggt    60
ggatttccat acactgaaat gattgttcat ctt                                93

<210> SEQ ID NO 648
<211> LENGTH: 93
<212> TYPE: DNA
<213> ORGANISM: Nicotiana tabacum

<400> SEQUENCE: 648
tcagcaacat atgggaaggt tctgactttg gatggagcaa ttcaacacac agagaatggt    60
ggatttccat acactgaaat gattgttcat ctt                                93

<210> SEQ ID NO 649
<211> LENGTH: 93
<212> TYPE: DNA
<213> ORGANISM: Nicotiana tabacum

<400> SEQUENCE: 649
tcagcaacat atgggaaggt tctgactttg gatggagcaa ttcaacacac agagaatggt    60
ggatttccat acactgaaat gattgttcat ctt                                93

<210> SEQ ID NO 650
<211> LENGTH: 93
<212> TYPE: DNA
<213> ORGANISM: Nicotiana tabacum

<400> SEQUENCE: 650
tcagcaacat atgggaaggt tctgactttg gatggagcaa ttcaacacac agagaatggt    60
ggatttccat acactgaaat gattgttcat ctt                                93

<210> SEQ ID NO 651
<211> LENGTH: 93
<212> TYPE: DNA
<213> ORGANISM: Nicotiana tabacum

<400> SEQUENCE: 651
tcagcaacat atgggaaggt tctgactttg gatggagcaa ttcaacacac agagaatggt    60
ggatttccat acactgaaat gattgttcat ctt                                93

<210> SEQ ID NO 652
<211> LENGTH: 93
<212> TYPE: DNA
<213> ORGANISM: Nicotiana tabacum

<400> SEQUENCE: 652
tcagcaacat atgggaaggt tctgactttg gatggagcaa ttcaacacac agagaatggt    60
ggatttccat acactgaaat gattgttcat ctt                                93

<210> SEQ ID NO 653
<211> LENGTH: 93
<212> TYPE: DNA
<213> ORGANISM: Nicotiana tabacum

<400> SEQUENCE: 653
tcagcaacat atgggaaggt tctgactttg gatggagcaa ttcaacacac agagaatggt    60
ggatttccat acactgaaat gattgttcat ctt                                93

<210> SEQ ID NO 654
<211> LENGTH: 93
<212> TYPE: DNA
<213> ORGANISM: Nicotiana tabacum

<400> SEQUENCE: 654
tcagcaacat atgggaaggt tctgactttg gatggagcaa ttcaacacac agagaatggt    60
ggatttccat acactgaaat gattgttcat ctt                                93

<210> SEQ ID NO 655
<211> LENGTH: 93
<212> TYPE: DNA
<213> ORGANISM: Nicotiana tabacum

<400> SEQUENCE: 655
tcagcaacat atgggaaggt tctgactttg gatggagcaa ttcaacacac agagaatggt    60
ggatttccat acactgaaat gattgttcat ctt                                93

<210> SEQ ID NO 656
<211> LENGTH: 93
<212> TYPE: DNA
<213> ORGANISM: Nicotiana tabacum

<400> SEQUENCE: 656
tcagcaacat atgggaaggt tctgactttg gatggagcaa ttcaacacac agagaatggt    60
ggatttccat acactgaaat gattgttcat ctt                                93

<210> SEQ ID NO 657
<211> LENGTH: 93
<212> TYPE: DNA
<213> ORGANISM: Nicotiana tabacum

<400> SEQUENCE: 657
tcagcaacat atgggaaggt tctgactttg gatggagcaa ttcaacacac agagaatggt    60
ggatttccat acactgaaat gattgttcat ctt                                93

```
<210> SEQ ID NO 658
<211> LENGTH: 93
<212> TYPE: DNA
<213> ORGANISM: Nicotiana tabacum

<400> SEQUENCE: 658
tcagcaacat atgggaaggt tctgactttg gatggagcaa ttcaacacac agagaatggt    60
ggatttccat acactgaaat gattgttcat ctt                                93

<210> SEQ ID NO 659
<211> LENGTH: 93
<212> TYPE: DNA
<213> ORGANISM: Nicotiana tabacum

<400> SEQUENCE: 659
tcagcaacat atgggaaggt tctgactttg gatggagcaa ttcaacacac agagaatggt    60
ggatttccat acactgaaat gattgttcat ctt                                93

<210> SEQ ID NO 660
<211> LENGTH: 93
<212> TYPE: DNA
<213> ORGANISM: Nicotiana tabacum

<400> SEQUENCE: 660
tcagcaacat atgggaaggt tctgactttg gatggagcaa ttcaacacac agagaatggt    60
ggatttccat acactgaaat gattgttcat ctt                                93

<210> SEQ ID NO 661
<211> LENGTH: 93
<212> TYPE: DNA
<213> ORGANISM: Nicotiana tabacum

<400> SEQUENCE: 661
tcagcaacat atgggaaggt tctgactttg gatggagcaa ttcaacacac agagaatggt    60
ggatttccat acactgaaat gattgttcat ctt                                93

<210> SEQ ID NO 662
<211> LENGTH: 93
<212> TYPE: DNA
<213> ORGANISM: Nicotiana tabacum

<400> SEQUENCE: 662
tcagcaacat atgggaaggt tctgactttg gatggagcaa ttcaacacac agagaatggt    60
ggatttccat acactgaaat gattgttcat ctt                                93

<210> SEQ ID NO 663
<211> LENGTH: 93
<212> TYPE: DNA
<213> ORGANISM: Nicotiana tabacum

<400> SEQUENCE: 663
tcagcaacat atgggaaggt tctgactttg gatggagcaa ttcaacacac agagaatggt    60
ggatttccat acactgaaat gattgttcat ctt                                93

<210> SEQ ID NO 664
<211> LENGTH: 93
<212> TYPE: DNA
<213> ORGANISM: Nicotiana tabacum

<400> SEQUENCE: 664
```
tcagcaacat atgggaaggt tctgactttg gatggagcaa ttcaacacac agagaatggt    60
ggatttccat acactgaaat gattgttcat ctt    93

<210> SEQ ID NO 665
<211> LENGTH: 93
<212> TYPE: DNA
<213> ORGANISM: Nicotiana tabacum

<400> SEQUENCE: 665
tcagcaacat atgggaaggt tctgactttg gatggagcaa ttcaacacac agagaatggt    60
ggatttccat acactgaaat gattgttcat ctt    93

<210> SEQ ID NO 666
<211> LENGTH: 89
<212> TYPE: DNA
<213> ORGANISM: Nicotiana tabacum

<400> SEQUENCE: 666
tcagcaacat atgggaaggt tttgactttg gatggagcaa ttcaacagag aatggtggat    60
ttccatacac tgaaatgatt gttcatctt    89

<210> SEQ ID NO 667
<211> LENGTH: 89
<212> TYPE: DNA
<213> ORGANISM: Nicotiana tabacum

<400> SEQUENCE: 667
tcagcaacat atgggaaggt tttgactttg gatggagcaa ttcaacagag aatggtggat    60
ttccatacac tgaaatgatt gttcatctt    89

<210> SEQ ID NO 668
<211> LENGTH: 88
<212> TYPE: DNA
<213> ORGANISM: Nicotiana tabacum

<400> SEQUENCE: 668
tcagcaacat atgggaaggt tttgactttg gatggagcaa ttcaacgaga atggtggatt    60
tccatacact gaaatgattg ttcatctt    88

<210> SEQ ID NO 669
<211> LENGTH: 88
<212> TYPE: DNA
<213> ORGANISM: Nicotiana tabacum

<400> SEQUENCE: 669
tcagcaacat atgggaaggt tttgactttg gatggagcaa ttcaacgaga atggtggatt    60
tccatacact gaaatgattg ttcatctt    88

<210> SEQ ID NO 670
<211> LENGTH: 88
<212> TYPE: DNA
<213> ORGANISM: Nicotiana tabacum

<400> SEQUENCE: 670
tcagcaacat atgggaaggt tttgactttg gatggagcaa ttcaaagaga atggtggatt    60
tccatacact gaaatgattg ttcatctt    88

<210> SEQ ID NO 671
<211> LENGTH: 88

```
<212> TYPE: DNA
<213> ORGANISM: Nicotiana tabacum

<400> SEQUENCE: 671
tcagcaacat atgggaaggt tttgactttg gatggagcaa ttcaaagaga atggtggatt    60
tccatacact gaaatgattg ttcatctt                                      88

<210> SEQ ID NO 672
<211> LENGTH: 89
<212> TYPE: DNA
<213> ORGANISM: Nicotiana tabacum

<400> SEQUENCE: 672
tcagcaacat atgggaaggt tttgactttg gatggagcaa ttcaacagag aatggtggat    60
ttccatacac tgaaatgatt gttcatctt                                     89

<210> SEQ ID NO 673
<211> LENGTH: 89
<212> TYPE: DNA
<213> ORGANISM: Nicotiana tabacum

<400> SEQUENCE: 673
tcagcaacat atgggaaggt tttgactttg gatggagcaa ttcaacagag aatggtggat    60
ttccatacac tgaaatgatt gttcatctt                                     89

<210> SEQ ID NO 674
<211> LENGTH: 91
<212> TYPE: DNA
<213> ORGANISM: Nicotiana tabacum

<400> SEQUENCE: 674
tcagcaacat atgggaaggt tttgactttg gatggagcaa ttcaacacag agaatggtgg    60
atttccatac actgaaatga ttgttcatct t                                  91

<210> SEQ ID NO 675
<211> LENGTH: 91
<212> TYPE: DNA
<213> ORGANISM: Nicotiana tabacum

<400> SEQUENCE: 675
tcagcaacat atgggaaggt tttgactttg gatggagcaa ttcaacacag agaatggtgg    60
atttccatac actgaaatga ttgttcatct t                                  91

<210> SEQ ID NO 676
<211> LENGTH: 91
<212> TYPE: DNA
<213> ORGANISM: Nicotiana tabacum

<400> SEQUENCE: 676
tcagcaacat atgggaaggt tttgactttg gatggagcaa ttcaacacag agaatggtgg    60
atttccatac actgaaatga ttgttcatct t                                  91

<210> SEQ ID NO 677
<211> LENGTH: 91
<212> TYPE: DNA
<213> ORGANISM: Nicotiana tabacum

<400> SEQUENCE: 677
tcagcaacat atgggaaggt tttgactttg gatggagcaa ttcaacacag agaatggtgg    60
```

```
atttccatac actgaaatga ttgttcatct t                                    91

<210> SEQ ID NO 678
<211> LENGTH: 91
<212> TYPE: DNA
<213> ORGANISM: Nicotiana tabacum

<400> SEQUENCE: 678
tcagcaacat atgggaaggt tttgactttg gatggagcaa ttcaacacag agaatggtgg     60
atttccatac actgaaatga ttgttcatct t                                    91

<210> SEQ ID NO 679
<211> LENGTH: 83
<212> TYPE: DNA
<213> ORGANISM: Nicotiana tabacum

<400> SEQUENCE: 679
tcagcaacat atgggaaggt tttgactttg gatggagcaa ttagaatggt ggatttccat     60
acactgaaat gattgttcat ctt                                             83

<210> SEQ ID NO 680
<211> LENGTH: 91
<212> TYPE: DNA
<213> ORGANISM: Nicotiana tabacum

<400> SEQUENCE: 680
tcagcaacat atgggaaggt tttgactttg gatggagcaa ttcaacacag agaatggtgg     60
atttccatac actgaaatga ttgttcatct t                                    91

<210> SEQ ID NO 681
<211> LENGTH: 83
<212> TYPE: DNA
<213> ORGANISM: Nicotiana tabacum

<400> SEQUENCE: 681
tcagcaacat atgggaaggt tttgactttg gatggagcaa ttagaatggt ggatttccat     60
acactgaaat gattgttcat ctt                                             83

<210> SEQ ID NO 682
<211> LENGTH: 89
<212> TYPE: DNA
<213> ORGANISM: Nicotiana tabacum

<400> SEQUENCE: 682
tcagcaacat atgggaaggt tttgactttg gatggagcaa ttcaacagag aatggtggat     60
ttccatacac tgaaatgatt gttcatctt                                       89

<210> SEQ ID NO 683
<211> LENGTH: 89
<212> TYPE: DNA
<213> ORGANISM: Nicotiana tabacum

<400> SEQUENCE: 683
tcagcaacat atgggaaggt tttgactttg gatggagcaa ttcaacagag aatggtggat     60
ttccatacac tgaaatgatt gttcatctt                                       89

<210> SEQ ID NO 684
<211> LENGTH: 91
<212> TYPE: DNA
<213> ORGANISM: Nicotiana tabacum
```

<400> SEQUENCE: 684
tcagcaacat atgggaaggt tttgactttg gatggagcaa ttcaacacag agaatggtgg    60
atttccatac actgaaatga ttgttcatct t                                   91

<210> SEQ ID NO 685
<211> LENGTH: 91
<212> TYPE: DNA
<213> ORGANISM: Nicotiana tabacum

<400> SEQUENCE: 685
tcagcaacat atgggaaggt tttgactttg gatggagcaa ttcaacacag agaatggtgg    60
atttccatac actgaaatga ttgttcatct t                                   91

<210> SEQ ID NO 686
<211> LENGTH: 89
<212> TYPE: DNA
<213> ORGANISM: Nicotiana tabacum

<400> SEQUENCE: 686
tcagcaacat atgggaaggt tttgactttg gatggagcaa ttcaacagag aatggtggat    60
ttccatacac tgaaatgatt gttcatctt                                      89

<210> SEQ ID NO 687
<211> LENGTH: 91
<212> TYPE: DNA
<213> ORGANISM: Nicotiana tabacum

<400> SEQUENCE: 687
tcagcaacat atgggaaggt tttgactttg gatggagcaa ttcaacacag agaatggtgg    60
atttccatac actgaaatga ttgttcatct t                                   91

<210> SEQ ID NO 688
<211> LENGTH: 91
<212> TYPE: DNA
<213> ORGANISM: Nicotiana tabacum

<400> SEQUENCE: 688
tcagcaacat atgggaaggt tttgactttg gatggagcaa ttcaacacag agaatggtgg    60
atttccatac actgaaatga ttgttcatct t                                   91

<210> SEQ ID NO 689
<211> LENGTH: 91
<212> TYPE: DNA
<213> ORGANISM: Nicotiana tabacum

<400> SEQUENCE: 689
tcagcaacat atgggaaggt tttgactttg gatggagcaa ttcaacacag agaatggtgg    60
atttccatac actgaaatga ttgttcatct t                                   91

<210> SEQ ID NO 690
<211> LENGTH: 89
<212> TYPE: DNA
<213> ORGANISM: Nicotiana tabacum

<400> SEQUENCE: 690
tcagcaacat atgggaaggt tttgactttg gatggagcaa ttcaacagag aatggtggat    60
ttccatacac tgaaatgatt gttcatctt                                      89

<210> SEQ ID NO 691
<211> LENGTH: 88
<212> TYPE: DNA
<213> ORGANISM: Nicotiana tabacum

<400> SEQUENCE: 691
tcagcaacat atgggaaggt tttgactttg gatggagcaa ttcaacaaga atggtggatt    60
tccatacact gaaatgattg ttcatctt                                      88

<210> SEQ ID NO 692
<211> LENGTH: 91
<212> TYPE: DNA
<213> ORGANISM: Nicotiana tabacum

<400> SEQUENCE: 692
tcagcaacat atgggaaggt tttgactttg gatggagcaa ttcaacacag agaatggtgg    60
atttccatac actgaaatga ttgttcatct t                                  91

<210> SEQ ID NO 693
<211> LENGTH: 89
<212> TYPE: DNA
<213> ORGANISM: Nicotiana tabacum

<400> SEQUENCE: 693
tcagcaacat atgggaaggt tttgactttg gatggagcaa ttcaacagag aatggtggat    60
ttccatacac tgaaatgatt gttcatctt                                     89

<210> SEQ ID NO 694
<211> LENGTH: 91
<212> TYPE: DNA
<213> ORGANISM: Nicotiana tabacum

<400> SEQUENCE: 694
tcagcaacat atgggaaggt tttgactttg gatggagcaa ttcaacacag agaatggtgg    60
atttccatac actgaaatga ttgttcatct t                                  91

<210> SEQ ID NO 695
<211> LENGTH: 91
<212> TYPE: DNA
<213> ORGANISM: Nicotiana tabacum

<400> SEQUENCE: 695
tcagcaacat atgggaaggt tttgactttg gatggagcaa ttcaacacag agaatggtgg    60
atttccatac actgaaatga ttgttcatct t                                  91

<210> SEQ ID NO 696
<211> LENGTH: 91
<212> TYPE: DNA
<213> ORGANISM: Nicotiana tabacum

<400> SEQUENCE: 696
tcagcaacat atgggaaggt tttgactttg gatggagcaa ttcaacacag agaatggtgg    60
atttccatac actgaaatga ttgttcatct t                                  91

<210> SEQ ID NO 697
<211> LENGTH: 85
<212> TYPE: DNA
<213> ORGANISM: Nicotiana tabacum

<400> SEQUENCE: 697
tcagcaacat atgggaaggt tttgactttg gatggagcaa ttcaagaatg gtggatttcc    60
atacactgaa atgattgttc atctt    85

<210> SEQ ID NO 698
<211> LENGTH: 93
<212> TYPE: DNA
<213> ORGANISM: Nicotiana tabacum

<400> SEQUENCE: 698
tcagcaacat atgggaaggt tttgactttg gatggagcaa ttcaacacac agagaatggt    60
ggatttccat acactgaaat gattgttcat ctt    93

<210> SEQ ID NO 699
<211> LENGTH: 93
<212> TYPE: DNA
<213> ORGANISM: Nicotiana tabacum

<400> SEQUENCE: 699
tcagcaacat atgggaaggt tttgactttg gatggagcaa ttcaacacac agagaatggt    60
ggatttccat acactgaaat gattgttcat ctt    93

<210> SEQ ID NO 700
<211> LENGTH: 93
<212> TYPE: DNA
<213> ORGANISM: Nicotiana tabacum

<400> SEQUENCE: 700
tcagcaacat atgggaaggt tttgactttg gatggagcaa ttcaacacac agagaatggt    60
ggatttccat acactgaaat gattgttcat ctt    93

<210> SEQ ID NO 701
<211> LENGTH: 93
<212> TYPE: DNA
<213> ORGANISM: Nicotiana tabacum

<400> SEQUENCE: 701
tcagcaacat atgggaaggt tttgactttg gatggagcaa ttcaacacac agagaatggt    60
ggatttccat acactgaaat gattgttcat ctt    93

<210> SEQ ID NO 702
<211> LENGTH: 93
<212> TYPE: DNA
<213> ORGANISM: Nicotiana tabacum

<400> SEQUENCE: 702
tcagcaacat atgggaaggt tttgactttg gatggagcaa ttcaacacac agagaatggt    60
ggatttccat acactgaaat gattgttcat ctt    93

<210> SEQ ID NO 703
<211> LENGTH: 93
<212> TYPE: DNA
<213> ORGANISM: Nicotiana tabacum

<400> SEQUENCE: 703
tcagcaacat atgggaaggt tttgactttg gatggagcaa ttcaacacac agagaatggt    60
ggatttccat acactgaaat gattgttcat ctt    93

<210> SEQ ID NO 704

```
<211> LENGTH: 93
<212> TYPE: DNA
<213> ORGANISM: Nicotiana tabacum

<400> SEQUENCE: 704
tcagcaacat atgggaaggt tttgactttg gatggagcaa ttcaacacac agagaatggt      60
ggatttccat acactgaaat gattgttcat ctt                                   93

<210> SEQ ID NO 705
<211> LENGTH: 93
<212> TYPE: DNA
<213> ORGANISM: Nicotiana tabacum

<400> SEQUENCE: 705
tcagcaacat atgggaaggt tttgactttg gatggagcaa ttcaacacac agagaatggt      60
ggatttccat acactgaaat gattgttcat ctt                                   93

<210> SEQ ID NO 706
<211> LENGTH: 93
<212> TYPE: DNA
<213> ORGANISM: Nicotiana tabacum

<400> SEQUENCE: 706
tcagcaacat atgggaaggt tttgactttg gatggagcaa ttcaacacac agagaatggt      60
ggatttccat acactgaaat gattgttcat ctt                                   93

<210> SEQ ID NO 707
<211> LENGTH: 93
<212> TYPE: DNA
<213> ORGANISM: Nicotiana tabacum

<400> SEQUENCE: 707
tcagcaacat atgggaaggt tttgactttg gatggagcaa ttcaacacac agagaatggt      60
ggatttccat acactgaaat gattgttcat ctt                                   93

<210> SEQ ID NO 708
<211> LENGTH: 93
<212> TYPE: DNA
<213> ORGANISM: Nicotiana tabacum

<400> SEQUENCE: 708
tcagcaacat atgggaaggt tttgactttg gatggagcaa ttcaacacac agagaatggt      60
ggatttccat acactgaaat gattgttcat ctt                                   93

<210> SEQ ID NO 709
<211> LENGTH: 93
<212> TYPE: DNA
<213> ORGANISM: Nicotiana tabacum

<400> SEQUENCE: 709
tcagcaacat atgggaaggt tttgactttg gatggagcaa ttcaacacac agagaatggt      60
ggatttccat acactgaaat gattgttcat ctt                                   93

<210> SEQ ID NO 710
<211> LENGTH: 93
<212> TYPE: DNA
<213> ORGANISM: Nicotiana tabacum

<400> SEQUENCE: 710
tcagcaacat atgggaaggt tttgactttg gatggagcaa ttcaacacac agagaatggt      60
```

```
ggatttccat acactgaaat gattgttcat ctt                            93

<210> SEQ ID NO 711
<211> LENGTH: 93
<212> TYPE: DNA
<213> ORGANISM: Nicotiana tabacum

<400> SEQUENCE: 711
tcagcaacat atgggaaggt tttgactttg gatggagcaa ttcaacacac agagaatggt   60
ggatttccat acactgaaat gattgttcat ctt                            93

<210> SEQ ID NO 712
<211> LENGTH: 93
<212> TYPE: DNA
<213> ORGANISM: Nicotiana tabacum

<400> SEQUENCE: 712
tcagcaacat atgggaaggt tttgactttg gatggagcaa ttcaacacac agagaatggt   60
ggatttccat acactgaaat gattgttcat ctt                            93

<210> SEQ ID NO 713
<211> LENGTH: 93
<212> TYPE: DNA
<213> ORGANISM: Nicotiana tabacum

<400> SEQUENCE: 713
tcagcaacat atgggaaggt tttgactttg gatggagcaa ttcaacacac agagaatggt   60
ggatttccat acactgaaat gattgttcat ctt                            93

<210> SEQ ID NO 714
<211> LENGTH: 93
<212> TYPE: DNA
<213> ORGANISM: Nicotiana tabacum

<400> SEQUENCE: 714
tcagcaacat atgggaaggt tttgactttg gatggagcaa ttcaacacac agagaatggt   60
ggatttccat acactgaaat gattgttcat ctt                            93

<210> SEQ ID NO 715
<211> LENGTH: 93
<212> TYPE: DNA
<213> ORGANISM: Nicotiana tabacum

<400> SEQUENCE: 715
tcagcaacat atgggaaggt tttgactttg gatggagcaa ttcaacacac agagaatggt   60
ggatttccat acactgaaat gattgttcat ctt                            93

<210> SEQ ID NO 716
<211> LENGTH: 93
<212> TYPE: DNA
<213> ORGANISM: Nicotiana tabacum

<400> SEQUENCE: 716
tcagcaacat atgggaaggt tttgactttg gatggagcaa ttcaacacac agagaatggt   60
ggatttccat acactgaaat gattgttcat ctt                            93

<210> SEQ ID NO 717
<211> LENGTH: 93
<212> TYPE: DNA
```

<213> ORGANISM: Nicotiana tabacum

<400> SEQUENCE: 717
tcagcaacat atgggaaggt tttgactttg gatggagcaa ttcaacacac agagaatggt     60
ggatttccat acactgaaat gattgttcat ctt                                 93

<210> SEQ ID NO 718
<211> LENGTH: 93
<212> TYPE: DNA
<213> ORGANISM: Nicotiana tabacum

<400> SEQUENCE: 718
tcagcaacat atgggaaggt tttgactttg gatggagcaa ttcaacacac agagaatggt     60
ggatttccat acactgaaat gattgttcat ctt                                 93

<210> SEQ ID NO 719
<211> LENGTH: 93
<212> TYPE: DNA
<213> ORGANISM: Nicotiana tabacum

<400> SEQUENCE: 719
tcagcaacat atgggaaggt tttgactttg gatggagcaa ttcaacacac agagaatggt     60
ggatttccat acactgaaat gattgttcat ctt                                 93

<210> SEQ ID NO 720
<211> LENGTH: 93
<212> TYPE: DNA
<213> ORGANISM: Nicotiana tabacum

<400> SEQUENCE: 720
tcagcaacat atgggaaggt tttgactttg gatggagcaa ttcaacacac agagaatggt     60
ggatttccat acactgaaat gattgttcat ctt                                 93

<210> SEQ ID NO 721
<211> LENGTH: 93
<212> TYPE: DNA
<213> ORGANISM: Nicotiana tabacum

<400> SEQUENCE: 721
tcagcaacat atgggaaggt tttgactttg gatggagcaa ttcaacacac agagaatggt     60
ggatttccat acactgaaat gattgttcat ctt                                 93

<210> SEQ ID NO 722
<211> LENGTH: 93
<212> TYPE: DNA
<213> ORGANISM: Nicotiana tabacum

<400> SEQUENCE: 722
tcagcaacat atgggaaggt tttgactttg gatggagcaa ttcaacacac agagaatggt     60
ggatttccat acactgaaat gattgttcat ctt                                 93

<210> SEQ ID NO 723
<211> LENGTH: 93
<212> TYPE: DNA
<213> ORGANISM: Nicotiana tabacum

<400> SEQUENCE: 723
tcagcaacat atgggaaggt tttgactttg gatggagcaa ttcaacacac agagaatggt     60
ggatttccat acactgaaat gattgttcat ctt                                 93

<210> SEQ ID NO 724
<211> LENGTH: 93
<212> TYPE: DNA
<213> ORGANISM: Nicotiana tabacum

<400> SEQUENCE: 724
tcagcaacat atgggaaggt tttgactttg gatggagcaa ttcaacacac agagaatggt      60
ggatttccat acactgaaat gattgttcat ctt                                  93

<210> SEQ ID NO 725
<211> LENGTH: 93
<212> TYPE: DNA
<213> ORGANISM: Nicotiana tabacum

<400> SEQUENCE: 725
tcagcaacat atgggaaggt tttgactttg gatggagcaa ttcaacacac agagaatggt      60
ggatttccat acactgaaat gattgttcat ctt                                  93

<210> SEQ ID NO 726
<211> LENGTH: 93
<212> TYPE: DNA
<213> ORGANISM: Nicotiana tabacum

<400> SEQUENCE: 726
tcagcaacat atgggaaggt tttgactttg gatggagcaa ttcaacacac agagaatggt      60
ggatttccat acactgaaat gattgttcat ctt                                  93

<210> SEQ ID NO 727
<211> LENGTH: 93
<212> TYPE: DNA
<213> ORGANISM: Nicotiana tabacum

<400> SEQUENCE: 727
tcagcaacat atgggaaggt tttgactttg gatggagcaa ttcaacacac agagaatggt      60
ggatttccat acactgaaat gattgttcat ctt                                  93

<210> SEQ ID NO 728
<211> LENGTH: 93
<212> TYPE: DNA
<213> ORGANISM: Nicotiana tabacum

<400> SEQUENCE: 728
tcagcaacat atgggaaggt tttgactttg gatggagcaa ttcaacacac agagaatggt      60
ggatttccat acactgaaat gattgttcat ctt                                  93

<210> SEQ ID NO 729
<211> LENGTH: 93
<212> TYPE: DNA
<213> ORGANISM: Nicotiana tabacum

<400> SEQUENCE: 729
tcagcaacat atgggaaggt tttgactttg gatggagcaa ttcaacacac agagaatggt      60
ggatttccat acactgaaat gattgttcat ctt                                  93

COMPOSITIONS AND METHODS BASED ON PMT ENGINEERING FOR PRODUCING TOBACCO PLANTS AND PRODUCTS HAVING ALTERED ALKALOID LEVELS

INCORPORATION OF SEQUENCE LISTING

A sequence listing contained in the file named "P34620US02_SL.txt" which is 200,704 bytes (measured in MS-Windows®) and created on Jul. 24, 2019, is filed electronically herewith and incorporated by reference in its entirety.

FIELD

The present disclosure provides tobacco genetic engineering for modulating alkaloid and nicotine levels.

BACKGROUND

Nicotine is the predominant alkaloid, usually accounting for more than 90-95% of the total alkaloids in commercial tobacco cultivars. The remaining alkaloid fraction is primarily comprised three additional alkaloids: nornicotine, anabasine, and anatabine. Tobacco plants with reduced nicotine levels have been achieved with varying and inconsistent results by modulating different nicotine biosynthetic genes and transcriptional regulators. There is a need for new technologies to reduce nicotine levels in tobacco leaves.

SUMMARY

The present disclosure provides tobacco plants with altered total alkaloid and nicotine levels and commercially acceptable leaf grade, their development via breeding or transgenic approaches, and production of tobacco products from these tobacco plants.

In an aspect, the present disclosure provides a tobacco plant, or part thereof, comprising one or more mutant alleles in at least one PMT gene selected from the group consisting of PMT1a, PMT1b, PMT2, PMT3, and PMT4, wherein the tobacco plant is capable of producing a leaf comprising a nicotine level less than the nicotine level of a leaf from a control tobacco plant not having the one or more mutant alleles when grown and processed under comparable conditions.

In another aspect, a tobacco plant comprises one or more mutant alleles in at least two PMT genes selected from the group consisting of PMT1a, PMT1b, PMT2, PMT3, and PMT4.

In a further aspect, a tobacco plant comprises one or more mutant alleles in at least three PMT genes selected from the group consisting of PMT1a, PMT1b, PMT2, PMT3, and PMT4.

In another aspect, a tobacco plant comprises one or more mutant alleles in at least four PMT genes selected from the group consisting of PMT1a, PMT1b, PMT2, PMT3, and PMT4.

In a further aspect, a tobacco plant comprises one or more mutant alleles in five PMT genes selected from the group consisting of PMT1a, PMT1b, PMT2, PMT3, and PMT4.

In an aspect, the present disclosure provides a tobacco plant selected from the group consisting of a single pmt mutant, a double pmt mutant, a triple mutant, a quadruple mutant, and a quintuple mutant, as listed in Tables 8A to 8E.

In an aspect, the present disclosure provides a tobacco plant as listed in Tables 4A to 4E or Table 10. In another aspect, the present disclosure provides a progeny plant of a tobacco plant in Tables 4A to 4E or Table 10, from either selfing or a cross with another plant in Tables 4A to 4E or Table 10.

In another aspect, the present disclosure provides a tobacco plant comprising various combinations of the pmt mutant alleles listed in Tables 5A to 5E or Tables 12A to 12E to give rise to a single pint mutant, a double pint mutant, a triple mutant, a quadruple mutant, or a quintuple mutant. In an aspect, the present disclosure provides a tobacco plant comprising a pint mutant allele sequence selected from the group consisting of SEQ ID Nos. 21 to 200, 410 to 441, 474 to 505, 538 to 569, 602 to 633, and 666 to 697.

The present disclosure further provides cured tobacco, tobacco blends, tobacco products comprising plant material from tobacco plants, lines, varieties or hybrids disclosed.

BRIEF DESCRIPTION OF THE SEQUENCES

SEQ ID Nos: 1 to 5 set forth exemplary genomic sequences of PMT1b, PMT1a, PMT2, PMT3, and PMT4, respectively, from a TN90 reference genome.

SEQ ID Nos: 6 to 10 set forth exemplary cDNA sequences of PMT1b, PMT1a, PMT2, PMT3, and PMT4, respectively, from TN90.

SEQ ID Nos: 11 to 15 set forth exemplary polypeptide sequences of PMT1b, PMT1a, PMT2, PMT3, and PMT4, respectively, from TN90.

SEQ ID Nos: 16 to 22 set forth exemplary guide RNA sequences.

SEQ ID Nos: 23 to 200, 410 to 441, 474 to 505, 538 to 569, 602 to 633, and 666 to 697 set forth exemplary edited pmt mutant sequences.

Figure 6A:
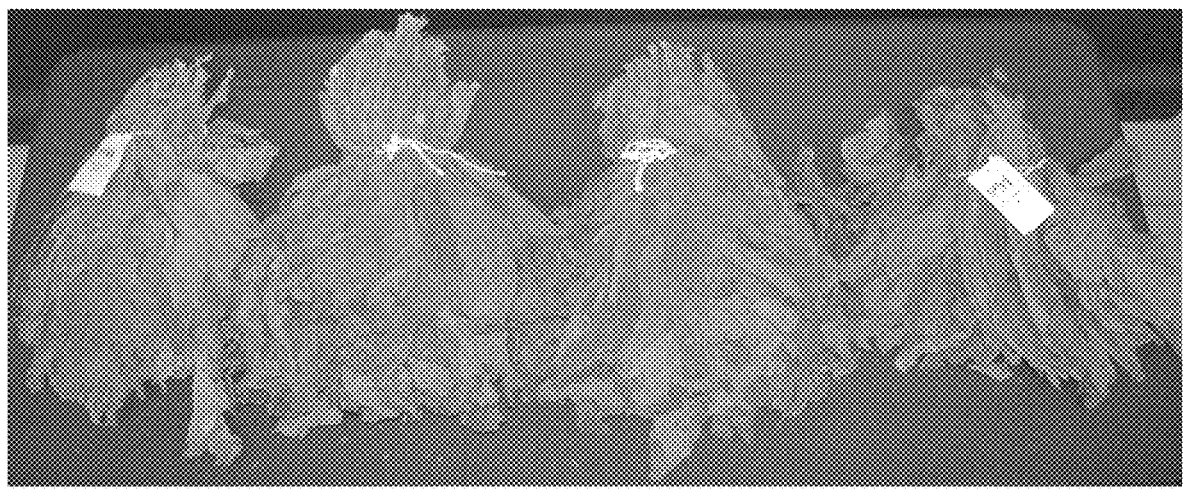
Figure 6B:
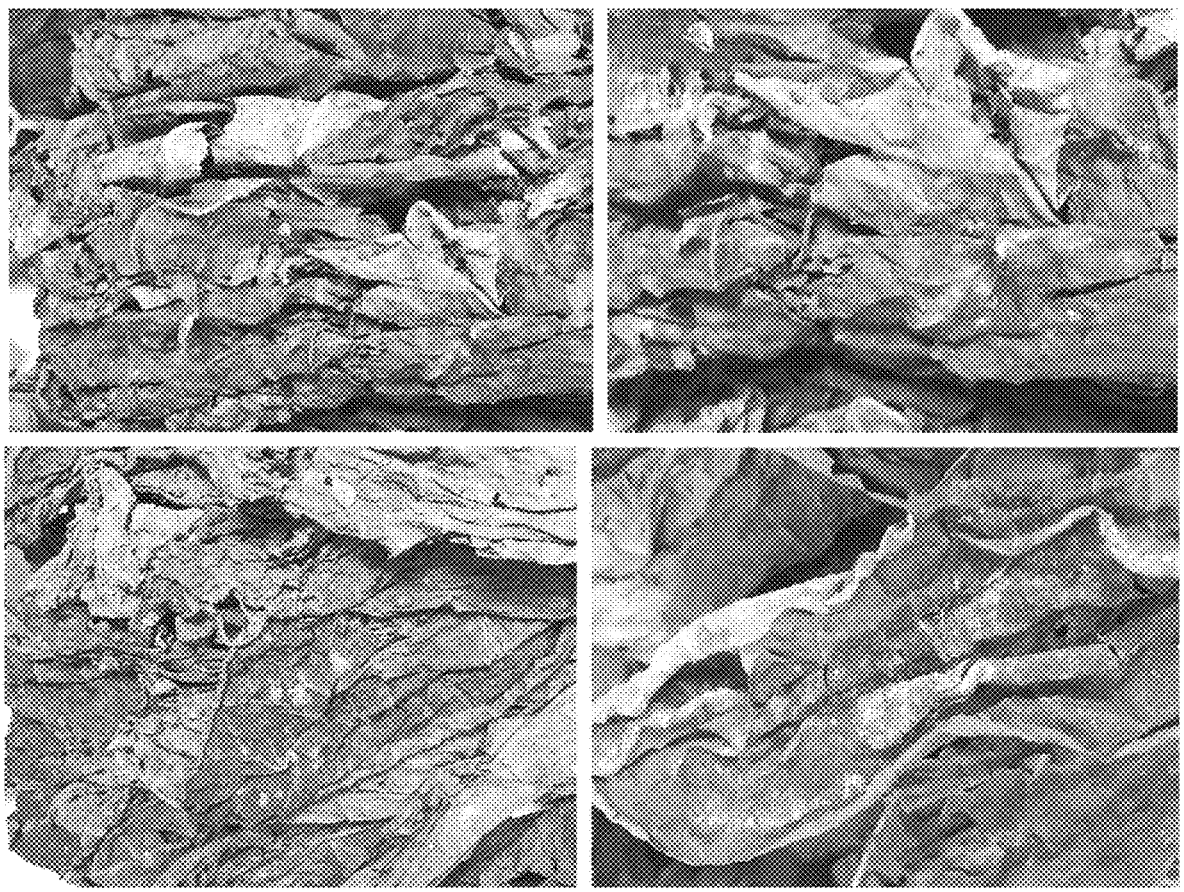
Figure 6C:
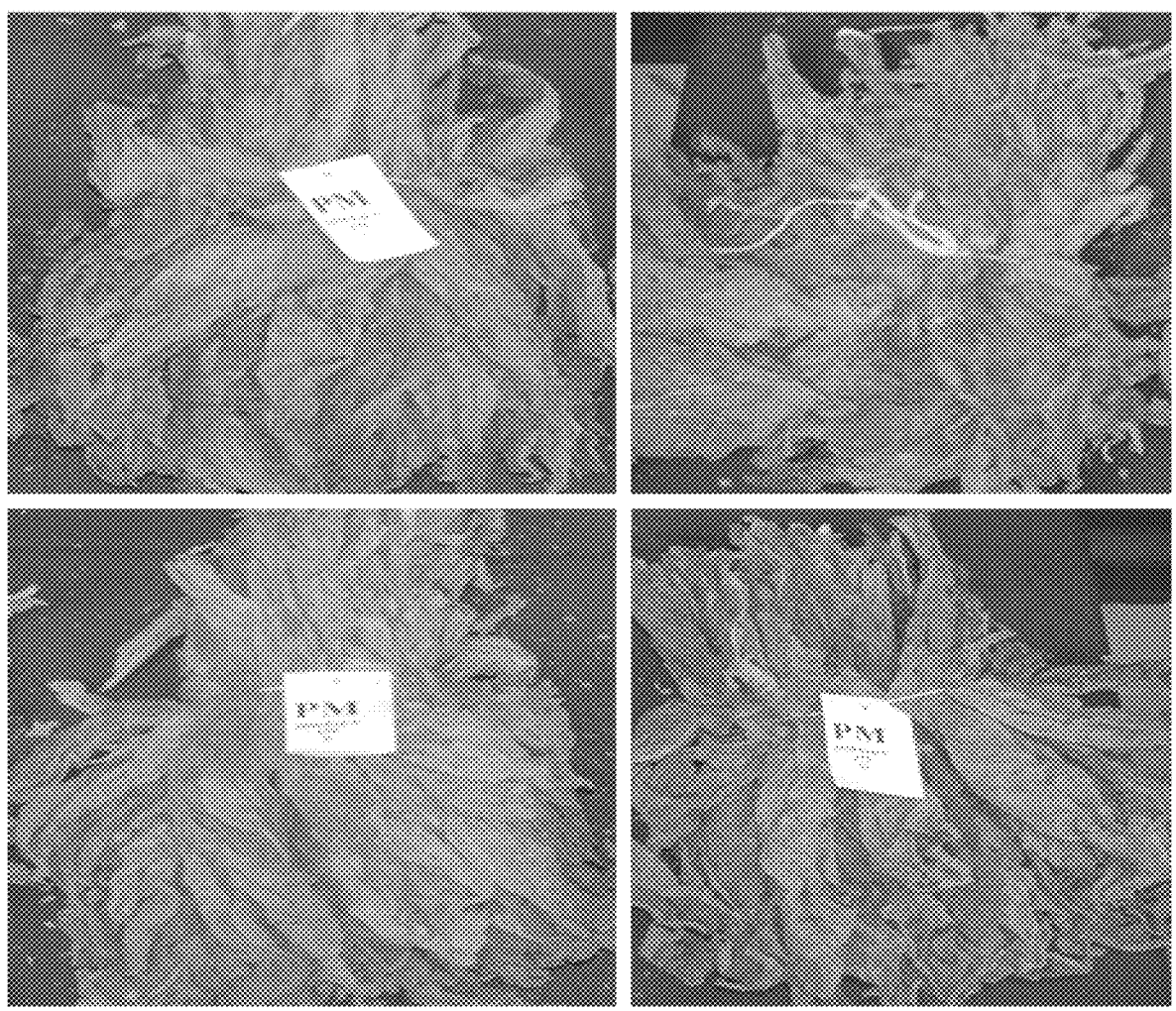
Figure 6D:
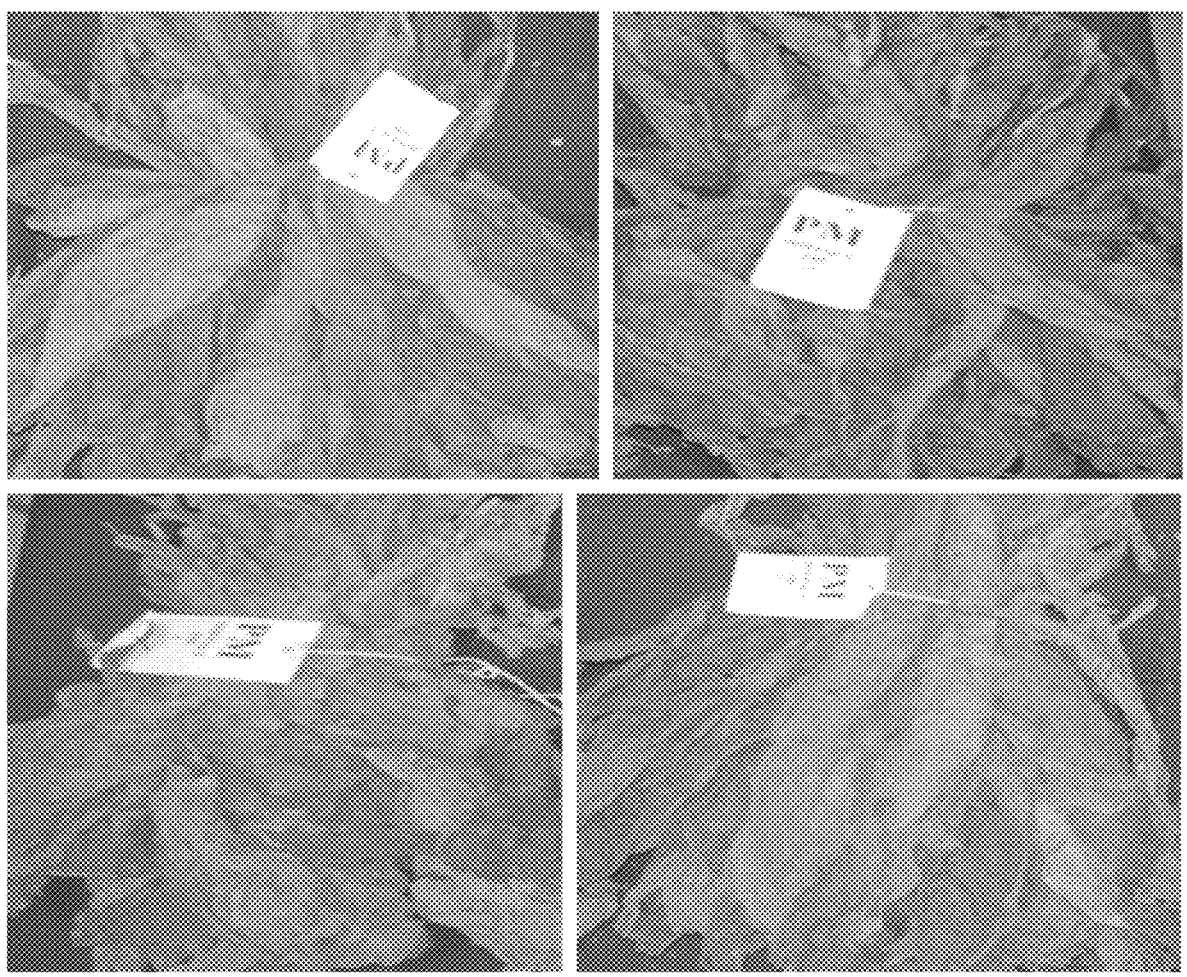
Figure 6E:
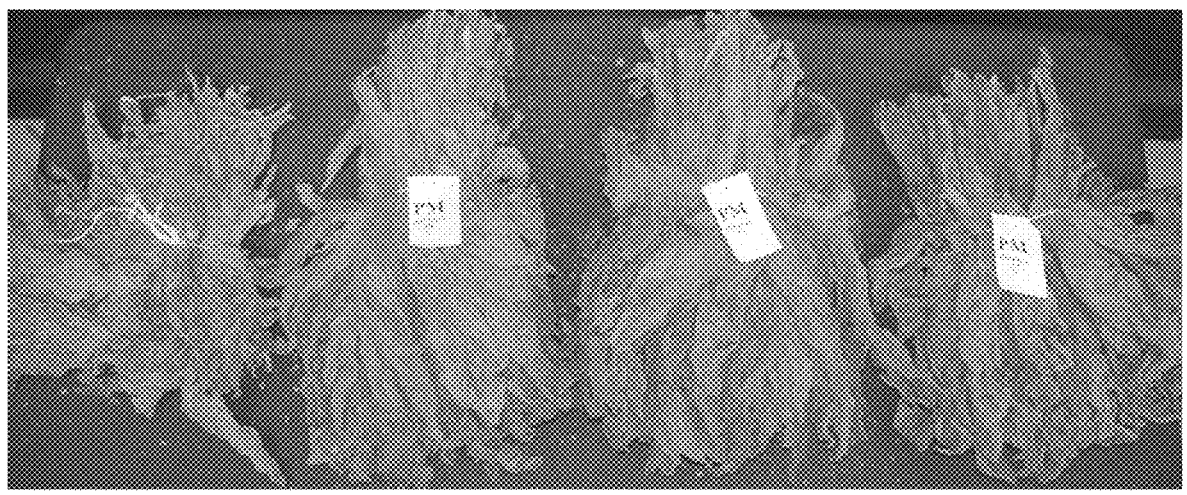

Photographs depicting mold growth on cured tobacco, including TN90 LC (FIG. 6A), LA BU 21 (FIG. 6B), TN90 comprising an RNAi construct to downregulate PR50 (FIG. 6C), TN90 comprising an RNAi construct to downregulate PMT genes (FIG. 6D), and TN90 comprising edits to all five PMT genes (FIG. 6E).

Figure 7:
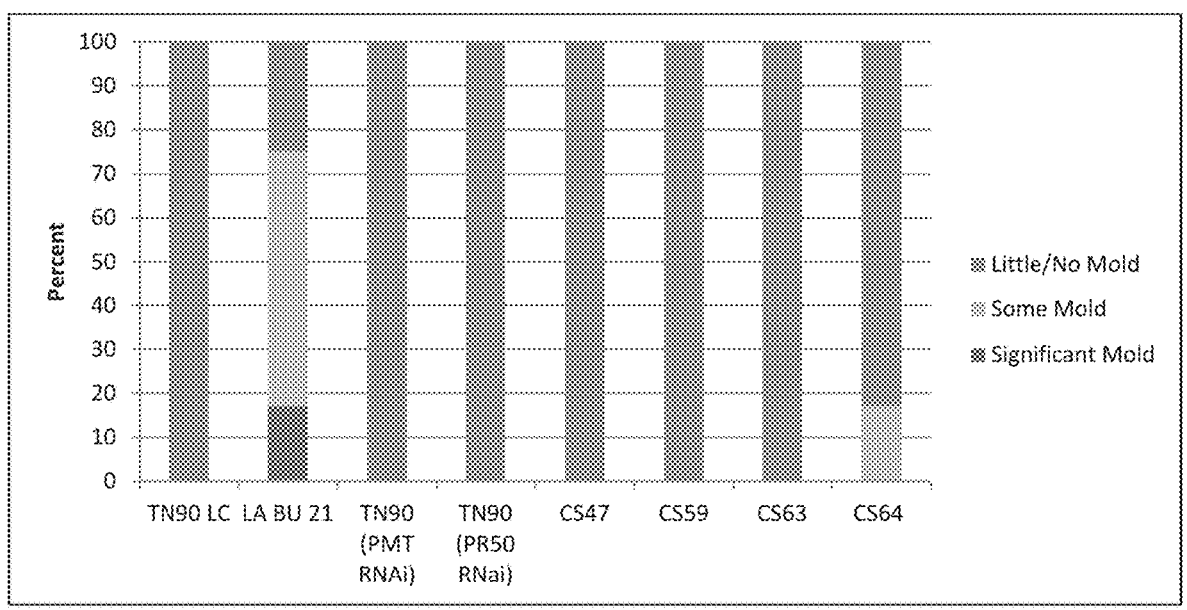

FIG. 7: Depiction of mold infection observed in the lines examined in FIGS. 6A-6E.

DETAILED DESCRIPTION

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents and publications are incorporated by reference in their entirety.

As used herein, the singular form "a," "an,' and "the" include plural references unless the context clearly dictates otherwise. For example, the term "a compound" or "at least one compound" may include a plurality of compounds, including mixtures thereof.

When the term "about" is used in conjunction with a numerical range, it modifies that range by extending the boundaries above and below the numerical values set forth by 10%.

As used herein, phrases such as "less than", "more than", "at least", "at most", "approximately", "below", "above", and "about", when used in conjunction with a series of numerical values, modify each and every value within the series. For example, an expression of "less than 1%, 2%, or 3%" is equivalent to "less than 1%, less than 2%, or less than 3%."

As used herein, a tobacco plant refers to a plant from the species *Nicotiana tabacum*.

Nicotine biosynthesis in tobacco starts with the methylation of the polyamine, putrescine, to N-methylputrescine by the enzyme, putrescine N-methyltransferase (PMT), using S-adenosyl-methionine as the co-factor. This is a step that commits precursor metabolites to nicotine biosynthesis. PMT enzymes are classified under the enzyme classification system as EC 2.1.1.53. In *Nicotiana tabacum*, five genes encode putrescine N-methyltransferases, designated PMT1a, PMT1b, PMT2, PMT3, and PMT4. Table 1A lists genomic DNA sequences, cDNA sequences, and protein sequences of these five PMT genes in a TN90 plant. The present disclosure describes compositions and methods that are used to edit PMT genes to produce pmt mutant plants having reduced nicotine levels while maintaining leaf quality.

As used herein, "PMT1b" or the "PMT1b gene" refers to a genic locus in tobacco encoding a polypeptide having an exemplary amino acid sequence in TN90 as set forth in SEQ ID No. 11.

As used herein, "PMT1a" or the "PMT1a gene" refers to a genic locus in tobacco encoding a polypeptide having an exemplary amino acid sequence in TN90 as set forth in SEQ ID No. 12.

As used herein, "PMT2" or the "PMT2 gene" refers to a genic locus in tobacco encoding a polypeptide having an exemplary amino acid sequence in TN90 as set forth in SEQ ID No. 13.

As used herein, "PMT3" or the "PMT3 gene" refers to a genic locus in tobacco encoding a polypeptide having an exemplary amino acid sequence in TN90 as set forth in SEQ ID No. 14.

As used herein, "PMT4" or the "PMT4 gene" refers to a genic locus in tobacco encoding a polypeptide having an exemplary amino acid sequence in TN90 as set forth in SEQ ID No. 15.

As used herein, a mutation refers to an inheritable genetic modification introduced into a gene to reduce, inhibit, or eliminate the expression or activity of a product encoded by the gene. Such a modification can be in any sequence region of a gene, for example, in a promoter, 5' UTR, exon, intron, 3' UTR, or terminator region. In an aspect, mutations are not natural polymorphisms that exist in a particular tobacco variety or cultivar. As used herein, a "mutant allele" refers to an allele from a locus where the allele comprises a mutation.

As used herein, a "pint mutant" refers to a tobacco plant comprising one or more mutations in one or more PMT genes. A pmt mutant can be a single mutant, a double mutant, a triple mutant, a quadruple mutant, or a quintuple mutant. As used herein, a single, double, triple, quadruple, or quintuple pmt mutant refers to a mutant having modifications in one, two, three, four, or five PMT genes, respectively. A pmt mutant can also be a homozygous mutant, a heterozygous mutant, or a heteroallelic mutant combination in one or more PMT genes.

As used herein, a gene name or a genic locus name is capitalized and shown in italic, e.g., PMT1a, PMT1b, PMT2, PMT3, and PMT4. A protein or polypeptide name is capitalized without being italicized, e.g., PMT1a, PMT1b, PMT2, PMT3, and PMT4. A mutant name (for either referencing to a general mutation in a gene or a group of genes, or referencing to a specific mutant allele) is shown in lower case and italic, e.g., pmt, pmt1a, pmt1b, pmt2, pmt3, and pmt4.

In an aspect, the present disclosure provides a tobacco plant, or part thereof, comprising one or more mutant alleles in at least one PMT gene selected from the group consisting of PMT1a, PMT1b, PMT2, PMT3, and PMT4, wherein the tobacco plant is capable of producing a leaf comprising a nicotine level less than the nicotine level of a leaf from a control tobacco plant not having the one or more mutant alleles when grown and processed under comparable conditions. In an aspect, a single pmt mutant tobacco plant is provided. In another aspect, a single pmt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the single pmt mutation when grown in similar growth conditions. In a further aspect, a single pmt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the single pmt mutation when grown in similar growth conditions.

In another aspect, a tobacco plant comprises one or more mutant alleles in at least two PMT genes selected from the group consisting of PMT1a, PMT1b, PMT2, PMT3, and PMT4. In an aspect, a double pmt mutant tobacco plant is provided. In another aspect, a double pmt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the double pmt mutations when grown in similar growth conditions. In a further aspect, a double pmt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the double pmt mutations when grown in similar growth conditions.

In a further aspect, a tobacco plant comprises one or more mutant alleles in at least three PMT genes selected from the group consisting of PMT1a, PMT1b, PMT2, PMT3, and PMT4. In an aspect, a triple pmt mutant tobacco plant is provided. In another aspect, a triple pmt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the triple pmt mutations when grown in similar growth conditions. In a further aspect, a triple pmt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the triple pmt mutations when grown in similar growth conditions.

In another aspect, a tobacco plant comprises one or more mutant alleles in at least four PMT genes selected from the group consisting of PMT1a, PMT1b, PMT2, PMT3, and PMT4. In an aspect, a quadruple pmt mutant tobacco plant is provided. In another aspect, a quadruple pmt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the quadruple pmt mutations when grown in similar growth conditions. In a further aspect, a quadruple pmt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the quadruple pmt mutations when grown in similar growth conditions.

In a further aspect, a tobacco plant comprises one or more mutant alleles in five PMT genes selected from the group consisting of PMT1a, PMT1b, PMT2, PMT3, and PMT4. In an aspect, a quintuple pmt mutant tobacco plant is provided. In another aspect, a quintuple pmt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the quintuple pmt mutations when grown in similar growth conditions. In a further aspect, a quintuple pmt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the quintuple pmt mutations when grown in similar growth conditions.

In an aspect, a tobacco plant is a single pmt mutant, a double pmt mutant, a triple mutant, a quadruple mutant, or a quintuple mutant as listed in Tables 8A to 8E. In another aspect, a tobacco plant comprises one or more pmt mutant alleles listed in Tables 5A to 5E and Tables 12A to 12E. Each and every combination of the pmt mutant alleles listed in Tables 5A to 5E and Tables 12A to 12E is also provided to give rise to a single pmt mutant, a double pmt mutant, a triple mutant, a quadruple mutant, or a quintuple mutant. Each of the mutated loci can be either homozygous or heterozygous, or comprises a heteroallelic combination. In another aspect, a tobacco plant comprises a pmt mutant genotype combination as shown for each individual line listed in Tables 4A to 4E and Table 10. In an aspect, a tobacco plant comprises a pmt mutant allele sequence selected from the group consisting of SEQ ID Nos. 21 to 200, 410 to 441, 474 to 505, 538 to 569, 602 to 633, and 666 to 697. In another aspect, the present disclosure provides a double pmt mutant, a triple mutant, a quadruple mutant, or a quintuple mutant comprising pmt mutant allele sequences selected from the group consisting of SEQ ID Nos. 21 to 200, 410 to 441, 474 to 505, 538 to 569, 602 to 633, and 666 to 697.

In an aspect, a tobacco plant is capable of producing a leaf comprising a nicotine level less than 90%, 80%, 70%, 60%, 50%, 40%, 30%, 20%, 15%, 10%, 9%, 8%, 7%, 6%, 5%, 4%, 3%, 2%, 1%, 0.5%, or 0.25% of the nicotine level of a leaf from a control tobacco plant when grown and processed under comparable conditions. In another aspect, a tobacco plant is capable of producing a leaf comprising a nicotine level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control tobacco plant when grown and processed under comparable conditions.

In another aspect, a tobacco plant is capable of producing a leaf comprising a total alkaloid level less than 90%, 80%, 70%, 60%, 50%, 40%, 30%, 20%, 15%, 10%, 9%, 8%, 7%, 6%, 5%, 4%, 3%, 2%, 1%, 0.5%, or 0.25% of the total alkaloid level of a leaf from a control tobacco plant when grown and processed under comparable conditions. In another aspect, a tobacco plant is capable of producing a leaf comprising a total alkaloid level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the total alkaloid level of a control tobacco plant when grown and processed under comparable conditions.

In a further aspect, a tobacco plant is capable of producing a leaf comprising a total alkaloid level less than 40%, 35%, 30%, 25%, 20%, 15%, 10%, or 5% of the total alkaloid level of a leaf from a control tobacco plant when grown and processed under comparable conditions.

In an aspect, a mutant pmt allele comprises a mutation in a PMT sequence region selected from the group consisting of a promoter, 5' UTR, first exon, first intron, second exon, second intron, third exon, third intron, fourth exon, fourth intron, fifth exon, fifth intron, sixth exon, sixth intron, seventh exon, seventh intron, eighth exon, 3' UTR, terminator, and any combination thereof. In another aspect, a mutant pmt allele comprises a mutation in a PMT genomic sequence region listed in Tables 1D to 1H.

In another aspect, a mutant pmt allele comprises one or more mutation types selected from the group consisting of a nonsense mutation, a missense mutation, a frameshift mutation, a splice-site mutation, and any combination thereof. In an aspect, a mutant pmt allele is a null allele or a knock-out allele.

In an aspect, a mutant pmt allele results in one or more of the following: a PMT protein truncation, a non-translatable PMT gene transcript, a non-functional PMT protein, a premature stop codon in a PMT gene, and any combination thereof.

In another aspect, a mutant pmt allele comprises a mutation selected from the group consisting of a substitution, a deletion, an insertion, a duplication, and an inversion of one or more nucleotides relative to a wild-type PMT gene.

In an aspect, a pmt mutant comprises a zygosity status selected from the group consisting of homozygous, heterozygous, and heteroallelic. In another aspect, a pmt mutant is homozygous or heteroallelic in at least 1, 2, 3, 4, or 5 PMT genes. In an aspect, a pmt mutant is homozygous or heteroallelic in at least 4 PMT genes. In another aspect, a pmt mutant is homozygous or heteroallelic in all five PMT genes. In another aspect, a pmt mutant comprises mutations in PMT1a and PMT3.

In an aspect, a tobacco plant is capable of producing a leaf comprising a nicotine level selected from the group consisting of less than 0.15%, less than 0.125%, less than 0.1%, less than 0.08%, less than 0.06%, less than 0.05%, less than 0.04%, less than 0.03%, less than 0.02%, and less than 0.01% dry weight.

In another aspect, a tobacco plant is capable of producing a leaf comprising a total alkaloid level selected from the group consisting of less than 1%, less than 0.8%, less than 0.7%, less than 0.6%, less than 0.5%, less than 0.4%, less than 0.3%, and less than 0.2% dry weight.

In a further aspect, a tobacco plant is capable of producing a cured leaf comprising a total TSNA level of between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm.

In an aspect, a tobacco plant is capable of producing leaves, when cured, having a USDA grade index value selected from the group consisting of 50 or more, 55 or more, 60 or more, 65 or more, 70 or more, 75 or more, 80 or more, 85 or more, 90 or more, and 95 or more. In another aspect, a tobacco plant is capable of producing leaves, when cured, having a USDA grade index value comparable to that of a control plant when grown and cured in similar conditions, where the control plant shares an essentially identical genetic background with the tobacco plant except for the modification. In a further aspect, a tobacco plant is capable of producing leaves, when cured, having a USDA grade index value of at least about 65%, at least about 70%, at least about 75%, at least about 80%, at least about 85%, at least about 90%, at least about 95%, or at least about 98% of the USDA grade index value of a control plant when grown in similar conditions, where the control plant shares an essentially identical genetic background with the tobacco plant except the modification. In a further aspect, a tobacco plant is capable of producing leaves, when cured, having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a control plant. In a further aspect, a tobacco plant is capable of producing leaves, when cured, having a USDA grade index value of between 70% and 125%, between 75% and 120%, between 80% and 115%, between 85% and 110%, or between 90% and 100% of the USDA grade index value of a control plant.

In an aspect, a tobacco plant comprises nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the control plant shares an essentially identical genetic background with the tobacco plant except for the modification.

In a further aspect, a tobacco plant comprises one or more pmt mutant alleles and further comprises a transgene or mutation directly suppressing the expression or activity of one or more genes encoding a product selected from the group consisting of MPO, QPT, BBL, A622, aspartate oxidase, agmatine deiminase (AIC), arginase, diamine oxidase, ornithine decarboxylase, arginine decarboxylase, nicotine uptake permease (NUP), and MATE transporter.

In an aspect, a tobacco plant comprises one or more pmt mutant alleles and further comprises a mutation in an ERF gene of Nic2 locus. In an aspect, a tobacco plant further comprises one or more mutations in two or more, three or more, four or more, five or more, six or more, or all seven genes selected from the group consisting of ERF189, ERF115, ERF221, ERF104, ERF179, ERF17, and ERF168. See Shoji et al., *Plant Cell*, (10):3390-409 (2010); and Kajikawa et al., *Plant physiol.* 2017, 174:999-1011. In an aspect, a tobacco plant further comprises one or more mutations in ERF189, ERF115, or both.

In an aspect, a tobacco plant comprises one or more qpt mutant alleles and further comprises a mutation in an ERF gene of Nic1 locus (or Nic1b locus as in PCT/US2019/013345 filed on Jan. 11, 2019, published as WO/2019/140297). See also WO/2018/237107. In an aspect, a tobacco plant further comprises one or more mutations in two or more, three or more, four or more, five or more, six or more, or seven or more genes selected from the group consisting of ERF101, ERF110, ERFnew, ERF199, ERF19, ERF130, ERF16, ERF29, ERF210, and ERF91L2. See Kajikawa et al., *Plant physiol.* 2017, 174:999-1011. In an aspect, a tobacco plant further comprises one or more mutations in one or more, two or more, three or more, four or more, five or more, or all six genes selected from the group consisting of ERFnew, ERF199, ERF19, ERF29, ERF210, and ERF91L2.

In an aspect, the present disclosure further provides a pmt mutant tobacco plant, or part thereof, comprising a nicotine or total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.025%, less than 0.01%, and less than 0.005%, where the tobacco plant is capable of producing leaves, when cured, having a USDA grade index value of 50 or more 55 or more, 60 or more, 65 or more, 70 or more, 75 or more, 80 or more, 85 or more, 90 or more, and 95 or more. In another aspect, such pmt mutant tobacco plant comprises a nicotine level of less than 0.02% and are capable of producing leaves, when cured, having a USDA grade index value of 70 or more. In a further aspect, such tobacco plant comprises a nicotine level of less than 0.01% and are capable of producing leaves, when cured, having a USDA grade index value of 70 or more.

In an aspect, the present disclosure also provides a tobacco plant, or part thereof, comprising a non-transgenic mutation, where the non-transgenic mutation reduces the nicotine or total alkaloid level of the tobacco plant to below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the tobacco plant is capable of producing leaves, when cured, having a USDA grade index value comparable to the USDA grade index value of the control plant, and where the control plant shares an essentially identical genetic background with the tobacco plant except the non-transgenic mutation.

In an aspect, a tobacco plant comprises a pint mutation introduced by an approach selected from the group consisting of random mutagenesis and targeted mutagenesis. In another aspect, a pmt mutation is introduced by a targeted mutagenesis approach selected from the group consisting of meganuclease, zinc finger nuclease, TALEN, and CRISPR.

Unless specified otherwise, measurements of alkaloid or nicotine levels (or another leaf chemistry or property characterization) or leaf grade index values mentioned herein for a tobacco plant, variety, cultivar, or line refer to average measurements, including, for example, an average of multiple leaves of a single plant or an average measurement from a population of tobacco plants from a single variety, cultivar, or line.

Unless specified otherwise, the nicotine or alkaloid level (or another leaf chemistry or property characterization) of a tobacco plant is measured after topping in a pooled leaf sample collected from leaf number 3, 4, and 5 after topping. As used herein, whenever a comparison between leaves from two plants (e.g., a mutant plant versus a control plant) is mentioned, leaves from the same or comparable stalk position(s) and developmental stage(s) are intended so that the comparison can demonstrate effects due to genotype differences, not from other factors. As an illustration, leaf 3 of a wild-type control plant is intended as a reference point for comparing with leaf 3 of a pmt mutant plant. In an aspect, a tobacco plant comprising at least one pmt mutation is compared to a control tobacco plant of the same tobacco variety.

Nicotine or alkaloid level (or another leaf chemistry or property characterization) of a tobacco plant can also be measured in alternative ways. In an aspect, the nicotine or alkaloid level (or another leaf chemistry or property characterization) of a tobacco plant is measured after topping in a leaf having the highest level of nicotine or alkaloid (or another leaf chemistry or property characterization). In an aspect, the nicotine or alkaloid level of a tobacco plant is measured after topping in leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In another aspect, the nicotine or alkaloid level (or another leaf chemistry or property characterization) of a tobacco plant is measured after topping in a pool of two or more leaves with consecutive leaf numbers selected from the group consisting of leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. In another aspect, the nicotine or alkaloid level (or another leaf chemistry or property characterization) of a tobacco plant is measured after topping in a leaf with a leaf number selected from the group consisting of between 1 and 5, between 6 and 10, between 11 and 15, between 16 and 20, between 21 and 25, and between 26 and 30. In another aspect, the nicotine or alkaloid level (or another leaf chemistry or property characterization) of a tobacco plant is measured after topping in a pool of two or more leaves with leaf numbers selected from the group consisting of between 1 and 5, between 6 and 10, between 11 and 15, between 16 and 20, between 21 and 25, and between 26 and 30. In another aspect, the nicotine or alkaloid level (or another leaf chemistry or property characterization) of a tobacco plant is measured after topping in a pool of three or more leaves with leaf numbers selected from the group consisting of between 1 and 5, between 6 and 10, between 11 and 15, between 16 and 20, between 21 and 25, and between 26 and 30.

As used herein, leaf numbering is based on the leaf position on a tobacco stalk with leaf number 1 being the youngest leaf (at the top) after topping and the highest leaf number assigned to the oldest leaf (at the bottom).

A population of tobacco plants or a collection of tobacco leaves for determining an average measurement (e.g., alkaloid or nicotine level or leaf grading) can be of any size, for example, 5, 10, 15, 20, 25, 30, 35, 40, or 50. Industry-accepted standard protocols are followed for determining average measurements and grad index values.

As used herein, "topping" refers to the removal of the stalk apex, including the SAM, flowers, and up to several adjacent leaves, when a tobacco plant is near vegetative maturity and around the start of reproductive growth. Typically, tobacco plants are topped in the button stage (soon after the flower begins to appear). For example, greenhouse or field-grown tobacco plants can be topped when 50% of the plants have at least one open flower. Topping a tobacco plant results in the loss of apical dominance and also induces increased alkaloid production.

Unless indicated otherwise, the nicotine or alkaloid level (or another leaf chemistry or property characterization) of a tobacco plant is measured 2 weeks after topping. Alternatively, other time points can be used. In an aspect, the nicotine or alkaloid level (or another leaf chemistry or property characterization) of a tobacco plant is measured about 1, 2, 3, 4, or 5 weeks after topping. In another aspect, the nicotine, alkaloid, or polyamine level (or another leaf chemistry or property characterization) of a tobacco plant is measured about 3, 5, 7, 10, 12, 14, 17, 19 or 21 days after topping.

As used herein, "similar growth conditions" or "comparable growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine. Minor tobacco alkaloids include nicotine-n-oxide, N-methyl anatabine, N-methyl anabasine, pseudooxynicotine, 2,3 dipyridyl and others.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E. See also Hibi et al., *Plant Physiology* 100: 826-35 (1992) for a method using gas-liquid chromatography equipped with a capillary column and an FID detector.

Unless specifically indicated otherwise, alkaloids and nicotine levels are measured using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009). Alternatively, tobacco total alkaloids can be measured using a segmented-flow colorimetric method developed for analysis of tobacco samples as adapted by Skalar Instrument Co (West Chester, Pa.) and described by Collins et al., *Tobacco Science* 13:79-81 (1969). In short, samples of tobacco can be dried, ground, and extracted prior to analysis of total alkaloids and reducing sugars. The method then employs an acetic acid/methanol/water extraction and charcoal for decolorization. Determination of total alkaloids is based on the reaction of cyanogen chloride with nicotine alkaloids in the presence of an aromatic amine to form a colored complex which is measured at 460 nm. Unless specified otherwise, total alkaloid levels or nicotine levels shown herein are on a dry weight basis (e.g., percent total alkaloid or percent nicotine).

In an aspect, a tobacco plant comprises an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, a tobacco plant comprises an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, between 3.5% and 3.6% on a dry weight basis. In a further aspect, a tobacco plant comprises an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides a tobacco plant having an altered nicotine level without negative impacts over other tobacco traits, e.g., leaf grade index value. In an aspect, a low-nicotine or nicotine-free tobacco variety provides cured tobacco of commercially acceptable grade. Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U. S. Type 62), Effective April 1971. A USDA grade index value can be determined according to an industry accepted grade index. See, e.g., Bowman et al, *Tobacco Science*, 32:39-40(1988); Legacy Tobacco Document Library (Bates Document #523267826-523267833, Jul. 1, 1988, Memorandum on the Proposed Burley Tobacco Grade Index); and Miller et al., 1990, *Tobacco Intern.*, 192:55-57 (all foregoing references are incorporated by inference in their entirety). In an aspect, a USDA grade index is a 0-100 numerical representation of federal grade received and is a weighted average of all stalk positions. A higher grade index indicates higher quality. Alternatively, leaf grade can be determined via hyperspectral imaging. See e.g., WO 2011/027315 (published on Mar. 10, 2011, and incorporated by inference in its entirety).

In an aspect, a tobacco plant provided herein comprises a similar level of one or more tobacco aroma compounds compared to a control tobacco plant when grown in similar growth conditions. In another aspect, a tobacco plant provided herein comprise a similar level of one or more tobacco aroma compounds selected from the group consisting of 3-methylvaleric acid, valeric acid, isovaleric acid, a labdenoid, a cembrenoid, a sugar ester, and a reducing sugar, compared to a control tobacco plant when grown in similar growth conditions.

As used herein, tobacco aroma compounds are compounds associated with the flavor and aroma of tobacco smoke. These compounds include, but are not limited to, 3-methylvaleric acid, valeric acid, isovaleric acid, cembrenoid and labdenoid diterpenes, and sugar esters. Concentrations of tobacco aroma compounds can be measured by any known metabolite profiling methods in the art including, without limitation, gas chromatography mass spectrometry (GC-MS), Nuclear Magnetic Resonance Spectroscopy, liquid chromatography-linked mass spectrometry. See The Handbook of Plant Metabolomics, edited by Weckwerth and Kahl, (Wiley-Blackwell) (May 28, 2013).

As used herein, "reducing sugar(s)" are any sugar (monosaccharide or polysaccharide) that has a free or potentially free aldehyde or ketone group. Glucose and fructose act as nicotine buffers in cigarette smoke by reducing smoke pH and effectively reducing the amount of "free" unprotonated nicotine. Reducing sugars balances smoke flavor, for example, by modifying the sensory impact of nicotine and other tobacco alkaloids. An inverse relationship between sugar content and alkaloid content has been reported across tobacco varieties, within the same variety, and within the same plant line caused by planting conditions. Reducing sugar levels can be measured using a segmented-flow colorimetric method developed for analysis of tobacco samples as adapted by Skalar Instrument Co (West Chester, Pa.) and described by Davis, Tobacco Science 20:139-144 (1976). For example, a sample is dialyzed against a sodium carbonate solution. Copper neocuproin is added to the sample and the solution is heated. The copper neocuproin chelate is reduced in the presence of sugars resulting in a colored complex which is measured at 460 nm.

In an aspect, a tobacco plant comprises one or more non-naturally existing mutant alleles in one or more PMT gene loci which reduce or eliminate PMT enzymatic activity from the one or more PMT gene loci. In an aspect, these mutant alleles result in lower nicotine levels. Mutant pmt alleles can be introduced by any method known in the art including random or targeted mutagenesis approaches.

Such mutagenesis methods include, without limitation, treatment of seeds with ethyl methylsulfate (EMS) (Hildering and Verkerk, In, The use of induced mutations in plant breeding. Pergamon press, pp 317-320, 1965) or UV-irradiation, X-rays, and fast neutron irradiation (see, for example, Verkerk, *Neth. J. Agric. Sci.* 19:197-203, 1971; and Poehlman, Breeding Field Crops, Van Nostrand Reinhold, N.Y. (3.sup.rd ed), 1987), transposon tagging (Fedoroff et al., 1984; U.S. Pat. Nos. 4,732,856 and 5,013,658), as well as T-DNA insertion methodologies (Hoekema et al., 1983; U.S. Pat. No. 5,149,645). EMS-induced mutagenesis consists of chemically inducing random point mutations over the length of the genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene. The types of mutations that may be present in a tobacco gene include, for example, point mutations, deletions, insertions, duplications, and inversions. Such mutations desirably are present in the coding region of a tobacco gene; however mutations in the promoter region, and intron, or an untranslated region of a tobacco gene may also be desirable.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes can be determined using methods that are well known in the art. Insertional mutations in gene exons usually result in null-mutants. Mutations in conserved residues can be particularly effective in inhibiting the function of a protein. In an aspect, tobacco plants comprise a nonsense (e.g., stop codon) mutation in one or more PMT genes described herein.

It will be appreciated that, when identifying a mutation, the endogenous reference DNA sequence should be from the same variety of tobacco. For example, if a modified tobacco plant comprising a mutation is from the variety TN90, then the endogenous reference sequence must be the endogenous TN90 sequence, not a homologous sequence from a different tobacco variety (e.g., K326). Similarly, if a modified tobacco cell comprising a mutation is a TN90 cell, then the endogenous reference sequence must be the endogenous TN90 sequence, not a homologous sequence from a tobacco cell from a different tobacco variety (e.g., K326).

In an aspect, the present disclosure also provides a tobacco line with altered nicotine levels while maintaining commercially acceptable leaf quality. This line can be produced by introducing mutations into one or more PMT genes via precise genome engineering technologies, for example, Transcription activator-like effector nucleases (TALENs), meganuclease, zinc finger nuclease, and a clustered regularly-interspaced short palindromic repeats (CRISPR)/Cas9 system, a CRISPR/Cpf1 system, a CRISPR/Csm1 system, and a combination thereof (see, for example, U.S. Patent Application publication 2017/0233756). See, e.g., Gaj et al., *Trends in Biotechnology,* 31(7):397-405 (2013).

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454), enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In an aspect, a tobacco plant or plant genome provided herein is mutated or edited by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, or a CRISPR/Csm1 nuclease.

As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide selected from the group consisting of SEQ ID NOs: 1 to 10, and fragments thereof. In another aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs: 11 to 15.

Meganucleases, ZFNs, TALENs, CRISPR/Cas9, CRISPR/Csm1 and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In an aspect, a method provided comprises editing a plant genome with a nuclease provided to mutate at least 1, at least 2, at least 3, at least 4, at least 5, at least 6, at least 7, at least 8, at least 9, at least 10, or more than 10 nucleotides in the plant genome via HR with a donor polynucleotide. In an aspect, a mutation provided is caused by genome editing using a nuclease. In another aspect, a mutation provided is caused by non-homologous end-joining or homologous recombination.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The *Xanthomonas* pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

A relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39:e82; and tale-nt.cac.cornell.edu/about.

A CRISPR/Cas9 system, CRISPR/Csm1, or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9, CRISPR/Csm1, and a CRISPR/Cpf1 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 and Csm1 act in a similar manner to Cas9, but Cpf1 and Csm1 do not require a tracrRNA.

In still another aspect, a tobacco plant provided here comprises one or more pint mutations and further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to a control plant lacking one or more mutations in one or more loci encoding a nicotine demethylase. In an aspect, a tobacco plant described further comprises reduced nicotine demethylase activity compared to a control plant when grown and cured under comparable conditions.

In an aspect, a pint mutant tobacco plant further comprises a mutation capable of producing a leaf comprising an anabasine level less than the anabasine level of a leaf from a wild-type control tobacco plant when grown and processed under comparable conditions. In another aspect, a pint mutant tobacco plant further comprises a mutation capable of producing a leaf comprising an anabasine level less than 5%, 10%, 20%, 25%, 30%, 40%, 50%, 60%, 70%, or 80% of the anabasine level of a leaf from a wild-type control tobacco plant when grown and processed under comparable conditions.

In an aspect, a pint mutant tobacco plant comprises a further mutation capable of producing a leaf comprising a more than 2 fold reduction of the anatabine level compared to a leaf from a control tobacco plant when grown and processed under comparable conditions. In another aspect, a pint mutant tobacco plant comprises a further mutation capable of producing a leaf comprising a more than 3, 4, 5, 6, 7, 8, 9, 10, 11, 12, or 13 fold reduction of the anatabine level compared to a leaf from a wild-type control tobacco plant when grown and processed under comparable conditions. In an aspect, a mutation providing lower level of anatabine is a mutation described in US Application Publication No. 2014/0283165 and US Application Publication No. 2016/0010103. In another aspect, a pint mutant further comprises a mutation in a quinolate phosphoribosyl transferase (QPT) or quinolinate synthase (QS) gene. In a further aspect, a pmt mutant plant further comprises a transgene or mutation suppressing the expression or activity of a QPT or QS gene.

In an aspect, a pint mutant tobacco plant further comprises a mutation capable of providing a nornicotine level less than 80%, 75%, 70%, 65%, 60%, 55%, 50%, 45%, 40%, or 35% of the nornicotine level of a leaf from a wild-type control tobacco plant when grown and processed under comparable conditions.

In an aspect, a pmt mutant tobacco plant is capable of producing a cured leaf comprising a total N-nitrosonornicotine (NNN) level of less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm.

In another aspect, a pmt mutant tobacco plant is capable of producing a cured leaf comprising a total NNN level of between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 parts per million (ppm).

In an aspect, a pmt mutant tobacco plant is capable of producing a cured leaf comprising a total nicotine-derived nitrosamine ketone (NNK) level of less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm.

In another aspect, a pmt mutant tobacco plant is capable of producing a cured leaf comprising a total NNK level of between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm.

In an aspect, a pint mutant tobacco plant further comprises a mutation or transgene providing an increased level of one or more antioxidants. In another aspect, a pmt mutant tobacco plant further comprises a genetic modification in an endogenous gene and further comprises an increased level of one or more antioxidants in a cured leaf compared to a control cured tobacco leaf lacking the genetic modification, where the endogenous gene encodes an antioxidant biosynthetic enzyme, a regulatory transcription factor of an antioxidant, an antioxidant transporter, an antioxidant metabolic enzyme, or a combination thereof. In a further aspect, a pint mutant tobacco plant further comprises a transgene and further comprises an increased level of one or more antioxidants in a cured leaf compared to a control cured tobacco leaf lacking the transgene, where the transgene encodes or directly modulates an antioxidant biosynthetic enzyme, a regulatory transcription factor of an antioxidant, an antioxidant transporter, an antioxidant metabolic enzyme, or a combination thereof. In an aspect, a pint mutant tobacco plant further comprises a transgene or a cisgenic construct expressing one or more genes selected from the group consisting of AtPAP1, NtAN2, NtAN1, NtJAF13, NtMyb3, chorismate mutase, and arogenate dehydrotase (ADT). In another aspect, a pint mutant tobacco plant further comprises one or more transgenes or genetic modification for increasing antioxidants or decreasing one or more TSNAs as described in WIPO Publication No. 2018/067985 or US Publication No. 2018/0119163.

In an aspect, a tobacco plant described is a modified tobacco plant. As used herein, "modified", in the context of a plant, refers to a plant comprising a genetic alteration introduced for certain purposes and beyond natural polymorphisms.

In an aspect, a tobacco plant described is a cisgenic plant. As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In an aspect, a plant, plant cell, or plant genome provided is cisgenic. Cisgenic plants, plant cells, and plant genomes provided can lead to ready-to-use tobacco lines. In another aspect, a tobacco plant provided comprises no non-tobacco genetic material or sequences.

As used herein, "gene expression" or expression of a gene refers to the biosynthesis or production of a gene product, including the transcription and/or translation of the gene product.

In an aspect, a tobacco plant provided comprises one or more pmt mutations and further comprises reduced expression or activity of one or more genes involved in nicotine biosynthesis or transport. Genes involved in nicotine biosynthesis include, but are not limited to, arginine decarboxylase (ADC), methylputrescine oxidase (MPO), NADH dehydrogenase, ornithine decarboxylase (ODC), phosphoribosylanthranilate isomerase (PRAI), quinolate phosphoribosyl transferase (QPT), and S-adenosyl-methionine synthetase (SAMS). Nicotine Synthase, which catalyzes the condensation step between a nicotinic acid derivative and methylpyrrolinium cation, has not been elucidated although two candidate genes (A622 and NBB1) have been proposed. See US 2007/0240728 A1 and US 2008/0120737A1. A622 encodes an isoflavone reductase-like protein. In addition, several transporters may be involved in the translocation of nicotine. A transporter gene, named MATE, has been cloned and characterized (Morita et al., PNAS 106:2447-52 (2009)).

In an aspect, a tobacco plant provided comprises one or more pmt mutations and further comprises a reduced level of mRNA, protein, or both of one or more genes encoding a product selected from the group consisting of MPO, QPT, ADC, ODC, PRAI, SAMS, BBL, MATE, A622, and NBB1, compared to a control tobacco plant. In another aspect, a tobacco plants provided comprises one or more pint mutations and further comprises a transgene directly suppressing the expression of one or more genes encoding a product selected from the group consisting of MPO, QPT, ADC, ODC, PRAI, SAMS, BBL, MATE, A622, and NBB1. In another aspect, a tobacco plant provided comprises one or more pmt mutations and further comprises a transgene or mutation suppressing the expression or activity of one or more genes encoding a product selected from the group consisting of MPO, QPT, ADC, ODC, PRAI, SAMS, BBL, MATE, A622, and NBB1.

In an aspect, a tobacco plant provided is from a tobacco type selected from the group consisting of flue-cured tobacco, air-cured tobacco, dark air-cured tobacco, dark fire-cured tobacco, Galpao tobacco, and Oriental tobacco. In another aspect, a tobacco plant provided is from a tobacco type selected from the group consisting of Burley tobacco, Maryland tobacco, and dark tobacco.

In an aspect, a tobacco plant provided is in a flue-cured tobacco background or exhibits one or more flue-cured tobacco characteristic described here. Flue-cured tobaccos (also called Virginia or bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In an aspect, a low-alkaloid or low-nicotine tobacco plant or seed provided is in a flue-cured tobacco background selected from the group consisting of CC 13, CC 27, CC 33, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, a low-alkaloid or low-nicotine tobacco plant or seed provided is in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-l11, Speight G-l17, Speight 168, Speight 179, Speight NF-3, Va 116, Va 182, and any variety essentially derived from any one of the foregoing varieties. See WO 2004/041006 A1. In a further aspect, low-alkaloid or low-nicotine tobacco plants, seeds, hybrids, varieties, or lines are in any flue cured background selected from the group consisting of K326, K346, and NC 196.

In an aspect, a tobacco plant provided is in an air-cured tobacco background or exhibits one or more air-cured tobacco characteristic described here. Air-cured tobaccos include Burley, Md., and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In an aspect, a low-alkaloid or low-nicotine tobacco plant or seed provided is in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, Bu 21×Ky 10, HB04P, Ky 14×L 8, Kt 200, Newton 98, Pedigo 561, Pf561 and Va 509. In a further aspect, low-alkaloid or low-nicotine tobacco plants, seeds, hybrids, varieties, or lines are in any Burley background selected from the group consisting of TN 90, KT 209, KT 206, KT212, and HB 4488. In another aspect, a low-alkaloid or low-nicotine tobacco plant or seed provided is in a Maryland tobacco background selected from the group consisting of Md 10, Md 40, Md 201, Md 609, Md 872 and Md 341.

In an aspect, a tobacco plant provided is in a dark air-cured tobacco background or exhibits one or more dark air-cured tobacco characteristic described here. Dark air-cured tobaccos are distinguished from other types primarily by its curing process which gives dark air-cured tobacco its medium- to dark-brown color and distinct aroma. Dark air-cured tobaccos are mainly used in the production of chewing tobacco and snuff. In an aspect, a low-alkaloid or low-nicotine tobacco plant or seed provided is in a dark air-cured tobacco background selected from the group consisting of Sumatra, Jatim, Dominican Cubano, Besuki, One sucker, Green River, Va. sun-cured, and Paraguan Passado.

In an aspect, a tobacco plant provided is in a dark fire-cured tobacco background or exhibits one or more dark fire-cured tobacco characteristic described here. Dark fire-cured tobaccos are generally cured with low-burning wood fires on the floors of closed curing barns. Their leaves have low sugar content but high nicotine content. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In an aspect, a low-alkaloid or low-nicotine tobacco plant or seed provided is in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

In an aspect, a tobacco plant provided is in an Oriental tobacco background or exhibits one or more Oriental tobacco characteristic described here. Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In an aspect, a low-alkaloid or low-nicotine tobacco plant or seed provided is in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In an aspect, low-alkaloid or low-nicotine tobacco plants, seeds, hybrids, varieties, or lines are essentially derived from or in the genetic background of BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359, Maryland 609, HB3307PLC, HB4488PLC, KT206LC, KT209LC, KT210LC, KT212LC, R610LC, PVH2310, NC196, KTD14LC, KTD6LC, KTD8LC, PD7302LC, PD7305LC, PD7309LC, PD7318LC, PD7319LC, PD7312LC, ShireyLC, or any commercial tobacco variety according to standard tobacco breeding techniques known in the art.

All foregoing mentioned specific varieties of dark air-cured, Burley, Md., dark fire-cured, or Oriental type are listed only for exemplary purposes. Any additional dark air-cured, Burley, Md., dark fire-cured, Oriental varieties are also contemplated in the present application.

Also provided are populations of tobacco plants described. In an aspect, a population of tobacco plants has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants is in a soil type with low to medium fertility.

Also provided are containers of seeds from tobacco plants described. A container of tobacco seeds of the present disclosure may contain any number, weight, or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Containers of tobacco seeds may be any container available in the art. By way of non-limiting example, a container may be a box, a bag, a packet, a pouch, a tape roll, a tube, or a bottle.

Also provided is cured tobacco material made from a low-alkaloid or low-nicotine tobacco plant described. Further provided is cured tobacco material made from a tobacco plant described with higher levels of total alkaloid or nicotine.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In an aspect, green leaf tobacco provided can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, e.g., U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cure, aged, and fermented tobacco can be further processed (e.g., cut, shredded, expanded, or blended). See, for example, U.S. Pat. Nos. 4,528,993; 4,660,577; and 4,987,907. In an aspect, the cured tobacco material of the present disclosure is sun-cured. In another aspect, the cured tobacco material of the present disclosure is flue-cured, air-cured, or fire-cured.

The presence of mold on cured tobacco can significantly reduce the quality and marketability (e.g., leaf grade) of the cured leaves. Mold growth is a common problem that can occur during extended periods of high humidity (e.g., greater than 70% relative humidity) at temperatures between approximately 10° C. (50° F.) and 32.2° C. (90° F.). Mold tends to be more prevalent at higher temperatures.

Tobacco plants, varieties, and lines provided herein comprising a mutant allele in one or more PMT genes, two or more PMT genes, three or more PMT genes, four or more PMT genes, or five PMT genes exhibit reduced mold infection as compared to the low alkaloid tobacco variety LA Burley 21 (LA BU 21). Similarly, tobacco plants, varieties, and lines provided herein comprising an RNAi construct that downregulates expression or translation of one or more PMT genes, two or more PMT genes, three or more PMT genes, four or more PMT genes, or five PMT genes exhibit reduced mold infection as compared to the low alkaloid tobacco variety LA Burley 21 (LA BU 21).

LA BU 21 is a low total alkaloid tobacco line produced by incorporation of a low alkaloid gene(s) from a Cuban cigar variety into Burley 21 through several backcrosses (Legg et al., *Crop Science*, 10:212 (1970)). It has approximately 0.2% total alkaloids (dry weight) compared to the about 3.5% (dry weight) of its parent, Burley 21. LA B U 21 has a leaf grade well below commercially acceptable standards.

In an aspect, a cured tobacco leaf comprising a mutant allele of pmt1a comprises no observable mold infection. In another aspect, a cured tobacco leaf comprising a mutant allele of pmt1b comprises no observable mold infection. In another aspect, a cured tobacco leaf comprising a mutant allele of pmt2 comprises no observable mold infection. In another aspect, a cured tobacco leaf comprising a mutant allele of pmt3 comprises no observable mold infection. In another aspect, a cured tobacco leaf comprising a mutant allele of pmt4 comprises no observable mold infection. In another aspect, a cured tobacco leaf comprising a mutant allele of pmt1a, a mutant allele of pmt1b, a mutant allele of pmt2, a mutant allele of pmt3, and a mutant allele of pmt4 comprises no observable mold infection.

In an aspect, a cured tobacco leaf comprising a mutant allele of pmt1a comprises a reduced mold infection as compared to a control cured tobacco leaf from the variety LA BU 21. In another aspect, a cured tobacco leaf comprising a mutant allele of pmt1b comprises a reduced mold infection as compared to a control cured tobacco leaf from the variety LA BU 21. In another aspect, a cured tobacco leaf comprising a mutant allele of pmt2 comprises a reduced mold infection as compared to a control cured tobacco leaf from the variety LA BU 21. In another aspect, a cured tobacco leaf comprising a mutant allele of pmt3 comprises a reduced mold infection as compared to a control cured tobacco leaf from the variety LA BU 21. In another aspect, a cured tobacco leaf comprising a mutant allele of pmt4 comprises a reduced mold infection as compared to a control cured tobacco leaf from the variety LA BU 21. In another aspect, a cured tobacco leaf comprising a mutant allele of pmt1a, a mutant allele of pmt1b, a mutant allele of pmt2, a mutant allele of pmt3, and a mutant allele of pmt4 comprises a reduced mold infection as compared to a control cured tobacco leaf from the variety LA BU 21.

In an aspect, a cured leaf from a tobacco plant, variety, or line provided in any one of Tables 4A to 4E, Table 10, or Table 14 comprises no observable mold infection. In another aspect, a cured leaf from a tobacco plant, variety, or line provided in any one of Tables 4A to 4E, Table 10, or Table 14 comprises a reduced mold infection as compared to a control cured tobacco leaf from the variety LA BU 21.

In an aspect, a cured leaf from a tobacco plant, variety, or line comprising one or more pint mutations provided in any one of Tables 5A to 5E and Tables 12A to 12E comprises no observable mold infection. In another aspect, a cured leaf from a tobacco plant, variety, or line comprising one or more pmt mutations provided in any one of Tables 5A to 5E and Tables 12A to 12E comprises a reduced mold infection as compared to a control cured leaf from the variety LA BU 21.

In an aspect, a cured leaf from a tobacco plant, variety, or line comprising a mutant allele of pmt1a comprises a higher leaf grade than a control cured leaf from the variety LA BU 21. In an aspect, a cured leaf from a tobacco plant, variety, or line comprising a mutant allele of pmt1b comprises a higher leaf grade than a control cured leaf from the variety LA BU 21. In an aspect, a cured leaf from a tobacco plant, variety, or line comprising a mutant allele of pmt2 comprises a higher leaf grade than a control cured leaf from the variety LA BU 21. In an aspect, a cured leaf from a tobacco plant, variety, or line comprising a mutant allele of pmt3 comprises a higher leaf grade than a control cured leaf from the variety LA BU 21. In an aspect, a cured leaf from a tobacco plant, variety, or line comprising a mutant allele of pmt4 comprises a higher leaf grade than a control cured leaf from the variety LA BU 21. In another aspect, a cured tobacco leaf from a plant, variety, or line comprising a mutant allele of pmt1a, a mutant allele of pmt1b, a mutant allele of pmt2, a mutant allele of pmt3, and a mutant allele of pmt4 comprises a higher leaf grade than a control cured leaf from the variety LA BU 21.

In an aspect, a cured leaf from a tobacco plant, variety, or line provided in any one of Tables 4A to 4E, Table 10, or Table 14 comprises a higher leaf grade than a control cured leaf from the variety LA BU 21.

In an aspect, a cured leaf from a tobacco plant, variety, or line comprising one or more pint mutations provided in any one of Tables 5A to 5E and Tables 12A to 12E comprises a higher leaf grade than a control cured leaf from the variety LA BU 21.

In an aspect, a "reduced mold infection" refers to a reduced area of infected leaf. In another aspect, a "reduced mold infection" refers to a reduced number of viable mold spores on an infected leaf. Standard methods of detecting and counting viable mold spores are known and available in the art.

In an aspect, a reduced mold infection comprises a reduction of infected leaf area of at least 1% as compared to a control leaf. In an aspect, a reduced mold infection comprises a reduction of infected leaf area of at least 2% as compared to a control leaf. In an aspect, a reduced mold infection comprises a reduction of infected leaf area of at least 3% as compared to a control leaf. In an aspect, a reduced mold infection comprises a reduction of infected leaf area of at least 4% as compared to a control leaf. In an aspect, a reduced mold infection comprises a reduction of infected leaf area of at least 5% as compared to a control leaf. In an aspect, a reduced mold infection comprises a reduction of infected leaf area of at least 10% as compared to a control leaf. In an aspect, a reduced mold infection comprises a reduction of infected leaf area of at least 15% as compared to a control leaf. In an aspect, a reduced mold infection comprises a reduction of infected leaf area of at least 20% as compared to a control leaf. In an aspect, a reduced mold infection comprises a reduction of infected leaf area of at least 25% as compared to a control leaf. In an aspect, a reduced mold infection comprises a reduction of infected leaf area of at least 30% as compared to a control leaf. In an aspect, a reduced mold infection comprises a reduction of infected leaf area of at least 35% as compared to a control leaf. In an aspect, a reduced mold infection comprises a reduction of infected leaf area of at least 40% as compared to a control leaf. In an aspect, a reduced mold infection comprises a reduction of infected leaf area of at least 50% as compared to a control leaf. In an aspect, a reduced mold infection comprises a reduction of infected leaf area of at least 60% as compared to a control leaf. In an aspect, a reduced mold infection comprises a reduction of infected leaf area of at least 70% as compared to a control leaf. In an aspect, a reduced mold infection comprises a reduction of infected leaf area of at least 75% as compared to a control leaf. In an aspect, a reduced mold infection comprises a reduction of infected leaf area of at least 80% as compared to a control leaf. In an aspect, a reduced mold infection comprises a reduction of infected leaf area of at least 90% as compared to a control leaf. In an aspect, a reduced mold infection comprises a reduction of infected leaf area of at least 95% as compared to a control leaf. In an aspect, a reduced mold infection comprises a reduction of infected leaf area of 100% as compared to a control leaf.

In an aspect, a reduced mold infection comprises a reduction of infected leaf area of between 1% and 100% as compared to a control leaf. In an aspect, a reduced mold infection comprises a reduction of infected leaf area of between 1% and 90% as compared to a control leaf. In an aspect, a reduced mold infection comprises a reduction of infected leaf area of between 1% and 80% as compared to a control leaf. In an aspect, a reduced mold infection comprises a reduction of infected leaf area of between 1% and 70% as compared to a control leaf. In an aspect, a reduced mold infection comprises a reduction of infected leaf area of between 1% and 60% as compared to a control leaf. In an aspect, a reduced mold infection comprises a reduction of infected leaf area of between 1% and 50% as compared to a control leaf. In an aspect, a reduced mold infection comprises a reduction of infected leaf area of between 1% and 40% as compared to a control leaf. In an aspect, a reduced mold infection comprises a reduction of infected leaf area of between 1% and 30% as compared to a control leaf. In an aspect, a reduced mold infection comprises a reduction of infected leaf area of between 1% and 20% as compared to a control leaf. In an aspect, a reduced mold infection comprises a reduction of infected leaf area of between 1% and 10% as compared to a control leaf. In an aspect, a reduced mold infection comprises a reduction of infected leaf area of between 10% and 100% as compared to a control leaf. In an aspect, a reduced mold infection comprises a reduction of infected leaf area of between 20% and 100% as compared to a control leaf. In an aspect, a reduced mold infection comprises a reduction of infected leaf area of between 30% and 100% as compared to a control leaf. In an aspect, a reduced mold infection comprises a reduction of infected leaf area of between 40% and 100% as compared to a control leaf. In an aspect, a reduced mold infection comprises a reduction of infected leaf area of between 50% and 100% as compared to a control leaf. In an aspect, a reduced mold infection comprises a reduction of infected leaf area of between 60% and 100% as compared to a control leaf. In an aspect, a reduced mold infection comprises a reduction of infected leaf area of between 70% and 100% as compared to a control leaf. In an aspect, a reduced mold infection comprises a reduction of infected leaf area of between 80% and 100% as compared to a control leaf. In an aspect, a reduced mold infection comprises a reduction of infected leaf area of between 90% and 100% as compared to a control leaf. In an aspect, a reduced mold infection comprises a reduction of infected leaf area of between 10% and 75% as compared to a control leaf. In an aspect, a reduced mold infection comprises a reduction of infected leaf area of between 25% and 75% as compared to a control leaf. In an aspect, a reduced mold infection comprises a reduction of infected leaf area of between 25% and 50% as compared to a control leaf.

In an aspect, mold infecting cured tobacco is of a genus selected from the group consisting of *Cladosporium, Penicillium, Alternaria, Aspergillus*, and *Mucor*.

Tobacco material obtained from the tobacco lines, varieties or hybrids of the present disclosure can be used to make tobacco products. As used herein, "tobacco product" is defined as any product made or derived from tobacco that is intended for human use or consumption.

Tobacco products provided include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

In an aspect, a tobacco product of the present disclosure can be a blended tobacco product. In another aspect, a tobacco product of the present disclosure can be a low nicotine tobacco product. In a further aspect, a tobacco product of the present disclosure may comprise nornicotine at a level of less than about 3 mg/g. For example, the nornicotine content in such a product can be 3.0 mg/g, 2.5 mg/g, 2.0 mg/g, 1.5 mg/g, 1.0 mg/g, 750 μg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable.

In an aspect, cured tobacco material or tobacco products provided comprise an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, cured tobacco material or tobacco products provided comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, cured tobacco material or tobacco products provided comprise an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides methods for breeding tobacco lines, cultivars, or varieties comprising a desirable level of total alkaloid or nicotine, e.g., low nicotine or nicotine free. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in a $F_2$ or backcross generation using F1 hybrid plants or further crossing the F1 hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. A recurrent parent in the present disclosure can be a flue-cured variety, a Burley variety, a dark air-cured variety, a dark fire-cured variety, or an Oriental variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using the tobacco plants described includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In an aspect, this disclosure provides a tobacco plant, variety, line, or cell comprising one or more pmt mutations provided in any one of Tables 5A to 5E and Tables 12A to 12E.

In another aspect, this disclosure provides a tobacco plant, variety, line, or cell derived from any tobacco plant, variety, or line provided in any one of Tables 4A to 4E, Table 10, or Table 14.

In an aspect, this disclosure provides the tobacco line 18GH203 and $F_1$ or $F_2$ tobacco plants, or male sterile tobacco plants, derived therefrom. In an aspect, this disclosure provides the tobacco line 18GH341 and $F_1$ or $F_2$ tobacco plants, or male sterile tobacco plants, derived therefrom. In an aspect, this disclosure provides the tobacco line 17GH1678 and $F_1$ or $F_2$ tobacco plants, or male sterile tobacco plants, derived therefrom. In an aspect, this disclosure provides the tobacco line 17GH1680 and $F_1$ or $F_2$ tobacco plants, or male sterile tobacco plants, derived therefrom. In an aspect, this disclosure provides the tobacco line 17GH1804 and $F_1$ or $F_2$ tobacco plants, or male sterile tobacco plants, derived therefrom. In an aspect, this disclosure provides the tobacco line 17GH1898 and $F_1$ or $F_2$ tobacco plants, or male sterile tobacco plants, derived therefrom. In an aspect, this disclosure provides the tobacco line 18GH207 and $F_1$ or $F_2$ tobacco plants, or male sterile tobacco plants, derived therefrom. In an aspect, this disclosure provides the tobacco line 18GH342 and $F_1$ or $F_2$ tobacco plants, or male sterile tobacco plants, derived therefrom. In an aspect, this disclosure provides the tobacco line 18GH343 and $F_1$ or $F_2$ tobacco plants, or male sterile tobacco plants, derived therefrom. In an aspect, this disclosure provides the tobacco line 18GH348 and $F_1$ or $F_2$ tobacco plants, or male sterile tobacco plants, derived therefrom. In an aspect, this disclosure provides the tobacco line 18GH349 and $F_1$ or $F_2$ tobacco plants, or male sterile tobacco plants, derived therefrom. In an aspect, this disclosure provides the tobacco line 18GH355 and $F_1$ or $F_2$ tobacco plants, or male sterile tobacco plants, derived therefrom. In an aspect, this disclosure provides the tobacco line 18GH359 and $F_1$ or $F_2$ tobacco plants, or male sterile tobacco plants, derived therefrom. In an aspect, this disclosure provides the tobacco line 18GH64 and $F_1$ or $F_2$ tobacco plants, or male sterile tobacco plants, derived therefrom. In an aspect, this disclosure provides the tobacco line 18GH682 and $F_1$ or $F_2$ tobacco plants, or male sterile tobacco plants, derived therefrom. In an aspect, this disclosure provides the tobacco line 18GH692 and $F_1$ or $F_2$ tobacco plants, or male sterile tobacco plants, derived therefrom. In an aspect, this disclosure provides the tobacco line 18GH697 and $F_1$ or $F_2$ tobacco plants, or male sterile tobacco plants, derived therefrom. In an aspect, this disclosure provides the tobacco line 18GH922 and $F_1$ or $F_2$ tobacco plants, or male sterile tobacco plants, derived therefrom. In an aspect, this disclosure provides the tobacco line 18GH957 and $F_1$ or $F_2$ tobacco plants, or male sterile tobacco plants, derived therefrom. In an aspect, this disclosure provides the tobacco line 17GH1808 and $F_1$ or $F_2$ tobacco plants, or male sterile tobacco plants, derived therefrom. In an aspect, this disclosure provides the tobacco line 17GH1810 and $F_1$ or $F_2$ tobacco plants, or male sterile tobacco plants, derived therefrom. In an aspect, this disclosure provides the tobacco line 17GH1886 and $F_1$ or $F_2$ tobacco plants, or male sterile tobacco plants, derived therefrom. In an aspect, this disclosure provides the tobacco line 17GH1888 and $F_1$ or $F_2$ tobacco plants, or male sterile tobacco plants, derived therefrom. In an aspect, this disclosure provides the tobacco line 17GH1889 and $F_1$ or $F_2$ tobacco plants, or male sterile tobacco plants, derived therefrom. In an aspect, this disclosure provides the tobacco line 17GH189 and $F_1$ or $F_2$ tobacco plants, or male sterile tobacco plants, derived therefrom. In an aspect, this disclosure provides the tobacco line 17GH1893 and $F_1$ or $F_2$ tobacco plants, or male sterile tobacco plants, derived therefrom. In an aspect, this disclosure provides the tobacco line 17GH1901 and $F_1$ or $F_2$ tobacco plants, or male sterile tobacco plants, derived therefrom. In an aspect, this disclosure provides the tobacco line 17GH1902 and $F_1$ or $F_2$ tobacco plants, or male sterile tobacco plants, derived therefrom. In an aspect, this disclosure provides the tobacco line 18GH3 and $F_1$ or $F_2$ tobacco plants, or male sterile tobacco plants, derived therefrom. In an aspect, this disclosure provides the tobacco line 18GH125 and $F_1$ or $F_2$ tobacco plants, or male sterile tobacco plants, derived therefrom. In an aspect, this disclosure provides the tobacco line 18GH208 and $F_1$ or $F_2$ tobacco plants, or male sterile tobacco plants, derived therefrom. In an aspect, this disclosure provides the tobacco line 18GH403 and $F_1$ or $F_2$ tobacco plants, or male sterile tobacco plants, derived therefrom. In an aspect, this disclosure provides the tobacco line 18GH414 and $F_1$ or $F_2$ tobacco plants, or male sterile tobacco plants, derived therefrom. In an aspect, this disclosure provides the tobacco line 18GH434 and $F_1$ or $F_2$ tobacco plants, or male sterile tobacco plants, derived therefrom. In an aspect, this disclosure provides the tobacco line 18GH436 and $F_1$ or $F_2$ tobacco plants, or male sterile tobacco plants, derived therefrom. In an aspect, this disclosure provides the tobacco line 18GH437 and $F_1$ or $F_2$ tobacco plants, or male sterile tobacco plants, derived therefrom. In an aspect, this disclosure provides the tobacco line 18GH449 and $F_1$ or $F_2$ tobacco plants, or male sterile tobacco plants, derived therefrom. In an aspect, this disclosure provides the tobacco line 18GH706 and $F_1$ or $F_2$ tobacco plants, or male sterile tobacco plants, derived therefrom. In an aspect, this disclosure provides the tobacco line 18GH709 and $F_1$ or $F_2$ tobacco plants, or male sterile tobacco plants, derived therefrom. In an aspect, this disclosure provides the tobacco line 18GH710 and $F_1$ or $F_2$ tobacco plants, or male sterile tobacco plants, derived therefrom. In an aspect, this disclosure provides the tobacco line 18GH716 and $F_1$ or $F_2$ tobacco plants, or male sterile tobacco plants, derived therefrom. In an aspect, this disclosure provides the tobacco line 18GH729 and $F_1$ or $F_2$ tobacco plants, or male sterile tobacco plants, derived therefrom. In an aspect, this disclosure provides the tobacco line 18GH731 and $F_1$ or $F_2$ tobacco plants, or male sterile tobacco plants, derived therefrom. In an aspect, this disclosure provides the tobacco line 18GH752 and $F_1$ or $F_2$ tobacco plants, or male sterile tobacco plants, derived therefrom. In an aspect, this disclosure provides the tobacco line 18GH756 and $F_1$ or $F_2$ tobacco plants, or male sterile tobacco plants, derived therefrom. In an aspect, this disclosure provides the tobacco line 18GH768 and $F_1$ or $F_2$ tobacco plants, or male sterile tobacco plants, derived therefrom. In an aspect, this disclosure provides the tobacco line 18GH771 and $F_1$ or $F_2$ tobacco plants, or male sterile tobacco plants, derived therefrom. In an aspect, this disclosure provides the tobacco line 18GH776 and $F_1$ or $F_2$ tobacco plants, or male sterile tobacco plants, derived therefrom. In an aspect, this disclosure provides the tobacco line 18GH800 and $F_1$ or $F_2$ tobacco plants, or male sterile tobacco plants, derived therefrom. In an aspect, this disclosure provides the tobacco line 18GH818 and $F_1$ or $F_2$ tobacco plants, or male sterile tobacco plants, derived therefrom. In an aspect, this disclosure provides the tobacco line 18GH10 and $F_1$ or $F_2$ tobacco plants, or male sterile tobacco plants, derived therefrom. In an aspect, this disclosure provides the tobacco line 18GH1004 and $F_1$ or $F_2$ tobacco plants, or male sterile tobacco plants, derived therefrom. In an aspect, this disclosure provides the tobacco line 18GH1033 and $F_1$ or $F_2$ tobacco plants, or male sterile tobacco plants, derived therefrom. In an aspect, this disclosure provides the tobacco line 18GH132 and $F_1$ or $F_2$ tobacco plants, or male sterile tobacco plants, derived therefrom. In an aspect, this disclosure provides the tobacco line 18GH134 and $F_1$ or $F_2$ tobacco plants, or male sterile tobacco plants, derived therefrom. In an aspect, this disclosure provides the tobacco line 18GH217 and $F_1$ or $F_2$ tobacco plants, or male sterile tobacco plants, derived therefrom. In an aspect, this disclosure provides the tobacco line 18GH456 and $F_1$ or $F_2$ tobacco plants, or male sterile tobacco plants, derived therefrom. In an aspect, this disclosure provides the tobacco line 18GH457 and $F_1$ or $F_2$ tobacco plants, or male sterile tobacco plants, derived therefrom. In an aspect, this disclosure provides the tobacco line 18GH460 and $F_1$ or $F_2$ tobacco plants, or male sterile tobacco plants, derived therefrom. In an aspect, this disclosure provides the tobacco line 18GH465 and $F_1$ or $F_2$ tobacco plants, or male sterile tobacco plants, derived therefrom. In an aspect, this disclosure provides the tobacco line 18GH71 and $F_1$ or $F_2$ tobacco plants, or male sterile tobacco plants, derived therefrom. In an aspect, this disclosure provides the tobacco line 18GH830 and $F_1$ or $F_2$ tobacco plants, or male sterile tobacco plants, derived therefrom. In an aspect, this disclosure provides the tobacco line 18GH831 and $F_1$ or $F_2$ tobacco plants, or male sterile tobacco plants, derived therefrom. In an aspect, this disclosure provides the tobacco line 18GH836 and $F_1$ or $F_2$ tobacco plants, or male sterile tobacco plants, derived therefrom. In an aspect, this disclosure provides the tobacco line 18GH841 and $F_1$ or $F_2$ tobacco plants, or male sterile tobacco plants, derived therefrom. In an aspect, this disclosure provides the tobacco line 18GH974 and $F_1$ or $F_2$ tobacco plants, or male sterile tobacco plants, derived therefrom. In an aspect, this disclosure provides the tobacco line 18GH981 and $F_1$ or $F_2$ tobacco plants, or male sterile tobacco plants, derived therefrom. In an aspect, this disclosure provides the tobacco line 18GH994 and $F_1$ or $F_2$ tobacco plants, or male sterile tobacco plants, derived therefrom. In an aspect, this disclosure provides the tobacco line 17GH1905 and $F_1$ or $F_2$ tobacco plants, or male sterile tobacco plants, derived therefrom. In an aspect, this disclosure provides the tobacco line 18GH128 and $F_1$ or $F_2$ tobacco plants, or male sterile tobacco plants, derived therefrom. In an aspect, this disclosure provides the tobacco line 18GH130 and $F_1$ or $F_2$ tobacco plants, or male sterile tobacco plants, derived therefrom. In an aspect, this disclosure provides the tobacco line 18GH131 and $F_1$ or $F_2$ tobacco plants, or male sterile tobacco plants, derived therefrom. In an aspect, this disclosure provides the tobacco line 18GH133 and $F_1$ or $F_2$ tobacco plants, or male sterile tobacco plants, derived therefrom. In an aspect, this disclosure provides the tobacco line 18GH136 and $F_1$ or $F_2$ tobacco plants, or male sterile tobacco plants, derived therefrom. In an aspect, this disclosure provides the tobacco line 18GH216 and $F_1$ or $F_2$ tobacco plants, or male sterile tobacco plants, derived therefrom. In an aspect, this disclosure provides the tobacco line 18GH227 and $F_1$ or $F_2$ tobacco plants, or male sterile tobacco plants, derived therefrom. In an aspect, this disclosure provides the tobacco line 18GH5 and $F_1$ or $F_2$ tobacco plants, or male sterile tobacco plants, derived therefrom. In an aspect, this disclosure provides the tobacco line 18GH6 and $F_1$ or $F_2$ tobacco plants, or male sterile tobacco plants, derived therefrom. In an aspect, this disclosure provides the tobacco line 18GH65 and $F_1$ or $F_2$ tobacco plants, or male sterile tobacco plants, derived therefrom. In an aspect, this disclosure provides the tobacco line 18GH66 and $F_1$ or $F_2$ tobacco plants, or male sterile tobacco plants, derived therefrom. In an aspect, this disclosure provides the tobacco line 18GH69 and $F_1$ or $F_2$ tobacco plants, or male sterile tobacco plants, derived therefrom. In an aspect, this disclosure provides the tobacco line 18GH72 and $F_1$ or $F_2$ tobacco plants, or male sterile tobacco plants, derived therefrom. In an aspect, this disclosure provides the tobacco line 18GH73 and $F_1$ or $F_2$ tobacco plants, or male sterile tobacco plants, derived therefrom. In an aspect, this disclosure provides the tobacco line 18GH74 and $F_1$ or $F_2$ tobacco plants, or male sterile tobacco plants, derived therefrom. In an aspect, this disclosure provides the tobacco line 18GH78 and $F_1$ or $F_2$ tobacco plants, or male sterile tobacco plants, derived therefrom. In an aspect, this disclosure provides the tobacco line 18GH79 and $F_1$ or $F_2$ tobacco plants, or male sterile tobacco plants, derived therefrom. In an aspect, this disclosure provides the tobacco line 18GH8 and $F_1$ or $F_2$ tobacco plants, or male sterile tobacco plants, derived therefrom. In an aspect, this disclosure provides the tobacco line 18GH9 and $F_1$ or $F_2$ tobacco plants, or male sterile tobacco plants, derived therefrom. In an aspect, this disclosure provides the tobacco line 17GH1696 and $F_1$ or $F_2$ tobacco plants, or male sterile tobacco plants, derived therefrom. In an aspect, this disclosure provides the tobacco line 17GH1717 and $F_1$ or $F_2$ tobacco plants, or male sterile tobacco plants, derived therefrom. In an aspect, this disclosure provides the tobacco line 17GH1719 and $F_1$ or $F_2$ tobacco plants, or male sterile tobacco plants, derived therefrom. In an aspect, this disclosure provides the tobacco line 17GH1729 and $F_1$ or $F_2$ tobacco plants, or male sterile tobacco plants, derived therefrom. In an aspect, this disclosure provides the tobacco line 17GH1736 and $F_1$ or $F_2$ tobacco plants, or male sterile tobacco plants, derived therefrom. In an aspect, this disclosure provides the tobacco line 17GH1737 and $F_1$ or $F_2$ tobacco plants, or male sterile tobacco plants, derived therefrom. In an aspect, this disclosure provides the tobacco line 17GH1739 and $F_1$ or $F_2$ tobacco plants, or male sterile tobacco plants, derived therefrom. In an aspect, this disclosure provides the tobacco line 17GH1740 and $F_1$ or $F_2$ tobacco plants, or male sterile tobacco plants, derived therefrom. In an aspect, this disclosure provides the tobacco line 17GH1835 and $F_1$ or $F_2$ tobacco plants, or male sterile tobacco plants, derived therefrom. In an aspect, this disclosure provides the tobacco line 17GH1848 and $F_1$ or $F_2$ tobacco plants, or male sterile tobacco plants, derived therefrom. In an aspect, this disclosure provides the tobacco line 17GH1849 and $F_1$ or $F_2$ tobacco plants, or male sterile tobacco plants, derived therefrom. In an aspect, this disclosure provides the tobacco line 17GH1912 and $F_1$ or $F_2$ tobacco plants, or male sterile tobacco plants, derived therefrom. In an aspect, this disclosure provides the tobacco line 17GH1937 and $F_1$ or $F_2$ tobacco plants, or male sterile tobacco plants, derived therefrom. In an aspect, this disclosure provides the tobacco line 17GH1940 and $F_1$ or $F_2$ tobacco plants, or male sterile tobacco plants, derived therefrom. In an aspect, this disclosure provides the tobacco line 17GH1943 and $F_1$ or $F_2$ tobacco plants, or male sterile tobacco plants, derived therefrom. In an aspect, this disclosure provides the tobacco line 17GH1944 and $F_1$ or $F_2$ tobacco plants, or male sterile tobacco plants, derived therefrom. In an aspect, this disclosure provides the tobacco line 18GH1051 and $F_1$ or $F_2$ tobacco plants, or male sterile tobacco plants, derived therefrom. In an aspect, this disclosure provides the tobacco line 18GH22 and $F_1$ or $F_2$ tobacco plants, or male sterile tobacco plants, derived therefrom. In an aspect, this disclosure provides the tobacco line 18GH34 and $F_1$ or $F_2$ tobacco plants, or male sterile tobacco plants, derived therefrom. In an aspect, this disclosure provides the tobacco line 18GH473 and $F_1$ or $F_2$ tobacco plants, or male sterile tobacco plants, derived therefrom. In an aspect, this disclosure provides the tobacco line 18GH49 and $F_1$ or $F_2$ tobacco plants, or male sterile tobacco plants, derived therefrom. In an aspect, this disclosure provides the tobacco line 18GH50 and $F_1$ or $F_2$ tobacco plants, or male sterile tobacco plants, derived therefrom. In an aspect, this disclosure provides the tobacco line 18GH848 and $F_1$ or $F_2$ tobacco plants, or male sterile tobacco plants, derived therefrom. In an aspect, this disclosure provides the tobacco line 18GH850 and $F_1$ or $F_2$ tobacco plants, or male sterile tobacco plants, derived therefrom. In an aspect, this disclosure provides the tobacco line 18GH851 and $F_1$ or $F_2$ tobacco plants, or male sterile tobacco plants, derived therefrom. In an aspect, this disclosure provides the tobacco line 17GH1699 and $F_1$ or $F_2$ tobacco plants, or male sterile tobacco plants, derived therefrom. In an aspect, this disclosure provides the tobacco line 17GH1708 and $F_1$ or $F_2$ tobacco plants, or male sterile tobacco plants, derived therefrom. In an aspect, this disclosure provides the tobacco line 17GH1722 and $F_1$ or $F_2$ tobacco plants, or male sterile tobacco plants, derived therefrom. In an aspect, this disclosure provides the tobacco line 17GH1724 and $F_1$ or $F_2$ tobacco plants, or male sterile tobacco plants, derived therefrom. In an aspect, this disclosure provides the tobacco line 17GH1725 and $F_1$ or $F_2$ tobacco plants, or male sterile tobacco plants, derived therefrom. In an aspect, this disclosure provides the tobacco line 17GH1845 and $F_1$ or $F_2$ tobacco plants, or male sterile tobacco plants, derived therefrom. In an aspect, this disclosure provides the tobacco line 17GH1846 and $F_1$ or $F_2$ tobacco plants, or male sterile tobacco plants, derived therefrom. In an aspect, this disclosure provides the tobacco line 17GH1847 and $F_1$ or $F_2$ tobacco plants, or male sterile tobacco plants, derived therefrom. In an aspect, this disclosure provides the tobacco line 17GH1911 and $F_1$ or $F_2$ tobacco plants, or male sterile tobacco plants, derived therefrom. In an aspect, this disclosure provides the tobacco line 17GH1912 and $F_1$ or $F_2$ tobacco plants, or male sterile tobacco plants, derived therefrom. In an aspect, this disclosure provides the tobacco line 17GH1915 and $F_1$ or $F_2$ tobacco plants, or male sterile tobacco plants, derived therefrom. In an aspect, this disclosure provides the tobacco line 17GH1918 and $F_1$ or $F_2$ tobacco plants, or male sterile tobacco plants, derived therefrom. In an aspect, this disclosure provides the tobacco line 17GH1928 and $F_1$ or $F_2$ tobacco plants, or male sterile tobacco plants, derived therefrom. In an aspect, this disclosure provides the tobacco line 17GH1932 and $F_1$ or $F_2$ tobacco plants, or male sterile tobacco plants, derived therefrom. In an aspect, this disclosure provides the tobacco line 17GH1933 and $F_1$ or $F_2$ tobacco plants, or male sterile tobacco plants, derived therefrom. In an aspect, this disclosure provides the tobacco line 17GH1936 and $F_1$ or $F_2$ tobacco plants, or male sterile tobacco plants, derived therefrom. In an aspect, this disclosure provides the tobacco line 18GH20 and $F_1$ or $F_2$ tobacco plants, or male sterile tobacco plants, derived therefrom. In an aspect, this disclosure provides the tobacco line 18GH28 and $F_1$ or $F_2$ tobacco plants, or male sterile tobacco plants, derived therefrom. In an aspect, this disclosure provides the tobacco line 18GH31 and $F_1$ or $F_2$ tobacco plants, or male sterile tobacco plants, derived therefrom. In an aspect, this disclosure provides the tobacco line 18GH47 and $F_1$ or $F_2$ tobacco plants, or male sterile tobacco plants, derived therefrom. In an aspect, this disclosure provides the tobacco line 18GH51 and $F_1$ or $F_2$ tobacco plants, or male sterile tobacco plants, derived therefrom. In an aspect, this disclosure provides the tobacco line 18GH52 and $F_1$ or $F_2$ tobacco plants, or male sterile tobacco plants, derived therefrom. In an aspect, this disclosure provides the tobacco line CS107 and $F_1$ or $F_2$ tobacco plants, or male sterile tobacco plants, derived therefrom. In an aspect, this disclosure provides the tobacco line CS106 and $F_1$ or $F_2$ tobacco plants, or male sterile tobacco plants, derived therefrom. In an aspect, this disclosure provides the tobacco line CS115 and $F_1$ or $F_2$ tobacco plants, or male sterile tobacco plants, derived therefrom. In an aspect, this disclosure provides the tobacco line 17GH1809-13 and $F_1$ or $F_2$ tobacco plants, or male sterile tobacco plants, derived therefrom. In an aspect, this disclosure provides the tobacco line CS111 and $F_1$ or $F_2$ tobacco plants, or male sterile tobacco plants, derived therefrom. In an aspect, this disclosure provides the tobacco line CS112 and $F_1$ or $F_2$ tobacco plants, or male sterile tobacco plants, derived therefrom. In an aspect, this disclosure provides the tobacco line 17GH1678-60 and $F_1$ or $F_2$ tobacco plants, or male sterile tobacco plants, derived therefrom. In an aspect, this disclosure provides the tobacco line CS131 and $F_1$ or $F_2$ tobacco plants, or male sterile tobacco plants, derived therefrom. In an aspect, this disclosure provides the tobacco line 18GH709-01 and $F_1$ or $F_2$ tobacco plants, or male sterile tobacco plants, derived therefrom. In an aspect, this disclosure provides the tobacco line 18GH709-08 and $F_1$ or $F_2$ tobacco plants, or male sterile tobacco plants, derived therefrom. In an aspect, this disclosure provides the tobacco line 18GH414-11 and $F_1$ or $F_2$ tobacco plants, or male sterile tobacco plants, derived therefrom. In an aspect, this disclosure provides the tobacco line 18GH414-19 and $F_1$ or $F_2$ tobacco plants, or male sterile tobacco plants, derived therefrom. In an aspect, this disclosure provides the tobacco line 18GH437-04 and $F_1$ or $F_2$ tobacco plants, or male sterile tobacco plants, derived therefrom. In an aspect, this disclosure provides the tobacco line 18GH437-08 and $F_1$ or $F_2$ tobacco plants, or male sterile tobacco plants, derived therefrom. In an aspect, this disclosure provides the tobacco line 18GH437-32 and $F_1$ or $F_2$ tobacco plants, or male sterile tobacco plants, derived therefrom. In an aspect, this disclosure provides the tobacco line 18GH437-39 and $F_1$ or $F_2$ tobacco plants, or male sterile tobacco plants, derived therefrom. In an aspect, this disclosure provides the tobacco line 18GH449-26 and $F_1$ or $F_2$ tobacco plants, or male sterile tobacco plants, derived therefrom. In an aspect, this disclosure provides the tobacco line 18GH449-33 and $F_1$ or $F_2$ tobacco plants, or male sterile tobacco plants, derived therefrom. In an aspect, this disclosure provides the tobacco line 18GH125-48 and $F_1$ or $F_2$ tobacco plants, or male sterile tobacco plants, derived therefrom. In an aspect, this disclosure provides the tobacco line CS102 and $F_1$ or $F_2$ tobacco plants, or male sterile tobacco plants, derived therefrom. In an aspect, this disclosure provides the tobacco line CS103 and $F_1$ or $F_2$ tobacco plants, or male sterile tobacco plants, derived therefrom. In an aspect, this disclosure provides the tobacco line 17GH1719-30 and $F_1$ or $F_2$ tobacco plants, or male sterile tobacco plants, derived therefrom. In an aspect, this disclosure provides the tobacco line 17GH1740-36 and F$_1$ or F$_2$ tobacco plants, or male sterile tobacco plants, derived therefrom. In an aspect, this disclosure provides the tobacco line 17GH1698-22 and F$_1$ or F$_2$ tobacco plants, or male sterile tobacco plants, derived therefrom. In an aspect, this disclosure provides the tobacco line 17GH1700-13 and F$_1$ or F$_2$ tobacco plants, or male sterile tobacco plants, derived therefrom. In an aspect, this disclosure provides the tobacco line 17GH1702-17 and F$_1$ or F$_2$ tobacco plants, or male sterile tobacco plants, derived therefrom. In an aspect, this disclosure provides the tobacco line 17GH1849-01 and F$_1$ or F$_2$ tobacco plants, or male sterile tobacco plants, derived therefrom. In an aspect, this disclosure provides the tobacco line 17GH1849-48 and F$_1$ or F$_2$ tobacco plants, or male sterile tobacco plants, derived therefrom. In an aspect, this disclosure provides the tobacco line 17GH1737-24 and F$_1$ or F$_2$ tobacco plants, or male sterile tobacco plants, derived therefrom. In an aspect, this disclosure provides the tobacco line CS118 and F$_1$ or F$_2$ tobacco plants, or male sterile tobacco plants, derived therefrom. In an aspect, this disclosure provides the tobacco line CS133 and F$_1$ or F$_2$ tobacco plants, or male sterile tobacco plants, derived therefrom. In an aspect, this disclosure provides the tobacco line CS120 and F$_1$ or F$_2$ tobacco plants, or male sterile tobacco plants, derived therefrom. In an aspect, this disclosure provides the tobacco line 18GH1108-07 and F$_1$ or F$_2$ tobacco plants, or male sterile tobacco plants, derived therefrom. In an aspect, this disclosure provides the tobacco line 18GH2162 and F$_1$ or F$_2$ tobacco plants, or male sterile tobacco plants, derived therefrom. In an aspect, this disclosure provides the tobacco line CS164 and F$_1$ or F$_2$ tobacco plants, or male sterile tobacco plants, derived therefrom. In an aspect, this disclosure provides the tobacco line CS163 and F$_1$ or F$_2$ tobacco plants, or male sterile tobacco plants, derived therefrom. In an aspect, this disclosure provides the tobacco line CS146 and F$_1$ or F$_2$ tobacco plants, or male sterile tobacco plants, derived therefrom. In an aspect, this disclosure provides the tobacco line CS147 and F$_1$ or F$_2$ tobacco plants, or male sterile tobacco plants, derived therefrom. In an aspect, this disclosure provides the tobacco line CS150 and F$_1$ or F$_2$ tobacco plants, or male sterile tobacco plants, derived therefrom. In an aspect, this disclosure provides the tobacco line CS151 and F$_1$ or F$_2$ tobacco plants, or male sterile tobacco plants, derived therefrom. In an aspect, this disclosure provides the tobacco line CS148 and F$_1$ or F$_2$ tobacco plants, or male sterile tobacco plants, derived therefrom. In an aspect, this disclosure provides the tobacco line CS149 and F$_1$ or F$_2$ tobacco plants, or male sterile tobacco plants, derived therefrom. In an aspect, this disclosure provides the tobacco line CS152 and F$_1$ or F$_2$ tobacco plants, or male sterile tobacco plants, derived therefrom. In an aspect, this disclosure provides the tobacco line CS153 and F$_1$ or F$_2$ tobacco plants, or male sterile tobacco plants, derived therefrom. In an aspect, this disclosure provides the tobacco line CS143 and F$_1$ or F$_2$ tobacco plants, or male sterile tobacco plants, derived therefrom. In an aspect, this disclosure provides the tobacco line 18GH2169 and F$_1$ or F$_2$ tobacco plants, or male sterile tobacco plants, derived therefrom. In an aspect, this disclosure provides the tobacco line 18GH2171 and F$_1$ or F$_2$ tobacco plants, or male sterile tobacco plants, derived therefrom. In an aspect, this disclosure provides the tobacco line CS165 and F$_1$ or F$_2$ tobacco plants, or male sterile tobacco plants, derived therefrom. In an aspect, this disclosure provides the tobacco line CS118 and F$_1$ or F$_2$ tobacco plants, or male sterile tobacco plants, derived therefrom. In an aspect, this disclosure provides the tobacco line 18GH2254-7 and F$_1$ or F$_2$ tobacco plants, or male sterile tobacco plants, derived therefrom.

In an aspect, the present disclosure provides a method of introgressing a low nicotine trait into a tobacco variety, the method comprising: (a) crossing a first tobacco variety comprising a low nicotine trait with a second tobacco variety without the low nicotine trait to produce one or more progeny tobacco plants; (b) genotyping the one or more progeny tobacco plants for a pmt mutant allele selected from those listed in Tables 4A to 4E, Tables 5A to 5E, Table 10, and Tables 12A to 12E; and (c) selecting a progeny tobacco plant comprising the pmt mutant allele. In another aspect, these methods further comprise backcrossing the selected progeny tobacco plant with the second tobacco variety. In a further aspect, these methods further comprise: (d) crossing the selected progeny plant with itself or with the second tobacco variety to produce one or more further progeny tobacco plants; and (e) selecting a further progeny tobacco plant comprising a low nicotine trait. In an aspect, the step (e) of selecting comprises marker-assisted selection. In an aspect, these methods produce a single gene conversion comprising a low nicotine trait. In an aspect, these methods produce a single gene conversion comprising a pmt mutant allele. In an aspect, the second tobacco variety is an elite variety. In another aspect, the genotyping step of these methods involve one or more molecular marker assays. In another aspect, the genotyping may involve a polymorphic marker comprising a polymorphism selected from the group consisting of single nucleotide polymorphisms (SNPs), insertions or deletions in DNA sequence (Indels), simple sequence repeats of DNA sequence (SSRs), a restriction fragment length polymorphism (RFLP), and a tag SNP.

As used herein, "locus" is a chromosomal locus or region where a polymorphic nucleic acid, trait determinant, gene, or marker is located. A "locus" can be shared by two homologous chromosomes to refer to their corresponding locus or region. As used herein, "allele" refers to an alternative nucleic acid sequence of a gene or at a particular locus (e.g., a nucleic acid sequence of a gene or locus that is different than other alleles for the same gene or locus). Such an allele can be considered (i) wild-type or (ii) mutant if one or more mutations or edits are present in the nucleic acid sequence of the mutant allele relative to the wild-type allele. A mutant allele for a gene may have a reduced or eliminated activity or expression level for the gene relative to the wild-type allele. For diploid organisms such as tobacco, a first allele can occur on one chromosome, and a second allele can occur at the same locus on a second homologous chromosome. If one allele at a locus on one chromosome of a plant is a mutant allele and the other corresponding allele on the homologous chromosome of the plant is wild-type, then the plant is described as being heterozygous for the mutant allele. However, if both alleles at a locus are mutant alleles, then the plant is described as being homozygous for the mutant alleles. A plant homozygous for mutant alleles at a locus may comprise the same mutant allele or different mutant alleles if heteroallelic or biallelic.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the F1 generation. The term "BC1" refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "single gene converted" or "single gene conversion" refers to plants that are developed using a plant breeding technique known as backcrossing, or via genetic engineering, where essentially all of the desired morphological and physiological characteristics of a variety are recovered in addition to the single gene transferred into the variety via the backcrossing technique or via genetic engineering.

As used herein, "elite variety" means any variety that has resulted from breeding and selection for superior agronomic performance.

As used herein, "selecting" or "selection" in the context of marker-assisted selection or breeding refer to the act of picking or choosing desired individuals, normally from a population, based on certain pre-determined criteria.

As used herein, the term "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "marker assay" means a method for detecting a polymorphism at a particular locus using a particular method, e.g., measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism (RFLP), and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed.

It is understood that any tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance; high yield; high grade index value; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves), or any combination. In an aspect, low-nicotine or nicotine-free tobacco plants or seeds disclosed comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants further comprise an introgressed trait conferring resistance to brown stem rot (U.S. Pat. No. 5,689,035) or resistance to cyst nematodes (U.S. Pat. No. 5,491,081).

The present disclosure also provides pmt mutant tobacco plants comprising an altered nicotine or total alkaloid level but having a yield comparable to the yield of corresponding initial tobacco plants without such a nicotine level alternation. In an aspect, a pmt mutant variety provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre. In another aspect, a pmt mutant tobacco variety provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre. In a further aspect, pmt mutant tobacco plants provide a yield between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the yield of a control plant having essentially identical genetic background except for pmt mutation(s). In a further aspect, pmt mutant tobacco plants provide a yield between 70% and 125%, between 75% and 120%, between 80% and 115%, between 85% and 110%, or between 90% and 100% of the yield of a control plant having essentially identical genetic background except for pmt mutations.

In an aspect, a tobacco plant disclosed (e.g., a low-nicotine, nicotine-free, or low-alkaloid tobacco variety) comprises a modification conferring a desired trait (e.g., low-nicotine, nicotine-free, or low-alkaloid) without substantially impacting a trait selected from the group consisting of yield, ripening and senescence, susceptibility to insect herbivory, polyamine content after topping, chlorophyll level, mesophyll cell number per unit leaf area, and end-product quality after curing.

In an aspect, a tobacco plant disclosed comprises a modification conferring a desired trait (e.g., low-nicotine, nicotine-free, or low-alkaloid) and further comprises a trait substantially comparable to an unmodified control plant, where the trait is selected from the group consisting of yield, ripening and senescence, susceptibility to insect herbivory, polyamine content after topping, chlorophyll level, mesophyll cell number per unit leaf area, and end-product quality after curing.

In an aspect, a tobacco plant disclosed comprises a modification conferring a desired trait (e.g., low-nicotine, nicotine-free, or low-alkaloid) and further comprises a yield which is more than 80%, more than 85%, more than 90%, more than 95%, more than 100%, more than 105%, more than 110%, more than 115%, more than 120%, more than 125%, more than 130%, more than 135%, or more than 140% relative to the yield of an unmodified control plant. In an aspect, a tobacco plant disclosed comprises a modification conferring a desired trait (e.g., low-nicotine, nicotine-free, or low-alkaloid) and further comprises a yield which is between 70% and 140%, between 75% and 135%, between 80% and 130%, between 85% and 125%, between 90% and 120%, between 95% and 115%, or between 100% and 110% relative to the yield of an unmodified control plant. In an aspect, a tobacco plant disclosed comprises a modification conferring a desired trait (e.g., low-nicotine, nicotine-free, or low-alkaloid) and further comprises a yield which is between 70% and 80%, between 75% and 85%, between 80% and 90%, between 85% and 95%, between 90% and 100%, between 95% and 105%, between 105% and 115%, between 110% and 120%, between 115% to 125%, between 120% and 130%, between 125 and 135%, or between 130% and 140% relative to the yield of an unmodified control plant.

In an aspect, a low-nicotine or nicotine-free tobacco variety disclosed is adapted for machine harvesting. In another aspect, a low-nicotine or nicotine-free tobacco variety disclosed is harvested mechanically.

In an aspect, tobacco plants provided are hybrid plants. Hybrids can be produced by preventing self-pollination of female parent plants (e.g., seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting F1 seed is harvested.

Plants can be used to form single-cross tobacco F1 hybrids. Pollen from a male parent plant is manually transferred to an emasculated female parent plant or a female parent plant that is male sterile to form F1 seed. Alternatively, three-way crosses can be carried out where a single-cross F1 hybrid is used as a female parent and is crossed with a different male parent. As another alternative, double-cross hybrids can be created where the F1 progeny of two different single-crosses are themselves crossed. Self-incompatibility can be used to particular advantage to prevent self-pollination of female parents when forming a double-cross hybrid.

In an aspect, a low-nicotine or nicotine-free tobacco variety is male sterile. In another aspect, a low-nicotine or nicotine-free tobacco variety is cytoplasmic male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

In an aspect, this disclosure provides a male sterile tobacco plant, variety, or line comprising one or more pmt mutations provided in any one of Tables 5A to 5E and Tables 12A to 12E.

In another aspect, this disclosure provides a male sterile tobacco plant, variety, or line derived from any tobacco plant, variety, or line provided in any one of Tables 4A to 4E, Table 10, or Table 14.

In an aspect, this disclosure provides the male sterile line dCS11. In another aspect, this disclosure provides the male sterile line dCS12. In another aspect, this disclosure provides the male sterile line dCS13. In another aspect, this disclosure provides the male sterile line dCS14. In another aspect, this disclosure provides the male sterile line dCS15.

In another aspect, this disclosure provides the male sterile line dCS16. In another aspect, this disclosure provides the male sterile line dCS17. In another aspect, this disclosure provides the male sterile line dCS18. In another aspect, this disclosure provides the male sterile line dS697.

In a further aspect, tobacco parts provided include, but are not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In an aspect, tobacco part provided does not include seed. In an aspect, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Cells, tissues and organs can be from seed, fruit, leaf, cotyledon, hypocotyl, meristem, embryos, endosperm, root, shoot, stem, pod, flower, infloresence, stalk, pedicel, style, stigma, receptacle, petal, sepal, pollen, anther, filament, ovary, ovule, pericarp, phloem, vascular tissue. In another aspect, this disclosure provides a tobacco plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco plants naturally reproduce via seeds, not via asexual reproduction or vegetative propagation. In an aspect, this disclosure provides tobacco endosperm. In another aspect, this disclosure provides tobacco endosperm cells. In a further aspect, this disclosure provides a male or female sterile tobacco plant, which cannot reproduce without human intervention.

In an aspect, the present disclosure provides a nucleic acid molecule comprising at least about 40%, 45%, 50%, 55%, 60%, 65%, 70% 75% 80%, 85%, 90%, 91%, 92%, 93%, 94%, 95%, 96%, 97%, 98%, 99%, or 100% identity to a sequence selected from the group consisting of SEQ ID NOs: 1 to 10, and fragments thereof. In an aspect, the present disclosure provides a polypeptide or protein comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to an amino acid sequence selected from the group consisting of SEQ ID NOs: 11 to 15.

As used herein, the term "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution.

The present disclosure further provides a method manufacturing a tobacco product comprising tobacco material from tobacco plants disclosed. In an aspect, methods comprise conditioning aged tobacco material made from tobacco plants to increase its moisture content from between about 12.5% and about 13.5% to about 21%, blending the conditioned tobacco material to produce a desirable blend. In an aspect, the method of manufacturing a tobacco product further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In an aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with the copolymer and optionally flavorants and other additives.

In an aspect, tobacco material provided can be processed to a desired size. In an aspect, tobacco fibers can be processed to have an average fiber size of less than 200 micrometers. In an aspect, tobacco fibers are between 75 and 125 micrometers. In another aspect, tobacco fibers are processed to have a size of 75 micrometers or less. In an aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. The oral product can have a different overall oven volatiles content than the oven volatiles content of the tobacco fibers used to make the oral product. The processing steps described can reduce or increase the oven volatiles content.

Having now generally described the disclosure, the same will be more readily understood through reference to the following examples that are provided by way of illustration, and are not intended to be limiting of the present disclosure, unless specified.

EXAMPLES

Example 1: Expression Profiling of Five PMT Genes

Figure 1:
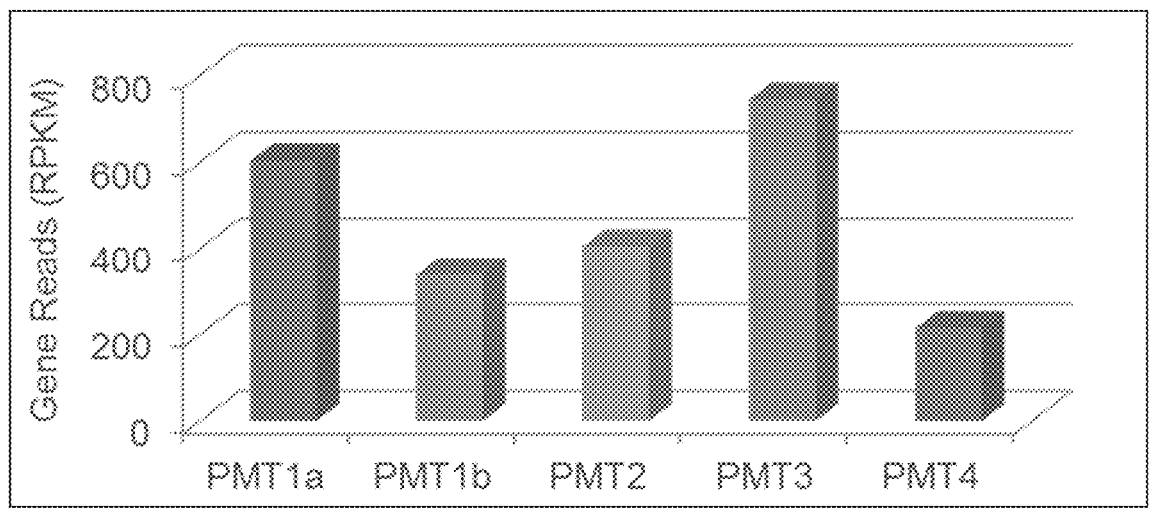
FIG. 1: RNA expression of five PMT genes in TN90 roots
Figure 2:
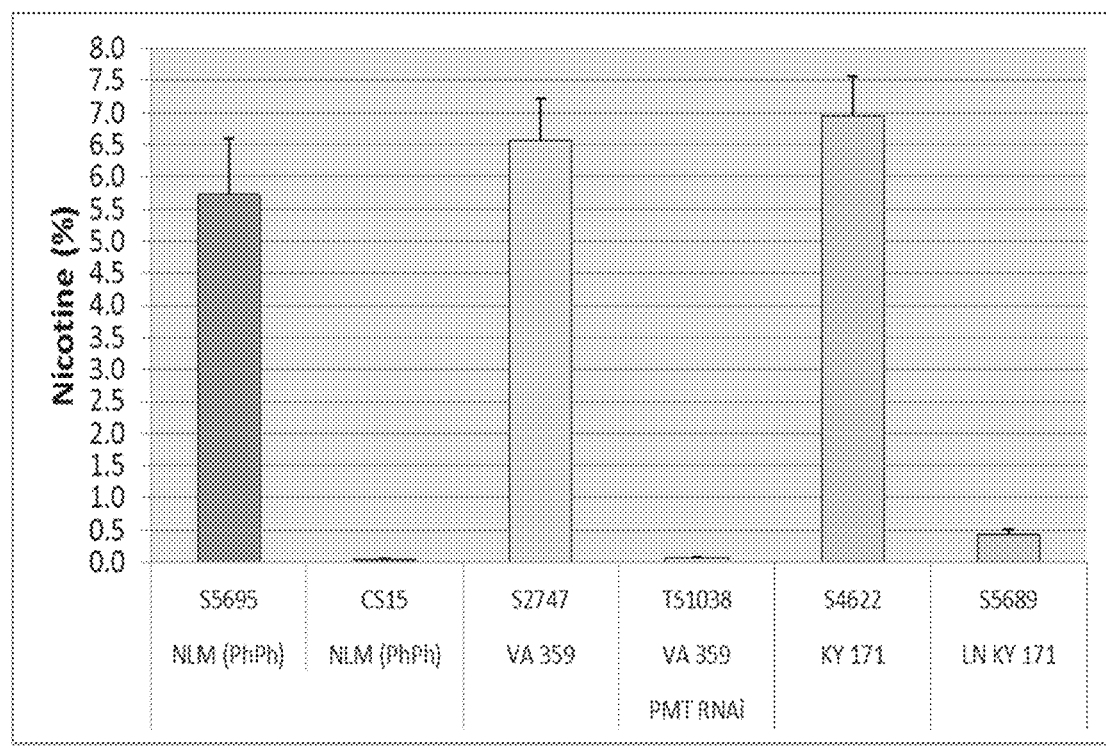
FIG. 2: Nicotine levels in various low-alkaloid lines: CS15 (a quintuple pmt knock-out mutant line CS15 in the NLM (Ph Ph) background), a PMT RNAi transgenic line in the VA359 background) and a low-nicotine KY171 ("LN KY171") variety (the KY 171 background harboring nic1 and nic2 double mutations), in comparison to their respective normal-alkaloid control line: NLM (Ph Ph), VA359, and KY171 background.
Figure 3:
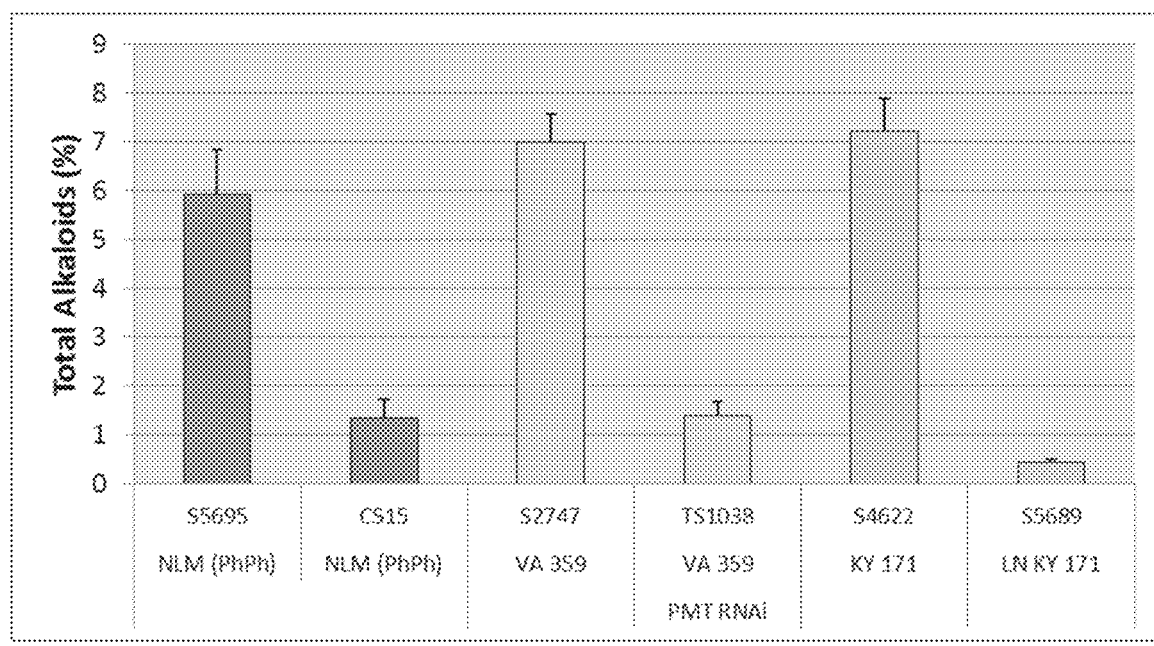
FIG. 3: Total alkaloid levels in various low-alkaloid lines: CS15, PMT RNAi, and LN KY171, in comparison to their respective normal-alkaloid control line: NLM (Ph Ph), VA359, and KY171 background.
Figure 4:
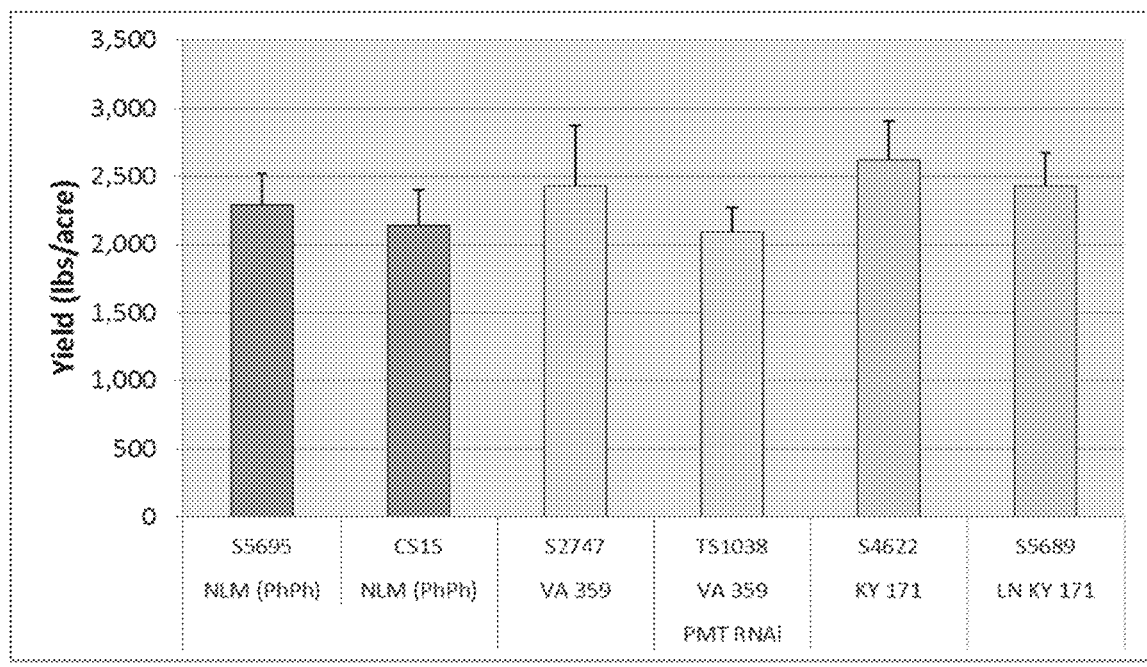
FIG. 4: Leaf yield in various low-alkaloid lines: CS15, PMT RNAi, and LN KY171, in comparison to their respective normal-alkaloid control line: NLM (Ph Ph), VA359, and KY171 background.
Figure 5:
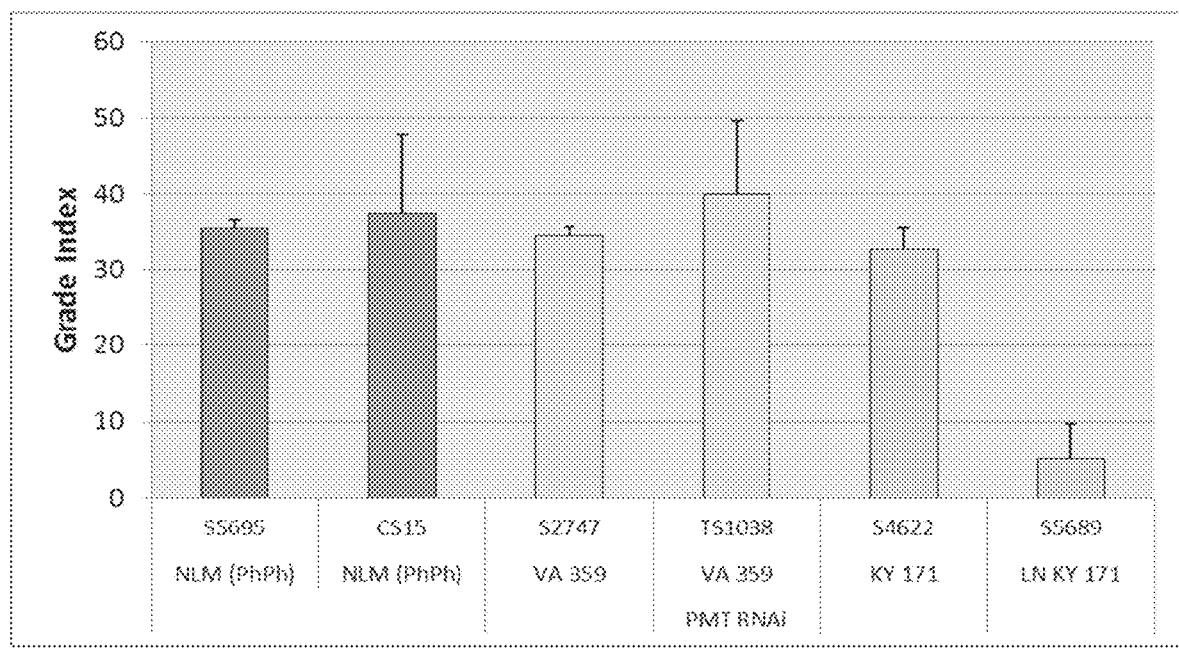
FIG. 5: Leaf quality in various low-alkaloid lines: CS15, PMT RNAi, and LN KY171, in comparison to their respective normal-alkaloid control line: NLM (Ph Ph), VA359, and KY171 background.

Nicotine biosynthesis starts with conversion of polyamine putrescine to N-methylputrescine by the enzyme putrescine N-methyl transferase (PMT). This is a step that commits precursor metabolites to nicotine biosynthesis. Genes encoding PMT (PMT1a, PMT1b, PMT2, PMT3 and PMT4) are present in the tobacco (Nicotiana tabacum) genome. Table 1A lists genomic DNA sequences, cDNA sequences, and protein sequences of five PMT genes. Tables 1B and 1C provide sequence identities among five PMT genes. Pooled expression levels from before topping to harvest provide support that, without being limited by any particular theory, PMT1a and PMT3 represent two major PMT genes (FIG. 1).

TABLE 1A

Sequences of five tobacco PMT genes.

| Gene Name | Genomic DNA Sequence (including regions such as promoter, 5' UTR, introns, 3' UTR, and terminator) (SEQ ID No.) | cDNA Sequence (SEQ ID No.) | Protein Sequence (SEQ ID No.) |
|---|---|---|---|
| PMT1b | 1 | 6 | 11 |
| PMT1a | 2 | 7 | 12 |
| PMT2 | 3 | 8 | 13 |
| PMT3 | 4 | 9 | 14 |
| PMT4 | 5 | 10 | 15 |

TABLE 1B cDNA sequence identity among five tobacco PMT genes determined by Clustal2.1.

| cDNA % identity | PMT1a | PMT1b | PMT2 | PMT3 | PMT4 |
|---|---|---|---|---|---|
| PMT1a | 100 | | | | |
| PMT1b | 98.85 | 100 | | | |
| PMT2 | 91.81 | 91.71 | 100 | | |
| PMT3 | 93.71 | 93.53 | 91.79 | 100 | |
| PMT4 | 94.24 | 94.06 | 92.75 | 94.59 | 100 |

TABLE 1C

Protein sequence identity among five tobacco PMT genes determined by Clustal2.1.

| Protein % identity | PMT1a | PMT1b | PMT2 | PMT3 | PMT4 |
|---|---|---|---|---|---|
| PMT1a | 100 | | | | |
| PMT1b | 98.4 | 100 | | | |
| PMT2 | 95.42 | 95.75 | 100 | | |
| PMT3 | 97.48 | 97.76 | 96.23 | 100 | |
| PMT4 | 96.27 | 96.8 | 96.32 | 97.63 | 100 |

TABLE 1D

PMT1b genomic sequence (SEQ ID No. 1) annotation.

| Element | location |
|---|---|
| 5' sequence | 1 . . . 1000 |
| exon 1 | 1001 . . . 1292 |
| intron 1 | 1293 . . . 1464 |
| exon 2 | 1465 . . . 1541 |
| intron 2 | 1542 . . . 1623 |
| exon 3 | 1624 . . . 1851 |
| intron 3 | 1852 . . . 1971 |
| exon 4 | 1972 . . . 2044 |
| intron 4 | 2045 . . . 2143 |
| exon 5 | 2144 . . . 2215 |
| intron 5 | 2216 . . . 2333 |
| exon 6 | 2334 . . . 2529 |
| intron 6 | 2530 . . . 3033 |
| exon 7 | 3034 . . . 3166 |
| intron 7 | 3167 . . . 3260 |
| exon 8 | 3261 . . . 3317 |
| 3' sequence | 3318 . . . 4317 |

TABLE 1E

PMT1a genomic sequence (SEQ ID No. 2) annotation.

| Element | location |
|---|---|
| 5' sequence | 1 . . . 1000 |
| exon 1 | 1001 . . . 1294 |
| intron 1 | 1295 . . . 1422 |
| exon 2 | 1423 . . . 1497 |
| intron 2 | 1498 . . . 1579 |
| exon 3 | 1580 . . . 1810 |
| intron 3 | 1811 . . . 1932 |
| exon 4 | 1933 . . . 2003 |
| intron 4 | 2004 . . . 2102 |
| exon 5 | 2103 . . . 2175 |
| intron 5 | 2176 . . . 2293 |
| exon 6 | 2294 . . . 2487 |
| intron 6 | 2488 . . . 2925 |
| exon 7 | 2926 . . . 3058 |
| intron 7 | 3059 . . . 3153 |
| exon 8 | 3154 . . . 3210 |
| 3' sequence | 3211 . . . 4210 |

TABLE 1F

PMT2 genomic sequence (SEQ ID No. 3) annotation.

| Element | location |
|---|---|
| 5' sequence | 1 . . . 792 |
| exon 1 | 793 . . . 1020 |
| intron 1 | 1021 . . . 1201 |
| exon 2 | 1202 . . . 1276 |
| intron 2 | 1277 . . . 1358 |
| exon 3 | 1359 . . . 1589 |
| intron 3 | 1590 . . . 1694 |

TABLE 1F-continued

PMT2 genomic sequence (SEQ ID No. 3) annotation.

| Element | location |
|---|---|
| exon 4 | 1695 . . . 1765 |
| intron 4 | 1766 . . . 1875 |
| exon 5 | 1876 . . . 1948 |
| intron 5 | 1949 . . . 2037 |
| exon 6 | 2038 . . . 2231 |
| intron 6 | 2232 . . . 2397 |
| exon 7 | 2398 . . . 2530 |
| intron 7 | 2531 . . . 2629 |
| exon 8 | 2630 . . . 2686 |
| 3' sequence | 2687 . . . 3686 |

TABLE 1G

PMT3 genomic sequence (SEQ ID No. 4) annotation.

| Element | location |
|---|---|
| 5' sequence | 1 . . . 1000 |
| exon 1 | 1001 . . . 1312 |
| intron 1 | 1313 . . . 1562 |
| exon 2 | 1563 . . . 1637 |
| intron 2 | 1638 . . . 1731 |
| exon 3 | 1732 . . . 1962 |
| intron 3 | 1963 . . . 2050 |
| exon 4 | 2051 . . . 2121 |
| intron 4 | 2122 . . . 2230 |
| exon 5 | 2231 . . . 2303 |
| intron 5 | 2304 . . . 2397 |
| exon 6 | 2398 . . . 2591 |
| intron 6 | 2592 . . . 2750 |
| exon 7 | 2751 . . . 2883 |
| intron 7 | 2884 . . . 2978 |
| exon 8 | 2979 . . . 3035 |
| 3' sequence | 3036 . . . 4035 |

TABLE 1H

PMT4 genomic sequence (SEQ ID No. 5) annotation.

| Element | location |
|---|---|
| 5' sequence | 1 . . . 1000 |
| exon 1 | 1001 . . . 1426 |
| intron 1 | 1427 . . . 1609 |
| exon 2 | 1610 . . . 1684 |
| intron 2 | 1685 . . . 1766 |
| exon 3 | 1767 . . . 1997 |
| intron 3 | 1998 . . . 2112 |

TABLE 1H-continued

PMT4 genomic sequence (SEQ ID No. 5) annotation.

| Element | location |
|---|---|
| exon 4 | 2113 . . . 2183 |
| intron 4 | 2184 . . . 2290 |
| exon 5 | 2291 . . . 2363 |
| intron 5 | 2364 . . . 2452 |
| exon 6 | 2453 . . . 2646 |
| intron 6 | 2647 . . . 3146 |
| exon 7 | 3147 . . . 3279 |
| intron 7 | 3280 . . . 3374 |
| exon 8 | 3375 . . . 3431 |
| 3' sequence | 3432 . . . 4431 |

Example 2: PMT Genome Editing and Tobacco Line Development

PMT knockout mutants are produced by editing various PMT genes. Tobacco protoplasts are transfected using polyethylene glycol (PEG) with plasmids encoding a genome editing technology 1 (GET 1) protein or a genome editing technology (GET) 2 protein and specific guide RNAs (gRNAs) targeting PMT genes at desired positions. Table 2 lists gRNA sequences used for PMT editing. Some gRNAs (e.g., Nos. 6 and 7) are pooled together for targeting multiple PMT genes in a single transfection.

Transfected protoplasts are then immobilized in 1% agarose bead and subjected to tissue culture. When calli grow up to ~1 mm in diameter, they are spread on TOM2 plates. Calli are screened for insertions or deletions (indels) at the target positions using fragment analysis. Candidates, showing size shifts compared to wildtype control, are selected for further culture and the consequent shoots are tested by fragment analysis again to confirm the presence of indels. Rooted shoots are potted and sequenced for the target positions to determine the exact sequences deleted. Young leaf from each plant is harvested and PCR amplified for PMT fragments using phirekit. PMT Libraries for each line is indexed and 384 lines are pooled and sequenced using Miseq.

SNP analysis is carried out to determine both the exact edited pmt mutant allele sequences and the zygosity state at each PMT gene locus. Table 3 provides the zygosity information of representative edited plants. Tables 4A to 4E provide indels sequence information in each edited line of various tobacco varieties (e.g., K326, TN90, NLM, oriental). Tables 5A to 5E provide genomic sequences of about 40 nucleotides from each pmt mutant allele with the edited site in the middle of the genomic sequence (e.g., 20 nucleotides on each side of the deleted or inserted sequence site).

TABLE 2 gRNA sequences used in 2 genome editing technologies and their target genes. "Y" represents that a gRNA targets that PMT gene, while "—" represents that a gRNA does not target that PMT gene.

| gRNA No. | Genome Editing Technology (GET) | gRNA sequence | Target genes | | | | |
|---|---|---|---|---|---|---|---|
| | | | PMT1b | PMT1a | PMT2 | PMT3 | PMT4 |
| 1 | GET 1 | CCCATGAACGGCCACCAAAA (SEQ ID NO: 16) | Y | Y | — | — | — |
| 2 | GET 1 | GGCACTTCCAAACACCAAAA (SEQ ID NO: 17) | Y | Y | Y | Y | Y |
| 3 | GET 1 | GTTGTTCGGATGTCCCATTC (SEQ ID NO: 18) | Y | Y | — | — | — |

TABLE 2-continued gRNA sequences used in 2 genome editing technologies and their target genes. "Y" represents that a gRNA targets that PMT gene, while "—" represents that a gRNA does not target that PMT gene.

| gRNA No. | Genome Editing Technology (GET) | gRNA sequence | Target genes PMT1b | PMT1a | PMT2 | PMT3 | PMT4 |
|---|---|---|---|---|---|---|---|
| 4 | GET 1 | CTAAACTCTGAAAACCAACC (SEQ ID NO: 19) | Y | — | Y | Y | — |
| 5 | GET 1 | TTTCAGAGTTTAGCGCATTA (SEQ ID NO: 20) | Y | Y | Y | Y | Y |
| 6 | GET 2 | GATGGAGCAATTCAACATACAGA (SEQ ID NO: 21) | Y | Y | — | — | — |
| 7 | GET 2 | GATGGAGCAATTCAACACACAGA (SEQ ID NO: 22) | — | — | Y | Y | Y |

TABLE 3

Zygosity of individual PMT genic locus in selected pmt mutants in various background produced by genome editing using GET2. Number one (1) represents homozygous for a single mutant allele. Numbers 2 to 5 represent a heteroallelic combination having 2 to 5 Indels. Hyphens indicate no data. Detailed genotype information is shown in Tables 4A to 4D.

| Variety | Line | PMT1b | PMT1a | PMT2 | PMT3 | PMT4 |
|---|---|---|---|---|---|---|
| Basma | 18GH203 | 1 | 2 | 2 | 2 | 1 |
| Basma | 18GH341 | 1 | 2 | 2 | 2 | 1 |
| K326 | 17GH1678 | 2 | 2 | 1 | 1 | 2 |
| K326 | 17GH1680 | 1 | 2 | 1 | 1 | 1 |
| K326 | 17GH1804 | 1 | 2 | 1 | 1 | 1 |
| K326 | 17GH1898 | 1 | 2 | 1 | 1 | 1 |
| K326 | 18GH207 | 1 | 2 | 1 | 1 | 1 |
| K326 | 18GH342 | 1 | 2 | 1 | 1 | 1 |
| K326 | 18GH343 | 1 | 2 | 1 | 1 | 1 |
| K326 | 18GH348 | 1 | 1 | 1 | 1 | 1 |
| K326 | 18GH349 | 1 | 1 | 1 | 1 | 1 |
| K326 | 18GH355 | 1 | 2 | 2 | 3 | 2 |
| K326 | 18GH359 | 1 | 2 | 1 | 1 | 1 |
| K326 | 18GH64 | 2 | 1 | 2 | 1 | 1 |
| K326 | 18GH682 | 1 | 2 | 2 | 2 | 2 |
| K326 | 18GH692 | 1 | 2 | 2 | 2 | 1 |
| K326 | 18GH697 | 1 | 1 | 1 | 1 | 1 |
| K326 | 18GH922 | 1 | 1 | 1 | 1 | 1 |
| K326 | 18GH957 | 1 | 1 | 2 | 1 | 1 |
| K326 | 17GH1808 | 1 | 2 | 1 | 2 | 1 |
| K326 | 17GH1810 | 1 | 1 | 1 | 2 | 2 |
| K326 | 17GH1886 | — | — | 2 | 1 | — |
| K326 | 17GH1888 | — | 1 | 1 | — | — |
| K326 | 17GH1889 | — | 1 | 1 | — | — |
| K326 | 17GH1892 | 3 | 1 | 2 | 2 | — |
| K326 | 17GH1893 | 1 | 1 | 1 | 1 | 1 |
| K326 | 17GH1901 | 1 | 1 | 1 | 2 | 2 |
| K326 | 17GH1902 | 1 | 1 | 1 | 2 | 2 |
| K326 | 18GH3 | — | 1 | 1 | 1 | — |
| Katerini | 18GH125 | 2 | 2 | 1 | 2 | 1 |
| Katerini | 18GH208 | 2 | 1 | 1 | 2 | 1 |
| Katerini | 18GH403 | 1 | 1 | 1 | 1 | — |
| Katerini | 18GH414 | 2 | 1 | 1 | 1 | 1 |
| Katerini | 18GH434 | 2 | 1 | 1 | 2 | 1 |
| Katerini | 18GH436 | 2 | 1 | 1 | 4 | 1 |
| Katerini | 18GH437 | 1 | 2 | 1 | 2 | 2 |
| Katerini | 18GH449 | 2 | 2 | 1 | 1 | 1 |
| Katerini | 18GH706 | 2 | 1 | 1 | 2 | 1 |
| Katerini | 18GH709 | 2 | 2 | 1 | 1 | 1 |
| Katerini | 18GH710 | 1 | 1 | 2 | 2 | 1 |
| Katerini | 18GH716 | 2 | 2 | 1 | 2 | 2 |
| Katerini | 18GH729 | 1 | 1 | 2 | 2 | 1 |
| Katerini | 18GH731 | 1 | 1 | 1 | 2 | 1 |
| Katerini | 18GH752 | 2 | 1 | 1 | 1 | 1 |
| Katerini | 18GH756 | 1 | 1 | 1 | 2 | 2 |
| Katerini | 18GH768 | 1 | 1 | 1 | 1 | 2 |
| Katerini | 18GH771 | 1 | 1 | 2 | 2 | 1 |
| Katerini | 18GH776 | 2 | 2 | 1 | 1 | 2 |
| Katerini | 18GH800 | 2 | 2 | 1 | 1 | 2 |
| Katerini | 18GH818 | 1 | 1 | 1 | 2 | — |
| NLMz | 18GH10 | 1 | 1 | 1 | 1 | 1 |
| NLMz | 18GH1004 | 2 | 1 | 1 | 2 | 2 |
| NLMz | 18GH1033 | 2 | 1 | 1 | 2 | 2 |
| NLMz | 18GH132 | 1 | 2 | 2 | 3 | 1 |
| NLMz | 18GH134 | 1 | 2 | 1 | 1 | 1 |
| NLMz | 18GH217 | 1 | 2 | 2 | 1 | 2 |
| NLMz | 18GH456 | 2 | 1 | 1 | 1 | 1 |
| NLMz | 18GH457 | 1 | 1 | 1 | 1 | 1 |
| NLMz | 18GH460 | 1 | 2 | 3 | 1 | 1 |
| NLMz | 18GH465 | 2 | 1 | 1 | 2 | 2 |
| NLMz | 18GH71 | 1 | 1 | 1 | 1 | 1 |
| NLMz | 18GH830 | 1 | 1 | 1 | 1 | 1 |
| NLMz | 18GH831 | 1 | 2 | 1 | — | 1 |
| NLMz | 18GH836 | 1 | 1 | 1 | 1 | 1 |
| NLMz | 18GH841 | 2 | 2 | 1 | — | 1 |
| NLMz | 18GH974 | 2 | 1 | 2 | 2 | 1 |
| NLMz | 18GH981 | 1 | 1 | 2 | 2 | 2 |
| NLMz | 18GH994 | 2 | 1 | 2 | 2 | 2 |
| NLMz | 17GH1905 | 1 | 2 | 1 | 2 | 2 |
| NLMz | 18GH128 | — | — | 2 | 2 | 1 |
| NLMz | 18GH130 | 2 | 2 | 1 | 1 | 1 |
| NLMz | 18GH131 | 1 | 3 | 2 | — | 1 |
| NLMz | 18GH133 | 2 | 3 | 2 | — | 1 |
| NLMz | 18GH136 | — | — | 1 | — | — |
| NLMz | 18GH216 | 2 | 2 | 1 | 1 | 2 |
| NLMz | 18GH227 | 1 | 1 | 1 | — | 1 |
| NLMz | 18GH5 | 1 | 2 | 1 | 2 | 2 |
| NLMz | 18GH6 | 1 | 1 | 3 | 1 | 1 |
| NLMz | 18GH65 | 2 | 2 | 2 | 2 | 1 |
| NLMz | 18GH66 | 1 | 2 | 1 | 2 | 2 |
| NLMz | 18GH69 | — | 1 | — | 2 | 1 |
| NLMz | 18GH72 | 2 | 2 | 2 | 2 | 1 |
| NLMz | 18GH73 | — | 2 | 2 | — | 1 |
| NLMz | 18GH74 | — | 1 | — | — | — |
| NLMz | 18GH78 | 1 | 1 | 1 | 3 | 2 |
| NLMz | 18GH79 | — | 2 | 2 | — | 1 |
| NLMz | 18GH8 | 1 | 2 | 2 | 1 | 2 |
| NLMz | 18GH9 | 1 | 2 | 1 | — | 1 |

TABLE 3-continued

Zygosity of individual PMT genic locus in selected pmt mutants in various background produced by genome editing using GET2. Number one (1) represents homozygous for a single mutant allele. Numbers 2 to 5 represent a heteroallelic combination having 2 to 5 Indels. Hyphens indicate no data. Detailed genotype information is shown in Tables 4A to 4D.

| Variety | Line | PMT1b | PMT1a | PMT2 | PMT3 | PMT4 |
|---|---|---|---|---|---|---|
| TN90 | 17GH1696 | 1 | 1 | 1 | 1 | 1 |
| TN90 | 17GH1717 | 1 | 2 | 2 | 2 | 1 |
| TN90 | 17GH1719 | 1 | 2 | 1 | 1 | 1 |
| TN90 | 17GH1729 | 2 | 1 | 1 | 1 | 1 |
| TN90 | 17GH1736 | 1 | 1 | 2 | 1 | 1 |
| TN90 | 17GH1737 | 1 | 2 | 2 | 2 | 1 |
| TN90 | 17GH1739 | 1 | 1 | 1 | 1 | 2 |
| TN90 | 17GH1740 | 1 | 2 | 1 | 2 | 1 |
| TN90 | 17GH1835 | 2 | 2 | 2 | 1 | 1 |
| TN90 | 17GH1848 | 1 | 2 | 1 | 1 | 1 |
| TN90 | 17GH1849 | 1 | 1 | 1 | 2 | 2 |
| TN90 | 17GH1912 | 1 | 2 | 1 | 1 | 1 |
| TN90 | 17GH1937 | 1 | 2 | 1 | 2 | 1 |
| TN90 | 17GH1940 | 1 | 2 | 1 | 1 | 1 |
| TN90 | 17GH1943 | 1 | 1 | 1 | 1 | 2 |
| TN90 | 17GH1944 | 1 | 1 | 1 | 1 | 2 |
| TN90 | 18GH1051 | 2 | 2 | 2 | 1 | 2 |
| TN90 | 18GH22 | 1 | 2 | 1 | 2 | 1 |
| TN90 | 18GH34 | 1 | 1 | 1 | 1 | 2 |
| TN90 | 18GH473 | 1 | 1 | 1 | 2 | 2 |
| TN90 | 18GH49 | 1 | 1 | 1 | 1 | 1 |
| TN90 | 18GH50 | 2 | 1 | 1 | 1 | 1 |
| TN90 | 18GH848 | 2 | 2 | 2 | 1 | 2 |
| TN90 | 18GH850 | 1 | 2 | 1 | 2 | 2 |
| TN90 | 18GH851 | 1 | 2 | 1 | 2 | 2 |
| TN90 | 17GH1699 | 3 | 2 | 2 | 2 | 1 |
| TN90 | 17GH1708 | 1 | 3 | 1 | 2 | — |
| TN90 | 17GH1722 | 2 | 1 | 2 | 2 | 1 |
| TN90 | 17GH1724 | 2 | 1 | 1 | 2 | 1 |
| TN90 | 17GH1725 | 2 | 1 | 1 | 2 | 1 |
| TN90 | 17GH1845 | 2 | 2 | 1 | 2 | 2 |
| TN90 | 17GH1846 | 2 | 1 | 2 | 2 | 1 |
| TN90 | 17GH1847 | 2 | 1 | 2 | 2 | 1 |
| TN90 | 17GH1911 | 1 | 2 | 1 | 1 | 1 |
| TN90 | 17GH1912 | 1 | 2 | 1 | 1 | 1 |
| TN90 | 17GH1915 | — | 1 | — | 1 | — |
| TN90 | 17GH1918 | 2 | 2 | 1 | 1 | 5 |
| TN90 | 17GH1928 | 2 | 2 | — | 2 | 1 |
| TN90 | 17GH1932 | 2 | 2 | — | — | 1 |
| TN90 | 17GH1933 | 2 | 2 | 2 | 5 | 1 |
| TN90 | 17GH1936 | 2 | 2 | 2 | 1 | 2 |
| TN90 | 18GH20 | — | 1 | 2 | 1 | 2 |
| TN90 | 18GH28 | 2 | 1 | 2 | 1 | 2 |
| TN90 | 18GH31 | 1 | 3 | 1 | 1 | 1 |
| TN90 | 18GH47 | 1 | 3 | 1 | 1 | 1 |
| TN90 | 18GH51 | — | — | — | 1 | — |
| TN90 | 18GH52 | — | — | — | 1 | — |

TABLE 4A

Mutant pmt alleles in K326 produced by genome editing using GET2. The position of each edited site (e.g.,, indels) is relative to the nucleotide number on the corresponding cDNA sequence of each PMT gene. For example, line 17GH1678 has bi-allelic mutations in PMT1b. One of the two alleles has a four-nucleotide deletion which corresponds to nucleotides 416 to 419 of the PMT1b cDNA sequence. The other allele has a two-nucleotide deletion which corresponds to nucleotides 418 to 419 of the PMT1b cDNA sequence. SEQ ID Numbers are assigned and shown for sequences of more than 10 nucleotides.

| | | PMT1b | | PMT1a | | PMT2 | |
|---|---|---|---|---|---|---|---|
| VARIETY | LINE | Position | Deleted sequence | Position | Deleted sequence | Position | Deleted sequence |
| K326 | 17GH1678 | 416..419 | ATAC | 415..421 | CATACAG | 348..349 | AC |
| | | 418..419 | AC | 417..420 | TACA | | |
| K326 | 17GH1680 | 414..417 | ACAT | 414..417 | ACAT | 348..349 | AC |
| | | | | 416..417 | AT | | |
| K326 | 17GH1804 | 414..417 | ACAT | 411..420 | TCAACATACA(379) | 348..349 | AC |
| | | | | 417..420 | TACA | | |
| K326 | 17GH1898 | 414..417 | ACAT | 411..420 | TCAACATACA(379) | 348..349 | AC |
| | | | | 417..420 | TACA | | |
| K326 | 18GH207 | 414..417 | ACAT | 415..415 | C | 348..351 | ACAC |
| | | | | 417..417 | T | | |
| K326 | 18GH343 | 414..417 | ACAT | 414..417 | ACAT | 348..349 | AC |
| | | | | 416..417 | AT | | |
| K326 | 18GH348 | 414..417 | ACAT | 414..417 | ACAT | 348..349 | AC |
| K326 | 18GH349 | 414..417 | ACAT | 414..417 | ACAT | 348..349 | AC |
| K326 | 18GH355 | 414..417 | ACAT | 414..417 | ACAT | 348..351 | ACAC |
| | | | | 416..417 | AT | 350..351 | AC |
| K326 | 18GH359 | 414..417 | ACAT | 411..420 | TCAACATACA(379) | 348..349 | AC |
| | | | | 417..420 | TACA | | |

TABLE 4A-continued

Mutant pmt alleles in K326 produced by genome editing using GET2. The position of each edited site (e.g., indels) is relative to the nucleotide number on the corresponding cDNA sequence of each PMT gene. For example, line 17GH1678 has bi-allelic mutations in PMT1b. One of the two alleles has a four-nucleotide deletion which corresponds to nucleotides 416 to 419 of the PMT1b cDNA sequence. The other allele has a two-nucleotide deletion which corresponds to nucleotides 418 to 419 of the PMT1b cDNA sequence. SEQ ID Numbers are assigned and shown for sequences of more than 10 nucleotides.

| Variety | Line | Pos1 | Seq1 | Pos2 | Seq2 | Pos3 | Seq3 |
|---|---|---|---|---|---|---|---|
| K326 | 18GH64 | 413..420<br>417..420 | AACATACA<br>TACA | 414..417 | ACAT | 349..352<br>354..359 | CACA<br>AGAGAA |
| K326 | 18GH682 | 415..421 | CATACAG | 413..422<br>417..420 | AACATACAGA(386)<br>TACA | 348..351<br>350..351 | ACAC<br>AC |
| K326 | 18GH692 | 414..417 | ACAT | 414..420<br>416..420 | ACATACA<br>ATACA | 348..351<br>350..351 | ACAC<br>AC |
| K326 | 18GH697 | 414..417 | ACAT | 414..417 | ACAT | 348..351 | ACAC |
| K326 | 18GH922 | 414..417 | ACAT | 414..417 | ACAT | 348..351 | ACAC |
| K326 | 18GH957 | 414..417 | ACAT | 414..417 | ACAT | 349..355<br>351..354 | CACACAG<br>CACA |
| K326 | 17GH1886 | — | — | — | — | 346..350<br>349..350 | CAACA<br>CA |
| K326 | 17GH1888 | — | — | 418..419 | AC | 348..349 | AC |
| K326 | 17GH1889 | — | — | 418..419 | AC | 348..349 | AC |
| K326 | 17GH1892 | 413..419<br>414..419<br>416..419 | AACATAC<br>ACATAC<br>ATAC | 414..417 | ACAT | 348..351<br>350..351 | ACAC<br>AC |
| K326 | 17GH1893 | 416..421 | ATACAG | 416..420 | ATACA | 348..349 | AC |
| K326 | 17GH1901 | 414..417 | ACAT | 417..420 | TACA | 348..355 | ACACACAG |
| K326 | 17GH1902 | 414..417 | ACAT | 417..420 | TACA | 348..355 | ACACACAG |
| K326 | 17GH1808 | 414..417 | ACAT | 413..421<br>418..421 | AACATACAG<br>ACAG | 352..354 | ACA |
| K326 | 17GH1810 | 414..417 | ACAT | 417..420 | TACA | 348..355 | ACACACAG |
| K326 | 18GH3 | — | — | 414..417 | ACAT | 348..349 | AC |
| K326 | 18GH4 | — | — | 414..417 | ACAT | 348..349 | AC |

| | | PMT3 | | PMT4 | |
|---|---|---|---|---|---|
| VARIETY | LINE | Position | Deleted sequence | Position | Deleted sequence |
| K326 | 17GH1678 | 432..435 | ACAC | 547..551<br>548..551 | CACAC<br>ACAC |
| K326 | 17GH1680 | 432..435 | ACAC | 546..547 | AC |
| K326 | 17GH1804 | 433..437 | CACAC | 548..552 | ACACA |
| K326 | 17GH1898 | 433..437 | CACAC | 548..552 | ACACA |
| K326 | 18GH207 | 432..433 | AC | 546..549 | ACAC |
| K326 | 18GH343 | 432..435 | ACAC | 546..547 | AC |
| K326 | 18GH348 | 429..439 | TCAACACACAG(396) | 546..547 | AC |
| K326 | 18GH349 | 429..439 | TCAACACACAG(396) | 546..547 | AC |
| K326 | 18GH355 | 431..438<br>435..438<br>440..442 | AACACACA<br>CACA<br>AGA | 546..547<br>550..553 | AC<br>ACAG |
| K326 | 18GH359 | 433..437 | CACAC | 548..552 | ACACA |
| K326 | 18GH64 | 432..433 | AC | 546..549 | ACAC |

TABLE 4A-continued

Mutant pmt alleles in K326 produced by genome editing using GET2. The position of each edited site (e.g.,, indels) is relative to the nucleotide number on the corresponding cDNA sequence of each PMT gene. For example, line 17GH1678 has bi-allelic mutations in PMT1b. One of the two alleles has a four-nucleotide deletion which corresponds to nucleotides 416 to 419 of the PMT1b cDNA sequence. The other allele has a two-nucleotide deletion which corresponds to nucleotides 418 to 419 of the PMT1b cDNA sequence. SEQ ID Numbers are assigned and shown for sequences of more than 10 nucleotides.

| | | | | | |
|---|---|---|---|---|---|
| K326 | 18GH682 | 432..439 | ACACACAG | 543..554 | TCAACACACAGA(404) |
| | | 437..438 | CA | 549..552 | CACA |
| K326 | 18GH692 | 432..439 | ACACACAG | 546..549 | ACAC |
| | | 437..438 | CA | | |
| K326 | 18GH697 | 430..436 | CAACACA | 546..549 | ACAC |
| K326 | 18GH922 | 430..436 | CAACACA | 546..549 | ACAC |
| K326 | 18GH957 | 431..438 | AACACACA | 546..547 | AC |
| K326 | 17GH1886 | 432..433 | AC | — | — |
| K326 | 17GH1888 | — | — | — | — |
| K326 | 17GH1889 | — | — | — | — |
| K326 | 17GH1892 | 432..435 | ACAC | — | — |
| | | 434..435 | AC | | |
| K326 | 17GH1893 | 430..436 | CAACACA | 546..547 | AC |
| K326 | 17GH1901 | 432..435 | ACAC | 548..552 | ACACA |
| | | 434..435 | AC | 550..552 | ACA |
| K326 | 17GH1902 | 432..435 | ACAC | 548..552 | ACACA |
| | | 434..435 | AC | 550..552 | ACA |
| K326 | 17GH1808 | 432..435 | ACAC | 546..547 | AC |
| | | 434..435 | AC | | |
| K326 | 17GH1810 | 432..435 | ACAC | 548..552 | ACACA |
| | | 434..435 | AC | 550..552 | ACA |
| K326 | 18GH3 | 432..435 | ACAC | — | — |
| K326 | 18GH4 | 429..439 | TCAACACACAG(396) | 546..547 | AC |

TABLE 4B

Mutant pmt alleles in TN90 produced by genome editing using GET2.

| VARIETY | LINE | PMT1b | | PMT1a | | PMT2 | |
|---|---|---|---|---|---|---|---|
| | | Position | Deleted sequence | Position | Deleted sequence | Position | Deleted sequence |
| TN90 | 17GH1696 | 414..417 | ACAT | 414..417 | ACAT | 348..349 | AC |
| TN90 | 17GH1717 | 414..417 | ACAT | 414..417 | ACAT | 346..352 | CAACACA |
| | | | | 415..416 | CA | 349..352 | CACA |
| TN90 | 17GH1719 | 414..417 | ACAT | 417..420 | TACA | 348..349 | AC |
| | | | | 417..423 | TACAGAG | | |
| TN90 | 17GH1729 | 412..421 | CAACATACAG(380) | 412..418 | CAACATA | 348..351 | ACAC |
| | | 414..420 | ACATACA | | | | |
| TN90 | 17GH1736 | 418..421 | ACAG | 414..417 | ACAT | 347..357 | AACACACAGAG(391) |
| | | | | | | 351..354 | CACA |
| TN90 | 17GH1737 | 414..417 | ACAT | 414..417 | ACAT | 346..352 | CAACACA |
| | | | | 415..416 | CA | 349..352 | CACA |

TABLE 4B-continued

Mutant pmt alleles in TN90 produced by genome editing using GET2.

| | | | | | | | |
|---|---|---|---|---|---|---|---|
| TN90 | 17GH1739 | 414..417 | ACAT | 414..417 | ACAT | 348..349 | AC |
| TN90 | 17GH1740 | 414..417 | ACAT | 416..419<br>418..419 | ATAC<br>AC | 348..351 | ACAC |
| TN90 | 17GH1835 | 413..421<br>417..420 | AACATACAG<br>TACA | 417..420<br>418..421 | TACA<br>ACAG | 350..354<br>351..362 | ACACA<br>CACAGAGAATGG<br>(394) |
| TN90 | 17GH1848 | 414..417 | ACAT | 417..420<br>417..423 | TACA<br>TACAGAG | 348..349 | AC |
| TN90 | 17GH1849 | 414..417 | ACAT | 414..417 | ACAT | 348..351 | ACAC |
| TN90 | 17GH1912 | 414..417 | ACAT | 417..420<br>417..423 | TACA<br>TACAGAG | 348..349 | AC |
| TN90 | 17GH1937 | 416..419 | ATAC | 412..421<br>(380)<br>417..420 | CAACATACAG<br>TACA | 348..351 | ACAC |
| TN90 | 17GH1940 | 414..417 | ACAT | 417..420<br>417..423 | TACA<br>TACAGAG | 348..349 | AC |
| TN90 | 17GH1943 | 414..417 | ACAT | 414..417 | ACAT | 348..349 | AC |
| TN90 | 17GH1944 | 414..417 | ACAT | 414..417 | ACAT | 348..349 | AC |
| TN90 | 18GH1051 | 414..418<br>415..421 | ACATA<br>CATACAG | 412..418<br>415..418 | CAACATA<br>CATA | 348..351<br>350..351 | ACAC<br>AC |
| TN90 | 18GH22 | 416..419 | ATAC | 412..421<br>(380)<br>417..420 | CAACATACAG<br>TACA | 348..351 | ACAC |
| TN90 | 18GH34 | 414..417 | ACAT | 414..417 | ACAT | 348..349 | AC |
| TN90 | 18GH473 | 414..417 | ACAT | 414..417 | ACAT | 348..351 | ACAC |
| TN90 | 18GH49 | 412..421 | CAACATACAG<br>(380) | 412..418 | CAACATA | 348..351 | ACAC |
| TN90 | 18GH50 | 412..421<br>414..420 | CAACATACAG<br>(380)<br>ACATACA | 412..418 | CAACATA | 348..351 | ACAC |
| TN90 | 18GH848 | 414..418<br>415..421 | ACATA<br>CATACAG | 412..418<br>415..418 | CAACATA<br>CATA | 348..351<br>350..351 | ACAC<br>AC |
| TN90 | 18GH850 | 414..417 | ACAT | 416..422<br>417..420 | ATACAGA<br>TACA | 348..349 | AC |
| TN90 | 18GH851 | 414..417 | ACAT | 416..422<br>417..420 | ATACAGA<br>TACA | 348..349 | AC |
| TN90 | 17GH1699 | 419..420<br>418..423<br>427..427 | CA<br>ACAGAG<br>G | 413..420<br>419..420 | AACATACA<br>CA | 348..351<br>349..349 | ACAC<br>C |
| TN90 | 17GH1708 | 414..417 | ACAT | 414..415<br>418..424<br>419..420 | AC<br>ACAGAGAA<br>CA | 346..355 | CAACACACAG(390) |
| TN90 | 17GH1722 | 415..420<br>418..421 | CATACA<br>ACAG | 414..417 | ACAT | 348..351<br>350..351 | ACAC<br>AC |
| TN90 | 17GH1724 | 416..421<br>417..420 | ATACAG<br>TACA | 414..417 | ACAT | 348..351 | ACAC |
| TN90 | 17GH1725 | 416..421<br>417..420 | ATACAG<br>TACA | 414..417 | ACAT | 348..351 | ACAC |
| TN90 | 17GH1845 | 416..418<br>418..419 | ATA<br>AC | 412..418<br>415..418 | CAACATA<br>CATA | 348..351 | ACAC |
| TN90 | 17GH1846 | 415..420<br>418..421 | CATACA<br>ACAG | 414..417 | ACAT | 348..351<br>350..351 | ACAC<br>AC |

TABLE 4B-continued

Mutant pmt alleles in TN90 produced by genome editing using GET2.

| TN90 | 17GH1847 | 415..420<br>418..421 | CATACA<br>ACAG | 414..417 | ACAT | 348..351<br>350..351 | ACAC<br>AC |
| --- | --- | --- | --- | --- | --- | --- | --- |
| TN90 | 17GH1911 | 414..417 | ACAT | 417..420<br>417..423 | TACA<br>TACAGAG | 348..349 | AC |
| TN90 | 17GH1912 | 414..417 | ACAT | 417..420<br>417..423 | TACA<br>TACAGAG | 348..349 | AC |
| TN90 | 17GH1915 | — | — | 414..417 | ACAT | — | — |
| TN90 | 17GH1918 | 414..419<br>416..419 | ACATAC<br>ATAC | 417..420<br>418..421 | TACA<br>ACAG | 353..361 | CAGAGAATG |
| TN90 | 17GH1928 | 412..418<br>415..418 | CAACATA<br>CATA | 414..417<br>419..421 | ACAT<br>CAG | — | — |
| TN90 | 17GH1932 | 414..419<br>416..419 | ACATAC<br>ATAC | 416..419<br>418..419 | ATAC<br>AC | — | — |
| TN90 | 17GH1933 | 414..419<br>416..419 | ACATAC<br>ATAC | 416..419<br>418..419 | ATAC<br>AC | 350..355<br>351..354 | ACACAG<br>CACA |
| TN90 | 17GH1936 | 413..421<br>417..420 | AACATACAG<br>TACA | 416..419<br>418..419 | ATAC<br>AC | 348..351<br>350..351 | ACAC<br>AC |
| TN90 | 18GH20 | | | 414..419 | ACATAC | 348..349<br>352..355 | AC<br>ACAG |
| TN90 | 18GH47 | 414..419 | ACATAC | 416..419<br>418..419<br>424..425 | ATAC<br>AC<br>AA | 348..349 | AC |
| TN90 | 18GH28 | 414..419<br>416..419 | ACATAC<br>ATAC | 414..417 | ACAT | 348..351<br>350..351 | ACAC<br>AC |
| TN90 | 18GH31 | 414..419 | ACATAC | 416..419<br>418..419<br>424..425 | ATAC<br>AC<br>AA | 348..349 | AC |

| | | PMT3 | | PMT4 | |
| --- | --- | --- | --- | --- | --- |
| VARIETY | LINE | Position | Deleted sequence | Position | Deleted sequence |
| TN90 | 17GH1696 | 436..439 | ACAG | 546..547 | AC |
| TN90 | 17GH1717 | 432..435<br>434..435 | ACAC<br>AC | 546..547 | AC |
| TN90 | 17GH1719 | 432..433 | AC | 546..549 | ACAC |
| TN90 | 17GH1729 | 432..433 | AC | 546..547 | AC |
| TN90 | 17GH1736 | 432..433 | AC | 546..547 | AC |
| TN90 | 17GH1737 | 432..435<br>434..435 | ACAC<br>AC | 546..547 | AC |
| TN90 | 17GH1739 | 432..433 | AC | 546..549<br>548..549 | ACAC<br>AC |
| TN90 | 17GH1740 | 435..438<br>436..439 | CACA<br>ACAG | 546..547 | AC |
| TN90 | 17GH1835 | 432..435 | ACAC | 546..547 | AC |
| TN90 | 17GH1848 | 432..433 | AC | 546..549 | ACAC |
| TN90 | 17GH1849 | 430..436<br>433..436 | CAACACA<br>CACA | 546..549<br>548..549 | ACAC<br>AC |
| TN90 | 17GH1912 | 432..433 | AC | 546..549 | ACAC |
| TN90 | 17GH1937 | 432..435<br>434..435 | ACAC<br>AC | 546..547 | AC |
| TN90 | 17GH1940 | 432..433 | AC | 546..549 | ACAC |

TABLE 4B-continued

Mutant pmt alleles in TN90 produced by genome editing using GET2.

| | | | | | |
|---|---|---|---|---|---|
| TN90 | 17GH1943 | 432..433 | AC | 546..549 | ACAC |
| TN90 | 17GH1944 | 432..433 | AC | 546..549<br>548..549 | ACAC<br>AC |
| TN90 | 18GH1051 | 432..433 | AC | 546..549<br>548..549 | ACAC<br>AC |
| TN90 | 18GH22 | 432..435<br>434..435 | ACAC<br>AC | 546..547 | AC |
| TN90 | 18GH34 | 432..433 | AC | 546..549<br>548..549 | ACAC<br>AC |
| TN90 | 18GH473 | 430..436<br>433..436 | CAACACA<br>CACA | 546..549<br>548..549 | ACAC<br>AC |
| TN90 | 18GH49 | 432..433 | AC | 546..547 | AC |
| TN90 | 18GH50 | 432..433 | AC | 546..547 | AC |
| TN90 | 18GH848 | 432..433 | AC | 546..549 | ACAC |
| TN90 | 18GH850 | 435..438<br>436..439 | CACA<br>ACAG | 546..547<br>550..553 | AC<br>ACAG |
| TN90 | 18GH851 | 435..438<br>436..439 | CACA<br>ACAG | 546..547<br>550..553 | AC<br>ACAG |
| TN90 | 17GH1699 | 429..438<br>432..446 | TCAACACACA<br>(395)<br>ACACACAG<br>AGAATGG<br>(399) | 546..547 | AC |
| TN90 | 17GH1708 | 432..437<br>440..443 | ACACAC<br>AGAA | — | — |
| TN90 | 17GH1722 | 432..433<br>435..439 | AC<br>CACAG | 546..549 | ACAC |
| TN90 | 17GH1724 | 432..435<br>434..435 | ACAC<br>AC | 550..553 | ACAG |
| TN90 | 17GH1725 | 432..435<br>434..435 | ACAC<br>AC | 550..553 | ACAG |
| TN90 | 17GH1845 | 433..437<br>436..437 | CACAC<br>AC | 546..551<br>550..551 | ACACAC<br>AC |
| TN90 | 17GH1846 | 432..433<br>435..439 | AC<br>CACAG | 546..549 | ACAC |
| TN90 | 17GH1847 | 432..433<br>435..439 | AC<br>CACAG | 546..549 | ACAC |
| TN90 | 17GH1911 | 432..433 | AC | 546..549 | ACAC |
| TN90 | 17GH1912 | 432..433 | AC | 546..549 | ACAC |
| TN90 | 17GH1915 | 432..435 | ACAC | — | — |
| TN90 | 17GH1918 | 432..435 | ACAC | 544..550<br>554..554<br>558..563<br>565..566<br>569..572 | CAACACA<br>A<br>TGGTGG<br>TT<br>CATA |
| TN90 | 17GH1928 | 432..448<br>437..438 | ACACACAG<br>AGAATGGTG<br>(400)<br>CA | 546..547 | AC |
| TN90 | 17GH1932 | — | — | 546..551 | ACACAC |

TABLE 4B-continued

Mutant pmt alleles in TN90 produced by genome editing using GET2.

| | | | | | |
|---|---|---|---|---|---|
| TN90 | 17GH1933 | 413..414 | CT | 546..551 | ACACAC |
| | | 418..419 | GA | | |
| | | 426..427 | AA | | |
| | | 431..432 | AA | | |
| | | 432..435 | ACAC | | |
| TN90 | 17GH1936 | 432..433 | AC | 544..550 | CAACACA |
| | | | | 547..550 | CACA |
| TN90 | 18GH20 | 432..433 | AC | 546..549 | ACAC |
| | | | | 548..549 | AC |
| TN90 | 18GH47 | 436..439 | ACAG | 546..549 | ACAC |
| TN90 | 18GH28 | 433..437 | CACAC | 546..549 | ACAC |
| | | | | 548..549 | AC |
| TN90 | 18GH31 | 436..439 | ACAG | 546..549 | ACAC |

TABLE 4C

Mutant pmt alleles in NLMz produced by genome editing using GET2. NLMz refers to the Narrow Leaf Madole variety containing triple loss-of-function mutations in three nicotine demethylase genes (CYP82E4, CYP82E5v2, and CYP82E10).

| | | PMT1b | | PMT1a | | PMT2 | |
|---|---|---|---|---|---|---|---|
| VARIETY | LINE | Position | Deleted sequence | Position | Deleted sequence | Position | Deleted sequence |
| NLMz | 18GH10 | 414..417 | ACAT | 414..417 | ACAT | 350..351 | AC |
| NLMz | 18GH1004 | 414..417<br>416..416 | ACAT<br>A | 412..418 | CAACATA | 348..349 | AC |
| NLMz | 18GH1033 | 414..417<br>416..416 | ACAT<br>A | 412..418 | CAACATA | 348..349 | AC |
| NLMz | 18GH132 | 417..418 | TA | 416..419<br>418..419 | ATAC<br>AC | 348..352<br>348..353 | ACACA<br>ACACAC |
| NLMz | 18GH134 | 414..417 | ACAT | 414..423<br>419..420 | ACATACAGAG (388)<br>CA | 348..351 | ACAC |
| NLMz | 18GH217 | 414..417 | ACAT | 415..419<br>417..418 | CATAC<br>TA | 346..352<br>351..352 | CAACACA<br>CA |
| NLMz | 18GH456 | 416..419<br>418..419 | ATAC<br>AC | 414..417 | ACAT | 348..349 | AC |
| NLMz | 18GH457 | 414..417 | ACAT | 414..417 | ACAT | 348..349 | AC |
| NLMz | 18GH460 | 414..417 | ACAT | 409..420<br>416..429 | ATTCAACATACA (383)<br>ATACAGAGAATGGT (389) | 350..363<br>351..354<br>353..354 | ACACAGAGAATGGT (393)<br>CACA<br>CA |
| NLMz | 18GH465 | 414..417<br>416..416 | ACAT<br>A | 412..418 | CAACATA | 348..349 | AC |
| NLMz | 18GH830 | 414..417 | ACAT | 414..417 | ACAT | 348..351 | ACAC |
| NLMz | 18GH831 | 413..428 | AACATACAGAGAATGG (381) | 413..428<br>417..420 | AACATACAGAGAATGG (381)<br>TACA | 348..351 | ACAC |
| NLMz | 18GH836 | 414..417 | ACAT | 414..417 | ACAT | 348..349 | AC |
| NLMz | 18GH841 | 415..421<br>419..420 | CATACAG<br>CA | 413..420<br>414..420 | AACATACA<br>ACATACA | 347..357 | AACACACAGAG (391) |

TABLE 4C-continued

Mutant pmt alleles in NLMz produced by genome editing using GET2. NLMz refers to the Narrow Leaf Madole variety containing triple loss-of-function mutations in three nicotine demethylase genes (CYP82E4, CYP82E5v2, and CYP82E10).

| | | | | | | | |
|---|---|---|---|---|---|---|---|
| NLMz | 18GH974 | 411..420 | TCAACATACA(379) | 411..420 | TCAACATACA (379) | 351..354 | CACA |
| | | 417..420 | TACA | | | 353..354 | CA |
| NLMz | 18GH981 | 412..418 | CAACATA | 414..417 | ACAT | 346..352 | CAACACA |
| | | | | | | 349..352 | CACA |
| NLMz | 18GH994 | 414..417 | ACAT | 412..418 | CAACATA | 348..349 | AC |
| | | 416..416 | A | | | | |
| NLMz | 18GH128 | — | — | 414..420 | ACATACA | 348..351 | ACAC |
| | | | | 417..421 | TACAG | 350..351 | AC |
| NLMz | 18GH130 | 414..437 | ACATACAGAG AATGGTGGAT TTCC (382) | 412..418 | CAACATA | 349..355 | CACACAG |
| | | 417..420 | TACA | 415..418 | CATA | | |
| NLMz | 18GH131 | 417..418 | TA | 416..419 | ATAC | 348..353 | ACACAC |
| | | | | 417..419 | TAC | 350..353 | ACAC |
| | | | | 418..419 | AC | | |
| NLMz | 18GH133 | 413..419 | AACATAC | 414..420 | ACATACA | 348..351 | ACAC |
| | | 414..419 | ACATAC | 417..420 | TACA | 350..351 | AC |
| | | | | 417..421 | TACAG | | |
| NLMz | 18GH136 | — | — | — | — | 348..349 | AC |
| NLMz | 18GH216 | 412..418 | CAACATA | 414..419 | ACATAC | 347..354 | AACACACA |
| | | 415..418 | CATA | 416..419 | ATAC | | |
| NLMz | 18GH227 | 418..419 | AC | 414..417 | ACAT | 348..351 | ACAC |
| NLMz | 18GH5 | 414..417 | ACAT | 414..420 | ACATACA | 352..355 | ACAG |
| | | | | 415..421 | CATACAG | | |
| NLMz | 18GH6 | 414..417 | ACAT | 416..429 | ATACAGAG AATGGT (389) | 350..363 | ACACAGA GAATGGT(393) |
| | | | | 417..422 | TACAGA | 351..356 | CACAGA |
| | | | | | | 353..356 | CAGA |
| NLMz | 18GH65 | 416..423 | ATACAGAG | 414..419 | ACATAC | 348..351 | ACAC |
| | | 418..420 | ACA | 417..419 | TAC | 350..351 | AC |
| NLMz | 18GH66 | 414..417 | ACAT | 414..420 | ACATACA | 352..355 | ACAG |
| | | | | 415..421 | CATACAG | | |
| NLMz | 18GH69 | | | 411..420 | TCAACATACA (379) | | |
| NLMz | 18GH72 | 416..423 | ATACAGAG | 414..419 | ACATAC | 348..351 | ACAC |
| | | 418..420 | ACA | 417..419 | TAC | 350..351 | AC |
| NLMz | 18GH73 | — | — | 414..420 | ACATACA | 348..351 | ACAC |
| | | | | 417..421 | TACAG | 350..351 | AC |
| NLMz | 18GH74 | — | — | 412..418 | CAACATA | — | — |
| NLMz | 18GH78 | 414..419 | ACATAC | 414..417 | ACAT | 348..349 | AC |
| NLMz | 18GH79 | — | — | 414..420 | ACATACA | 348..351 | ACAC |
| | | | | 417..421 | TACAG | 350..351 | AC |
| NLMz | 18GH8 | 417..420 | TACA | 416..421 | ATACAG | 348..354 | ACACACA |
| | | | | 417..420 | TACA | 350..354 | ACACA |
| NLMz | 18GH9 | 417..418 | TA | 416..419 | ATAC | 348..353 | ACACAC |
| | | | | 418..419 | AC | | |
| NLMz | 18GH71 | 414..417 | ACAT | 414..417 | ACAT | 348..351 | ACAC |
| NLMz | 17GH1905 | 414..417 | ACAT | 414..420 | ACATACA | 352..355 | ACAG |
| | | | | 415..421 | CATACAG | | |

TABLE 4C-continued

Mutant pmt alleles in NLMz produced by genome editing using GET2. NLMz refers to the Narrow Leaf Madole variety containing triple loss-of-function mutations in three nicotine demethylase genes (CYP82E4, CYP82E5v2, and CYP82E10).

| VARIETY | LINE | PMT3 Position | PMT3 Deleted sequence | PMT4 Position | PMT4 Deleted sequence |
|---|---|---|---|---|---|
| NLMz | 18GH10 | 431..441 | AACACACAGAG (391) | 546..549 | ACAC |
| NLMz | 18GH1004 | 430..436<br>435..436 | CAACACA<br>CA | 546..553<br>551..552 | ACACACAG<br>CA |
| NLMz | 18GH1033 | 430..436<br>435..436 | CAACACA<br>CA | 546..553<br>551..552 | ACACACAG<br>CA |
| NLMz | 18GH132 | 432..437<br>434..437<br>436..437 | ACACAC<br>ACAC<br>AC | 546..547 | AC |
| NLMz | 18GH134 | 433..439 | CACACAG | 550..556 | ACAGAGA |
| NLMz | 18GH217 | 432..435 | ACAC | 545..557<br>551..552 | AACACACAGAGAA(407)<br>CA |
| NLMz | 18GH456 | 432..433 | AC | 546..549 | ACAC |
| NLMz | 18GH457 | 432..433 | AC | 546..549 | ACAC |
| NLMz | 18GH460 | 436..439 | ACAG | 550..553 | ACAG |
| NLMz | 18GH465 | 430..436<br>435..436 | CAACACA<br>CA | 546..553<br>551..552 | ACACACAG<br>CA |
| NLMz | 18GH830 | 432..435 | ACAC | 550..553 | ACAG |
| NLMz | 18GH831 | | | 546..547 | AC |
| NLMz | 18GH836 | 432..433 | AC | 546..549 | ACAC |
| NLMz | 18GH841 | | | 546..547 | AC |
| NLMz | 18GH974 | 432..433<br>436..439 | AC<br>ACAG | 546..549 | ACAC |
| NLMz | 18GH981 | 429..439<br>431..441 | TCAACACACAG(396)<br>AACACACAGAG(391) | 546..552<br>546..553 | ACACACA<br>ACACACAG |
| NLMz | 18GH994 | 430..436<br>435..436 | CAACACA<br>CA | 546..553<br>551..552 | ACACACAG<br>CA |
| NLMz | 18GH128 | — | — | 546..547 | AC |
| NLMz | 18GH130 | 430..436 | CAACACA | 546..549 | ACAC |
| NLMz | 18GH131 | — | — | 546..547 | AC |
| NLMz | 18GH133 | — | — | 546..547 | AC |
| NLMz | 18GH136 | — | — | — | — |
| NLMz | 18GH216 | 432..433 | AC | 546..549<br>548..549 | ACAC<br>AC |
| NLMz | 18GH227 | | | 546..549 | ACAC |
| NLMz | 18GH5 | 429..435<br>432..435 | TCAACAC<br>ACAC | 546..551<br>548..551 | ACACAC<br>ACAC |
| NLMz | 18GH6 | 436..439 | ACAG | 550..553 | ACAG |
| NLMz | 18GH65 | 433..437<br>436..437 | CACAC<br>AC | 546..549 | ACAC |

TABLE 4C-continued

Mutant pmt alleles in NLMz produced by genome editing using GET2. NLMz refers to the Narrow Leaf Madole variety containing triple loss-of-function mutations in three nicotine demethylase genes (CYP82E4, CYP82E5v2, and CYP82E10).

| | | | | | |
|---|---|---|---|---|---|
| NLMz | 18GH66 | 429..435 | TCAACAC | 546..551 | ACACAC |
| | | 432..435 | ACAC | 548..551 | ACAC |
| NLMz | 18GH69 | 432..433 | AC | 546..549 | ACAC |
| | | 436..439 | ACAG | | |
| NLMz | 18GH72 | 433..437 | CACAC | 546..549 | ACAC |
| | | 436..437 | AC | | |
| NLMz | 18GH73 | — | — | 546..547 | AC |
| NLMz | 18GH74 | — | — | — | — |
| NLMz | 18GH78 | 431..431 | A | 546..549 | ACAC |
| | | 434..438 | ACACA | 548..549 | AC |
| | | 435..438 | CACA | | |
| NLMz | 18GH79 | — | — | 546..547 | AC |
| NLMz | 18GH8 | 435..447 | CACAGAGA | 549..552 | CACA |
| | | | ATGGT(401) | 549..553 | CACAG |
| NLMz | 18GH9 | — | — | 546..547 | AC |
| NLMz | 18GH71 | 431..441 | AACACACA | 546..549 | ACAC |
| | | | GAG(391) | | |
| NLMz | 17GH1905 | 429..435 | TCAACAC | 546..551 | ACACAC |
| | | 432..435 | ACAC | 548..551 | ACAC |

TABLE 4D

Mutant pmt alleles in oriental tobacco produced by genome editing using GET2.

| | | PMT1b | | PMT1a | | PMT2 | |
|---|---|---|---|---|---|---|---|
| VARIETY | LINE | Position | Deleted sequence | Position | Deleted sequence | Position | Deleted sequence |
| Katerini | 18GH125 | 412..418 | CAACATA | 416..419 | ATAC | 348..355 | ACACACAG |
| | | 414..418 | ACATA | 418..419 | AC | | |
| Basma | 18GH203 | 414..417 | ACAT | 412..418 | CAACATA | 348..357 | ACACACAGAG(392) |
| | | | | 415..418 | CATA | 353..354 | CA |
| Katerini | 18GH208 | 416..419 | ATAC | 414..417 | ACAT | 352..355 | ACAG |
| | | 418..419 | AC | | | | |
| Basma | 18GH341 | 414..417 | ACAT | 412..418 | CAACATA | 348..357 | ACACACAGAG(392) |
| | | | | 415..418 | CATA | 353..354 | CA |
| Katerini | 18GH403 | 414..417 | ACAT | 414..417 | ACAT | 348..351 | ACAC |
| Katerini | 18GH414 | 412..418 | CAACATA | 414..417 | ACAT | 348..349 | AC |
| | | 415..418 | CATA | | | | |
| Katerini | 18GH434 | 413..420 | AACATACA | 414..417 | ACAT | 351..357 | CACAGAG |
| | | 417..420 | TACA | | | | |
| Katerini | 18GH436 | 412..418 | CAACATA | 414..421 | ACATACAG | 346..352 | CAACACA |
| | | 415..416 | CA | | | | |
| Katerini | 18GH437 | 414..417 | ACAT | 414..417 | ACAT | 348..349 | AC |
| | | | | 416..417 | AT | | |
| Katerini | 18GH449 | 414..417 | ACAT | 413..419 | AACATAC | 348..349 | AC |
| | | 415..416 | CA | 418..419 | AC | | |
| Katerini | 18GH706 | 416..420 | ATACA | 414..417 | ACAT | 348..351 | ACAC |
| | | 419..420 | CA | | | | |

TABLE 4D-continued

Mutant pmt alleles in oriental tobacco produced by genome editing using GET2.

| | | | | | | | |
|---|---|---|---|---|---|---|---|
| Katerini | 18GH709 | 412..418 417..418 | CAACATA TA | 414..417 416..417 | ACAT AT | 348..349 | AC |
| Katerini | 18GH710 | 414..417 | ACAT | 414..417 | ACAT | 351..354 352..355 | CACA ACAG |
| Katerini | 18GH716 | 416..419 418..419 | ATAC AC | 417..420 417..421 | TACA TACAG | 348..351 | ACAC |
| Katerini | 18GH729 | 414..417 | ACAT | 414..417 | ACAT | 350..357 353..354 | ACACAGAG CA |
| Katerini | 18GH731 | 414..417 | ACAT | 414..417 | ACAT | 348..351 | ACAC |
| Katerini | 18GH752 | 416..419 418..419 | ATAC AC | 414..417 | ACAT | 348..349 | AC |
| Katerini | 18GH756 | 416..419 416..419 | ATAC ATAC | 414..417 414..417 | ACAT ACAT | 353..354 353..354 | CA CA |
| Katerini | 18GH768 | 416..419 | ATAC | 414..417 | ACAT | 348..351 | ACAC |
| Katerini | 18GH771 | 416..419 | ATAC | 414..417 | ACAT | 346..352 349..352 | CAACACA CACA |
| Katerini | 18GH776 | 409..415 418..419 | ATTCAAC AC | 411..417 414..417 | TCAACAT ACAT | 348..351 | ACAC |
| Katerini | 18GH800 | 412..418 415..418 | CAACATA CATA | 414..420 416..420 | ACATACA ATACA | 348..351 | ACAC |
| Katerini | 18GH818 | 414..417 | ACAT | 409..415 | ATTCAAC | 348..351 | ACAC |

| | | PMT3 | | PMT4 | |
|---|---|---|---|---|---|
| VARIETY | LINE | Position | Deleted sequence | Position | Deleted sequence |
| Katerini | 18GH125 | 432..435 434..435 | ACAC AC | 546..547 | AC |
| Basma | 18GH203 | 432..435 434..435 | ACAC AC | 546..549 | ACAC |
| Katerini | 18GH208 | 432..441 435..438 | ACACACAGAG(392) CACA | 546..553 | ACACACAG |
| Basma | 18GH341 | 432..435 434..435 | ACAC AC | 546..549 | ACAC |
| Katerini | 18GH403 | 432..435 | ACAC | | |
| Katerini | 18GH414 | 430..436 | CAACACA | 546..547 | AC |
| Katerini | 18GH434 | 433..439 437..438 | CACACAG CA | 546..547 | AC |
| Katerini | 18GH436 | 432..433 436..443 445..449 451..463 | AC ACAGAGAA GGTGG TTTCCATACACTG (402) | 546..547 | AC |
| Katerini | 18GH437 | 433..439 435..438 | CACACAG CACA | 544..553 551..552 | CAACACACAG(390) CA |
| Katerini | 18GH449 | 432..435 | ACAC | 546..549 | ACAC |
| Katerini | 18GH706 | 432..439 435..438 | ACACACAG CACA | 545..555 | AACACACAGAG(391) |
| Katerini | 18GH709 | 432..435 | ACAC | 546..547 | AC |
| Katerini | 18GH710 | 432..435 434..435 | ACAC AC | 546..547 | AC |

TABLE 4D-continued

Mutant pmt alleles in oriental tobacco produced by genome editing using GET2.

| | | | | | |
|---|---|---|---|---|---|
| Katerini | 18GH716 | 432..439 | ACACACAG | 546..549 | ACAC |
| | | 435..438 | CACA | 548..549 | AC |
| Katerini | 18GH729 | 432..435 | ACAC | 546..547 | AC |
| Katerini | 18GH731 | 433..433 | C | 544..553 | CAACACACAG(390) |
| | | 435..439 | CACAG | | |
| Katerini | 18GH752 | 432..435 | ACAC | 546..549 | ACAC |
| Katerini | 18GH756 | 433..439 | CACACAG | 545..555 | AACACACAGAG(391) |
| | | 433..439 | CACACAG | 545..555 | AACACACAGAG(391) |
| | | 437..438 | CA | 549..552 | CACA |
| Katerini | 18GH768 | 432..433 | AC | 544..550 | CAACACA |
| | | | | 547..550 | CACA |
| Katerini | 18GH771 | 432..435 | ACAC | 546..547 | AC |
| | | 434..435 | AC | | |
| Katerini | 18GH776 | 441..441 | G | 546..549 | ACAC |
| | | | | 548..549 | AC |
| Katerini | 18GH800 | 432..435 | ACAC | 541..551 | ATTCAACACAC(403) |
| | | | | 548..551 | ACAC |
| Katerini | 18GH818 | 432..435 | ACAC | — | — |
| | | 434..435 | AC | | |

TABLE 4E

Mutant pmt alleles in NLM (Ph Ph) tobacco produced by genome editing using GET1.

| | | PMT1b | | PMT1a | | PMT2 | | PMT3 | | PMT4 | |
|---|---|---|---|---|---|---|---|---|---|---|---|
| LINE | Modification | | Position from ATG | | Position from ATG | | Position from ATG | | Position from ATG | | Position from ATG |
| CS15 | A-deleted | | 131 | A-inserted | 132 | A-deleted T-deleted | 98 196 | A-deleted T-deleted | 98 282 | A-del | 131 |
| | T-deleted | | 262 | | | | | | | | |

TABLE 5A

A list of exemplary mutant alleles obtained in the PMT1b gene. Mutant allele sequences listed here and Tables 5B to 5E represent about 40-nucleotide-long genomic sequences from each edited PMT gene with the edited site in the middle of the genomic sequence (e.g., 20 nucleotides on each side of the deleted or inserted sequence site). These mutant alleles corresponds to those listed in Tables 4A to 4E.
PMT1b

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 131...131 | A | 23 | TGGCATTTCCAAACACCAA ACGGGCACCAGAATGGCACTT | 201 | TGGCATTTCCAAACACCAAAaCGGGCACCA GAATGGCACTT |
| 262...262 | T | 24 | CCAACTCTATTAAGCCTGGT GGTTTTCAGAGTTTAGCGCA | 202 | CCAACTCTATTAAGCCTGGTtGGTTTTCAGA GTTTAGCGCA |
| 409..415 | ATTCAAC | 25 | TTCTGACTTTGGATGGAGCA ATACAGAGAATGGTGGATTT | 203 | TTCTGACTTTGGATGGAGCAattcaacATACAG AGAATGGTGGATTT |
| 411..420 | TCAACATACA (379) | 26 | CTGACTTTGGATGGAGCAA TGAGAATGGTGGATTTCCATA | 204 | CTGACTTTGGATGGAGCAATtcaacatacaGAGA ATGGTGGATTTCCATA |
| 412..418 | CAACATA | 27 | TGACTTTGGATGGAGCAAT TCAGAGAATGGTGGATTTCCA | 205 | TGACTTTGGATGGAGCAATTcaacataCAGAGA ATGGTGGATTTCCA |

TABLE 5A-continued

A list of exemplary mutant alleles obtained in the PMT1b gene. Mutant allele sequences listed here and Tables 5B to 5E represent about 40-nucleotide-long genomic sequences from each edited PMT gene with the edited site in the middle of the genomic sequence (e.g., 20 nucleotides on each side of the deleted or inserted sequence site). These mutant alleles corresponds to those listed in Tables 4A to 4E.

PMT1b

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 412..421 | CAACATACAG (380) | 28 | TGACTTTGGATGGAGCAAT TAGAATGGTGGATTTCCATAC | 206 | TGACTTTGGATGGAGCAATTcaacatacagAGAA TGGTGGATTTCCATAC |
| 413..419 | AACATAC | 29 | GACTTTGGATGGAGCAATT CAGAGAATGGTGGATTTCCAT | 207 | GACTTTGGATGGAGCAATTCaacatacAGAGAA TGGTGGATTTCCAT |
| 413..420 | AACATACA | 30 | GACTTTGGATGGAGCAATT CGAGAATGGTGGATTTCCATA | 208 | GACTTTGGATGGAGCAATTCaacatacaGAGAA TGGTGGATTTCCATA |
| 413..421 | AACATACAG | 31 | GACTTTGGATGGAGCAATT CAGAATGGTGGATTTCCATAC | 209 | GACTTTGGATGGAGCAATTCaacatacagAGAA TGGTGGATTTCCATAC |
| 413..428 | AACATACAGAGA ATGG (381) | 32 | GACTTTGGATGGAGCAATT CTGGATTTCCATACACTGAAA | 210 | GACTTTGGATGGAGCAATTCaacatacagagaatgg TGGATTTCCATACACTGAAA |
| 414..417 | ACAT | 33 | ACTTTGGATGGAGCAATTC AtACAGAGAATGGTGGATTT CC | 211 | ACTTTGGATGGAGCAATTCAacatACAGAGA ATGGTGGATTTCC |
| 414..418 | ACATA | 34 | ACTTTGGATGGAGCAATTC ACAGAGAATGGTGGATTTCCA | 212 | ACTTTGGATGGAGCAATTCAacataCAGAGAA TGGTGGATTTCCA |
| 414..419 | ACATAC | 35 | ACTTTGGATGGAGCAATTC AAGAGAATGGTGGATTTCCAT | 213 | ACTTTGGATGGAGCAATTCAacatacAGAGAA TGGTGGATTTCCAT |
| 414..420 | ACATACA | 36 | ACTTTGGATGGAGCAATTC AGAGAATGGTGGATTTCCATA | 214 | ACTTTGGATGGAGCAATTCAacatacaGAGAAT GGTGGATTTCCATA |
| 414..437 | ACATACAGAGAA TGGTGGATTTCC (382) | 37 | ACTTTGGATGGAGCAATTC AATACACTGAAATGATTGT TC | 215 | ACTTTGGATGGAGCAATTCAacatacagagaatggt ggatttccATACACTGAAATGATTGTTC |
| 415..416 | CA | 38 | CTTTGGATGGAGCAATTCA ATACAGAGAATGGTGGATTTC | 216 | CTTTGGATGGAGCAATTCAAcaTACAGAGAA TGGTGGATTTC |
| 415..418 | CATA | 39 | CTTTGGATGGAGCAATTCA ACAGAGAATGGTGGATTTCCA | 217 | CTTTGGATGGAGCAATTCAAcataCAGAGAAT GGTGGATTTCCA |
| 415..420 | CATACA | 40 | CTTTGGATGGAGCAATTCA AGAGAATGGTGGATTTCCATA | 218 | CTTTGGATGGAGCAATTCAAcatacaGAGAAT GGTGGATTTCCATA |
| 415..421 | CATACAG | 41 | CTTTGGATGGAGCAATTCA AAGAATGGTGGATTTCCATAC | 219 | CTTTGGATGGAGCAATTCAAcatacagAGAATG GTGGATTTCCATAC |
| 416..416 | A | 42 | TTTGGATGGAGCAATTCAA CTACAGAGAATGGTGGATTTC | 220 | TTTGGATGGAGCAATTCAACaTACAGAGAA TGGTGGATTTC |
| 416..418 | ATA | 43 | TTTGGATGGAGCAATTCAA CCAGAGAATGGTGGATTTCCA | 221 | TTTGGATGGAGCAATTCAACataCAGAGAAT GGTGGATTTCCA |
| 416..419 | ATAC | 44 | TTTGGATGGAGCAATTCAA CAGAGAATGGTGGATTTCCAT | 222 | TTTGGATGGAGCAATTCAACatacAGAGAATG GTGGATTTCCAT |
| 416..420 | ATACA | 45 | TTTGGATGGAGCAATTCAA CGAGAATGGTGGATTTCCATA | 223 | TTTGGATGGAGCAATTCAACatacaGAGAATG GTGGATTTCCATA |
| 416..421 | ATACAG | 46 | TTTGGATGGAGCAATTCAA CAGAATGGTGGATTTCCATAC | 224 | TTTGGATGGAGCAATTCAACatacagAGAATG GTGGATTTCCATAC |
| 416..423 | ATACAGAG | 47 | TTTGGATGGAGCAATTCAA CAATGGTGGATTTCCATACAC | 225 | TTTGGATGGAGCAATTCAACatacagagAATGG TGGATTTCCATACAC |
| 417..418 | TA | 48 | TTGGATGGAGCAATTCAAC ACAGAGAATGGTGGATTTCCA | 226 | TTGGATGGAGCAATTCAACAtaCAGAGAATG GTGGATTTCCA |

TABLE 5A-continued

A list of exemplary mutant alleles obtained in the PMT1b gene. Mutant allele sequences listed here and Tables 5B to 5E represent about 40-nucleotide-long genomic sequences from each edited PMT gene with the edited site in the middle of the genomic sequence (e.g., 20 nucleotides on each side of the deleted or inserted sequence site). These mutant alleles corresponds to those listed in Tables 4A to 4E.

PMT1b

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 417..420 | TACA | 49 | TTGGATGGAGCAATTCAAC AGAGAATGGTGGATTTCCATA | 227 | TTGGATGGAGCAATTCAACAtacaGAGAATG GTGGATTTCCATA |
| 418..419 | AC | 50 | TGGATGGAGCAATTCAACA TAGAGAATGGTGGATTTCCAT | 228 | TGGATGGAGCAATTCAACATacAGAGAATG GTGGATTTCCAT |
| 418..420 | ACA | 51 | TGGATGGAGCAATTCAACA TGAGAATGGTGGATTTCCATA | 229 | TGGATGGAGCAATTCAACATacaGAGAATGG TGGATTTCCATA |
| 418..421 | ACAG | 52 | TGGATGGAGCAATTCAACA TAGAATGGTGGATTTCCATAC | 230 | TGGATGGAGCAATTCAACATacagAGAATGG TGGATTTCCATAC |
| 418..423 | ACAGAG | 53 | TGGATGGAGCAATTCAACA TAATGGTGGATTTCCATACAC | 231 | TGGATGGAGCAATTCAACATacagagAATGGT GGATTTCCATACAC |
| 419..420 | CA | 54 | GGATGGAGCAATTCAACAT AGAGAATGGTGGATTTCCATA | 232 | GGATGGAGCAATTCAACATAcaGAGAATGG TGGATTTCCATA |
| 427..427 | G | 55 | CAATTCAACATACAGAGAA TGTGGATTTCCATACACTGA A | 233 | CAATTCAACATACAGAGAATgGTGGATTTC CATACACTGAA |

TABLE 5B

A list of exemplary mutant alleles obtained in the PMT1a gene.

PMT1a

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 132...132 | A inserted | 56 | GCACTTCCAAACACCAAAACa GGGCACCAGAATGGCACTTT | 234 | GCACTTCCAAACACCAAAACGGGCA CCAGAATGGCACTTT |
| 409..415 | ATTCAAC | 57 | TTCTGACTTTGGATGGAGCAA TACAGAGAATGGTGGATTT | 235 | TTCTGACTTTGGATGGAGCAattcaacAT ACAGAGAATGGTGGATTT |
| 409..420 | ATTCAACATACA (383) | 58 | TTCTGACTTTGGATGGAGCAG AGAATGGTGGATTTCCATA | 236 | TTCTGACTTTGGATGGAGCAattcaacatac aGAGAATGGTGGATTTCCATA |
| 411..417 | TCAACAT | 59 | CTGACTTTGGATGGAGCAATA CAGAGAATGGTGGATTTCC | 237 | CTGACTTTGGATGGAGCAATtcaacatAC AGAGAATGGTGGATTTCC |
| 411..420 | TCAACATACA (384) | 60 | CTGACTTTGGATGGAGCAATG AGAATGGTGGATTTCCATA | 238 | CTGACTTTGGATGGAGCAATtcaacataca GAGAATGGTGGATTTCCATA |
| 412..418 | CAACATA | 61 | TGACTTTGGATGGAGCAATTC AGAGAATGGTGGATTTCCA | 239 | TGACTTTGGATGGAGCAATTcaacataCA GAGAATGGTGGATTTCCA |
| 412..421 | CAACATACAG (385) | 62 | TGACTTTGGATGGAGCAATTA GAATGGTGGATTTCCATAC | 240 | TGACTTTGGATGGAGCAATTcaacatacag AGAATGGTGGATTTCCATAC |
| 413..419 | AACATAC | 63 | GACTTTGGATGGAGCAATTCA GAGAATGGTGGATTTCCAT | 241 | GACTTTGGATGGAGCAATTCaacatacA GAGAATGGTGGATTTCCAT |
| 413..420 | AACATACA | 64 | GACTTTGGATGGAGCAATTCG AGAATGGTGGATTTCCATA | 242 | GACTTTGGATGGAGCAATTCaacatacaG AGAATGGTGGATTTCCATA |
| 413..421 | AACATACAG | 65 | GACTTTGGATGGAGCAATTCA GAATGGTGGATTTCCATAC | 243 | GACTTTGGATGGAGCAATTCaacatacag AGAATGGTGGATTTCCATAC |

TABLE 5B-continued

A list of exemplary mutant alleles obtained in the PMT1a gene.

PMT1a

| Position | Deleted sequence (SEQ ID No.) | Mutant Allele sequence (SEQ ID No.) | Mutant Allele Sequence | Reference Allele sequence (SEQ ID No.) | Reference Allele Sequence |
| --- | --- | --- | --- | --- | --- |
| 413..422 | AACATACAGA (386) | 66 | GACTTTGGATGGAGCAATTCG AATGGTGGATTTCCATACA | 244 | GACTTTGGATGGAGCAATTCaacatacag aGAATGGTGGATTTCCATACA |
| 413..428 | AACATACAGAG AATGG(387) | 67 | GACTTTGGATGGAGCAATTCT GGATTTCCATACACTGAAA | 245 | GACTTTGGATGGAGCAATTCaacatacag agaatggTGGATTTCCATACACTGAAA |
| 414..415 | AC | 68 | ACTTTGGATGGAGCAATTCAA TACAGAGAATGGTGGATTT | 246 | ACTTTGGATGGAGCAATTCAacATAC AGAGAATGGTGGATTT |
| 414..417 | ACAT | 69 | ACTTTGGATGGAGCAATTCAA CAGAGAATGGTGGATTTCC | 247 | ACTTTGGATGGAGCAATTCAacatACA GAGAATGGTGGATTTCC |
| 414..419 | ACATAC | 70 | ACTTTGGATGGAGCAATTCAA GAGAATGGTGGATTTCCAT | 248 | ACTTTGGATGGAGCAATTCAacatacAG AGAATGGTGGATTTCCAT |
| 414..420 | ACATACA | 71 | ACTTTGGATGGAGCAATTCAG AGAATGGTGGATTTCCATA | 249 | ACTTTGGATGGAGCAATTCAacatacaG AGAATGGTGGATTTCCATA |
| 414..421 | ACATACAG | 72 | ACTTTGGATGGAGCAATTCAA GAATGGTGGATTTCCATAC | 250 | ACTTTGGATGGAGCAATTCAacatacagA GAATGGTGGATTTCCATAC |
| 414..423 | ACATACAGAG (388) | 73 | ACTTTGGATGGAGCAATTCAA ATGGTGGATTTCCATACAC | 251 | ACTTTGGATGGAGCAATTCAacatacaga gAATGGTGGATTTCCATACAC |
| 415..415 | C | 74 | CTTTGGATGGAGCAATTCAAA TACAGAGAATGGTGGATTT | 252 | CTTTGGATGGAGCAATTCAAcATACA GAGAATGGTGGATTT |
| 415..416 | CA | 75 | CTTTGGATGGAGCAATTCAAT ACAGAGAATGGTGGATTTC | 253 | CTTTGGATGGAGCAATTCAAcaTACA GAGAATGGTGGATTTC |
| 415..418 | CATA | 76 | CTTTGGATGGAGCAATTCAAC AGAGAATGGTGGATTTCCA | 254 | CTTTGGATGGAGCAATTCAAcataCAG AGAATGGTGGATTTCCA |
| 415..419 | CATAC | 77 | CTTTGGATGGAGCAATTCAAA GAGAATGGTGGATTTCCAT | 255 | CTTTGGATGGAGCAATTCAAcatacAGA GAATGGTGGATTTCCAT |
| 415..421 | CATACAG | 78 | CTTTGGATGGAGCAATTCAAA GAATGGTGGATTTCCATAC | 256 | CTTTGGATGGAGCAATTCAAcatacagA GAATGGTGGATTTCCATAC |
| 416..417 | AT | 79 | TTTGGATGGAGCAATTCAACtA CAGAGAATGGTGGATTTCC | 257 | TTTGGATGGAGCAATTCAAcatACAGA GAATGGTGGATTTCC |
| 416..419 | ATAC | 80 | TTTGGATGGAGCAATTCAACA GAGAATGGTGGATTTCCAT | 258 | TTTGGATGGAGCAATTCAACatacAGA GAATGGTGGATTTCCAT |
| 416..420 | ATACA | 81 | TTTGGATGGAGCAATTCAACG AGAATGGTGGATTTCCATA | 259 | TTTGGATGGAGCAATTCAACatacaGAG AATGGTGGATTTCCATA |
| 416..421 | ATACAG | 82 | TTTGGATGGAGCAATTCAACA GAATGGTGGATTTCCATAC | 260 | TTTGGATGGAGCAATTCAACatacagAG AATGGTGGATTTCCATAC |
| 416..422 | ATACAGA | 83 | TTTGGATGGAGCAATTCAACG AATGGTGGATTTCCATACA | 261 | TTTGGATGGAGCAATTCAACatacagaG AATGGTGGATTTCCATACA |
| 416..429 | ATACAGAGAAT GGT(389) | 84 | TTTGGATGGAGCAATTCAACG GATTTCCATACACTGAAAT | 262 | TTTGGATGGAGCAATTCAACatacagaga atggtGGATTTCCATACACTGAAAT |
| 417..417 | T | 85 | TTGGATGGAGCAATTCAACAA CAGAGAATGGTGGATTTCC | 263 | TTGGATGGAGCAATTCAACAtACAGA GAATGGTGGATTTCC |
| 417..418 | TA | 86 | TTGGATGGAGCAATTCAACAC AGAGAATGGTGGATTTCCA | 264 | TTGGATGGAGCAATTCAACAtaCAGA GAATGGTGGATTTCCA |
| 417..419 | TAC | 87 | TTGGATGGAGCAATTCAACAA GAGAATGGTGGATTTCCAT | 265 | TTGGATGGAGCAATTCAACAtacAGAG AATGGTGGATTTCCAT |
| 417..420 | TACA | 88 | TTGGATGGAGCAATTCAACAG AGAATGGTGGATTTCCATA | 266 | TTGGATGGAGCAATTCAACAtacaGAG AATGGTGGATTTCCATA |

TABLE 5B-continued

A list of exemplary mutant alleles obtained in the PMT1a gene.

PMT1a

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 417..421 | TACAG | 89 | TTGGATGGAGCAATTCAACAA GAATGGTGGATTTCCATAC | 267 | TTGGATGGAGCAATTCAACAtacagAG AATGGTGGATTTCCATAC |
| 417..422 | TACAGA | 90 | TTGGATGGAGCAATTCAACAG AATGGTGGATTTCCATACA | 268 | TTGGATGGAGCAATTCAACAtacagaGA ATGGTGGATTTCCATACA |
| 417.423 | TACAGAG | 91 | TTGGATGGAGCAATTCAACAA ATGGTGGATTTCCATACAC | 269 | TTGGATGGAGCAATTCAACAtacagagA ATGGTGGATTTCCATACAC |
| 418..419 | AC | 92 | TGGATGGAGCAATTCAACATA GAGAATGGTGGATTTCCAT | 270 | TGGATGGAGCAATTCAACATacAGAG AATGGTGGATTTCCAT |
| 418..421 | ACAG | 93 | TGGATGGAGCAATTCAACATA GAATGGTGGATTTCCATAC | 271 | TGGATGGAGCAATTCAACATacagAGA ATGGTGGATTTCCATAC |
| 418..424 | ACAGAGA | 94 | TGGATGGAGCAATTCAACATA TGGTGGATTTCCATACACT | 272 | TGGATGGAGCAATTCAACATacagagaA TGGTGGATTTCCATACACT |
| 419..420 | CA | 95 | GGATGGAGCAATTCAACATAG AGAATGGTGGATTTCCATA | 273 | GGATGGAGCAATTCAACATAcaGAGA ATGGTGGATTTCCATA |
| 419..421 | CAG | 96 | GGATGGAGCAATTCAACATAA GAATGGTGGATTTCCATAC | 274 | GGATGGAGCAATTCAACATAcagAGA ATGGTGGATTTCCATAC |
| 424..425 | AA | 97 | GAGCAATTCAACATACAGAGT GGTGGATTTCCATACACTG | 275 | GAGCAATTCAACATACAGAGaaTGGT GGATTTCCATACACTG |

TABLE 5C

A list of exemplary mutant alleles obtained in the PMT2 gene.

PMT2

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 98...98 | A | 98 | TGGCACTTCCAAACACCA AACGGCCACAAGAATGGG ACTT | 276 | TGGCACTTCCAAACACCAAAaCG GCCACAAGAATGGGACTT |
| 196...619 | T | 99 | CCAATTGTATTAAGCCTGG TGGTTTTCAGAGTTTAGCGCA | 277 | CCAATTGTATTAAGCCTGGtGG TTTTCAGAGTTTAGCGCA |
| 346..350 | CAACA | 100 | TGACTTTGGATGGAGCAAT TCACAGAGAATGGTGGATTTC | 278 | TGACTTTGGATGGAGCAATTcaac aCACAGAGAATGGTGGATTTC |
| 346..352 | CAACACA | 101 | TGACTTTGGATGGAGCAAT TCAGAGAATGGTGGATTTCCA | 279 | TGACTTTGGATGGAGCAATTcaac acaCAGAGAATGGTGGATTTCCA |
| 346..355 | CAACACACAG (390) | 102 | TGACTTTGGATGGAGCAAT TAGAATGGTGGATTTCCATAC | 280 | TGACTTTGGATGGAGCAATTcaac acacagAGAATGGTGGATTTCCATAC |
| 347..354 | AACACACA | 103 | GACTTTGGATGGAGCAATT CGAGAATGGTGGATTTCCATA | 281 | GACTTTGGATGGAGCAATTcaaca cacAGAGAATGGTGGATTTCCATA |
| 347..357 | AACACACAGAG (391) | 104 | GACTTTGGATGGAGCAATT CAATGGTGGATTTCCATACAC | 282 | GACTTTGGATGGAGCAATTcaaca cacagagAATGGTGGATTTCCATACAC |
| 348..349 | AC | 105 | ACTTTGGATGGAGCAATTC AACACAGAGAATGGTGGATTT | 283 | ACTTTGGATGGAGCAATTCAacA CACAGAGAATGGTGGATTT |
| 348..351 | ACAC | 106 | ACTTTGGATGGAGCAATTC AACAGAGAATGGTGGATTTCC | 284 | ACTTTGGATGGAGCAATTCAacac ACAGAGAATGGTGGATTTCC |

TABLE 5C-continued

A list of exemplary mutant alleles obtained in the PMT2 gene.

PMT2

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 348..352 | ACACA | 107 | ACTTTGGATGGAGCAATTC ACAGAGAATGGTGGATTTCCA | 285 | ACTTTGGATGGAGCAATTCAacac aCAGAGAATGGTGGATTTCCA |
| 348..353 | ACACAC | 108 | ACTTTGGATGGAGCAATTC AAGAGAATGGTGGATTTCCAT | 286 | ACTTTGGATGGAGCAATTCAacac acAGAGAATGGTGGATTTCCAT |
| 348..354 | ACACACA | 109 | ACTTTGGATGGAGCAATTC AGAGAATGGTGGATTTCCATA | 287 | ACTTTGGATGGAGCAATTCAacac acaGAGAATGGTGGATTTCCATA |
| 348..355 | ACACACAG | 110 | ACTTTGGATGGAGCAATTC AAGAATGGTGGATTTCCATAC | 288 | ACTTTGGATGGAGCAATTCAacac acagAGAATGGTGGATTTCCATAC |
| 348..357 | ACACACAGAG (392) | 111 | ACTTTGGATGGAGCAATTC AAATGGTGGATTTCCATACAC | 289 | ACTTTGGATGGAGCAATTCAacac acagagAATGGTGGATTTCCATACAC |
| 349..349 | C | 112 | CTTTGGATGGAGCAATTCA AACACAGAGAATGGTGGATTT | 290 | CTTTGGATGGAGCAATTCAAcAC ACAGAGAATGGTGGATTT |
| 349..350 | CA | 113 | CTTTGGATGGAGCAATTCA ACACAGAGAATGGTGGATTTC | 291 | CTTTGGATGGAGCAATTCAAcaC ACAGAGAATGGTGGATTTC |
| 349..352 | CACA | 114 | CTTTGGATGGAGCAATTCA ACAGAGAATGGTGGATTT CCA | 292 | CTTTGGATGGAGCAATTCAAcaca CAGAGAATGGTGGATTTCCA |
| 349..355 | CACACAG | 115 | CTTTGGATGGAGCAATTCA AAGAATGGTGGATTTCCATAC | 293 | CTTTGGATGGAGCAATTCAAcaca cagAGAATGGTGGATTTCCATAC |
| 350..351 | AC | 116 | TTTGGATGGAGCAATTCAA CACAGAGAATGGTGGATTTCC | 294 | TTTGGATGGAGCAATTCAACacA CAGAGAATGGTGGATTTCC |
| 350..353 | ACAC | 117 | TTTGGATGGAGCAATTCAA CAGAGAATGGTGGATTTCCAT | 295 | TTTGGATGGAGCAATTCAACacac AGAGAATGGTGGATTTCCAT |
| 350..354 | ACACA | 118 | TTTGGATGGAGCAATTCAA CGAGAATGGTGGATTTCCATA | 296 | TTTGGATGGAGCAATTCAACacac aGAGAATGGTGGATTTCCATA |
| 350..355 | ACACAG | 119 | TTTGGATGGAGCAATTCAA CAGAATGGTGGATTTCCATAC | 297 | TTTGGATGGAGCAATTCAACacac agAGAATGGTGGATTTCCATAC |
| 350..357 | ACACAGAG | 120 | TTTGGATGGAGCAATTCAA CAATGGTGGATTTCCATACAC | 298 | TTTGGATGGAGCAATTCAACacac agagAATGGTGGATTTCCATACAC |
| 350..363 | ACACAGAGA ATGGT(393) | 121 | TTTGGATGGAGCAATTCAA CGGATTTCCATACACTGAAAT | 299 | TTTGGATGGAGCAATTCAACacac agagaatggtGGATTTCCATACACTG AAAT |
| 351..352 | CA | 122 | TTGGATGGAGCAATTCAA CACAGAGAATGGTGGATT TCCA | 300 | TTGGATGGAGCAATTCAACAcaC AGAGAATGGTGGATTTCCA |
| 351..354 | CACA | 123 | TTGGATGGAGCAATTCAA CAGAGAATGGTGGATTTC CATA | 301 | TTGGATGGAGCAATTCAACAcaca GAGAATGGTGGATTTCCATA |
| 351..356 | CACAGA | 124 | TTGGATGGAGCAATTCAA CAGAATGGTGGATTTCCAT ACA | 302 | TTGGATGGAGCAATTCAACAcaca gaGAATGGTGGATTTCCATACA |
| 351..357 | CACAGAG | 125 | TTGGATGGAGCAATTCAA CAAATGGTGGATTTCCATA CAC | 303 | TTGGATGGAGCAATTCAACAcaca gagAATGGTGGATTTCCATACAC |
| 351..362 | CACAGAGAA TGG(394) | 126 | TTGGATGGAGCAATTCAA CATGGATTTCCATACACTG AAA | 304 | TTGGATGGAGCAATTCAACAcaca gagaatggTGGATTTCCATACACTGA AA |
| 352..354 | ACA | 127 | TGGATGGAGCAATTCAAC ACGAGAATGGTGGATTTC CATA | 305 | TGGATGGAGCAATTCAACACaca GAGAATGGTGGATTTCCATA |

TABLE 5C-continued

A list of exemplary mutant alleles obtained in the PMT2 gene.

PMT2

| Position | Deleted sequence (SEQ ID No.) | Mutant Allele sequence (SEQ ID No.) | Mutant Allele Sequence | Reference Allele sequence (SEQ ID No.) | Reference Allele Sequence |
| --- | --- | --- | --- | --- | --- |
| 352..355 | ACAG | 128 | TGGATGGAGCAATTCAACACAGAATGGTGGATTTCCATAC | 306 | TGGATGGAGCAATTCAACACacagAGAATGGTGGATTTCCATAC |
| 353..354 | CA | 129 | GGATGGAGCAATTCAACACAGAGAATGGTGGATTTCCATA | 307 | GGATGGAGCAATTCAACACAcaGAGAATGGTGGATTTCCATA |
| 353..356 | CAGA | 130 | GGATGGAGCAATTCAACACAGAATGGTGGATTTCCATACA | 308 | GGATGGAGCAATTCAACACAcagaGAATGGTGGATTTCCATACA |
| 353..361 | CAGAGAATG | 131 | GGATGGAGCAATTCAACACAGTGGATTTCCATACACTGAA | 309 | GGATGGAGCAATTCAACACAcagagaatgGTGGATTTCCATACACTGAA |
| 354..359 | AGAGAA | 132 | GATGGAGCAATTCAACACACTGGTGGATTTCCATACACTG | 310 | GATGGAGCAATTCAACACACagagaaTGGTGGATTTCCATACACTG |

TABLE 5D

A list of exemplary mutant alleles obtained in the PMT3 gene.

PT3

| Position | Deleted sequence (SEQ ID No.) | Mutant Allele sequence (SEQ ID No.) | Mutant Allele Sequence | Reference Allele sequence (SEQ ID No.) | Reference Allele Sequence |
| --- | --- | --- | --- | --- | --- |
| 98...98 | A | 133 | TGGCACTTCCAAACACCAAACGGCCACCAGAATGGCACTT | 311 | TGGCACTTCCAAACACCAAAaCGGCCACCAGAATGGCACTT |
| 280...280 | T | 134 | CCAACTCTATTAAGCCTGGTGGTTTTCAGAGTTTAGCGCA | 312 | CCAACTCTATTAAGCCTGGTtGGTTTTCAGAGTTTAGCGCA |
| 413..414 | CT | 135 | AACATATGGGAAGGTTCTGATTGGATGGAGCAATTCAACA | 313 | AACATATGGGAAGGTTCTGActTTGGATGGAGCAATTCAACA |
| 418..419 | GA | 136 | ATGGGAAGGTTCTGACTTTGTGGAGCAATTCAACACACAG | 314 | ATGGGAAGGTTCTGACTTTGgaTGGAGCAATTCAACACACAG |
| 426..427 | AA | 137 | GTTCTGACTTTGGATGGAGCTTCAACACACAGAGAATGGT | 315 | GTTCTGACTTTGGATGGAGCaaTTCAACACACAGAGAATGGT |
| 429..435 | TCAACAC | 138 | CTGACTTTGGATGGAGCAATACAGAGAATGGTGGATTTCC | 316 | CTGACTTTGGATGGAGCAATtcaacacACAGAGAATGGTGGATTTCC |
| 429..438 | TCAACACACA (395) | 139 | CTGACTTTGGATGGAGCAATGAGAATGGTGGATTTCCATA | 317 | CTGACTTTGGATGGAGCAATtcaacacacaGAGAATGGTGGATTTCCATA |
| 429..439 | TCAACACACAG (396) | 140 | CTGACTTTGGATGGAGCAATAGAATGGTGGATTTCCATAC | 318 | CTGACTTTGGATGGAGCAATtcaacacacagAGAATGGTGGATTTCCATAC |
| 430..436 | CAACACA | 141 | TGACTTTGGATGGAGCAATTCAGAGAATGGTGGATTTCCA | 319 | TGACTTTGGATGGAGCAATTcaacacaCAGAGAATGGTGGATTTCCA |
| 431..431 | A | 142 | GACTTTGGATGGAGCAATTCACACACAGAGAATGGTGGAT | 320 | GACTTTGGATGGAGCAATTCaACACACAGAGAATGGTGGAT |
| 431..432 | AA | 143 | GACTTTGGATGGAGCAATTCCACACAGAGAATGGTGGATT | 321 | GACTTTGGATGGAGCAATTCaaCACACAGAGAATGGTGGATT |

TABLE 5D-continued

A list of exemplary mutant alleles obtained in the PMT3 gene.

PT3

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 431..438 | AACACACA | 144 | GACTTTGGATGGAGCAATTCGAGA ATGGTGGATTTCCATA | 322 | GACTTTGGATGGAGCAATTCaacacacaGA GAATGGTGGATTTCCATA |
| 431..441 | AACACACAGAG (397) | 145 | GACTTTGGATGGAGCAATTCAATG GTGGATTTCCATACAC | 323 | GACTTTGGATGGAGCAATTCaacacacagag AATGGTGGATTTCCATACAC |
| 432..433 | AC | 146 | ACTTTGGATGGAGCAATTCAACAC AGAGAATGGTGGATTT | 324 | ACTTTGGATGGAGCAATTCAacACACAG AGAATGGTGGATTT |
| 432..435 | ACAC | 147 | ACTTTGGATGGAGCAATTCAACAG AGAATGGTGGATTTCC | 325 | ACTTTGGATGGAGCAATTCAacacACAGA GAATGGTGGATTTCC |
| 432..437 | ACACAC | 148 | ACTTTGGATGGAGCAATTCAAGAG AATGGTGGATTTCCAT | 326 | ACTTTGGATGGAGCAATTCAacacacAGA GAATGGTGGATTTCCAT |
| 432..439 | ACACACAG | 149 | ACTTTGGATGGAGCAATTCAAGAA TGGTGGATTTCCATAC | 327 | ACTTTGGATGGAGCAATTCAacacacagAG AATGGTGGATTTCCATAC |
| 432...441 | ACACACAGAG (398) | 150 | ACTTTGGATGGAGCAATTCAAATG GTGGATTTCCATACAC | 328 | ACTTTGGATGGAGCAATTCAacacacagagA ATGGTGGATTTCCATACAC |
| 432..446 | ACACACAGAG AATGG(399) | 151 | ACTTTGGATGGAGCAATTCATGGA TTTCCATACACTGAAA | 329 | ACTTTGGATGGAGCAATTCAacacacagaga atggTGGATTTCCATACACTGAAA |
| 432..448 | ACACACAGAG AATGGTG(400) | 152 | ACTTTGGATGGAGCAATTCAGATT TCCATACACTGAAATG | 330 | ACTTTGGATGGAGCAATTCAacacacagaga atggtgGATTTCCATACACTGAAATG |
| 433..433 | C | 153 | CTTTGGATGGAGCAATTCAAACAC AGAGAATGGTGGATTT | 331 | CTTTGGATGGAGCAATTCAAcACACAG AGAATGGTGGATTT |
| 433..436 | CACA | 154 | CTTTGGATGGAGCAATTCAACAGA GAATGGTGGATTTCCA | 332 | CTTTGGATGGAGCAATTCAAcacaCAGAG AATGGTGGATTTCCA |
| 433..437 | CACAC | 155 | CTTTGGATGGAGCAATTCAAAGAG AATGGTGGATTTCCAT | 333 | CTTTGGATGGAGCAATTCAAcacacAGAG AATGGTGGATTTCCAT |
| 433..439 | CACACAG | 156 | CTTTGGATGGAGCAATTCAAAGAA TGGTGGATTTCCATAC | 334 | CTTTGGATGGAGCAATTCAAcacacagAGA ATGGTGGATTTCCATAC |
| 434..435 | AC | 157 | TTTGGATGGAGCAATTCAACACAG AGAATGGTGGATTTCC | 335 | TTTGGATGGAGCAATTCAACacACAGAG AATGGTGGATTTCC |
| 434..437 | ACAC | 158 | TTTGGATGGAGCAATTCAACAGAG AATGGTGGATTTCCAT | 336 | TTTGGATGGAGCAATTCAACacacAGAG AATGGTGGATTTCCAT |
| 434..438 | ACACA | 159 | TTTGGATGGAGCAATTCAACGAGA ATGGTGGATTTCCATA | 337 | TTTGGATGGAGCAATTCAACacacaGAGA ATGGTGGATTTCCATA |
| 435..436 | CA | 160 | TTGGATGGAGCAATTCAACACAGA GAATGGTGGATTTCCA | 338 | TTGGATGGAGCAATTCAACAcaCAGAGA ATGGTGGATTTCCA |
| 435..438 | CACA | 161 | TTGGATGGAGCAATTCAACAGAGA ATGGTGGATTTCCATA | 339 | TTGGATGGAGCAATTCAACAcacaGAGA ATGGTGGATTTCCATA |
| 435..439 | CACAG | 162 | TTGGATGGAGCAATTCAACAAGAA TGGTGGATTTCCATAC | 340 | TTGGATGGAGCAATTCAACAcacagAGAA TGGTGGATTTCCATAC |
| 435..447 | CACAGAGAAT GGT(401) | 163 | TTGGATGGAGCAATTCAACAGGAT TTCCATACACTGAAAT | 341 | TTGGATGGAGCAATTCAACAcacagagaatg gtGGATTTCCATACACTGAAAT |
| 436..437 | AC | 164 | TGGATGGAGCAATTCAACACAGAG AATGGTGGATTTCCAT | 342 | TGGATGGAGCAATTCAACACacAGAGA ATGGTGGATTTCCAT |
| 436..439 | ACAG | 165 | TGGATGGAGCAATTCAACACAGAA TGGTGGATTTCCATAC | 343 | TGGATGGAGCAATTCAACACacagAGAA TGGTGGATTTCCATAC |
| 436..443 | ACAGAGAA | 166 | TGGATGGAGCAATTCAACACTGGT GGATTTCCATACACTG | 344 | TGGATGGAGCAATTCAACACacagagaaTG GTGGATTTCCATACACTG |

TABLE 5D-continued

A list of exemplary mutant alleles obtained in the PMT3 gene.

PT3

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 437..438 | CA | 167 | GGATGGAGCAATTCAACACAGAGAAATGGTGGATTTCCATA | 345 | GGATGGAGCAATTCAACACAcaGAGAAATGGTGGATTTCCATA |
| 440..442 | AGA | 168 | TGGAGCAATTCAACACACAGATGGTGGATTTCCATACACT | 346 | TGGAGCAATTCAACACACAGagaATGGTGGATTTCCATACACT |
| 440..443 | AGAA | 169 | TGGAGCAATTCAACACACAGTGGTGGATTTCCATACACTG | 347 | TGGAGCAATTCAACACACAGagaaTGGTGGATTTCCATACACTG |
| 441..441 | G | 170 | GGAGCAATTCAACACACAGAAATGGTGGATTTCCATACAC | 348 | GGAGCAATTCAACACACAGAgAATGGTGGATTTCCATACAC |
| 445..449 | GGTGG | 171 | CAATTCAACACACAGAGAATATTTCCATACACTGAAATGA | 349 | CAATTCAACACACAGAGAATggtggATTTCCATACACTGAAATGA |
| 451..463 | TTTCCATACACTG(402) | 172 | AACACACAGAGAATGGTGGAAAATGATTGTTCATCTTCCA | 350 | AACACACAGAGAATGGTGGAtttccatacactgAAATGATTGTTCATCTTCCA |

TABLE 5E

A list of exemplary mutant alleles obtained in the PMT4 gene.

PMT4

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 131...131 | A | 173 | CGGCACTTCCAAACACCAAACGGCCACCCATAATGGCACTT | 351 | CGGCACTTCCAAACACCAAAaCGGCCACCATAATGGCACTT |
| 541..551 | ATTCAACACAC (403) | 174 | TTTTGACTTTGGATGGAGCAAGAGAATGGTGGATTTCCAT | 352 | TTTTGACTTTGGATGGAGCAattcaacacacAGAGAATGGTGGATTTCCAT |
| 543..554 | TCAACACACAGA (404) | 175 | TTGACTTTGGATGGAGCAATGAATGGTGGATTTCCATACA | 353 | TTGACTTTGGATGGAGCAATtcaacacacagaGAATGGTGGATTTCCATACA |
| 544..550 | CAACACA | 176 | TGACTTTGGATGGAGCAATTCAGAGAATGGTGGATTTCCA | 354 | TGACTTTGGATGGAGCAATTcaacacaCAGAGAATGGTGGATTTCCA |
| 544..553 | CAACACACAG (405) | 177 | TGACTTTGGATGGAGCAATTAGAATGGTGGATTTCCATAC | 355 | TGACTTTGGATGGAGCAATTcaacacacagAGAATGGTGGATTTCCATAC |
| 545..555 | AACACACAGAG (406) | 178 | GACTTTGGATGGAGCAATTCAATGGTGGATTTCCATACAC | 356 | GACTTTGGATGGAGCAATTCaacacacagagAATGGTGGATTTCCATACAC |
| 545..557 | AACACACAGAGAA (407) | 179 | GACTTTGGATGGAGCAATTCTGGTGGATTTCCATACACTG | 357 | GACTTTGGATGGAGCAATTCaacacacagagaaTGGTGGATTTCCATACACTG |
| 546..547 | AC | 180 | ACTTTGGATGGAGCAATTCAACACAGAGAATGGTGGATTT | 358 | ACTTTGGATGGAGCAATTCAacACACAGAGAATGGTGGATTT |
| 546..549 | ACAC | 181 | ACTTTGGATGGAGCAATTCAACACAGAGAATGGTGGATTTCC | 359 | ACTTTGGATGGAGCAATTCAacacACAGAGAATGGTGGATTTCC |
| 546..551 | ACACAC | 182 | ACTTTGGATGGAGCAATTCAAGAAATGGTGGATTTCCAT | 360 | ACTTTGGATGGAGCAATTCAacacacAGAGAATGGTGGATTTCCAT |
| 546..552 | ACACACA | 183 | ACTTTGGATGGAGCAATTCAGAGAATGGTGGATTTCCATA | 361 | ACTTTGGATGGAGCAATTCAacacacaGAGAATGGTGGATTTCCATA |
| 546..553 | ACACACAG | 184 | ACTTTGGATGGAGCAATTCAAGAATGGTGGATTTCCATAC | 362 | ACTTTGGATGGAGCAATTCAacacacagAGAATGGTGGATTTCCATAC |

TABLE 5E-continued

A list of exemplary mutant alleles obtained in the PMT4 gene.

PMT4

| Position | Deleted sequence (SEQ ID No.) | Mutant Allele sequence (SEQ ID No.) | Mutant Allele Sequence | Reference Allele sequence (SEQ ID No.) | Reference Allele Sequence |
|---|---|---|---|---|---|
| 547..550 | CACA | 185 | CTTTGGATGGAGCAATTCAACAGAGA ATGGTGGATTTCCA | 363 | CTTTGGATGGAGCAATTCAAcacaCAGAG AATGGTGGATTTCCA |
| 547..551 | CACAC | 186 | CTTTGGATGGAGCAATTCAAAGAGAA TGGTGGATTTCCAT | 364 | CTTTGGATGGAGCAATTCAAcacacAGAG AATGGTGGATTTCCAT |
| 548..549 | AC | 187 | TTTGGATGGAGCAATTCAACACAGAG AATGGTGGATTTCC | 365 | TTTGGATGGAGCAATTCAACacACAGAG AATGGTGGATTTCC |
| 548..551 | ACAC | 188 | TTTGGATGGAGCAATTCAACAGAGAA TGGTGGATTTCCAT | 366 | TTTGGATGGAGCAATTCAACacacAGAGA ATGGTGGATTTCCAT |
| 548..552 | ACACA | 189 | TTTGGATGGAGCAATTCAACGAGAAT GGTGGATTTCCATA | 367 | TTTGGATGGAGCAATTCAACacacaGAGA ATGGTGGATTTCCATA |
| 549..552 | CACA | 190 | TTGGATGGAGCAATTCAACAGAGAAT GGTGGATTTCCATA | 368 | TTGGATGGAGCAATTCAACAcacaGAGAA TGGTGGATTTCCATA |
| 549..553 | CACAG | 191 | TTGGATGGAGCAATTCAACAAGAATG GTGGATTTCCATAC | 369 | TTGGATGGAGCAATTCAACAcacagAGAA TGGTGGATTTCCATAC |
| 550..551 | AC | 192 | TGGATGGAGCAATTCAACACAGAGAA TGGTGGATTTCCAT | 370 | TGGATGGAGCAATTCAACACacAGAGAA TGGTGGATTTCCAT |
| 550..552 | ACA | 193 | TGGATGGAGCAATTCAACACGAGAAT GGTGGATTTCCATA | 371 | TGGATGGAGCAATTCAACACacaGAGAA TGGTGGATTTCCATA |
| 550..553 | ACAG | 194 | TGGATGGAGCAATTCAACACAGAATG GTGGATTTCCATAC | 372 | TGGATGGAGCAATTCAACACacagAGAAT GGTGGATTTCCATAC |
| 550..556 | ACAGAGA | 195 | TGGATGGAGCAATTCAACACATGGTG GATTTCCATACACT | 373 | TGGATGGAGCAATTCAACACacagagaATG GTGGATTTCCATACACT |
| 551..552 | CA | 196 | GGATGGAGCAATTCAACACAGAGAAT GGTGGATTTCCATA | 374 | GGATGGAGCAATTCAACACAcaGAGAAT GGTGGATTTCCATA |
| 554..554 | A | 197 | TGGAGCAATTCAACACACAGGAATGG TGGATTTCCATACA | 375 | TGGAGCAATTCAACACACAGaGAATGGT GGATTTCCATACA |
| 558..563 | TGGTGG | 198 | GCAATTCAACACACAGAGAAATTTCC ATACACTGAAATGA | 376 | GCAATTCAACACACAGAGAAtggtggATTT CCATACACTGAAATGA |
| 565..566 | TT | 199 | AACACACAGAGAATGGTGGATCCATA CACTGAAATGATTG | 377 | AACACACAGAGAATGGTGGAttTCCATAC ACTGAAATGATTG |
| 569..572 | CATA | 200 | CACAGAGAATGGTGGATTTCCACTGA AATGATTGTTCATC | 378 | CACAGAGAATGGTGGATTTCcataCACTG AAATGATTGTTCATC |

Example 3: Alkaloid Analysis of PMT Edited Lines

Genome edited tobacco plants along with controls are grown in 10" pots in green house with 75 PPM fertilizer. At flowering stage, plants are topped and 2 weeks post topping lamina samples were collected from 3, 4, 5 leaves from top and alkaloid levels are measured (Tables 6A to 6C) using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009).

Briefly, approximately 0.5 g of tobacco is extracted using liquid/liquid extraction into an organic solvent containing an internal standard and analyzed by gas chromatography (GC) with flame ionization detection (FID). Results can be reported as weight percent (Wt %) on either an as is or dry weight basis. Reporting data on a dry weight basis requires an oven volatiles (OV) determination. Unless specified otherwise, total or individual alkaloid levels or nicotine levels shown herein are on a dry weight basis (e.g., percent total alkaloid or percent nicotine).

Plants are also planted in the field, harvested, and tested for alkaloids and TSNA levels in cured tobacco. Both leaf yield and leaf grade are also assessed for PMT edited plants. Further, different mutant combinations of individual PMT genes are generated and tested (e.g., single, double, triple, or quadruple mutants).

Example 4: Comparing a Quintuple Pmt Knock-Out Mutant with Other Low-Alkaloid Tobacco Plants A quintuple pmt knock-out mutant line CS15 (see Table 4E for genotype, in the NLM (Ph Ph) background) is grown side by side with a PMT RNAi transgenic line (in the VA359 background, as described in US 2015/0322451) and a low-nicotine KY171 ("LN KY171") variety (the KY 171 background harboring nic1 and nic2 double mutations). Leaves are harvested and cured via a dark fire curing method. Each line is analyzed for nicotine and total alkaloid levels, leaf yield, and leaf quality (FIGS. 2 to 5). The data shows that suppressing PMT gene activity by editing all five PMT genes reduces nicotine level without compromising leaf yield or quality.

Example 5: Obtaining Tobacco Lines with Edited Mutant Alleles in One or More PMT Genes Tobacco lines with mutations in individual PMT genes or selected combinations of PMT genes are obtained from the tobacco lines listed in Table 3. Crossing a quintuple, quadruple, triple, or double mutant (having mutations in five, four, three, or two PMT genes, respectively) to a non-mutated control line and selecting segregating progeny plants can be performed to obtain specific PMT mutation combinations. Tables 8A to 8E represents possible mutant combinations being obtained. Each mutated gene can be either homozygous or heterozygous for the mutation. Each of the mutant alleles listed in Tables 4A to 4E and Table 10 can be used to generate single, double, triple, quintuple, or quadruple mutants. Exemplary individual pmt mutant alleles are listed in Tables 5A to 5E.

Example 6: Further Reduction of Total Alkaloids by Combining Pmt Mutations with Mutations in Other Genes To further reduce total alkaloids and/or selected individual alkaloids, pmt mutants are combined with mutations in additional genes related to alkaloid biosynthesis in tobacco, such as quinolate phosphoribosyl transferase (QPT) or quinolinate synthase (QS). Briefly, gene editing is used to mutant selected QPT and/or QS genes in a desired pmt mutant background (e.g., a quadruple or quintuple pmt mutant). In the resulting combined qpt/pmt or qs/pmt mutants, alkaloids and TSNA levels are tested in cured tobacco. Both leaf yield and leaf grade are also assessed.

TABLE 6A

Alkaloid levels in PMT edited lines in K326 (shown here and Tables 6B, 6C, and 7 as weight percentage per gram leaf lamina (dry weight))

| Variety | Plant ID | % Alkaloids Nicotine | Total Alkaloids |
|---|---|---|---|
| K326 Control | 17GH1811 | 1.17 | 1.23 |
| | 17GH1822 | 1.63 | 1.71 |
| | 17GH1806 | 1.69 | 1.76 |
| | 17GH1899 | 1.7893 | 1.9194 |
| | 17GH1812 | 1.91 | 2 |
| | 17GH1900 | 2.088 | 2.239 |
| | 17GH1821 | 2.16 | 2.26 |
| | 17GH1896 | 2.6006 | 2.7359 |

TABLE 6A-continued

Alkaloid levels in PMT edited lines in K326 (shown here and Tables 6B, 6C, and 7 as weight percentage per gram leaf lamina (dry weight))

| Variety | Plant ID | % Alkaloids Nicotine | Total Alkaloids |
|---|---|---|---|
| K326 Edited | 17GH1810 | 0.0013 | 0.3 |
| | 17GH1808 | 0.0044 | 0.24 |
| | 17GH1901 | 0.006 | 0.6958 |
| | 17GH1893 | 0.0072 | 0.7351 |
| | 17GH1804 | 0.0078 | 0.44 |
| | 17GH1902 | 0.008 | 0.6245 |
| | 18GH4 | 0.0102 | 0.2688 |
| | 17GH1892 | 0.0209 | 0.1281 |

TABLE 6B

Alkaloid levels in PMT edited lines in TN90

| Variety | Plant ID | % Alkaloids Nicotine | Total Alkaloids |
|---|---|---|---|
| TN90 Control | 17GH1838 | 1.88 | 1.98 |
| | 17GH1923 | 2.0868 | 2.2136 |
| | 17GH1924 | 2.2099 | 2.3394 |
| | 17GH1718 | 2.29 | 2.42 |
| | 17GH1839 | 2.6 | 2.74 |
| | 17GH1909 | 2.7639 | 2.9429 |
| | 17GH1910 | 2.9346 | 3.1283 |
| TN90 Edited | 17GH1699 | 0.0011 | 0.58 |
| | 17GH1708 | 0.0014 | 0.56 |
| | 17GH1847 | 0.0016 | 0.6 |
| | 17GH1848 | 0.0018 | 0.42 |
| | 17GH1724 | 0.0022 | 0.59 |
| | 17GH1846 | 0.0022 | 0.41 |
| | 17GH1722 | 0.0023 | 0.62 |
| | 17GH1725 | 0.003 | 0.69 |
| | 17GH1717 | 0.0035 | 0.7 |
| | 17GH1719 | 0.0042 | 0.75 |
| | 17GH1845 | 0.0047 | 0.45 |
| | 17GH1943 | 0.007 | 0.3464 |
| | 18GH47 | 0.0072 | 1.0455 |
| | 17GH1944 | 0.0074 | 0.403 |
| | 17GH1932 | 0.0074 | 0.4758 |
| | 17GH1936 | 0.0074 | 1.4394 |
| | 17GH1918 | 0.0075 | 0.458 |
| | 17GH1912 | 0.0078 | 0.5234 |
| | 18GH31 | 0.0079 | 1.0902 |
| | 18GH28 | 0.008 | 0.8748 |
| | 17GH1928 | 0.0081 | 1.1024 |
| | 17GH1933 | 0.0083 | 0.6517 |
| | 17GH1911 | 0.0088 | 0.281 |

TABLE 6C

Alkaloid levels in PMT edited lines in Narrow Leaf Madole (NLM)

| Variety | Plant ID | % Alkaloids Nicotine | Total Alkaloids |
|---|---|---|---|
| NLM Control | 18GH126 | 2.0844 | 2.1734 |
| | 18GH7 | 3.3504 | 3.5136 |
| NLM Edited | 18GH10 | 0.001 | 1.14 |
| | 18GH9 | 0.0012 | 0.92 |
| | 18GH6 | 0.0019 | 1.46 |
| | 18GH8 | 0.0022 | 1.46 |
| | 17GH1905 | 0.0032 | 1.49 |
| | 18GH5 | 0.0038 | 0.92 |
| | 18GH130 | 0.0041 | 0.8756 |

TABLE 6C-continued

Alkaloid levels in PMT edited lines in Narrow Leaf Madole (NLM)

| Variety | Plant ID | % Alkaloids | |
|---|---|---|---|
| | | Nicotine | Total Alkaloids |
| | 18GH132 | 0.0044 | 0.6335 |
| | 18GH79 | 0.0045 | 0.6182 |
| | 18GH69 | 0.0069 | 0.7495 |
| | 18GH71 | 0.007 | 0.7726 |
| | 18GH131 | 0.0077 | 0.4289 |
| | 18GH66 | 0.0081 | 0.6951 |
| | 18GH227 | 0.0086 | 0.8726 |
| | 18GH78 | 0.0086 | 0.662 |
| | 18GH72 | 0.0087 | 1.0048 |
| | 18GH216 | 0.0089 | 1.2758 |
| | 18GH65 | 0.0094 | 0.7018 |

TABLE 7

Relative changes in nicotine and total alkaloid levels in quintuple pmt knock-out mutants in various varieties. Average percent levels of nicotine and total alkaloids are calculated based on percent level data from individual lines as shown in Tables 6A to 6C. Relative changes reflect the nicotine or total alkaloid level in a quintuple pmt mutant relative to its control.

| | Nicotine | Total Alkaloids |
|---|---|---|
| K326 Control | 1.880 | 1.982 |
| K326 quintuple pmt mutant | 0.008 | 0.429 |
| Relative change | 0.44% | 21.65% |
| TN90 Control | 2.395 | 2.538 |
| TN90 quintuple pmt mutant | 0.005 | 0.655 |
| Relative change | 0.22% | 25.80% |
| NLM Control | 2.717 | 2.844 |
| NLM quintuple pmt mutant | 0.006 | 0.927 |
| Relative change | 0.20% | 32.59% |

TABLE 8A

A list of mutants obtained with various genotypic combinations for five PMT genes: single gene mutations

| | PMT1a | PMT1b | PMT2 | PMT3 | PMT4 |
|---|---|---|---|---|---|
| 1 | Mutant | WT | WT | WT | WT |
| 2 | WT | Mutant | WT | WT | WT |
| 3 | WT | WT | Mutant | WT | WT |
| 4 | WT | WT | WT | Mutant | WT |
| 5 | WT | WT | WT | WT | Mutant |

TABLE 8B

A list of mutants obtained with various genotypic combinations for five PMT genes: double gene mutations

| | PMT1a | PMT1b | PMT2 | PMT3 | PMT4 |
|---|---|---|---|---|---|
| 1 | Mutant | Mutant | WT | WT | WT |
| 2 | Mutant | WT | Mutant | WT | WT |
| 3 | Mutant | WT | WT | Mutant | WT |
| 4 | Mutant | WT | WT | WT | Mutant |
| 5 | WT | Mutant | Mutant | WT | WT |
| 6 | WT | Mutant | WT | Mutant | WT |
| 7 | WT | Mutant | WT | WT | Mutant |
| 8 | WT | WT | Mutant | Mutant | WT |
| 9 | WT | WT | Mutant | WT | Mutant |
| 10 | WT | WT | WT | Mutant | Mutant |

TABLE 8C

A list of mutants obtained with various genotypic combinations for five PMT genes: triple gene combinations

| | PMT1a | PMT1b | PMT2 | PMT3 | PMT4 |
|---|---|---|---|---|---|
| 1 | Mutant | Mutant | Mutant | WT | WT |
| 2 | Mutant | Mutant | WT | Mutant | WT |
| 3 | Mutant | Mutant | WT | WT | Mutant |
| 4 | Mutant | WT | Mutant | Mutant | WT |
| 5 | Mutant | WT | Mutant | WT | Mutant |
| 6 | Mutant | WT | WT | Mutant | Mutant |
| 7 | WT | Mutant | Mutant | Mutant | WT |
| 8 | WT | Mutant | Mutant | WT | Mutant |
| 9 | WT | WT | Mutant | Mutant | Mutant |
| 10 | WT | Mutant | Mutant | WT | Mutant |

TABLE 8D

A list of mutants obtained with various genotypic combinations for five PMT genes: quadruple gene combinations

| | PMT1a | PMT1b | PMT2 | PMT3 | PMT4 |
|---|---|---|---|---|---|
| 1 | Mutant | Mutant | Mutant | Mutant | WT |
| 2 | WT | Mutant | Mutant | Mutant | Mutant |
| 3 | Mutant | WT | Mutant | Mutant | Mutant |
| 4 | Mutant | Mutant | WT | Mutant | Mutant |
| 5 | Mutant | Mutant | Mutant | WT | Mutant |

TABLE 8E

A list of mutants obtained with various genotypic combinations for five PMT genes: quintuple gene combinations

| | PMT1a | PMT1b | PMT2 | PMT3 | PMT4 |
|---|---|---|---|---|---|
| 1 | Mutant | Mutant | Mutant | Mutant | Mutant |

Example 7: PMT Genome Editing and Tobacco Line Development

Additional PMT knockout mutants are produced by editing all five PMT genes (PMT1a, PMT1b, PMT2, PMT3, and PMT4) in different tobacco lines. Tobacco protoplasts are transfected using polyethylene glycol (PEG) with plasmids encoding a genome editing technology (GET2) protein and specific guide RNAs (gRNAs) targeting PMT genes at desired positions. Table 9 lists gRNA sequences used for PMT editing. Some gRNAs (e.g., Nos. 6 and 7) are pooled together for targeting multiple PMT genes in a single transfection.

TABLE 9

Guide RNAs for GET2 used in Example 7. "Y" indicates that a gRNA is capable of targeting that PMT gene, while "—" represents that a gRNA does not target that PMT gene.

| gRNA Sequence | PMT1a | PMT1b | PMT2 | PMT3 | PMT4 |
|---|---|---|---|---|---|
| GATGGAGCAATTCAACATACAGA (SEQ ID NO: 730) | Y | Y | — | — | — |
| GATGGAGCAATTCAACACACAGA (SEQ ID NO: 731) | — | — | Y | Y | Y |

Transfected protoplasts are then immobilized in 1% agarose bead and subjected to tissue culture. When calli grow up to ~1 mm in diameter, they are spread on TOM2 plates. Calli are screened for insertions or deletions (indels) at the target positions using fragment analysis. Candidates, showing size shifts compared to wildtype control, are selected for further culture and the consequent shoots are tested by fragment analysis again to confirm the presence of indels. Rooted shoots are potted and sequenced for the target positions to determine the exact sequences deleted. Young leaf from each plant is harvested and PCR amplified for PMT fragments using phirekit. PMT Libraries for each line is indexed and 384 lines are pooled and sequenced using Miseq.

SNP analysis is carried out to determine both the exact edited pmt mutant allele sequences and the zygosity state at each PMT gene locus. Table 10 provides indels sequence information in each edited line of various tobacco varieties (e.g., Basma, K326, Katerini, TN90, Izmir).

TABLE 10

Mutant pmt alleles in various lines produced by genome editing using GET2. The position of each edited site (e.g., indels) is relative to the nucleotide number on the corresponding cDNA sequence of each PMT gene (e.g., SEQ ID NO: 6 for PMT1b; SEQ ID NO: 7 for PMT1a; SEQ ID NO: 8 for PMT2; SEQ ID NO: 9 for PMT3; SEQ ID NO: 10 for PMT4). SEQ ID Numbers are assigned and shown for sequences of more than 10 nucleotides.

| Genotype | Line | PMT1a Deleted Sequence | Position | PMT1b Deleted Sequence | Position | PMT2 Deleted Sequence | Position |
|---|---|---|---|---|---|---|---|
| BASMA | CS107 | CAACATA | 412..418 | ACAT | 414..417 | AC | 348..349 |
| BASMA | CS106 | ACAT | 414..417 | ACAT | 414..417 | AC | 348..349 |
| K326 | CS115 | TCAACATACA (SEQ ID NO: 379) | 411..420 | ACAT | 414..417 | AC | 348..349 |
| K326 | 18GH2162 | ACAT | 414..417 | ACAT | 414..417 | ACACACAG | 348..355 |
| K326 | CS111 | ACAT | 414..417 | ACAT | 414..417 | AC | 348..349 |
| K326 | CS112 | CATACAG | 415..421 | AC | 418..419 | AC | 348..349 |
| K326 | 17GH1678-60 | CATACAG | 415..421 | AC | 418..419 | AC | 348..349 |
| K326 | CS131 | ACAT | 414..417 | ACAT | 414..417 | ACAC | 348..351 |
| KATERINI | CS164 | AT | 416..417 | CAACATA | 412..418 | AC | 348..349 |
| KATERINI | CS163 | ACAT | 414..417 | AT | 416..417 | AC | 348..349 |
| KATERINI | CS146 | GAGCAATTCAACATACAGA (SEQ ID NO: 408) | 404..422 | ACAT | 414..417 | AC | 348..349 |
| KATERINI | CS147 | ACAT | 414..417 | CAACATA | 412..418 | AC | 348..349 |
| KATERINI | CS150 | AT | 416..417 | ACAT | 414..417 | AC | 348..349 |
| KATERINI | CS151 | AT | 416..417 | ACAT | 414..417 | AC | 348..349 |
| KATERINI | CS148 | ACAT | 414..417 | ACAT | 414..417 | AC | 348..349 |
| KATERINI | CS149 | ACAT | 414..417 | ACAT | 414..417 | AC | 348..349 |
| KATERINI | CS152 | AC | 418..419 | ACAT | 414..417 | AC | 348..349 |
| KATERINI | CS153 | CAACATA | 412..418 | AC | 414..415 | AC | 348..349 |
| KATERINI | CS102 | ACAT | 414..417 | AACAT | 413..417 | ACACACAG | 348..355 |
| KATERINI | CS103 | AC | 418..419 | CAACATA | 412..418 | ACACACAG | 348..355 |
| TN90 | CS143 | TACAGAG | 417..423 | ACAT | 414..417 | AC | 348..349 |
| TN90 | 18GH2169 | AC | 418..419 | ACAT | 414..417 | ACAC | 348..351 |
| TN90 | CS120 | ACAT | 414..417 | ACAG | 418..421 | ACAC | 348..351 |
| TN90 | 17GH1698-22 | ACAT | 414..417 | ACAT | 414..417 | AC | 348..349 |
| TN90 | 17GH1700-13 | ACAT | 414..417 | AACAT | 413..417 | AC | 348..349 |
| TN90 | 17GH1702-17 | ACAT | 414..417 | ACAT | 414..417 | AC | 348..349 |
| TN90 | 18GH2171 | ACAT | 414..417 | ACAT | 414..417 | ACAC | 348..351 |
| TN90 | CS165 | ACAT | 414..417 | ACAT | 414..417 | ACAC | 348..351 |
| TN90 | CS118 | ACAT | 414..417 | ACAT | 414..417 | AC | 348..349 |

TABLE 10-continued

Mutant pmt alleles in various lines produced by genome editing using GET2. The position of each edited site (e.g., indels) is relative to the nucleotide number on the corresponding cDNA sequence of each PMT gene (e.g., SEQ ID NO: 6 for PMT1b; SEQ ID NO: 7 for PMT1a; SEQ ID NO: 8 for PMT2; SEQ ID NO: 9 for PMT3; SEQ ID NO: 10 for PMT4). SEQ ID Numbers are assigned and shown for sequences of more than 10 nucleotides.

| TN90 | CS133 | GGAGCA ATTCAAC (SEQ ID NO: 409) | 403..415 | CAACAT ACAG (SEQ ID NO: 380) | 412..421 | ACAC | 348..351 |
|---|---|---|---|---|---|---|---|
| TN90 | 17GH1737-24 | CA | 415..416 | ACAT | 414..417 | ACAC | 348..351 |
| IZMIR | 18GH2254-7 | CAACATA | 412..418 | ATAGAGAA | 416..417 & 420..425 | ACAC | 348..351 |

| | PMT3 | | PMT4 | |
|---|---|---|---|---|
| | Deleted Sequence | Position | Deleted Sequence | Position |
| | ACAC | 432..435 | ACAC | 546..549 |
| | ACAC | 432..435 | ACAC | 546..549 |
| | CACAC | 433..437 | ACACA | 548..552 |
| | AC | 432..433 | ACACA | 548..552 |
| | ACAC | 432..435 | CACAC | 547..551 |
| | ACAC | 432..435 | CACAC | 547..551 |
| | ACAC | 432..435 | ACAC | 546..549 |
| | AACACACAG | 431..439 | ACAC | 546..549 |
| | ACAC | 432..435 | AC | 546..547 |
| | ACAC | 432..435 | AC | 546..547 |
| | CAACACA | 430..436 | AC | 546..547 |
| | CAACACA | 430..436 | AC | 546..547 |
| | CACACAG | 433..439 | AC | 546..547 |
| | ACAC | 432..435 | CAACACACAG (SEQ ID NO: 390) | 544..553 |
| | CACACAG | 433..439 | AC | 546..547 |
| | ACAC | 432..435 | CAACACACAG (SEQ ID NO: 390) | 544..553 |
| | ACAC | 432..435 | ACAC | 546..549 |
| | ACAC | 432..435 | ACAC | 546..549 |
| | AC | 432..433 | AC | 546..547 |
| | AC | 432..433 | AC | 546..547 |
| | AC | 432..433 | ACAC | 546..549 |
| | ACAC | 432..435 | AC | 546..547 |
| | AC | 432..433 | AC | 546..547 |
| | ACAG | 436..439 | AC | 546..547 |
| | AC | 432..433 | ACAC | 546..549 |
| | AC | 432..433 | CACAG | 549..553 |
| | CAACACA | 430..436 | AC | 546..547 |
| | ACAC | 432..435 | ACAC | 546..549 |
| | AC | 432..433 | ACAC | 546..549 |
| | AC | 432..433 | AC | 546..547 |
| | AC | 432..433 | AC | 546..547 |
| | ACAC | 432..435 | ACACACAG | 546..553 |

TABLE 11 provides the length (in nucleotides) of each PMT indel for each gene in each line as provided in Table 10.
Table 11. The length (in nucleotides) of each indel for selected lines provided in Table 10.

| Genotype | Line | Seed Ids | PMT1a | PMT1b | PMT2 | PMT3 | PMT4 |
|---|---|---|---|---|---|---|---|
| BASMA | CS107 | CS107 | 7 | 4 | 2 | 4 | 4 |
| BASMA | CS106 | CS106 | 4 | 4 | 2 | 4 | 4 |
| K326 | CS115 | CS115 | 10 | 4 | 2 | 5 | 5 |
| K326 | 17GH1809-13 | 18GH2162 | 4 | 4 | 8 | 2 | 5 |
| K326 | CS111 | CS111 | 4 | 4 | 2 | 4 | 5 |
| K326 | CS112 | CS112 | 7 | 2 | 2 | 4 | 5 |
| K326 | 17GH1678-60 | 17GH1678-60 | 7 | 2 | 2 | 4 | 4 |

TABLE 11-continued provides the length (in nucleotides) of each PMT indel for each gene in each line as provided in Table 10.
Table 11. The length (in nucleotides) of each indel for selected lines provided in Table 10.

| Genotype | Line | Seed Ids | PMT1a | PMT1b | PMT2 | PMT3 | PMT4 |
|---|---|---|---|---|---|---|---|
| K326 | CS131 | CS131 | 4 | 4 | 4 | 9 | 4 |
| KATERINI | 18GH709-01 | CS164 | 2 | 7 | 2 | 4 | 2 |
| KATERINI | 18GH709-08 | CS163 | 4 | 2 | 2 | 4 | 2 |
| KATERINI | 18GH414-11 | CS146 | 19 | 4 | 2 | 7 | 2 |
| KATERINI | 18GH414-19 | CS147 | 4 | 7 | 2 | 7 | 2 |
| KATERINI | 18GH437-04 | CS150 | 2 | 4 | 2 | 7 | 2 |
| KATERINI | 18GH437-08 | CS151 | 2 | 4 | 2 | 4 | 10 |
| KATERINI | 18GH437-32 | CS148 | 4 | 4 | 2 | 7 | 2 |
| KATERINI | 18GH437-39 | CS149 | 4 | 4 | 2 | 4 | 10 |
| KATERINI | 18GH449-26 | CS152 | 2 | 4 | 2 | 4 | 4 |
| KATERINI | 18GH449-33 | CS153 | 7 | 2 | 2 | 4 | 4 |
| KATERINI | 18GH125-48 | CS162 | 2 | 7 | 8 | 2 | 2 |
| KATERINI | CS102 | CS102 | 4 | 5 | 8 | 2 | 2 |
| KATERINI | CS103 | CS103 | 2 | 7 | 8 | 2 | 2 |
| TN90 | 17GH1719-30 | CS143 | 7 | 4 | 2 | 2 | 4 |
| TN90 | 17GH1740-36 | 18GH2169 | 2 | 4 | 4 | 4 | 2 |
| TN90 | 17GH1698-22 | 17GH1698-22 | 4 | 4 | 2 | 4 | 2 |
| TN90 | 17GH1700-13 | 17GH1700-13 | 4 | 5 | 2 | 2 | 4 |
| TN90 | 17GH1702-17 | 17GH1702-17 | 4 | 4 | 2 | 2 | 5 |
| TN90 | 17GH1849-01 | 18GH2171 | 4 | 4 | 4 | 7 | 2 |
| TN90 | 17GH1849-48 | CS165 | 4 | 4 | 4 | 4 | 4 |
| TN90 | 17GH1737-24 | 17GH1737-24 | 2 | 4 | 4 | 2 | 2 |
| TN90 | CS118 | CS118 | 4 | 4 | 2 | 2 | 4 |
| TN90 | CS133 | CS133 | 13 | 10 | 4 | 2 | 2 |
| TN90 | CS120 | CS120 | 4 | 4 | 4 | 2 | 2 |
| IZMIR | 18GH1108-07 | 18GH2254-7 | 7 | 8 | 4 | 4 | 8 |

Tables 12A to 12E provide genomic sequences of approximately 90 nucleotides from each pmt mutant allele with the edited site in the middle of the genomic sequence (e.g., 45 nucleotides on each side of the deleted or inserted sequence site).

TABLE 12A

A list of exemplary mutant alleles obtained in the PMT1b gene. Mutant allele sequences listed here represent approximately 90-nucleotide-long genomic sequences from each edited PMT1b gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 6) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| BASMA | CS107 | TCAGCAACTTATGGGAAGGTTCTGACTTTGGATGGAGCAATTCAGAGAATGGTGGATTTCCATACACTGAAATGATTGTTCATCTA | 410 | TCAGCAACTTATGGGAAGGTTCTGACTTTGGATGGAGCAATTCAacatacaGAGAATGGTGGATTTCCATACACTGAAATGATTGTTCATCTA | 442 |
| BASMA | CS106 | TCAGCAACTTATGGGAAGGTTCTGACTTTGGATGGAGCAATTCAACAGAGAATGGTGGATTTCCATACACTGAAATGATTGTTCATCTA | 411 | TCAGCAACTTATGGGAAGGTTCTGACTTTGGATGGAGCAATTCAacatACAGAGAATGGTGGATTTCCATACACTGAAATGATTGTTCATCTA | 443 |
| K326 | CS115 | TCAGCAACTTATGGGAAGGTTCTGACTTTGGATGGAGCAATGAGAATGGTGGATTTCCATACACTGAAATGATTGTTCATCTA | 412 | TCAGCAACTTATGGGAAGGTTCTGACTTTGGATGGAGCAATtcaacatacaGAGAATGGTGGATTTCCATACACTGAAATGATTGTTCATCTA | 444 |
| K326 | 18GH2162 | TCAGCAACTTATGGGAAGGTTCTGACTTTGGATGGAGCAATTCAACAGAGAATGGTGGATTTCCATACACTGAAATGATTGTTCATCTA | 413 | TCAGCAACTTATGGGAAGGTTCTGACTTTGGATGGAGCAATTCAacatACAGAGAATGGTGGATTTCCATACACTGAAATGATTGTTCATCTA | 445 |
| K326 | CS111 | TCAGCAACTTATGGGAAGGTTCTGACTTTGGATGGAGCAATTCAACAGAGAATGGTGGATTTCCATACACTGAAATGATTGTTCATCTA | 414 | TCAGCAACTTATGGGAAGGTTCTGACTTTGGATGGAGCAATTCAacatACAGAGAATGGTGGATTTCCATACACTGAAATGATTGTTCATCTA | 446 |

TABLE 12A-continued

A list of exemplary mutant alleles obtained in the PMT1b gene. Mutant allele sequences listed here represent approximately 90-nucleotide-long genomic sequences from each edited PMT1b gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 6) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| K326 | CS112 | TCAGCAACTTATGGGAAGGTTCTGACT TTGGATGGAGCAATTCAAAGAATGGTG GATTTCCATACACTGAAATGATTGTTC ATCTA | 415 | TCAGCAACTTATGGGAAGGTTCTGACT TTGGATGGAGCAATTCAAcatacagAG AATGGTGGATTTCCATACACTGAAATG ATTGTTCATCTATCAAAGAATGG | 447 |
| K326 | 17GH1678-60 | TCAGCAACTTATGGGAAGGTTCTGACT TTGGATGGAGCAATTCAAAGAATGGTG GATTTCCATACACTGAAATGATTGTTC ATCTA | 416 | TCAGCAACTTATGGGAAGGTTCTGACT TTGGATGGAGCAATTCAAcatacagAG AATGGTGGATTTCCATACACTGAAATG ATTGTTCATCTATCAAAGAATGG | 448 |
| K326 | CS131 | TCAGCAACTTATGGGAAGGTTCTGACT TTGGATGGAGCAATTCAACAGAGAATG GTGGATTTCCATACACTGAAATGATTG TTCATCTA | 417 | TCAGCAACTTATGGGAAGGTTCTGACT TTGGATGGAGCAATTCAacatACAGAG AATGGTGGATTTCCATACACTGAAATG ATTGTTCATCTA | 449 |
| KATERINI | CS164 | TCAGCAACTTATGGGAAGGTTCTGACT TTGGATGGAGCAATTCAACACAGAGAA TGGTGGATTTCCATACACTGAAATGAT TGTTCATCTA | 418 | TCAGCAACTTATGGGAAGGTTCTGACT TTGGATGGAGCAATTCAACatACAGAG AATGGTGGATTTCCATACACTGAAATG ATTGTTCATCTA | 450 |
| KATERINI | CS163 | TCAGCAACTTATGGGAAGGTTCTGACT TTGGATGGAGCAATTCAACAGAGAATG GTGGATTTCCATACACTGAAATGATTG TTCATCTA | 419 | TCAGCAACTTATGGGAAGGTTCTGACT TTGGATGGAGCAATTCAacatACAGAG AATGGTGGATTTCCATACACTGAAATG ATTGTTCATCTA | 451 |
| KATERINI | CS146 | TCAGCAACTTATGGGAAGGTTCTGACT TTGGATGGAATGGTGGATTTCCATACA CTGAAATGATTGTTCATCTA | 420 | TCAGCAACTTATGGGAAGGTTCTGACT TTGGATGGAgcaattcaacatacagag aATGGTGGATTTCCATACACTGAAATG ATTGTTCATCTA | 452 |
| KATERINI | CS147 | TCAGCAACTTATGGGAAGGTTCTGACT TTGGATGGAGCAATTCAACAGAGAATG GTGGATTTCCATACACTGAAATGATTG TTCATCTA | 421 | TCAGCAACTTATGGGAAGGTTCTGACT TTGGATGGAGCAATTCAacatACAGAG AATGGTGGATTTCCATACACTGAAATG ATTGTTCATCTA | 453 |
| KATERINI | CS150 | TCAGCAACTTATGGGAAGGTTCTGACT TTGGATGGAGCAATTCAACACAGAGAA TGGTGGATTTCCATACACTGAAATGAT TGTTCATCTA | 422 | TCAGCAACTTATGGGAAGGTTCTGACT TTGGATGGAGCAATTCAACatACAGAG AATGGTGGATTTCCATACACTGAAATG ATTGTTCATCTA | 454 |
| KATERINI | CS151 | TCAGCAACTTATGGGAAGGTTCTGACT TTGGATGGAGCAATTCAACACAGAGAA TGGTGGATTTCCATACACTGAAATGAT TGTTCATCTA | 423 | TCAGCAACTTATGGGAAGGTTCTGACT TTGGATGGAGCAATTCAACatACAGAG AATGGTGGATTTCCATACACTGAAATG ATTGTTCATCTA | 455 |
| KATERINI | CS148 | TCAGCAACTTATGGGAAGGTTCTGACT TTGGATGGAGCAATTCAACAGAGAATG GTGGATTTCCATACACTGAAATGATTG TTCATCTA | 424 | TCAGCAACTTATGGGAAGGTTCTGACT TTGGATGGAGCAATTCAacatACAGAG AATGGTGGATTTCCATACACTGAAATG ATTGTTCATCTA | 456 |
| KATERINI | CS149 | TCAGCAACTTATGGGAAGGTTCTGACT TTGGATGGAGCAATTCAACAGAGAATG GTGGATTTCCATACACTGAAATGATTG TTCATCTA | 425 | TCAGCAACTTATGGGAAGGTTCTGACT TTGGATGGAGCAATTCAacatACAGAG AATGGTGGATTTCCATACACTGAAATG ATTGTTCATCTA | 457 |
| KATERINI | CS152 | TCAGCAACTTATGGGAAGGTTCTGACT TTGGATGGAGCAATTCAACATAGAGAA TGGTGGATTTCCATACACTGAAATGAT TGTTCATCTA | 426 | TCAGCAACTTATGGGAAGGTTCTGACT TTGGATGGAGCAATTCAACATacAGAG AATGGTGGATTTCCATACACTGAAATG ATTGTTCATCTA | 458 |
| KATERINI | CS153 | TCAGCAACTTATGGGAAGGTTCTGACT TTGGATGGAGCAATTCAGAGAATGGTG GATTTCCATACACTGAAATGATTGTTC ATCTA | 427 | TCAGCAACTTATGGGAAGGTTCTGACT TTGGATGGAGCAATTCAacatacagAG AATGGTGGATTTCCATACACTGAAATG ATTGTTCATCTA | 459 |
| KATERINI | CS102 | TCAGCAACTTATGGGAAGGTTCTGACT TTGGATGGAGCAATTCAACAGAGAATG GTGGATTTCCATACACTGAAATGATTG TTCATCTA | 428 | TCAGCAACTTATGGGAAGGTTCTGACT TTGGATGGAGCAATTCAacatACAGAG AATGGTGGATTTCCATACACTGAAATG ATTGTTCATCTA | 460 |

TABLE 12A-continued

A list of exemplary mutant alleles obtained in the PMT1b gene. Mutant allele sequences listed here represent approximately 90-nucleotide-long genomic sequences from each edited PMT1b gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 6) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| KATERINI | CS103 | TCAGCAACTTATGGGAAGGTTCTGACTTTGGATGGAGCAATTCAACATAGAGAATGGTGGATTTCCATACACTGAAATGATTGTTCATCTA | 429 | TCAGCAACTTATGGGAAGGTTCTGACTTTGGATGGAGCAATTCAACATacAGAGAATGGTGGATTTCCATACACTGAAATGATTGTTCATCTA | 461 |
| TN90 | CS143 | TCAGCAACTTATGGGAAGGTTCTGACTTTGGATGGAGCAATTCAACAAATGGTGGATTTCCATACACTGAAATGATTGTTCATCTA | 430 | TCAGCAACTTATGGGAAGGTTCTGACTTTGGATGGAGCAATTCAACAtacagagAATGGTGGATTTCCATACACTGAAATGATTGTTCATCTA | 462 |
| TN90 | 18GH2169 | TCAGCAACTTATGGGAAGGTTCTGACTTTGGATGGAGCAATTCAACATAGAGAATGGTGGATTTCCATACACTGAAATGATTGTTCATCTA | 431 | TCAGCAACTTATGGGAAGGTTCTGACTTTGGATGGAGCAATTCAACATacAGAGAATGGTGGATTTCCATACACTGAAATGATTGTTCATCTA | 463 |
| TN90 | CS120 | TCAGCAACTTATGGGAAGGTTCTGACTTTGGATGGAGCAATTCAACAGAGAATGGTGGATTTCCATACACTGAAATGATTGTTCATCTA | 432 | TCAGCAACTTATGGGAAGGTTCTGACTTTGGATGGAGCAATTCAacatACAGAGAATGGTGGATTTCCATACACTGAAATGATTGTTCATCTA | 464 |
| TN90 | 17GH1698-22 | TCAGCAACTTATGGGAAGGTTCTGACTTTGGATGGAGCAATTCAACAGAGAATGGTGGATTTCCATACACTGAAATGATTGTTCATCTA | 433 | TCAGCAACTTATGGGAAGGTTCTGACTTTGGATGGAGCAATTCAacatACAGAGAATGGTGGATTTCCATACACTGAAATGATTGTTCATCTA | 465 |
| TN90 | 17GH1700-13 | TCAGCAACTTATGGGAAGGTTCTGACTTTGGATGGAGCAATTCAACAGAGAATGGTGGATTTCCATACACTGAAATGATTGTTCATCTA | 434 | TCAGCAACTTATGGGAAGGTTCTGACTTTGGATGGAGCAATTCAacatACAGAGAATGGTGGATTTCCATACACTGAAATGATTGTTCATCTA | 466 |
| TN90 | 17GH1702-17 | TCAGCAACTTATGGGAAGGTTCTGACTTTGGATGGAGCAATTCAACAGAGAATGGTGGATTTCCATACACTGAAATGATTGTTCATCTA | 435 | TCAGCAACTTATGGGAAGGTTCTGACTTTGGATGGAGCAATTCAacatACAGAGAATGGTGGATTTCCATACACTGAAATGATTGTTCATCTA | 467 |
| TN90 | 18GH2171 | TCAGCAACTTATGGGAAGGTTCTGACTTTGGATGGAGCAATTCAACAGAGAATGGTGGATTTCCATACACTGAAATGATTGTTCATCTA | 436 | TCAGCAACTTATGGGAAGGTTCTGACTTTGGATGGAGCAATTCAacatACAGAGAATGGTGGATTTCCATACACTGAAATGATTGTTCATCTA | 468 |
| TN90 | CS165 | TCAGCAACTTATGGGAAGGTTCTGACTTTGGATGGAGCAATTCAACAGAGAATGGTGGATTTCCATACACTGAAATGATTGTTCATCTA | 437 | TCAGCAACTTATGGGAAGGTTCTGACTTTGGATGGAGCAATTCAacatACAGAGAATGGTGGATTTCCATACACTGAAATGATTGTTCATCTA | 469 |
| TN90 | CS118 | TCAGCAACTTATGGGAAGGTTCTGACTTTGGATATACAGAATGGTGGATTTCCATACACTGAAATGATTGTTCATCTA | 438 | TCAGCAACTTATGGGAAGGTTCTGACTTTGGATggagcaattcaacATACAGAGAATGGTGGATTTCCATACACTGAAATGATTGTTCATCTA | 470 |
| TN90 | CS113 | TCAGCAACTTATGGGAAGGTTCTGACTTTGGATGGAGCAATTCAACAGAGAATGGTGGATTTCCATACACTGAAATGATTGTTCATCTA | 439 | TCAGCAACTTATGGGAAGGTTCTGACTTTGGATGGAGCAATTCAacatACAGAGAATGGTGGATTTCCATACACTGAAATGATTGTTCATCTA | 471 |
| TN90 | 17GH1737-24 | TCAGCAACTTATGGGAAGGTTCTGACTTTGGATGGAGCAATTCAATACAGAGAATGGTGGATTTCCATACACTGAAATGATTGTTCATCTA | 440 | TCAGCAACTTATGGGAAGGTTCTGACTTTGGATGGAGCAATTCAAcaTACAGAGAATGGTGGATTTCCATACACTGAAATGATTGTTCATCTA | 472 |
| IZMIR | 18GH2254-7 | TCAGCAACTTATGGGAAGGTTCTGACTTTGGATGGAGCAATTCAGAGAATGGTGGATTTCCATACACTGAAATGATTGTTCATCTA | 441 | TCAGCAACTTATGGGAAGGTTCTGACTTTGGATGGAGCAATTCAacatacaGAGAATGGTGGATTTCCATACACTGAAATGATTGTTCATCTA | 473 |

TABLE 12B

A list of exemplary mutant alleles obtained in the PMT1a gene. Mutant allele sequences listed here represent approximately 90-nucleotide-long genomic sequences from each edited PMT1a gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 7) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| BASMA | CS107 | TCAGCAACTTATGGGAAGGTTCTGACTTTGGATGGAGCAATTCAACAGAGAATGGTGGATTTCCATACACTGAAATGATTGTTCATCTA | 474 | TCAGCAACTTATGGGAAGGTTCTGACTTTGGATGGAGCAATTCAacatACAGAGAATGGTGGATTTCCATACACTGAAATGATTGTTCATCTA | 506 |
| BASMA | CS106 | TCAGCAACTTATGGGAAGGTTCTGACTTTGGATGGAGCAATTCAACAGAGAATGGTGGATTTCCATACACTGAAATGATTGTTCATCTA | 475 | TCAGCAACTTATGGGAAGGTTCTGACTTTGGATGGAGCAATTCAacatACAGAGAATGGTGGATTTCCATACACTGAAATGATTGTTCATCTA | 507 |
| K326 | CS115 | TCAGCAACTTATGGGAAGGTTCTGACTTTGGATGGAGCAATTCAACAGAGAATGGTGGATTTCCATACACTGAAATGATTGTTCATCTA | 476 | TCAGCAACTTATGGGAAGGTTCTGACTTTGGATGGAGCAATTCAacatACAGAGAATGGTGGATTTCCATACACTGAAATGATTGTTCATCTA | 508 |
| K326 | 18GH2162 | TCAGCAACTTATGGGAAGGTTCTGACTTTGGATGGAGCAATTCAACAGAGAATGGTGGATTTCCATACACTGAAATGATTGTTCATCTA | 477 | TCAGCAACTTATGGGAAGGTTCTGACTTTGGATGGAGCAATTCAacatACAGAGAATGGTGGATTTCCATACACTGAAATGATTGTTCATCTA | 509 |
| K326 | CS111 | TCAGCAACTTATGGGAAGGTTCTGACTTTGGATGGAGCAATTCAACAGAGAATGGTGGATTTCCATACACTGAAATGATTGTTCATCTA | 478 | TCAGCAACTTATGGGAAGGTTCTGACTTTGGATGGAGCAATTCAacatACAGAGAATGGTGGATTTCCATACACTGAAATGATTGTTCATCTA | 510 |
| K326 | CS112 | TCAGCAACTTATGGGAAGGTTCTGACTTTGGATGGAGCAATTCAACATAGAGAATGGTGGATTTCCATACACTGAAATGATTGTTCATCTA | 479 | TCAGCAACTTATGGGAAGGTTCTGACTTTGGATGGAGCAATTCAACATacAGAGAATGGTGGATTTCCATACACTGAAATGATTGTTCATCTA | 511 |
| K326 | 17GH1678-60 | TCAGCAACTTATGGGAAGGTTCTGACTTTGGATGGAGCAATTCAACATAGAGAATGGTGGATTTCCATACACTGAAATGATTGTTCATCTA | 480 | TCAGCAACTTATGGGAAGGTTCTGACTTTGGATGGAGCAATTCAACATacAGAGAATGGTGGATTTCCATACACTGAAATGATTGTTCATCTA | 512 |
| K326 | CS131 | TCAGCAACTTATGGGAAGGTTCTGACTTTGGATGGAGCAATTCAACAGAGAATGGTGGATTTCCATACACTGAAATGATTGTTCATCTA | 481 | TCAGCAACTTATGGGAAGGTTCTGACTTTGGATGGAGCAATTCAacatACAGAGAATGGTGGATTTCCATACACTGAAATGATTGTTCATCTA | 513 |
| KATERINI | CS164 | TCAGCAACTTATGGGAAGGTTCTGACTTTGGATGGAGCAATTCAGAGAATGGTGGATTTCCATACACTGAAATGATTGTTCATCTA | 482 | TCAGCAACTTATGGGAAGGTTCTGACTTTGGATGGAGCAATTCAacatacaGAGAATGGTGGATTTCCATACACTGAAATGATTGTTCATCTA | 514 |
| KATERINI | CS163 | TCAGCAACTTATGGGAAGGTTCTGACTTTGGATGGAGCAATTCAACACAGAGAATGGTGGATTTCCATACACTGAAATGATTGTTCATCTA | 483 | TCAGCAACTTATGGGAAGGTTCTGACTTTGGATGGAGCAATTCAACatACAGAGAATGGTGGATTTCCATACACTGAAATGATTGTTCATCTA | 515 |
| KATERINI | CS146 | TCAGCAACTTATGGGAAGGTTCTGACTTTGGATGGAGCAATTCAACAGAGAATGGTGGATTTCCATACACTGAAATGATTGTTCATCTA | 484 | TCAGCAACTTATGGGAAGGTTCTGACTTTGGATGGAGCAATTCAacatACAGAGAATGGTGGATTTCCATACACTGAAATGATTGTTCATCTA | 516 |
| KATERINI | CS147 | TCAGCAACTTATGGGAAGGTTCTGACTTTGGATGGAGCAATTCAGAGAATGGTGGATTTCCATACACTGAAATGATTGTTCATCTA | 485 | TCAGCAACTTATGGGAAGGTTCTGACTTTGGATGGAGCAATTCAacatacaGAGAATGGTGGATTTCCATACACTGAAATGATTGTTCATCTA | 517 |
| KATERINI | CS150 | TCAGCAACTTATGGGAAGGTTCTGACTTTGGATGGAGCAATTCAACAGAGAATGGTGGATTTCCATACACTGAAATGATTGTTCATCTA | 486 | TCAGCAACTTATGGGAAGGTTCTGACTTTGGATGGAGCAATTCAacatACAGAGAATGGTGGATTTCCATACACTGAAATGATTGTTCATCTA | 518 |
| KATERINI | CS151 | TCAGCAACTTATGGGAAGGTTCTGACTTTGGATGGAGCAATTCAACAGAGAATGGTGGATTTCCATACACTGAAATGATTGTTCATCTA | 487 | TCAGCAACTTATGGGAAGGTTCTGACTTTGGATGGAGCAATTCAacatACAGAGAATGGTGGATTTCCATACACTGAAATGATTGTTCATCTA | 519 |

TABLE 12B-continued

A list of exemplary mutant alleles obtained in the PMT1a gene. Mutant allele sequences listed here represent approximately 90-nucleotide-long genomic sequences from each edited PMT1a gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 7) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| KATERINI | CS148 | TCAGCAACTTATGGGAAGGTTCTGACTTTGGATGGAGCAATTCAACAGAGAATGGTGGATTTCCATACACTGAAATGATTGTTCATCTA | 488 | TCAGCAACTTATGGGAAGGTTCTGACTTTGGATGGAGCAATTCAacatACAGAGAATGGTGGATTTCCATACACTGAAATGATTGTTCATCTA | 520 |
| KATERINI | CS149 | TCAGCAACTTATGGGAAGGTTCTGACTTTGGATGGAGCAATTCAACAGAGAATGGTGGATTTCCATACACTGAAATGATTGTTCATCTA | 489 | TCAGCAACTTATGGGAAGGTTCTGACTTTGGATGGAGCAATTCAacatACAGAGAATGGTGGATTTCCATACACTGAAATGATTGTTCATCTA | 521 |
| KATERINI | CS152 | TCAGCAACTTATGGGAAGGTTCTGACTTTGGATGGAGCAATTCAACAGAGAATGGTGGATTTCCATACACTGAAATGATTGTTCATCTA | 490 | TCAGCAACTTATGGGAAGGTTCTGACTTTGGATGGAGCAATTCAacatACAGAGAATGGTGGATTTCCATACACTGAAATGATTGTTCATCTA | 522 |
| KATERINI | CS153 | TCAGCAACTTATGGGAAGGTTCTGACTTTGGATGGAGCAATTCAATACAGAGAATGGTGGATTTCCATACACTGAAATGATTGTTCATCTA | 491 | TCAGCAACTTATGGGAAGGTTCTGACTTTGGATGGAGCAATTCAAcaTACAGAGAATGGTGGATTTCCATACACTGAAATGATTGTTCATCTA | 523 |
| KATERINI | CS102 | TCAGCAACTTATGGGAAGGTTCTGACTTTGGATGGAGCAATTCACAGAGAATGGTGGATTTCCATACACTGAAATGATTGTTCATCTA | 492 | TCAGCAACTTATGGGAAGGTTCTGACTTTGGATGGAGCAATTCAacataCAGAGAATGGTGGATTTCCATACACTGAAATGATTGTTCATCTA | 524 |
| KATERINI | CS103 | TCAGCAACTTATGGGAAGGTTCTGACTTTGGATGGAGCAATTCAGAGAATGGTGGATTTCCATACACTGAAATGATTGTTCATCTA | 493 | TCAGCAACTTATGGGAAGGTTCTGACTTTGGATGGAGCAATTCAacatacaGAGAATGGTGGATTTCCATACACTGAAATGATTGTTCATCTA | 525 |
| TN90 | CS143 | TCAGCAACTTATGGGAAGGTTCTGACTTTGGATGGAGCAATTCAACAGAGAATGGTGGATTTCCATACACTGAAATGATTGTTCATCTA | 494 | TCAGCAACTTATGGGAAGGTTCTGACTTTGGATGGAGCAATTCAacatACAGAGAATGGTGGATTTCCATACACTGAAATGATTGTTCATCTA | 526 |
| TN90 | 18GH2169 | TCAGCAACTTATGGGAAGGTTCTGACTTTGGATGGAGCAATTCAACAGAGAATGGTGGATTTCCATACACTGAAATGATTGTTCATCTA | 495 | TCAGCAACTTATGGGAAGGTTCTGACTTTGGATGGAGCAATTCAacatACAGAGAATGGTGGATTTCCATACACTGAAATGATTGTTCATCTA | 527 |
| TN90 | CS120 | TCAGCAACTTATGGGAAGGTTCTGACTTTGGATGGAGCAATTCAACATAGAATGGTGGATTTCCATACACTGAAATGATTGTTCATCTA | 496 | TCAGCAACTTATGGGAAGGTTCTGACTTTGGATGGAGCAATTCAACATacagAGAATGGTGGATTTCCATACACTGAAATGATTGTTCATCTA | 528 |
| TN90 | 17GH1698-22 | TCAGCAACTTATGGGAAGGTTCTGACTTTGGATGGAGCAATTCAACAGAGAATGGTGGATTTCCATACACTGAAATGATTGTTCATCTA | 497 | TCAGCAACTTATGGGAAGGTTCTGACTTTGGATGGAGCAATTCAacatACAGAGAATGGTGGATTTCCATACACTGAAATGATTGTTCATCTA | 529 |
| TN90 | 17GH1700-13 | TCAGCAACTTATGGGAAGGTTCTGACTTTGGATGGAGCAATTCACAGAGAATGGTGGATTTCCATACACTGAAATGATTGTTCATCTA | 498 | TCAGCAACTTATGGGAAGGTTCTGACTTTGGATGGAGCAATTCAacataCAGAGAATGGTGGATTTCCATACACTGAAATGATTGTTCATCTA | 530 |
| TN90 | 17GH1702-17 | TCAGCAACTTATGGGAAGGTTCTGACTTTGGATGGAGCAATTCAACAGAGAATGGTGGATTTCCATACACTGAAATGATTGTTCATCTA | 499 | TCAGCAACTTATGGGAAGGTTCTGACTTTGGATGGAGCAATTCAacatACAGAGAATGGTGGATTTCCATACACTGAAATGATTGTTCATCTA | 531 |
| TN90 | 18GH2171 | TCAGCAACTTATGGGAAGGTTCTGACTTTGGATGGAGCAATTCAACAGAGAATGGTGGATTTCCATACACTGAAATGATTGTTCATCTA | 500 | TCAGCAACTTATGGGAAGGTTCTGACTTTGGATGGAGCAATTCAacatACAGAGAATGGTGGATTTCCATACACTGAAATGATTGTTCATCTA | 532 |

TABLE 12B-continued

A list of exemplary mutant alleles obtained in the PMT1a gene. Mutant allele sequences listed here represent approximately 90-nucleotide-long genomic sequences from each edited PMT1a gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 7) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| TN90 | CS165 | TCAGCAACTTATGGGAAGGTTCTGACTTTGGATGGAGCAATTCAACAGAGAATGGTGGATTTCCATACACTGAAATGATTGTTCATCTA | 501 | TCAGCAACTTATGGGAAGGTTCTGACTTTGGATGGAGCAATTCAacatACAGAGAATGGTGGATTTCCATACACTGAAATGATTGTTCATCTA | 533 |
| TN90 | CS118 | TCAGCAACTTATGGGAAGGTTCTGACTTTGGATGGAGCAATTAGAATGGTGGATTTCCATACACTGAAATGATTGTTCATCTA | 502 | TCAGCAACTTATGGGAAGGTTCTGACTTTGGATGGAGCAATTcaacatacagAGAATGGTGGATTTCCATACACTGAAATGATTGTTCATCTA | 534 |
| TN90 | CS113 | TCAGCAACTTATGGGAAGGTTCTGACTTTGGATGGAGCAATTCAACATAGAATGGTGGATTTCCATACACTGAAATGATTGTTCATCTA | 503 | TCAGCAACTTATGGGAAGGTTCTGACTTTGGATGGAGCAATTCAACATAcagAGAATGGTGGATTTCCATACACTGAAATGATTGTTCATCTA | 535 |
| TN90 | 17GH1737-24 | TCAGCAACTTATGGGAAGGTTCTGACTTTGGATGGAGCAATTCAACAGAGAATGGTGGATTTCCATACACTGAAATGATTGTTCATCTA | 504 | TCAGCAACTTATGGGAAGGTTCTGACTTTGGATGGAGCAATTCAacatACAGAGAATGGTGGATTTCCATACACTGAAATGATTGTTCATCTA | 536 |
| IZMIR | 18GH2254-7 | TCAGCAACTTATGGGAAGGTTCTGACTTTGGATGGAGCAATTCAACACTGGTGGATTTCCATACACTGAAATGATTGTTCATCTA | 505 | TCAGCAACTTATGGGAAGGTTCTGACTTTGGATGGAGCAATTCAacatacagagACTGGTGGATTTCCATACACTGAAATGATTGTTCATCTA | 537 |

TABLE 12C

A list of exemplary mutant alleles obtained in the PMT2 gene. Mutant allele sequences listed here represent approximately 90-nucleotide-long genomic sequences from each edited PMT2 gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 8) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| BASMA | CS107 | TCAGCAACTTATGGGAAGGTTCTGACTTTGGATGGAGCAATTCAACACAGAGAATGGTGGATTTCCATACACTGAAATGATTGTTCATCTT | 538 | TCAGCAACTTATGGGAAGGTTCTGACTTTGGATGGAGCAATTCAacACACAGAGAATGGTGGATTTCCATACACTGAAATGATTGTTCATCTT | 570 |
| BASMA | CS106 | TCAGCAACTTATGGGAAGGTTCTGACTTTGGATGGAGCAATTCAACACAGAGAATGGTGGATTTCCATACACTGAAATGATTGTTCATCTT | 539 | TCAGCAACTTATGGGAAGGTTCTGACTTTGGATGGAGCAATTCAacACACAGAGAATGGTGGATTTCCATACACTGAAATGATTGTTCATCTT | 571 |
| K326 | CS115 | TCAGCAACTTATGGGAAGGTTCTGACTTTGGATGGAGCAATTCAACACAGAGAATGGTGGATTTCCATACACTGAAATGATTGTTCATCTT | 540 | TCAGCAACTTATGGGAAGGTTCTGACTTTGGATGGAGCAATTCAacACACAGAGAATGGTGGATTTCCATACACTGAAATGATTGTTCATCTT | 572 |
| K326 | 18GH2162 | TCAGCAACTTATGGGAAGGTTCTGACTTTGGATGGAGCAATTCAAGAATGGTGGATTTCCATACACTGAAATGATTGTTCATCTT | 541 | TCAGCAACTTATGGGAAGGTTCTGACTTTGGATGGAGCAATTCAacacacagAGAATGGTGGATTTCCATACACTGAAATGATTGTTCATCTT | 573 |
| K326 | CS111 | TCAGCAACTTATGGGAAGGTTCTGACTTTGGATGGAGCAATTCAACACAGAGAATGGTGGATTTCCATACACTGAAATGATTGTTCATCTT | 542 | TCAGCAACTTATGGGAAGGTTCTGACTTTGGATGGAGCAATTCAacACACAGAGAATGGTGGATTTCCATACACTGAAATGATTGTTCATCTT | 574 |

TABLE 12C-continued

A list of exemplary mutant alleles obtained in the PMT2 gene. Mutant allele sequences listed here represent approximately 90-nucleotide-long genomic sequences from each edited PMT2 gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 8) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| K326 | CS112 | TCAGCAACTTATGGGAAGGTTCTGACTTTGGATGGAGCAATTCAACACAGAGAATGGTGGATTTCCATACACTGAAATGATTGTTCATCTT | 543 | TCAGCAACTTATGGGAAGGTTCTGACTTTGGATGGAGCAATTCAacACACAGAGAATGGTGGATTTCCATACACTGAAATGATTGTTCATCTT | 575 |
| K326 | 17GH1678-60 | TCAGCAACTTATGGGAAGGTTCTGACTTTGGATGGAGCAATTCAACACAGAGAATGGTGGATTTCCATACACTGAAATGATTGTTCATCTT | 544 | TCAGCAACTTATGGGAAGGTTCTGACTTTGGATGGAGCAATTCAacACACAGAGAATGGTGGATTTCCATACACTGAAATGATTGTTCATCTT | 576 |
| K326 | CS131 | TCAGCAACTTATGGGAAGGTTCTGACTTTGGATGGAGCAATTCAACACAGAGAATGGTGGATTTCCATACACTGAAATGATTGTTCATCTT | 545 | TCAGCAACTTATGGGAAGGTTCTGACTTTGGATGGAGCAATTCAacacACAGAGAATGGTGGATTTCCATACACTGAAATGATTGTTCATCTT | 577 |
| KATERINI | CS164 | TCAGCAACTTATGGGAAGGTTCTGACTTTGGATGGAGCAATTCAACACAGAGAATGGTGGATTTCCATACACTGAAATGATTGTTCATCTT | 546 | TCAGCAACTTATGGGAAGGTTCTGACTTTGGATGGAGCAATTCAacACACAGAGAATGGTGGATTTCCATACACTGAAATGATTGTTCATCTT | 578 |
| KATERINI | CS163 | TCAGCAACTTATGGGAAGGTTCTGACTTTGGATGGAGCAATTCAACACAGAGAATGGTGGATTTCCATACACTGAAATGATTGTTCATCTT | 547 | TCAGCAACTTATGGGAAGGTTCTGACTTTGGATGGAGCAATTCAacACACAGAGAATGGTGGATTTCCATACACTGAAATGATTGTTCATCTT | 579 |
| KATERINI | CS146 | TCAGCAACTTATGGGAAGGTTCTGACTTTGGATGGAGCAATTCAACACAGAGAATGGTGGATTTCCATACACTGAAATGATTGTTCATCTT | 548 | TCAGCAACTTATGGGAAGGTTCTGACTTTGGATGGAGCAATTCAacACACAGAGAATGGTGGATTTCCATACACTGAAATGATTGTTCATCTT | 580 |
| KATERINI | CS147 | TCAGCAACTTATGGGAAGGTTCTGACTTTGGATGGAGCAATTCAACACAGAGAATGGTGGATTTCCATACACTGAAATGATTGTTCATCTT | 549 | TCAGCAACTTATGGGAAGGTTCTGACTTTGGATGGAGCAATTCAacACACAGAGAATGGTGGATTTCCATACACTGAAATGATTGTTCATCTT | 581 |
| KATERINI | CS150 | TCAGCAACTTATGGGAAGGTTCTGACTTTGGATGGAGCAATTCAACACAGAGAATGGTGGATTTCCATACACTGAAATGATTGTTCATCTT | 550 | TCAGCAACTTATGGGAAGGTTCTGACTTTGGATGGAGCAATTCAacACACAGAGAATGGTGGATTTCCATACACTGAAATGATTGTTCATCTT | 582 |
| KATERINI | CS151 | TCAGCAACTTATGGGAAGGTTCTGACTTTGGATGGAGCAATTCAACACAGAGAATGGTGGATTTCCATACACTGAAATGATTGTTCATCTT | 551 | TCAGCAACTTATGGGAAGGTTCTGACTTTGGATGGAGCAATTCAacACACAGAGAATGGTGGATTTCCATACACTGAAATGATTGTTCATCTT | 583 |
| KATERINI | CS148 | TCAGCAACTTATGGGAAGGTTCTGACTTTGGATGGAGCAATTCAACACAGAGAATGGTGGATTTCCATACACTGAAATGATTGTTCATCTT | 552 | TCAGCAACTTATGGGAAGGTTCTGACTTTGGATGGAGCAATTCAacACACAGAGAATGGTGGATTTCCATACACTGAAATGATTGTTCATCTT | 584 |
| KATERINI | CS149 | TCAGCAACTTATGGGAAGGTTCTGACTTTGGATGGAGCAATTCAACACAGAGAATGGTGGATTTCCATACACTGAAATGATTGTTCATCTT | 553 | TCAGCAACTTATGGGAAGGTTCTGACTTTGGATGGAGCAATTCAacACACAGAGAATGGTGGATTTCCATACACTGAAATGATTGTTCATCTT | 585 |
| KATERINI | CS152 | TCAGCAACTTATGGGAAGGTTCTGACTTTGGATGGAGCAATTCAACACAGAGAATGGTGGATTTCCATACACTGAAATGATTGTTCATCTT | 554 | TCAGCAACTTATGGGAAGGTTCTGACTTTGGATGGAGCAATTCAacACACAGAGAATGGTGGATTTCCATACACTGAAATGATTGTTCATCTT | 586 |
| KATERINI | CS153 | TCAGCAACTTATGGGAAGGTTCTGACTTTGGATGGAGCAATTCAACACAGAGAATGGTGGATTTCCATACACTGAAATGATTGTTCATCTT | 555 | TCAGCAACTTATGGGAAGGTTCTGACTTTGGATGGAGCAATTCAacACACAGAGAATGGTGGATTTCCATACACTGAAATGATTGTTCATCTT | 587 |

TABLE 12C-continued

A list of exemplary mutant alleles obtained in the PMT2 gene. Mutant allele sequences listed here represent approximately 90-nucleotide-long genomic sequences from each edited PMT2 gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 8) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| KATERINI | CS102 | TCAGCAACTTATGGGAAGGTTCTGACT TTGGATGGAGCAATTCAAGAATGGTGG ATTTCCATACACTGAAATGATTGTTCA TCTT | 556 | TCAGCAACTTATGGGAAGGTTCTGAC TTTGGATGGAGCAATTCAacacacag AGAATGGTGGATTTCCATACACTGAA ATGATTGTTCATCTT | 588 |
| KATERINI | CS103 | TCAGCAACTTATGGGAAGGTTCTGACT TTGGATGGAGCAATTCAAGAATGGTGG ATTTCCATACACTGAAATGATTGTTCA TCTT | 557 | TCAGCAACTTATGGGAAGGTTCTGAC TTTGGATGGAGCAATTCAacacacag AGAATGGTGGATTTCCATACACTGAA ATGATTGTTCATCTT | 589 |
| TN90 | CS143 | TCAGCAACTTATGGGAAGGTTCTGACT TTGGATGGAGCAATTCAACACAGAGAA TGGTGGATTTCCATACACTGAAATGAT TGTTCATCTT | 558 | TCAGCAACTTATGGGAAGGTTCTGAC TTTGGATGGAGCAATTCAacACACAG AGAATGGTGGATTTCCATACACTGAA ATGATTGTTCATCTT | 590 |
| TN90 | 18GH2169 | TCAGCAACTTATGGGAAGGTTCTGACT TTGGATGGAGCAATTCAACAGAGAATG GTGGATTTCCATACACTGAAATGATTG TTCATCTT | 559 | TCAGCAACTTATGGGAAGGTTCTGAC TTTGGATGGAGCAATTCAacACACAG AGAATGGTGGATTTCCATACACTGAA ATGATTGTTCATCTT | 591 |
| TN90 | CS120 | TCAGCAACTTATGGGAAGGTTCTGACT TTGGATGGAGCAATTCAACAGAGAATG GTGGATTTCCATACACTGAAATGATTG TTCATCTT | 560 | TCAGCAACTTATGGGAAGGTTCTGAC TTTGGATGGAGCAATTCAacACACAG AGAATGGTGGATTTCCATACACTGAA ATGATTGTTCATCTT | 592 |
| TN90 | 17GH1698-22 | TCAGCAACTTATGGGAAGGTTCTGACT TTGGATGGAGCAATTCAACACAGAGAA TGGTGGATTTCCATACACTGAAATGAT TGTTCATCTT | 561 | TCAGCAACTTATGGGAAGGTTCTGAC TTTGGATGGAGCAATTCAacACACAG AGAATGGTGGATTTCCATACACTGAA ATGATTGTTCATCTT | 593 |
| TN90 | 17GH1700-13 | TCAGCAACTTATGGGAAGGTTCTGACT TTGGATGGAGCAATTCAACACAGAGAA TGGTGGATTTCCATACACTGAAATGAT TGTTCATCTT | 562 | TCAGCAACTTATGGGAAGGTTCTGAC TTTGGATGGAGCAATTCAacACACAG AGAATGGTGGATTTCCATACACTGAA ATGATTGTTCATCTT | 594 |
| TN90 | 17GH1702-17 | TCAGCAACTTATGGGAAGGTTCTGACT TTGGATGGAGCAATTCAACACAGAGAA TGGTGGATTTCCATACACTGAAATGAT TGTTCATCTT | 563 | TCAGCAACTTATGGGAAGGTTCTGAC TTTGGATGGAGCAATTCAacACACAG AGAATGGTGGATTTCCATACACTGAA ATGATTGTTCATCTT | 595 |
| TN90 | 18GH2171 | TCAGCAACTTATGGGAAGGTTCTGACT TTGGATGGAGCAATTCAACAGAGAATG GTGGATTTCCATACACTGAAATGATTG TTCATCTT | 564 | TCAGCAACTTATGGGAAGGTTCTGAC TTTGGATGGAGCAATTCAacacACAG AGAATGGTGGATTTCCATACACTGAA ATGATTGTTCATCTT | 596 |
| TN90 | CS165 | TCAGCAACTTATGGGAAGGTTCTGACT TTGGATGGAGCAATTCAACAGAGAATG GTGGATTTCCATACACTGAAATGATTG TTCATCTT | 565 | TCAGCAACTTATGGGAAGGTTCTGAC TTTGGATGGAGCAATTCAacacACAG AGAATGGTGGATTTCCATACACTGAA ATGATTGTTCATCTT | 597 |
| TN90 | CS118 | TCAGCAACTTATGGGAAGGTTCTGACT TTGGATGGAGCAATTCAACAGAGAATG GTGGATTTCCATACACTGAAATGATTG TTCATCTT | 566 | TCAGCAACTTATGGGAAGGTTCTGAC TTTGGATGGAGCAATTCAacacACAG AGAATGGTGGATTTCCATACACTGAA ATGATTGTTCATCTT | 598 |
| TN90 | CS113 | TCAGCAACTTATGGGAAGGTTCTGACT TTGGATGGAGCAATTCAACAGAGAATG GTGGATTTCCATACACTGAAATGATTG TTCATCTT | 567 | TCAGCAACTTATGGGAAGGTTCTGAC TTTGGATGGAGCAATTCAacacACAG AGAATGGTGGATTTCCATACACTGAA ATGATTGTTCATCTT | 599 |
| TN90 | 17GH1737-24 | TCAGCAACTTATGGGAAGGTTCTGACT TTGGATGGAGCAATTCAACAGAGAATG GTGGATTTCCATACACTGAAATGATTG TTCATCTT | 568 | TCAGCAACTTATGGGAAGGTTCTGAC TTTGGATGGAGCAATTCAacacACAG AGAATGGTGGATTTCCATACACTGAA ATGATTGTTCATCTT | 600 |

TABLE 12C-continued

A list of exemplary mutant alleles obtained in the PMT2 gene. Mutant allele sequences listed here represent approximately 90-nucleotide-long genomic sequences from each edited PMT2 gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 8) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| IZMIR | 18GH2254-7 | TCAGCAACTTATGGGAAGGTTCTGACT TTGGATGGAGCAATTCAACAGAGAATG GTGGATTTCCATACACTGAAATGATTG TTCATCTT | 569 | TCAGCAACTTATGGGAAGGTTCTGAC TTTGGATGGAGCAATTCAacacACAG AGAATGGTGGATTTCCATACACTGAA ATGATTGTTCATCTT | 601 |

TABLE 12D

A list of exemplary mutant alleles obtained in the PMT3 gene. Mutant allele sequences listed here represent approximately 90-nucleotide-long genomic sequences from each edited PMT3 gene with the edited site in the middle of the genomic sequence (e.g., 4 nucleotides on each side of the deleted sequence site). The mutant allele corresponds to the indel provided for each line in Table 10. The lowercase letters in the reference allele sequence (SEQ ID NO: 9) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| BASMA | CS107 | TCAGCAACATATGGGAAGGTTCTGACT TTGGATGGAGCAATTCAACAGAGAATG GTGGATTTCCATACACTGAAATGATTG TTCATCTT | 602 | TCAGCAACATATGGGAAGGTTCTGACT TTGGATGGAGCAATTCAacacACAGAG AATGGTGGATTTCCATACACTGAAATG ATTGTTCATCTT | 634 |
| BASMA | CS106 | TCAGCAACATATGGGAAGGTTCTGACT TTGGATGGAGCAATTCAACAGAGAATG GTGGATTTCCATACACTGAAATGATTG TTCATCTT | 603 | TCAGCAACATATGGGAAGGTTCTGACT TTGGATGGAGCAATTCAacacACAGAG AATGGTGGATTTCCATACACTGAAATG ATTGTTCATCTT | 635 |
| K326 | CS115 | TCAGCAACATATGGGAAGGTTCTGACT TTGGATGGAGCAATTCAAAGAGAATGG TGGATTTCCATACACTGAAATGATTGT TCATCTT | 604 | TCAGCAACATATGGGAAGGTTCTGACT TTGGATGGAGCAATTCAACacacAGAG AATGGTGGATTTCCATACACTGAAATG ATTGTTCATCTT | 636 |
| K326 | 18GH2162 | TCAGCAACATATGGGAAGGTTCTGACT TTGGATGGAGCAATTCAACACAGAGAA TGGTGGATTTCCATACACTGAAATGAT TGTTCATCTT | 605 | TCAGCAACATATGGGAAGGTTCTGACT TTGGATGGAGCAATTCAacACACAGAG AATGGTGGATTTCCATACACTGAAATG ATTGTTCATCTT | 637 |
| K326 | CS111 | TCAGCAACATATGGGAAGGTTCTGACT TTGGATGGAGCAATTCAACAGAGAATG GTGGATTTCCATACACTGAAATGATTG TTCATCTT | 606 | TCAGCAACATATGGGAAGGTTCTGACT TTGGATGGAGCAATTCAacacACAGAG AATGGTGGATTTCCATACACTGAAATG ATTGTTCATCTT | 638 |
| K326 | CS112 | TCAGCAACATATGGGAAGGTTCTGACT TTGGATGGAGCAATTCAACAGAGAATG GTGGATTTCCATACACTGAAATGATTG TTCATCTT | 607 | TCAGCAACATATGGGAAGGTTCTGACT TTGGATGGAGCAATTCAacacACAGAG AATGGTGGATTTCCATACACTGAAATG ATTGTTCATCTT | 639 |
| K326 | 17GH1678-60 | TCAGCAACATATGGGAAGGTTCTGACT TTGGATGGAGCAATTCAACAGAGAATG GTGGATTTCCATACACTGAAATGATTG TTCATCTT | 608 | TCAGCAACATATGGGAAGGTTCTGACT TTGGATGGAGCAATTCAacacACAGAG AATGGTGGATTTCCATACACTGAAATG ATTGTTCATCTT | 640 |
| K326 | CS131 | TCAGCAACATATGGGAAGGTTCTGACT TTGGATGGAGCAATTCAGAATGGTGGA TTTCCATACACTGAAATGATTGTTCAT CTT | 609 | TCAGCAACATATGGGAAGGTTCTGACT TTGGATGGAGCAATTCAacacacagAG AATGGTGGATTTCCATACACTGAAATG ATTGTTCATCTT | 641 |
| KATERINI | CS164 | TCAGCAACATATGGGAAGGTTCTGACT TTGGATGGAGCAATTCAACAGAGAATG GTGGATTTCCATACACTGAAATGATTG TTCATCTT | 610 | TCAGCAACATATGGGAAGGTTCTGACT TTGGATGGAGCAATTCAacacACAGAG AATGGTGGATTTCCATACACTGAAATG ATTGTTCATCTT | 642 |

TABLE 12D-continued

A list of exemplary mutant alleles obtained in the PMT3 gene. Mutant allele sequences listed here represent approximately 90-nucleotide-long genomic sequences from each edited PMT3 gene with the edited site in the middle of the genomic sequence (e.g., 4nucleotides on each side of the deleted sequence site). The mutant allele corresponds to the indel provided for each line in Table 10. The lowercase letters in the reference allele sequence (SEQ ID NO: 9) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| KATERINI | CS163 | TCAGCAACATATGGGAAGGTTCTGACTTTGGATGGAGCAATTCAACAGAGAATGGTGGATTTCCATACACTGAAATGATTGTTCATCTT | 611 | TCAGCAACATATGGGAAGGTTCTGACTTTGGATGGAGCAATTCAacacACAGAGAATGGTGGATTTCCATACACTGAAATGATTGTTCATCTT | 643 |
| KATERINI | CS146 | TCAGCAACATATGGGAAGGTTCTGACTTTGGATGGAGCAATTCAGAGAATGGTGGATTTCCATACACTGAAATGATTGTTCATCTT | 612 | TCAGCAACATATGGGAAGGTTCTGACTTTGGATGGAGCAATTcaacacaCAGAGAATGGTGGATTTCCATACACTGAAATGATTGTTCATCTT | 644 |
| KATERINI | CS147 | TCAGCAACATATGGGAAGGTTCTGACTTTGGATGGAGCAATTCAGAGAATGGTGGATTTCCATACACTGAAATGATTGTTCATCTT | 613 | TCAGCAACATATGGGAAGGTTCTGACTTTGGATGGAGCAATTcaacacaCAGAGAATGGTGGATTTCCATACACTGAAATGATTGTTCATCTT | 645 |
| KATERINI | CS150 | TCAGCAACATATGGGAAGGTTCTGACTTTGGATGGAGCAATTCAAAGAATGGTGGATTTCCATACACTGAAATGATTGTTCATCTT | 614 | TCAGCAACATATGGGAAGGTTCTGACTTTGGATGGAGCAATTCAacacacagAGAATGGTGGATTTCCATACACTGAAATGATTGTTCATCTT | 646 |
| KATERINI | CS151 | TCAGCAACATATGGGAAGGTTCTGACTTTGGATGGAGCAATTCAACAGAGAATGGTGGATTTCCATACACTGAAATGATTGTTCATCTT | 615 | TCAGCAACATATGGGAAGGTTCTGACTTTGGATGGAGCAATTCAacacACAGAGAATGGTGGATTTCCATACACTGAAATGATTGTTCATCTT | 647 |
| KATERINI | CS148 | TCAGCAACATATGGGAAGGTTCTGACTTTGGATGGAGCAATTCAAAGAATGGTGGATTTCCATACACTGAAATGATTGTTCATCTT | 616 | TCAGCAACATATGGGAAGGTTCTGACTTTGGATGGAGCAATTCAAcacacagAGAATGGTGGATTTCCATACACTGAAATGATTGTTCATCTT | 648 |
| KATERINI | CS149 | TCAGCAACATATGGGAAGGTTCTGACTTTGGATGGAGCAATTCAACAGAGAATGGTGGATTTCCATACACTGAAATGATTGTTCATCTT | 617 | TCAGCAACATATGGGAAGGTTCTGACTTTGGATGGAGCAATTCAacacACAGAGAATGGTGGATTTCCATACACTGAAATGATTGTTCATCTT | 649 |
| KATERINI | CS152 | TCAGCAACATATGGGAAGGTTCTGACTTTGGATGGAGCAATTCAACAGAGAATGGTGGATTTCCATACACTGAAATGATTGTTCATCTT | 618 | TCAGCAACATATGGGAAGGTTCTGACTTTGGATGGAGCAATTCAacacACAGAGAATGGTGGATTTCCATACACTGAAATGATTGTTCATCTT | 650 |
| KATERINI | CS153 | TCAGCAACATATGGGAAGGTTCTGACTTTGGATGGAGCAATTCAACAGAGAATGGTGGATTTCCATACACTGAAATGATTGTTCATCTT | 619 | TCAGCAACATATGGGAAGGTTCTGACTTTGGATGGAGCAATTCAacacACAGAGAATGGTGGATTTCCATACACTGAAATGATTGTTCATCTT | 651 |
| KATERINI | CS102 | TCAGCAACATATGGGAAGGTTCTGACTTTGGATGGAGCAATTCAACACAGAGAATGGTGGATTTCCATACACTGAAATGATTGTTCATCTT | 620 | TCAGCAACATATGGGAAGGTTCTGACTTTGGATGGAGCAATTCAacACACAGAGAATGGTGGATTTCCATACACTGAAATGATTGTTCATCTT | 652 |
| KATERINI | CS103 | TCAGCAACATATGGGAAGGTTCTGACTTTGGATGGAGCAATTCAACACAGAGAATGGTGGATTTCCATACACTGAAATGATTGTTCATCTT | 621 | TCAGCAACATATGGGAAGGTTCTGACTTTGGATGGAGCAATTCAacACACAGAGAATGGTGGATTTCCATACACTGAAATGATTGTTCATCTT | 653 |
| TN90 | CS143 | TCAGCAACATATGGGAAGGTTCTGACTTTGGATGGAGCAATTCAACACAGAGAATGGTGGATTTCCATACACTGAAATGATTGTTCATCTT | 622 | TCAGCAACATATGGGAAGGTTCTGACTTTGGATGGAGCAATTCAacACACAGAGAATGGTGGATTTCCATACACTGAAATGATTGTTCATCTT | 654 |
| TN90 | 18GH2169 | TCAGCAACATATGGGAAGGTTCTGACTTTGGATGGAGCAATTCAACAGAGAATGGTGGATTTCCATACACTGAAATGATTGTTCATCTT | 623 | TCAGCAACATATGGGAAGGTTCTGACTTTGGATGGAGCAATTCAacacACAGAGAATGGTGGATTTCCATACACTGAAATGATTGTTCATCTT | 655 |
| TN90 | CS120 | TCAGCAACATATGGGAAGGTTCTGACTTTGGATGGAGCAATTCAACACAGAGAA | 624 | TCAGCAACATATGGGAAGGTTCTGACTTTGGATGGAGCAATTCAacACACAGAG | 656 |

TABLE 12D-continued

A list of exemplary mutant alleles obtained in the PMT3 gene. Mutant allele sequences listed here represent approximately 90-nucleotide-long genomic sequences from each edited PMT3 gene with the edited site in the middle of the genomic sequence (e.g., 4nucleotides on each side of the deleted sequence site). The mutant allele corresponds to the indel provided for each line in Table 10. The lowercase letters in the reference allele sequence (SEQ ID NO: 9) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| | | TGGTGGATTTCCATACACTGAAATGAT TGTTCATCTT | | AATGGTGGATTTCCATACACTGAAATG ATTGTTCATCTT | |
| TN90 | 17GH1698-22 | TCAGCAACATATGGGAAGGTTCTGACT TTGGATGGAGCAATTCAACACAGAATG GTGGATTTCCATACACTGAAATGATTG TTCATCTT | 625 | TCAGCAACATATGGGAAGGTTCTGACT TTGGATGGAGCAATTCAACACacagAG AATGGTGGATTTCCATACACTGAAATG ATTGTTCATCTT | 657 |
| TN90 | 17GH1700-13 | TCAGCAACATATGGGAAGGTTCTGACT TTGGATGGAGCAATTCAACACAGAGAA TGGTGGATTTCCATACACTGAAATGAT TGTTCATCTT | 626 | TCAGCAACATATGGGAAGGTTCTGACT TTGGATGGAGCAATTCAacACACAGAG AATGGTGGATTTCCATACACTGAAATG ATTGTTCATCTT | 658 |
| TN90 | 17GH1702-17 | TCAGCAACATATGGGAAGGTTCTGACT TTGGATGGAGCAATTCAACACAGAGAA TGGTGGATTTCCATACACTGAAATGAT TGTTCATCTT | 627 | TCAGCAACATATGGGAAGGTTCTGACT TTGGATGGAGCAATTCAacACACAGAG AATGGTGGATTTCCATACACTGAAATG ATTGTTCATCTT | 659 |
| TN90 | 18GH2171 | TCAGCAACATATGGGAAGGTTCTGACT TTGGATGGAGCAATTCAGAGAATGGTG GATTTCCATACACTGAAATGATTGTTC ATCTT | 628 | TCAGCAACATATGGGAAGGTTCTGACT TTGGATGGAGCAATTcaacacaCAGAG AATGGTGGATTTCCATACACTGAAATG ATTGTTCATCTT | 660 |
| TN90 | CS165 | TCAGCAACATATGGGAAGGTTCTGACT TTGGATGGAGCAATTCAACAGAGAATG GTGGATTTCCATACACTGAAATGATTG TTCATCTT | 629 | TCAGCAACATATGGGAAGGTTCTGACT TTGGATGGAGCAATTCAacacACACAG AATGGTGGATTTCCATACACTGAAATG ATTGTTCATCTT | 661 |
| TN90 | CS118 | TCAGCAACATATGGGAAGGTTCTGACT TTGGATGGAGCAATTCAACACAGAGAA TGGTGGATTTCCATACACTGAAATGAT TGTTCATCTT | 630 | TCAGCAACATATGGGAAGGTTCTGACT TTGGATGGAGCAATTCAacACACAGAG AATGGTGGATTTCCATACACTGAAATG ATTGTTCATCTT | 662 |
| TN90 | CS113 | TCAGCAACATATGGGAAGGTTCTGACT TTGGATGGAGCAATTCAACACAGAGAA TGGTGGATTTCCATACACTGAAATGAT TGTTCATCTT | 631 | TCAGCAACATATGGGAAGGTTCTGACT TTGGATGGAGCAATTCAacACACAGAG AATGGTGGATTTCCATACACTGAAATG ATTGTTCATCTT | 663 |
| TN90 | 17GH1737-24 | TCAGCAACATATGGGAAGGTTCTGACT TTGGATGGAGCAATTCAACACAGAGAA TGGTGGATTTCCATACACTGAAATGAT TGTTCATCTT | 632 | TCAGCAACATATGGGAAGGTTCTGACT TTGGATGGAGCAATTCAacACACAGAG AATGGTGGATTTCCATACACTGAAATG ATTGTTCATCTT | 664 |
| IZMIR | 18GH2254-7 | TCAGCAACATATGGGAAGGTTCTGACT TTGGATGGAGCAATTCAACAGAGAATG GTGGATTTCCATACACTGAAATGATTG TTCATCTT | 633 | TCAGCAACATATGGGAAGGTTCTGACT TTGGATGGAGCAATTCAacacACACAG AATGGTGGATTTCCATACACTGAAATG ATTGTTCATCTT | 665 |

TABLE 12E

A list of exemplary mutant alleles obtained in the PMT4 gene. Mutant allele sequences listed here represent approximately 90-nucleotide-long genomic sequences from each edited PMT4 gene with the edited site in the middle of the genomic sequence (e.g., 45 nucleotides oneach side of the deleted sequence site). The mutant allele corresponds to the indel provided for each line in Table 10. The lowercase letters in the reference allele sequence (SEQ ID NO: 10) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| BASMA | CS107 | TCAGCAACATATGGGAAGGTTTTGACT TTGGATGGAGCAATTCAACAGAGAATG GTGGATTTCCATACACTGAAATGATTG TTCATCTT | 666 | TCAGCAACATATGGGAAGGTTTTGAC TTTGGATGGAGCAATTCAacacACAG AGAATGGTGGATTTCCATACACTGAA ATGATTGTTCATCTT | 698 |

TABLE 12E-continued

A list of exemplary mutant alleles obtained in the PMT4 gene. Mutant allele sequences listed here represent approximately 90-nucleotide-long genomic sequences from each edited PMT4 gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 10) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| BASMA | CS106 | TCAGCAACATATGGGAAGGTTTTGACTTTGGATGGAGCAATTCAACGAGAATGGTGGATTTCCATACACTGAAATGATTGTTCATCTT | 667 | TCAGCAACATATGGGAAGGTTTTGACTTTGGATGGAGCAATTCAacacACAGAGAATGGTGGATTTCCATACACTGAAATGATTGTTCATCTT | 699 |
| K326 | CS115 | TCAGCAACATATGGGAAGGTTTTGACTTTGGATGGAGCAATTCAACGAGAATGGTGGATTTCCATACACTGAAATGATTGTTCATCTT | 668 | TCAGCAACATATGGGAAGGTTTTGACTTTGGATGGAGCAATTCAACacacaGAGAATGGTGGATTTCCATACACTGAAATGATTGTTCATCTT | 700 |
| K326 | 18GH2162 | TCAGCAACATATGGGAAGGTTTTGACTTTGGATGGAGCAATTCAACGAGAATGGTGGATTTCCATACACTGAAATGATTGTTCATCTT | 669 | TCAGCAACATATGGGAAGGTTTTGACTTTGGATGGAGCAATTCAACacacaGAGAATGGTGGATTTCCATACACTGAAATGATTGTTCATCTT | 701 |
| K326 | CS111 | TCAGCAACATATGGGAAGGTTTTGACTTTGGATGGAGCAATTCAAAGAGAATGGTGGATTTCCATACACTGAAATGATTGTTCATCTT | 670 | TCAGCAACATATGGGAAGGTTTTGACTTTGGATGGAGCAATTCAAcacacAGAGAATGGTGGATTTCCATACACTGAAATGATTGTTCATCTT | 702 |
| K326 | CS112 | TCAGCAACATATGGGAAGGTTTTGACTTTGGATGGAGCAATTCAAAGAGAATGGTGGATTTCCATACACTGAAATGATTGTTCATCTT | 671 | TCAGCAACATATGGGAAGGTTTTGACTTTGGATGGAGCAATTCAAcacacAGAGAATGGTGGATTTCCATACACTGAAATGATTGTTCATCTT | 703 |
| K326 | 17GH1678-60 | TCAGCAACATATGGGAAGGTTTTGACTTTGGATGGAGCAATTCAACGAGAATGGTGGATTTCCATACACTGAAATGATTGTTCATCTT | 672 | TCAGCAACATATGGGAAGGTTTTGACTTTGGATGGAGCAATTCAacacACAGAGAATGGTGGATTTCCATACACTGAAATGATTGTTCATCTT | 704 |
| K326 | CS131 | TCAGCAACATATGGGAAGGTTTTGACTTTGGATGGAGCAATTCAACGAGAATGGTGGATTTCCATACACTGAAATGATTGTTCATCTT | 673 | TCAGCAACATATGGGAAGGTTTTGACTTTGGATGGAGCAATTCAacacACAGAGAATGGTGGATTTCCATACACTGAAATGATTGTTCATCTT | 705 |
| KATERINI | CS164 | TCAGCAACATATGGGAAGGTTTTGACTTTGGATGGAGCAATTCAACACAGAGAATGGTGGATTTCCATACACTGAAATGATTGTTCATCTT | 674 | TCAGCAACATATGGGAAGGTTTTGACTTTGGATGGAGCAATTCAacACAGAGAATGGTGGATTTCCATACACTGAAATGATTGTTCATCTT | 706 |
| KATERINI | CS163 | TCAGCAACATATGGGAAGGTTTTGACTTTGGATGGAGCAATTCAACACAGAGAATGGTGGATTTCCATACACTGAAATGATTGTTCATCTT | 675 | TCAGCAACATATGGGAAGGTTTTGACTTTGGATGGAGCAATTCAacACAGAGAATGGTGGATTTCCATACACTGAAATGATTGTTCATCTT | 707 |
| KATERINI | CS146 | TCAGCAACATATGGGAAGGTTTTGACTTTGGATGGAGCAATTCAACACAGAGAATGGTGGATTTCCATACACTGAAATGATTGTTCATCTT | 676 | TCAGCAACATATGGGAAGGTTTTGACTTTGGATGGAGCAATTCAacACACAGAGAATGGTGGATTTCCATACACTGAAATGATTGTTCATCTT | 708 |
| KATERINI | CS147 | TCAGCAACATATGGGAAGGTTTTGACTTTGGATGGAGCAATTCAACACAGAGAATGGTGGATTTCCATACACTGAAATGATTGTTCATCTT | 677 | TCAGCAACATATGGGAAGGTTTTGACTTTGGATGGAGCAATTCAACACAGAGAATGGTGGATTTCCATACACTGAAATGATTGTTCATCTT | 709 |
| KATERINI | CS150 | TCAGCAACATATGGGAAGGTTTTGACTTTGGATGGAGCAATTCAACACAGAGAATGGTGGATTTCCATACACTGAAATGATTGTTCATCTT | 678 | TCAGCAACATATGGGAAGGTTTTGACTTTGGATGGAGCAATTCAacACACAGAGAATGGTGGATTTCCATACACTGAAATGATTGTTCATCTT | 710 |
| KATERINI | CS151 | TCAGCAACATATGGGAAGGTTTTGACTTTGGATGGAGCAATTAGAATGGTGGATTTCCATACACTGAAATGATTGTTCATCTT | 679 | TCAGCAACATATGGGAAGGTTTTGACTTTGGATGGAGCAATTcaacacagAGAATGGTGGATTTCCATACACTGAAATGATTGTTCATCTT | 711 |
| KATERINI | CS148 | TCAGCAACATATGGGAAGGTTTTGACTTTGGATGGAGCAATTCAACACAGAGAATGGTGGATTTCCATACACTGAAATGATTGTTCATCTT | 680 | TCAGCAACATATGGGAAGGTTTTGACTTTGGATGGAGCAATTCAacACACAGAGAATGGTGGATTTCCATACACTGAAATGATTGTTCATCTT | 712 |

TABLE 12E-continued

A list of exemplary mutant alleles obtained in the PMT4 gene. Mutant allele sequences listed here represent approximately 90-nucleotide-long genomic sequences from each edited PMT4 gene with the edited site in the middle of the genomic sequence (e.g., 45 nucleotides on each side of the deleted sequence site). The mutant allele corresponds to the indel provided for each line in Table 10. The lowercase letters in the reference allele sequence (SEQ ID NO: 10) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| KATERINI | CS149 | TCAGCAACATATGGGAAGGTTTTGACTTTGGATGGAGCAATTAGAATGGTGGATTTCCATACACTGAAATGATTGTTCATCTT | 681 | TCAGCAACATATGGGAAGGTTTTGACTTTGGATGGAGCAATTcaacacacagAGAATGGTGGATTTCCATACACTGAAATGATTGTTCATCTT | 713 |
| KATERINI | CS152 | TCAGCAACATATGGGAAGGTTTTGACTTTGGATGGAGCAATTCAACAGAGAATGGTGGATTTCCATACACTGAAATGATTGTTCATCTT | 682 | TCAGCAACATATGGGAAGGTTTTGACTTTGGATGGAGCAATTCAacacACAGAGAATGGTGGATTTCCATACACTGAAATGATTGTTCATCTT | 714 |
| KATERINI | CS153 | TCAGCAACATATGGGAAGGTTTTGACTTTGGATGGAGCAATTCAACAGAGAATGGTGGATTTCCATACACTGAAATGATTGTTCATCTT | 683 | TCAGCAACATATGGGAAGGTTTTGACTTTGGATGGAGCAATTCAacacACAGAGAATGGTGGATTTCCATACACTGAAATGATTGTTCATCTT | 715 |
| KATERINI | CS102 | TCAGCAACATATGGGAAGGTTTTGACTTTGGATGGAGCAATTCAACACAGAGAATGGTGGATTTCCATACACTGAAATGATTGTTCATCTT | 684 | TCAGCAACATATGGGAAGGTTTTGACTTTGGATGGAGCAATTCAacACACAGAGAATGGTGGATTTCCATACACTGAAATGATTGTTCATCTT | 716 |
| KATERINI | CS103 | TCAGCAACATATGGGAAGGTTTTGACTTTGGATGGAGCAATTCAACACAGAGAATGGTGGATTTCCATACACTGAAATGATTGTTCATCTT | 685 | TCAGCAACATATGGGAAGGTTTTGACTTTGGATGGAGCAATTCAacACACAGAGAATGGTGGATTTCCATACACTGAAATGATTGTTCATCTT | 717 |
| TN90 | CS143 | TCAGCAACATATGGGAAGGTTTTGACTTTGGATGGAGCAATTCAACAGAGAATGGTGGATTTCCATACACTGAAATGATTGTTCATCTT | 686 | TCAGCAACATATGGGAAGGTTTTGACTTTGGATGGAGCAATTCAacACACAGAGAATGGTGGATTTCCATACACTGAAATGATTGTTCATCTT | 718 |
| TN90 | 18GH2169 | TCAGCAACATATGGGAAGGTTTTGACTTTGGATGGAGCAATTCAACACAGAGAATGGTGGATTTCCATACACTGAAATGATTGTTCATCTT | 687 | TCAGCAACATATGGGAAGGTTTTGACTTTGGATGGAGCAATTCAacACACAGAGAATGGTGGATTTCCATACACTGAAATGATTGTTCATCTT | 719 |
| TN90 | CS120 | TCAGCAACATATGGGAAGGTTTTGACTTTGGATGGAGCAATTCAACACAGAGAATGGTGGATTTCCATACACTGAAATGATTGTTCATCTT | 688 | TCAGCAACATATGGGAAGGTTTTGACTTTGGATGGAGCAATTCAacACACAGAGAATGGTGGATTTCCATACACTGAAATGATTGTTCATCTT | 720 |
| TN90 | 17GH1698-22 | TCAGCAACATATGGGAAGGTTTTGACTTTGGATGGAGCAATTCAACACAGAGAATGGTGGATTTCCATACACTGAAATGATTGTTCATCTT | 689 | TCAGCAACATATGGGAAGGTTTTGACTTTGGATGGAGCAATTCAacACACAGAGAATGGTGGATTTCCATACACTGAAATGATTGTTCATCTT | 721 |
| TN90 | 17GH1700-13 | TCAGCAACATATGGGAAGGTTTTGACTTTGGATGGAGCAATTCAACAGAGAATGGTGGATTTCCATACACTGAAATGATTGTTCATCTT | 690 | TCAGCAACATATGGGAAGGTTTTGACTTTGGATGGAGCAATTCAacacACAGAGAATGGTGGATTTCCATACACTGAAATGATTGTTCATCTT | 722 |
| TN90 | 17GH1702-17 | TCAGCAACATATGGGAAGGTTTTGACTTTGGATGGAGCAATTCAACAAGAATGGTGGATTTCCATACACTGAAATGATTGTTCATCTT | 691 | TCAGCAACATATGGGAAGGTTTTGACTTTGGATGGAGCAATTCAACacacagAGAATGGTGGATTTCCATACACTGAAATGATTGTTCATCTT | 723 |
| TN90 | 18GH2171 | TCAGCAACATATGGGAAGGTTTTGACTTTGGATGGAGCAATTCAACACAGAGAATGGTGGATTTCCATACACTGAAATGATTGTTCATCTT | 692 | TCAGCAACATATGGGAAGGTTTTGACTTTGGATGGAGCAATTCAacACACAGAGAATGGTGGATTTCCATACACTGAAATGATTGTTCATCTT | 724 |
| TN90 | CS165 | TCAGCAACATATGGGAAGGTTTTGACTTTGGATGGAGCAATTCAACAGAGAATGGTGGATTTCCATACACTGAAATGATTGTTCATCTT | 693 | TCAGCAACATATGGGAAGGTTTTGACTTTGGATGGAGCAATTCAacacACAGAGAATGGTGGATTTCCATACACTGAAATGATTGTTCATCTT | 725 |

TABLE 12E-continued

A list of exemplary mutant alleles obtained in the PMT4 gene. Mutant allele sequences listed here represent approximately 90-nucleotide-long genomic sequences from each edited PMT4 gene with the edited site in the middle of the genomic sequence (e.g., 45 nucleotides oneach side of the deleted sequence site). The mutant allele corresponds to the indel provided for each line in Table 10. The lowercase letters in the reference allele sequence (SEQ ID NO: 10) denote which nucleotides are deleted in the mutant allele.

| Genotype | Line | Mutant Allele Sequence | Mutant Allele SEQ ID NO. | Reference Allele Sequence | Reference Allele SEQ ID NO. |
|---|---|---|---|---|---|
| TN90 | CS118 | TCAGCAACATATGGGAAGGTTTTGACTTTGGATGGAGCAATTCAACACAGAGAATGGTGGATTTCCATACACTGAAATGATTGTTCATCTT | 694 | TCAGCAACATATGGGAAGGTTTTGACTTTGGATGGAGCAATTCAacACACAGAGAATGGTGGATTTCCATACACTGAAATGATTGTTCATCTT | 726 |
| TN90 | CS113 | TCAGCAACATATGGGAAGGTTTTGACTTTGGATGGAGCAATTCAACACAGAGAATGGTGGATTTCCATACACTGAAATGATTGTTCATCTT | 695 | TCAGCAACATATGGGAAGGTTTTGACTTTGGATGGAGCAATTCAacACACAGAGAATGGTGGATTTCCATACACTGAAATGATTGTTCATCTT | 727 |
| TN90 | 17GH1737-24 | TCAGCAACATATGGGAAGGTTTTGACTTTGGATGGAGCAATTCAACACAGAGAATGGTGGATTTCCATACACTGAAATGATTGTTCATCTT | 696 | TCAGCAACATATGGGAAGGTTTTGACTTTGGATGGAGCAATTCAacACACAGAGAATGGTGGATTTCCATACACTGAAATGATTGTTCATCTT | 728 |
| IZMIR | 18GH2254-7 | TCAGCAACATATGGGAAGGTTTTGACTTTGGATGGAGCAATTCAAGAATGGTGGATTTCCATACACTGAAATGATTGTTCATCTT | 697 | TCAGCAACATATGGGAAGGTTTTGACTTTGGATGGAGCAATTCAacacacagAGAATGGTGGATTTCCATACACTGAAATGATTGTTCATCTT | 729 |

Example 8. Alkaloid Analysis of PMT Edited Lines

Homozygous genome edited tobacco lines from Example 7, along with control lines, are grown in a field. At flowering stage, plants are topped and two-weeks post topping, lamina samples are collected from the third, fourth, and fifth leaves from the top of the plant and alkaloid levels are measured (see Tables 13A-13C) using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009).

Approximately 0.5 g of tobacco is extracted using liquid/liquid extraction into an organic solvent containing an internal standard and analyzed by gas chromatography (GC) with flame ionization detection (FID). Results can be reported as weight percent (Wt %) on either on as is or dry weight basis. Reporting data on a dry weight basis requires an oven volatiles (OV) determination. Unless specified otherwise, total or individual alkaloid levels or nicotine levels shown herein are on a dry weight basis (e.g., percent total alkaloid or percent nicotine).

Plants are also planted in the field, harvested, and tested for alkaloids and TSNA levels in cured tobacco. Both leaf yield and leaf grade are also assessed for PMT edited plants.

TABLE 13A

Nicotine analysis of K326 and TN90 PMT edited lines after two weeks after flowering.

| Variety | Line | Replicate | Nicotine (mg/g tissue) |
|---|---|---|---|
| K 326 | CS111 | 1 | 0.023 |
|  |  | 2 | 0.024 |

TABLE 13A-continued

Nicotine analysis of K326 and TN90 PMT edited lines after two weeks after flowering.

| Variety | Line | Replicate | Nicotine (mg/g tissue) |
|---|---|---|---|
|  | CS131 | 1 | 0.022 |
|  |  | 2 | 0.018 |
|  |  | 3 | 0.021 |
|  | CS115 | 1 | 0.023 |
|  |  | 2 | 0.015 |
|  | Control | 1 | 16.8 |
|  |  | 2 | 17.2 |
|  |  | 3 | 16.6 |
| TN 90 LC | CS116 | 1 | 0.029 |
|  |  | 2 | 0.022 |
|  | CS133 | 1 | 0.016 |
|  |  | 2 | 0.018 |
|  | CS135 | 1 | 0.027 |
|  |  | 2 | 0.031 |
|  | CS120 | 1 | 0.022 |
|  |  | 2 | 0.045 |
|  | CS137 | 1 | 0.07 |
|  |  | 2 | 0.048 |
|  | Control | 1 | 29.5 |
|  |  | 2 | 29.8 |
|  |  | 3 | 24.2 |

TABLE 13B

Nicotine analysis of K326 and TN90 PMT edited lines after two-weeks after topping.

| Variety | Group | Replicate | Nicotine (mg/g tissue) |
|---|---|---|---|
| K 326 | CS111 | 1 | 0.024 |
|  |  | 2 | 0.025 |
|  | CS131 | 1 | 0.021 |
|  |  | 2 | 0.02 |
|  |  | 3 | 0.019 |

TABLE 13B-continued

Nicotine analysis of K326 and TN90 PMT edited lines after two-weeks after topping.

| Variety | Group | Replicate | Nicotine (mg/g tissue) |
|---|---|---|---|
| | CS115 | 1 | 0.018 |
| | Control | 1 | 16.771 |
| | | 2 | 17.212 |
| | | 3 | 16.581 |
| | | 4 | 22.734 |
| TN 90 LC | CS116 | 1 | 0.015 |
| | CS133 | 1 | 0.036 |
| | | 2 | 0.018 |
| | CS135 | 1 | 0.018 |
| | | 2 | 0.019 |
| | CS120 | 1 | 0.04 |
| | | 2 | 0.025 |
| | CS137 | 1 | 0.051 |
| | | 2 | 0.057 |
| | Control | 1 | 29.472 |
| | | 2 | 29.776 |
| | | 3 | 24.22 |
| | | 4 | 24.939 |

TABLE 13C

Nicotine analysis of Katerini and Basma PMT edited lines after two-weeks after flowering.

| Variety | Group | Replicate | Nicotine (mg/g tissue) |
|---|---|---|---|
| Katerini | CS102 | 1 | 0.032 |
| | | 2 | 0.028 |
| | CS103 | 1 | 0.017 |
| | Control | 1 | 26.109 |
| | | 2 | 26.466 |
| | | 3 | 27.091 |
| Basma | CS107 | 1 | 0.029 |
| | CS108 | 1 | 0.014 |
| | | 2 | 0.018 |
| | Control | 1 | 21.979 |
| | | 2 | 20.88 |
| | | 3 | 23.499 |

Example 9. Development of Male Sterile PMT Edited Lines

PMT edited hybrid lines are developed using the lines from Example 7. Hybrid lines are grown in the field and used as progenitors for male sterile lines. See Table 14.

TABLE 14

PMT edited very low nicotine male sterile lines

| Male Sterile Variety | Pollen source (line) | F1 hybrid seed (line) |
|---|---|---|
| MS Katerini | CS102 | dCS11 |
| | CS103 | dCS12 |
| MS Basma | CS106 | dCS13 |
| | CS107 | dCS14 |
| MS K326 | CS111 | dCS15 |
| | CS115 | dCS16 |
| MS TN90 | CS118 | dCS17 |
| | CS120 | dCS18 |
| MS Izmir | 18GH2254 | dS2697 |

Example 10. PMT Edited Lines Resist Mold During Curing

Tobacco leaf harvested from several low alkaloid tobacco lines is subjected to standard air curing practices. The tobacco leaves are examined for mold after the completion of curing.

Tobacco from the LA BU 21 exhibits more mold infestation than TN90 LC, a TN90 variety comprising an RNAi construct to downregulate all five PMT genes, a TN90 variety comprising an RNAi construct to downregulate the alkaloid biosynthesis gene PR50, and four PMT edited lines (CS47, CS59, CS63, and CS64) in a TN90 genetic background. See Table 15 and FIGS. 6A to 6E and 7.

TABLE 15

Mold damage exhibited by tobacco lines.

| Variety | Mold Rating | | | | | | | | | | | | Significant Mold | Some Mold | Little/No Mold |
|---|---|---|---|---|---|---|---|---|---|---|---|---|---|---|---|
| | Replicate 1 | | | Replicate 2 | | | Replicate 3 | | | Replicate 4 | | | | | |
| TN90 LC | G | G | G | G | G | G | G | G | G | G | G | G | 0% | 0% | 100% |
| LA BU 21 | G | S | G | B | S | G | S | S | S | B | S | S | 17% | 58% | 25% |
| TN90 (PMT RNAi) | G | G | G | G | G | G | G | G | G | G | G | G | 0% | 0% | 100% |
| TN90 (PR50 RNai) | G | G | G | G | G | G | G | G | G | G | G | G | 0% | 0% | 100% |
| CS47 | G | G | G | G | G | G | G | G | G | G | G | G | 0% | 0% | 100% |
| CS59 | G | G | G | G | G | G | G | G | G | G | G | G | 0% | 0% | 100% |
| CS63 | G | G | G | G | G | G | G | G | G | G | G | G | 0% | 0% | 100% |
| CS64 | G | G | G | G | G | G | G | G | S | S | G | | 0% | 17% | 83% |

"G" refers to little/no mold;
"S" refers to some mold; and
"B" refers to significant mold.
Percentage of Mold refers to the percentage of air cured sticks of tobacco exhibited each category of mold damage.

The invention claimed is:

1. A tobacco plant, or part thereof, comprising:
   (a) a first knockout mutant allele in a putrescine N-methyltransferase (PMT)1a gene (PMT1a), wherein a wildtype allele of the PMT1a gene encodes the polypeptide of SEQ ID NO: 12, and wherein the first knockout mutant allele in the PMT1a gene comprises the sequence of SEQ ID NO: 432; and
   (b) a second knockout mutant allele in a PMT1b gene, wherein a wildtype allele of the PMT1b gene encodes the polypeptide of SEQ ID NO: 11; and
   (c) a third knockout mutant allele in a PMT2 gene, wherein a wildtype allele of the PMT2 gene encodes the polypeptide of SEQ ID NO: 13; and
   (d) a fourth knockout mutant allele in a PMT3 gene, wherein a wildtype allele of the PMT3 gene encodes the polypeptide of SEQ ID NO: 14; and
   (e) a fifth knockout mutant allele in a PMT4 gene, wherein a wildtype allele of the PMT4 gene encodes the polypeptide of SEQ ID NO: 15,
wherein said tobacco plant produces a leaf comprising a nicotine level less than the nicotine level of a leaf from a control tobacco plant not having each of the first, second, third, fourth, and fifth knockout mutant alleles when grown and processed under comparable conditions.

2. The tobacco plant, or part thereof, of claim 1, wherein said tobacco plant produces a leaf comprising a nicotine level less than 90% of the nicotine level of a leaf from a control tobacco plant not having said one or more mutant alleles when grown and processed under comparable conditions.

3. The tobacco plant, or part thereof, of claim 1, wherein said tobacco plant produces a leaf comprising a total alkaloid level less than 90% of the total alkaloid level of a leaf from said control tobacco plant when grown and processed under comparable conditions.

4. The tobacco plant, or part thereof, of claim 1, wherein one or more mutant alleles comprise a mutation in a sequence region selected from the group consisting of a promoter, 5' untranslated region (UTR), first exon, first intron, second exon, second intron, third exon, 3' UTR, terminator, and any combination thereof.

5. The tobacco plant, or part thereof, of claim 1, wherein one or more mutant alleles comprise one or more mutation types selected from the group consisting of a nonsense mutation, a missense mutation, a frameshift mutation, a splice-site mutation, and any combination thereof.

6. The tobacco plant, or part thereof, of claim 1, wherein one or more mutant alleles result in one or more of the following: a PMT protein truncation, a non-translatable PMT gene transcript, a non-functional PMT protein, a premature stop codon in a PMT gene, and any combination thereof.

7. The tobacco plant, or part thereof, of claim 1, wherein one or more mutant alleles comprise a mutation selected from the group consisting of a substitution, a deletion, an insertion, a duplication, and an inversion of one or more nucleotides relative to a wild-type PMT gene.

8. The tobacco plant, or part thereof, of claim 1, wherein said tobacco plant produces a leaf comprising a nicotine level of less than 0.15% dry weight.

* * * * *